United States Patent
Walji et al.

(10) Patent No.: US 11,066,396 B2
(45) Date of Patent: Jul. 20, 2021

(54) 3-ARYL- HETEROARYL SUBSTITUTED 5-TRIFLUOROMETHYL OXADIAZOLES AS HISTONEDEACETYLASE 6 (HDAC6) INHIBITORS

(71) Applicant: Merck Sharp & Dohme Corp., Rahway, NJ (US)

(72) Inventors: Abbas Walji, Lansdale, PA (US); Richard Berger, Harleysville, PA (US); Craig A. Stump, Pottstown, PA (US); Kelly-Ann S. Schlegel, Fleetwood, PA (US); James J. Mulhearn, Elkins, PA (US); Thomas J. Greshock, Collegeville, PA (US); Deping Wang, Furlong, PA (US); Mark E. Fraley, North Wales, PA (US); Kristen G. Jones, Oreland, PA (US)

(73) Assignee: MERCK SHARP & DOHME CORP., Rahway, NJ (US)

( * ) Notice: Subject to any disclaimer, the term of this patent is extended or adjusted under 35 U.S.C. 154(b) by 0 days.

(21) Appl. No.: 16/309,390

(22) PCT Filed: Jun. 19, 2017

(86) PCT No.: PCT/US2017/038067
§ 371 (c)(1),
(2) Date: Dec. 12, 2018

(87) PCT Pub. No.: WO2017/222951
PCT Pub. Date: Dec. 28, 2017

(65) Prior Publication Data
US 2019/0185462 A1    Jun. 20, 2019

Related U.S. Application Data

(60) Provisional application No. 62/353,854, filed on Jun. 23, 2016.

(51) Int. Cl.
| | |
|---|---|
| *C07D 413/04* | (2006.01) |
| *C07D 413/10* | (2006.01) |
| *C07D 413/14* | (2006.01) |
| *C07D 413/12* | (2006.01) |
| *C07D 417/14* | (2006.01) |
| *C07D 471/04* | (2006.01) |
| *C07D 471/14* | (2006.01) |
| *C07D 487/04* | (2006.01) |
| *C07D 491/048* | (2006.01) |
| *C07D 491/052* | (2006.01) |

(Continued)

(52) U.S. Cl.
CPC ............ *C07D 413/10* (2013.01); *A61K 45/06* (2013.01); *A61P 3/10* (2018.01); *A61P 9/00* (2018.01); *A61P 11/06* (2018.01); *A61P 25/18* (2018.01); *A61P 25/28* (2018.01); *A61P 29/00* (2018.01); *A61P 35/00* (2018.01); *A61P 37/00* (2018.01); *A61P 37/02* (2018.01); *C07D 271/06* (2013.01); *C07D 271/113* (2013.01); *C07D 413/04* (2013.01); *C07D 413/12* (2013.01); *C07D 413/14* (2013.01); *C07D 417/12* (2013.01); *C07D 417/14* (2013.01); *C07D 471/04* (2013.01); *C07D 471/14* (2013.01); *C07D 487/04* (2013.01); *C07D 491/048* (2013.01); *C07D 491/052* (2013.01); *C07D 498/04* (2013.01); *C07D 513/04* (2013.01); *C07F 7/0807* (2013.01)

(58) Field of Classification Search
CPC ... C07D 413/04; C07D 413/10; C07D 413/14
See application file for complete search history.

(56) References Cited

U.S. PATENT DOCUMENTS

| | | |
|---|---|---|
| 2,789,118 A | 4/1957 | Bernstein |
| 2,990,401 A | 6/1961 | Bernstein |

(Continued)

FOREIGN PATENT DOCUMENTS

| | | | |
|---|---|---|---|
| EP | 1870401 A1 | 12/2007 | |
| EP | 15200959.3 | * 12/2015 | ............. A01N 25/04 |

(Continued)

OTHER PUBLICATIONS

Pearce et al., Failure modes in anticancer drug discovery and development, Cancer Drug Design and Discovery Edited by Stephen Neidle, Chapter 18, pp. 424-435 (2008).*

Johnson et al., Relationships between drug activity in NCI preclinical in vitro and in vivo models and early clinical trials, British Journal of Cancer, 84(10): 1424-1431,2001.*

Gura et al., Systems for identifying new drugs are often faulty, Science, 278:1041-1042, 1997.*

(Continued)

*Primary Examiner* — Deepak R Rao
(74) *Attorney, Agent, or Firm* — Nicole M. Beeler; John C. Todaro

(57) ABSTRACT

The present invention is directed to substituted 5-trifluoromethyl oxadiazole compounds of generic formula (I) or a pharmaceutically acceptable salt thereof. In particular, the invention is directed to a class of aryl and heteroaryl substituted 5-trifluoromethyl oxadiazole compounds of formula I which may be useful as HDAC6 inhibitors for treating cellular proliferative diseases, including cancer, neurodegenerative diseases, such as schizophrenia and stroke, as well as other diseases.

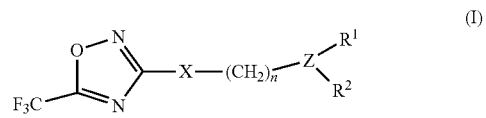

(I)

9 Claims, No Drawings

(51) Int. Cl.

| | |
|---|---|
| C07D 271/06 | (2006.01) |
| C07D 498/04 | (2006.01) |
| C07D 513/04 | (2006.01) |
| A61P 25/28 | (2006.01) |
| A61P 29/00 | (2006.01) |
| A61P 35/00 | (2006.01) |
| A61P 25/18 | (2006.01) |
| A61P 11/06 | (2006.01) |
| A61P 3/10 | (2006.01) |
| A61K 45/06 | (2006.01) |
| A61P 9/00 | (2006.01) |
| C07F 7/08 | (2006.01) |
| A61P 37/00 | (2006.01) |
| C07D 271/113 | (2006.01) |
| A61P 37/02 | (2006.01) |
| C07D 417/12 | (2006.01) |

(56) References Cited

U.S. PATENT DOCUMENTS

| | | | |
|---|---|---|---|
| 3,048,581 A | 8/1962 | Fried | |
| 3,126,375 A | 3/1964 | Ringold | |
| 3,749,712 A | 7/1973 | Cavazza | |
| 3,928,326 A | 12/1975 | Brattsand | |
| 3,929,768 A | 12/1975 | Brattsand | |
| 3,996,359 A | 12/1976 | Brattsand | |
| 4,782,084 A | 11/1988 | Vyas et al. | |
| 4,885,314 A | 12/1989 | Vyas et al. | |
| 5,719,147 A | 2/1998 | Dorn | |
| 6,061,934 A | 5/2000 | Baggen | |
| 6,284,781 B1 | 9/2001 | Danishefsky et al. | |
| 6,288,237 B1 | 9/2001 | Hoefle et al. | |
| 8,101,618 B2 * | 1/2012 | Kawamoto | C07D 417/14 514/252.02 |
| 8,158,677 B2 | 4/2012 | Munger et al. | |
| 8,981,084 B2 * | 3/2015 | Baloglu | C07D 271/06 540/575 |
| 10,081,624 B2 | 9/2018 | Kaieda et al. | |
| 2005/0249730 A1 | 11/2005 | Goetsch | |

FOREIGN PATENT DOCUMENTS

| | | | | |
|---|---|---|---|---|
| EP | 16157729.1 | * | 2/2016 | .......... C07D 471/08 |
| WO | 0050032 | | 8/2000 | |
| WO | 200044777 | | 8/2000 | |
| WO | 200061186 A1 | | 10/2000 | |
| WO | 2003013526 A1 | | 8/2002 | |
| WO | 2003059951 | | 7/2003 | |
| WO | 2005013958 | | 2/2005 | |
| WO | 2011088181 A1 | | 7/2011 | |
| WO | 2011088192 A1 | | 7/2011 | |
| WO | 006408 | | 1/2013 | |
| WO | 2013008162 | | 1/2013 | |
| WO | WO-2013008162 A1 * | | 1/2013 | ......... A61K 31/5377 |
| WO | 066831 A1 | | 5/2013 | |
| WO | 066839 A2 | | 5/2013 | |
| WO | 2013066835 A2 | | 5/2013 | |
| WO | WO-2013066831 A1 * | | 5/2013 | .......... C07D 413/14 |
| WO | WO2013066833 | | 5/2013 | |
| WO | 2013080120 | | 6/2013 | |
| WO | 2016031815 A1 | | 3/2016 | |
| WO | 2017085100 A1 | | 5/2017 | |
| WO | 2017093348 A1 | | 6/2017 | |
| WO | WO-2017093348 A1 * | | 6/2017 | .......... C07D 471/08 |
| WO | WO-2017103219 A1 * | | 6/2017 | .......... C07D 413/04 |
| WO | WO-2017110862 A1 * | | 6/2017 | ............. A01N 25/04 |
| WO | 2017118689 A1 | | 7/2017 | |
| WO | WO-2017222952 A1 * | | 12/2017 | ............. A61P 35/00 |
| WO | WO-2018080859 A1 * | | 5/2018 | .......... C07D 413/12 |
| WO | WO-2018187553 A1 * | | 10/2018 | .......... C07D 417/12 |

OTHER PUBLICATIONS

Simone, Oncology: Introduction, Cecil Textbook of Medicine, 20th Edition, vol. 1, pp. 1004-1010, 1996.*
Damasio, Alzheimer's Disease and related dementias, Cecil Textbook of Medicine, 20th Edition, vol. 2, pp. 1992-1996, 1996.*
Layzer, Degenerative diseases of the nervous system, Cecil Textbook of Medicine, 20th Edition, vol. 2, pp. 2050-2057, 1996.*
Takai et al., "Human Ovarian Carcinoma Cells: Histone Deacetylase Inhibitors Exhibit Antiproliferative Activity and Potently Induce Apoptosis", American Cancer Society, 2004, 101(12), 2760-2770.*
Glaser, "HDAC Inhibitors: Clinical Update and Mechanism-Based Potential," Biochemical Pharmacology, 2007 74(5), 659-671.*
Acute Leukemia, Merck Manual (Online Edition) 6 pages, pp. 1-6 (2013).*
Arts et al., Histone Deacetylase Inhibitors :From Chromatin Remodeling to Experimental Cancer Therapeutics, Current Medicinal Chemistry, 2003, 2343-2350, 10.
Ben-Av et al., Induction of Vascular Endothielial Growth Factor Expression in Synovial fibroblasts by Prostaglandin and Interleukin-1: A Potential mechanism for Inflammatory Angiogenesis, FEBS Letters, 1995, 83-87, 372.
Benezra et al., In Vivo Angiogenic Activity of Interleukins, Arch Ophthalmol, 1990, 573-576, 108.
Berge, S.M., et al.,, "Pharmaceutical Salts", J. Pharm. Sci, 1977, pp. 1-19, vol. 66, No. 1.
Bingham, A.L., et al.,, "Over One Hundred Solvates of sulfathiazole", Chem. Commun., 2001, pp. 603-604.
Blanchard et al., Histone Deacetylase Inhibitors: New Drugs for the Treatment of Inflammatory Diseases?, DDT, 2005, 197-204, 10.
Bouma et al., Thrombin Activable Fibrinolysis Inhibitor (TAFI, Plasma Procarboxypeptidedase B, Procarboxypeptidase R, Procarboxypeptidase U), Thrombosis Research, 2001, 329-354, 101.
Brower, Tumor Angiogenesis New Drugs on the Block, Nature America, 1999, 963-968, 17.
Caira, M.R., et al.,, "Preparation and Crystal Characterization of a Polymorph,a Monohydrate, and an Ethyl Acetate Solvate of the Antifungal Fluconazole", J. Pharmaceutical Sci., 2004, pp. 601-611, vol. 93, No. 3.
Chakraborty et al., Developmental Expression of the Cyclo-Oxygenase-1 and Cyclo-oxygenase-2 genes in the Peri-implantation Mouse Uterus and their differential regulation by the blastocyst and ovarian steroids, J. Mol Endocrinol, 1996, 107-122, 16.
Chiarugi et al., Cox-2, iNOS and p53 as play-makers of tumor angiogenesis (Review), International J. of Molecular Medicine, 1998, 715-719, 2.
Diaz-Flores et al., Intense Vascular Sprouting From Rat Femoral Vein Induced by Prostaglandins E1 and E2, The Anatomical Record, 1994, 68-76, 238.
Eliel et al., Stereochemistry of Organic Compounds, Stereochemistry of Carbon Compounds, 1994, pp. 1119-1190, John Wiley and Sons, New York.
Fathallah-Shaykh et al., Gene Transfer of IFN-y into Established Brain Tumors Represses Grwoth by Antiangiogenesis, J. of Immunology, 2000, 217-222, 164.
Fernandez et al., Neovascularization Produced by Angiotensin II, Clinical Mediicne, 1985, 141-145, 105.
Gould, Salt selection for basic drugs, International J. of Pharmaceutics, 1986, 201-217, 33.
Gralinkski et al., Effects of Troglitazone and Pioglitazone on Cytokine-Mediated Endothelial Cell Proliferation in Vitro, J. of Cardiovascular Pharmacology, 1998, 909-913, 31.
Gu et al., Effect of Novel CAAX Peptidomimetic Farnesyltransferase Inhibitor on Angiogenesis In Vitro and In Vivo, European J. of Cancer, 1999, 1394-1401, 35.
Hall et al., The Promise and Reality of Cancer Gene Therapy, Am. J. Hum. Genet, 1997, 785-789, 61.
Harada et al., Expression and Regulation of Vascular Endothelial Growth Factor in Osteoblasts, Clinical Ortho, 1995, 76-80, 313.
Higuchi et al., Pro-Drugs as Novel Delivery Systems, vol. 14 of the A.C.S. Symposium Series.
Hla et al., Human Cyclooxygenase-2 cDNA, Proc. Natl. Acad. Sci., 1992, 7384-7388, 89.

(56) References Cited

OTHER PUBLICATIONS

Kalin et al., Development and Therapeutic Implications of Selective Histone, J. of Medicinal Chemistry, 2013, pp. 6297-6313, 56.

Kim et al., Inhibition of Endothelial Growth Factor-Induced Angiogenesis Suppreses Tumour Growth in Vivo, Nature, 1993, 841-844, 362.

Korte et al., Changes of the Coagulation and Fibrinolysis System n Malignancy: Their possible Impact on Future Diagnostic and Therapeutic Procedures, Clin Chem Lab Med, 2000, 679-692, 38 (8), 38.

Kufe et al., Principles of Gene Therapy, Cancer Medicine, 2000, pp. 876-889, 5th Ed.

Leoni et al., The Antitumor Histone Deacetylase Inhibitor Suberoylanilide Hydroxamic Acid Exhibits Antiinflammatory Properties Via Suppression of Cytokines, PNAS, 2002, 2995-3000, 99.

Li et al., Adenovirus-Mediated Delivery of a uPA/uPAR Antagonist Suppresses Angiogenesis-Dependent Tumor Growth and Dissemination in Mice, Gene Therapy, 1998, 1105-1113, 5.

Majima et al., Significant Roles of Inducible Cyclooxygenase (COX)-2 in Angiogenesis in Rat Sponge Implants, Jpn. J. Pharmacol., 1997, 105-114, 75.

Miller et al., Histone Deacetylase Inhibitors, J. of Medicinal Chemistry, 2003, 5097-5116, 46.

Murata et al., Peroxisome Proliferator-Activated Receptor-y Ligands Inhibit Choroidal Neovascularization, Inestigative Ophthalmology & visual Science, 2000, 2309-2317, 41.

Murata et al., Response of Experimental Retinal Neovascularization to Thiazolidinediones, Arch Ophthamol, 2001, 709-717, 119.

Pubchem CID 2781559, "3-(4-Methylphenyl)-5-(Trifluoromethyl)-1,2,4-Oxadiazole", 2005.

Roche et al., Bioversible Carriers in Drug Design, American Pharmaceutical Association and Pergamon Press, 1987.

Seed et al., The Inhibition of Colon-26 Adenocarcinoma Development and Angiogenesis by Topical Diclofenac in 2.5% Hyaluronan, Cancer Research, 1997, 1625-1629, 57.

Simoes-Pires et al., HDAC6 as a target for neurodegenerative Diseases: What Makes it Different from the Other HDACs?, Molecular Neurodegeneration, 2013, 1-16, 8.

Stahl et al., Aminoquinazoline Compounds As A2A Antagonist, Handbook of Pharmaceutical Salts Properties, Selection, and Use, 2002, 330-331.

Suuronen et al., Regulation of Microglial Inflammatory Response by Histone, J. of Neurochemistry, 2003, 407-416, 87.

Tsujii et al., Cyclooxgenase Regulates Angiogenesis Induced by Colon Cancer Cells, Cell, 1998, 705-716, 93.

Van Tonder, E.C., et al.,, "Preparation and Physicochemical Characterization of 5 Niclosamide Solvates and 1 Hemisolvate", AAPS Pharm Sci Tech, 2004, pp. 1-10, vol. 5, No. US.

Xin et al., Peroxisome Proliferator Activated Receptor y Ligands are Potent Inhibitors of Angiogenesis in Vitro and in Vivo, J. Biol Chem,, 1999, 9116-9121, 13.

Yalpani et al., Coronary Heart Disease is the most Serious Threat to life in the Western World, but Progress is Being Made in Finding Ways to Reduce the Risks of Suffering Such a Fate, Chemistry & Industry, 1996, 85-89.

Zacharski et al., Heparin and Cancer, Thromb Haemost, 1998, 10-23, 80.

Zhang et al., Class II Histone Deacetylases Act as Signal-Responsive Repressors of Cardiac Hypertrophy, Cell, 2002, pp. 479-488, 110.

Ziche et al., Role of Prostaglandin E, and Copper in Angiogenesis, JNCI, 1982, 475-482, 69.

Bakharev, V.V. et al., Reactions of 1,3,5-Triazinylnitroformaldoxime 4.* Synthesis of (5-R-1,2,4-Oxadiazol-3-yl)-1,3,5-Triazines, Chemistry of Heterocyclic Compounds, 2012, 1258-1267, 47(10).

Supplementary European Search Report and Written Opinion for 17815984.4 dated Jan. 7, 2020. 9 pages.

\* cited by examiner

3-ARYL- HETEROARYL SUBSTITUTED 5-TRIFLUOROMETHYL OXADIAZOLES AS HISTONEDEACETYLASE 6 (HDAC6) INHIBITORS

CROSS REFERENCE TO RELATED APPLICATIONS

This application is the National Stage of International Application No. PCT/US17/38067, filed Jun. 19, 2017 which claims priority to 62/353,854 filed Jun. 23, 2016.

BACKGROUND OF THE INVENTION

Histone deacetylases (HDACs) and histone acetyl transferases (HATs) determine the pattern of histone acetylation, which together with other dynamic sequential post-translational modifications might represent a 'code' that can be recognised by non-histone proteins forming complexes involved in the regulation of gene expression. This and the ability of histone deacetylases (HDACs) to also modify non-histonic substrates and participate in multi-protein complexes contributes to the regulation of gene transcription, cell cycle progression and differentiation, genome stability and stress responses.

Eleven members of the HDAC family have been identified in humans, which share a conserved catalytic domain and are grouped into two classes: class I (1, 2, 3, 8), homologous to yeast Rpd3; class IIa (4, 5, 7, 9) and IIb (6, 10), homologous to yeast Hdal. HDAC11 shares homologies with both classes, but is at the same time distinct from all the other ten subtypes. Interest in these enzymes is growing because HDAC inhibitors (HDACi) are promising therapeutic agents against cancer and other diseases. The first generation of HDAC11 were discovered from cell-based functional assays and only later identified as HDAC class I/II inhibitors. Present HDAC inhibitors are pan-specific or lowly selective. Those that entered clinical trials all show similar adverse effects, mainly fatigue, anorexia, hematologic and GI-toxicity, that becomes dose-limiting in clinical trials.

HDAC6 is one of the best characterized deacetylase enzymes regulating many important biological processes via the formation of complexes with specific client proteins. In contrast to other deacetylases, HDAC6 has unique substrate specificity for nonhistone proteins such as α-tubulin, Hsp90, cortactin and peroxiredoxins. The diverse function of HDAD6 in conjuction with published data over the past few years suggest it could serve as a potential therapeutic target for the treatment of a wide range of diseases and may be overexpressed or deregulated in various cancers, neurodegenerative diseases and inflammatory disorders. Despite extensive efforts, very few HDAC6-selective inhibitors have been identified. The majority of the reported compounds use the hydroxamic acid pharmacophore as the zinc-binding group. See WO2013080120, WO2013008162, WO2013066835, WO2013066839, WO2013066831, WO2013066833, WO2013006408, WO2011088192, WO2011088181, J. Kalin et al., J. Med Chem 2013, 56, 6297-6313; and Simoes-Pires, et al., Molecular Neuro-degeneration 2013 8:7. See also WO2016031815 containing compounds that have not used the hydroxamic acid pharmacophore as the zinc-binding group.

To date, HDAC inhibitors that have been approved for use by the FDA can be divided into two categories: 1) non-selective pan HDAC inhibitors such as vorinostat (SAHA); and 2) HDAC inhibitors such as entinostat that only target Class I HDACs. The potential advantage of isoform-selective inhibitors over pan-HDAC inhbitors is based both in terms of efficacy and toxicity. The development of potent and highly selective HDAC inhbitors would be critical for better understanding of the cellular pathways related to their therapeutic effects, while also providing a reasonable basis to explore synergistic interactions with other clinically active compounds. It is also valuable because it is expected that the selective inhibition of a mostly cytoplasmic HDAC6 should avoid toxicity resulting from inhibition of other HDACs mainly involved in epigenetic modulation.

SUMMARY OF THE INVENTION

The invention is directed to a class of aryl and heteroaryl substituted 5-trifluoromethyl oxadiazole compounds of formula I below, their salts, pharmaceutical compositions comprising them, diagnostic and therapeutic uses and processes for making such compounds. In particular, the invention is directed to a class of aryl and heteroaryl substituted 5-trifluoromethyl oxadiazole compounds of formula I which may be useful as HDAC6 inhibitors for treating cellular proliferative diseases, including cancer, neurodegenerative diseases, such as schizophrenia and stroke, as well as other diseases. Uses for the claimed compounds include treating autoimmune diseases and/or inflammatory diseases (e.g., inflammatory bowel disease, rheumatoid arthritis, psoriasis, multiple sclerosis, Sjogren's syndrome, Behcet's disease, systemic erythematodes etc), graft-versus-host disease (GvHD), cellular proliferative diseases, including cancer (e.g., multiple myeloma, leukemia, uterus smooth muscle sarcoma, prostate cancer, intestinal cancer, lung cancer, cachexia, bone marrow fibrosis, etc.), central nervous system diseases, including neurodegenerative diseases such as Alzheimer's disease, Parkison's disease, Huntington's disease, schizophrenia and stroke, amongst other diseases.

DETAILED DESCRIPTION OF THE INVENTION

The present invention is directed to substituted 5-trifluoromethyl oxadiazole compounds of generic formula (I)

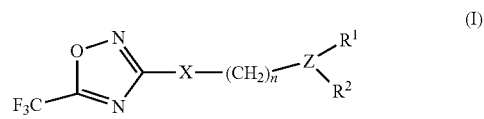

or a pharmaceutically acceptable salt thereof wherein;
X represents phenyl or a nitrogen containing six membered heteroaryl, said phenyl and heteroaryl optionally substituted with 1 to 3 groups of $R^c$;
Z is selected from the group consisting of —CH—, —N—, —O(CH$_2$)$_{0-1}$—, —SO$_2$N—, and —C(O)N—, provided that when Z is —O(CH$_2$) then $R^2$ is absent;
R represents hydrogen, halo, haloalkyl, or —C$_{1-6}$alkyl;
$R^1$ represents hydrogen, C$_{1-6}$alkyl, —(CHR)$_p$C$_{3-12}$ heterocyclyl, —(CH$_2$)$_p$C(O)(CRR)$_p$C$_{3-12}$heterocyclyl, —(CHR)$_p$C$_{6-10}$ aryl; —C(O)C$_{6-10}$ aryl, —(CH$_2$)$_p$C$_{3-10}$cycloalkyl, C(O)NHR$^2$, or —C(O)C$_{3-6}$cycloalkyl, said alkyl, aryl, cycloalkyl, and heterocyclyl optionally substituted with 1 to 3 groups of $R^a$;
$R^2$ is absent when Z is —O—, or represents hydrogen, —C$_{1-6}$alkyl, —C(O)C$_{1-6}$alkyl, —(CH$_2$)$_p$C$_{3-10}$ heterocyclyl, —C(O)(C(R$_2$)$_p$C$_{3-6}$heterocyclyl, —(CHR)$_p$C$_{6-10}$ aryl, —C(O)C$_{6-10}$ aryl, —C$_{3-6}$cycloalkyl, —C(O)C$_{3-6}$cycloalkyl, C(O)(CH$_2$)$_p$N(R)$_2$, C(O)(CH$_2$)$_p$OR, —NHC(O)CF$_3$, —NHC(O)R, —NHSO$_2$R, —NHC(O)NHR, —NHC(O)OR, NHC(O)(CH$_2$)$_p$C$_{3-10}$heterocyclyl, NHC(O)(CH$_2$)$_p$C$_{6-10}$aryl, NHC(O)(CH$_2$)$_p$OR, SO$_2$R, SO$_2$C$_{3-6}$ heterocyclyl, C(O)(CH$_2$)$_p$NHC(O)C$_{1-6}$alkyl, C(O)OR, C(O)(CH$_2$)$_p$SO$_2$R, said alkyl, cycloalkyl, aryl, and heterocyclyl optionally substituted with 1 to 4 groups of R$^a$;

or R$^1$ and R$^2$ can combine together with the atoms to which they are attached to form a five to fifteen membered monocyclic, bicyclic or tricyclic heterocyclic aromatic, partially aromatic, or non-aromatic ring optionally interrupted by 1 to 2 heteroatoms selected from N, S, and O, said heterocyclic ring optionally substituted with 1 to 4 groups of R$^a$;

R$^a$ is selected from the group consisting of H, —C$_{1-6}$alkyl, —C$_{3-10}$cycloalkyl, =O, —C$_{1-6}$alkylOR, -haloalkyl, —(CH$_2$)$_p$C$_{6-10}$aryl; —(CH$_2$)$_p$C$_{3-10}$ heterocyclyl, —C(O)C$_{3-10}$ heterocyclyl, —C(O)C$_{1-6}$alkyl, —C(O)NHC$_{3-6}$cycloalkyl, C(O)OC$_{1-6}$alkyl, C(O)N(R)$_2$, C(O)NH(CH$_2$)$_p$C$_{6-10}$aryl, C(O)NH(CH$_2$)$_p$C$_{3-10}$heterocyclyl, N(R)$_2$, CN, halo, —SO$_2$C$_{1-6}$alkyl, said alkyl, aryl, and heterocyclyl optionally substituted with 1 to 3 groups of R;

R$^b$ is selected from the group consisting of C$_{1-6}$alkyl, OC$_{1-6}$alkylOR, —(CH$_2$)$_p$C$_{6-10}$ aryl; —(CH$_2$)$_p$C$_{5-10}$ heteroaryl, halo, N(R)$_2$, hydroxyl, and -haloalkyl, said aryl and heteroaryl optionally substituted with 1 to 3 groups of C$_{1-6}$alkyl, R$^c$ is selected from the group consisting of C$_{1-6}$alkyl, halo, OR, N(R)$_2$, and SO$_2$R;

n represents 0-2; and p represents 0-4.

An embodiment of this invention is realized when X is optionally substituted C$_{6-10}$aryl. A subembodiment of this aspect of the invention is realized when aryl is optionally substituted pyridyl.

Another embodiment of this invention is realized when X is an optionally substituted nitrogen containing six membered heteroaryl. A subembodiment of this aspect of the invention is realized when the nitrogen containing six membered heteroaryl is linked to the trifluoromethyl oxadiazole group through a carbon atom. A subembodiment of this aspect of the invention is realized when the six membered heteroaryl contains at least one nitrogen atom.

Another subembodiment of the invention is realizded when the six membered heteroaryl containing at least one nitrogen atom is linked to the trifluoromethyl oxadiazole group through a carbon atom.

An embodiment of this invention if realized when X is selected from the group consisting of optionally substituted phenyl, pyridyl, pyrimidinyl, pyridazinyl, and pyrazinyl.

Another embodiment of this invention is realized when X is optionally substituted phenyl. A subembodiment of this invention is realized when X is phenyl substituted with 1 to 3, 1 to 2, or 1 halogen. A further subembodiment of this invention is realized when the halogen is selected from fluorine and chlorine.

Another embodiment of this invention is realized when X is optionally substituted pyridyl. Still another embodiment of this invention is realized when X is optionally substituted pyridyl linked to the trifluoromethyl oxadiazole group through a carbon atom. A subembodiment of this invention is realized when X is pyridyl substituted with 1 to 3, 1 to 2, or 1 C$_{1-6}$alkyl, halogen, OR, N(R)$_2$, or SO$_2$R. A further subembodiment of this invention is realized when the halogen is selected from fluorine and chlorine.

Another embodiment of this invention is realized when X is optionally substituted pyrimidinyl. Still another embodiment of this invention is realized when X is optionally substituted pyrimidinyl linked to the trifluoromethyl oxadiazole group through a carbon atom. A subembodiment of this invention is realized when X is pyrimidinyl substituted with 1 to 3, 1 to 2, or 1 C$_{1-6}$alkyl, halo, OR, N(R)$_2$, and SO$_2$R. A further subembodiment of this invention is realized when the halogen is selected from fluorine and chlorine.

Another embodiment of this invention is realized when X is optionally substituted pyridazinyl. Still another embodiment of this invention is realized when X is optionally substituted pyridazinyl linked to the trifluoromethyl oxadiazole group through a carbon atom. A subembodiment of this invention is realized when X is pyridazinyl substituted with 1 to 3, 1 to 2, or 1 C$_{1-6}$alkyl, halo, OR, N(R)$_2$, and/or SO$_2$R. A further subembodiment of this invention is realized when the halogen is selected from fluorine and chlorine.

Another embodiment of this invention is realized when X is optionally substituted pyrazinyl. Still another embodiment of this invention is realized when X is optionally substituted pyrazinyl linked to the trifluoromethyl oxadiazole group through a carbon atom. A subembodiment of this invention is realized when X is pyrazinyl substituted with 1 to 3, 1 to 2, or 1 C$_{1-6}$alkyl, halo, OR, N(R)$_2$, or SO$_2$R. A further subembodiment of this invention is realized when the halogen is selected from fluorine and chlorine.

Another embodiment of this invention is realized when n is 0. Another embodiment of this invention is realized when n is 1. Another embodiment of this invention is realized when n is 2.

Another embodiment of this invention is realized when p is 0. Another embodiment of this invention is realized when p is 1. Another embodiment of this invention is realized when p is 2. Another embodiment of this invention is realized when p is 3. Another embodiment of this invention is realized when p is 4.

Another embodiment of this invention is realized when Z is —CH—. A subembodiment of this aspect of the invention is realized when Z is —CH— and n is 0. Another subembodiment of this aspect of the invention is realized when Z is —CH— and n is 1.

Another embodiment of this invention is realized when Z is —N—. A subembodiment of this aspect of the invention is realized when Z is —N— and n is 0. Another subembodiment of this aspect of the invention is realized when Z is —N— and n is 1.

Another embodiment of this invention is realized when Z is —O— and R$^2$ is absent, and R$^1$ is phenyl optionally substituted with 1 to 3 groups of R$^a$.

Another embodiment of this invention is realized when Z is —O— and R$^2$ is absent. A subembodiment of this aspect of the invention is realized when Z is —O—, R$^2$ is absent, and R$^1$ is —(CHR)$_p$C$_{3-10}$ heterocyclyl, said heterocyclyl optionally substituted with 1 to 3 groups of R$^a$.

A further subembodiment of this aspect of the invention is realized when the heterocyclyl is quinolinyl, pyridyl, tetrahydropyranyl, imidazopyrimidinyl, pyrimidinyl, pyridazinyl, triazolopyridyl, triazolyl, pyrazolopyrimidinyl, tetrahydropyranpyrazolyl, benzimidazolyl, pyrrolopyridinyl, naphthyridinyl, benzotriazine, tetrahydroisoquinolinyl, indazolyl, imidazopyridinyl, oxadiazolyl, thiazolyl, quinazolyl, pyrazolyl, or pyrazinyl.

Another embodiment of this invention is realized when Z is —O(CH$_2$)— and R$^2$ is absent.

Another embodiment of this invention is realized when Z is —SO$_2$N—.

Another embodiment of this invention is realized when Z is —C(O)N—.

Still another embodiment of this invention is realized when $R^1$ is selected from the group consisting of —(CHR)$_p$C$_{3\text{-}12}$ heterocyclyl, —(CHR)$_p$C$_{6\text{-}10}$ aryl, —C$_{3\text{-}10}$cycloalkyl, said aryl and heterocyclyl optionally substituted with 1 to 3 groups of R$^a$. A subembodiment of this aspect of the invention is realized when the aryl and heterocyclyl is selected from the group consisting of optionally substituted phenyl, isoindolinone, and pyridyl. Another subembodiment of this aspect of the invention is realized when $R^1$ is optionally substituted phenyl. A further subembodiment of this aspect of the invention is realized when phenyl is substituted with 1 to 3 groups of R$^a$ selected from halogen and C$_{1\text{-}4}$ haloalkyl such as fluorine, chlorine, CF$_3$, and the like. Another subembodiment of this aspect of the invention is realized when $R^1$ is optionally substituted pyridyl. A further subembodiment of this aspect of the invention is realized when pyridyl is substituted with 1 to 3 groups of R$^a$ selected from halogen and C$_{1\text{-}4}$ haloalkyl such as fluorine, chlorine, CF$_3$, and the like. Another subembodiment of this aspect of the invention is realized when $R^1$ is optionally substituted cycloalkyl. A further subembodiment of this aspect of the invention is realized when $R^1$ is cyclopropyl, cyclobutyl, cyclopentyl or cyclohexyl.

Yet another embodiment of this invention is realized when $R^2$ is absent when Z is —O—.

Another embodiment of this invention is realized when $R^2$ is selected from the group consisting of —C(O)(CRR)$_p$ C$_{3\text{-}6}$heterocyclyl, —C(O)C$_{6\text{-}10}$ aryl, said aryl and heterocyclyl optionally substituted with 1 to 3 groups of R$^a$. A subembodiment of this aspect of the invention is realized when the aryl and heterocyclyl of $R^2$ is selected from the group consisting of optionally substituted pyridyl, pyrimidinyl, pyrazinyl, piperidinyl, tetrahydropyranyl, oxadiazolyl, morpholinyl, tetrahydrothiopyranyl, dihydropyridazinone, dioxanyl, benzimidazolyl, piperazinyl, oxopyridazinyl, triazolyl, dihydropyrazolyl, isoxazolyl, pyrazolyl, pyridazinyl, oxetanyl, dioxidothiomorpholinyl. A further subembodiment of this aspect of the invention is realized when the aryl and heterocyclyl of $R^2$ is selected from the group consisting of optionally substituted CH$_2$pyrazolyl, pyridyl, morpholinyl, triazolyl, piperidinyl, pyrimidinyl, pyrazinyl, pyridazinyl, and piperazinyl. Another subembodiment of this aspect of the invention is realized when $R^2$ is selected from the group consisting of optionally substituted pyridyl, C(O) tetrahydrothiophene, C(O)morpholinyl, C(O)pyrimidinyl, C(O)tetrahydrothiophene, C(O)pyrazine, C(O)piperidinyl, C(O)tetrahydropyranyl, C(O)oxadiazolyl, C(O)dioxanyl, C(O)dihydropyridazinone, C(O)CH$_2$morpholinyl, C(O) CH$_2$dioxidothiomorpholinyl, C(O)CH$_2$oxetanyl, C(O)CH$_2$ isoxazolyl, C(O)CH$_2$dihydropyrazolyl, C(O) CH$_2$piperazinyl, C(O)CH$_2$pyrimidinyl, C(O)CH$_2$pyrazinyl, C(O)CH$_2$benzimidazolyl, C(O)CH(CH$_3$)CH$_2$triazolyl, C(O) (CH$_2$)$_3$triazolyl, C(O)CH$_2$triazolyl, C(O)(CH$_2$)$_2$triazolyl, C(O)CH(CH$_3$)pyrazolyl, and C(O)CH(CH$_3$)triazolyl.

Another embodiment of this invention is realized when $R^2$ is selected from the group consisting of —C(O)C$_{1\text{-}6}$alkyl, C(O)(CH$_2$)$_p$N(R)$_2$, C(O)(CH$_2$)$_p$OR, C(O)(CH$_2$)$_p$NHC(O) C$_{1\text{-}6}$alkyl, C(O)OR, —C(O)C$_{3\text{-}6}$cycloalkyl and C(O) (CH$_2$)$_p$SO$_2$R, said alkyl and cycloalkyl optionally substituted with 1 to 3 groups of R$^a$. A subembodiment of this aspect of the invention is realized when the cycloalkyl of $R^2$ is selected from the group consisting of optionally substituted cyclopropyl, cyclobutyl, cyclopentyl and cyclohexyl. Another subembodiment of this aspect of the invention is realized when $R^2$ is selected from the group consisting of —C(O)OC(CH$_3$)$_3$, —C(O)C(CH$_3$)CN, —C(O)CH$_2$CH$_3$, —C(O)CH$_2$SO$_2$CH$_3$, and —C(O)CH$_2$N(CH$_3$)$_2$.

Still another embodiment of the invention is realized when $R^1$ and $R^2$ combine together with the atoms to which they are attached to form a five to fifteen membered monocyclic, bicyclic or tricyclic heterocyclic aromatic, partially aromatic, or non-aromatic ring optionally interrupted by 1 to 2 heteroatoms selected from N, S, and O, said heterocyclic ring optionally substituted with 1 to 3 groups of R$^a$. A subembodiment of this aspect of the invention is realized when the ring is aromatic. Another subembodiment of this aspect of the invention is realized when the ring is partially aromatic. Another subembodiment of this aspect of the invention is realized when the ring is non-aromatic.

A subembodiment of this aspect of the invention is realized when Z is nitrogen, and $R^1$ and $R^2$ combine together with the nitrogen atom to which they are attached to form an optionally substituted five or six membered monocyclic ring optionally interrupted by 1 to 2 heteroatoms selected from N, S, and O. A further subembodiment of this aspect of the invention is realized when $R^1$ and $R^2$ combine together with the nitrogen atom to which they are attached to form optionally substituted morpholinyl, morpholinonyl, piperazinyl, pyrrolidinonyl, piperidinonyl, oxazolidinonyl, piperidinyl, piperazinonyl, dihydroquinolinyl, imidazolidinonyl, or pyrollidinyl. Still a further subembodiment of this aspect of the invention is realized when $R^1$ and $R^2$ combine together with the nitrogen atom to which they are attached to form optionally substituted morpholinyl or morpholinonyl. A further subembodiment of this aspect of the invention is realized when $R^1$ and $R^2$ combine together with the nitrogen atom to which they are attached to form optionally substituted piperazinyl or piperazinonyl. A further subembodiment of this aspect of the invention is realized when $R^1$ and $R^2$ combine together with the nitrogen atom to which they are attached to form optionally substituted pyrollidinyl or pyrrolidinonyl. A further subembodiment of this aspect of the invention is realized when $R^1$ and $R^2$ combine together with the nitrogen atom to which they are attached to form optionally substituted piperidinonyl or piperidinyl. A further subembodiment of this aspect of the invention is realized when $R^1$ and $R^2$ combine together with the nitrogen atom to which they are attached to form optionally substituted oxazolidinonyl. A further subembodiment of this aspect of the invention is realized when $R^1$ and $R^2$ combine together with the nitrogen atom to which they are attached to form optionally substituted imidazolidinonyl. A further subembodiment of this aspect of the invention is realized when $R^1$ and $R^2$ combine together with the nitrogen atom to which they are attached to form optionally substituted dihydroquinolinyl.

Yet another aspect of this embodiment of the invention is realized when $R^1$ and $R^2$ combine together with the nitrogen atom to which they are attached to form morpholinyl, morpholinonyl, piperazinyl, pyrrolidinonyl, piperidinonyl, oxazolidinonyl, piperidinyl, piperazinonyl, or pyrollidinyl, said groups optionally substituted with 1 to 3 R$^a$ selected from the group consisting of —C$_{1\text{-}6}$alkyl, halo, —(CH$_2$)$_p$ C$_{6\text{-}10}$ aryl; —(CH$_2$)$_p$C$_{5\text{-}10}$ heterocyclyl, C(O)OC$_{1\text{-}6}$alkyl, C(O)N(R)$_2$, C(O)NH(CH$_2$)$_p$C$_{6\text{-}10}$ aryl, N(R)$_2$, said alkyl, aryl, and heterocyclyl optionally substituted with 1 to 3 groups of R$^b$. A further aspect of this embodiment is realized when R$_a$ selected from the group consisting of C(O)OC (CH$_3$)$_3$, C(O)OCH$_2$CH$_3$, C(O)NHC(CH$_3$)$_3$, CH$_2$OH, C(O) NC(CH$_3$)$_2$CH$_3$, —C$_{1\text{-}6}$alkyl, and optionally substituted phenyl, benzoxazolyl, benzimidazolyl, oxadiazolyl, piperidinyl, tetrahydropyranyl, pyridyl, benzythiazolyl, C(O)NHphenyl, and C(O)NH(CH$_2$)$_p$phenyl.

Yet a further subembodiment of this aspect of the invention is realized when $R^1$ and $R^2$ combine together with the nitrogen atom to which they are attached to form morpholinyl, morpholinonyl, piperazinyl, pyrrolidinonyl, piperidinonyl, oxazolidinonyl, piperidinyl, piperazinonyl, or pyrrolidinyl and at least one $R^a$ is present and is positioned adjacent to the nitrogen atom to which $R^1$ and $R^2$ originally are attached. Another subembodiment of this aspect of the invention is realized when the $R^a$ substituent attached adjacent to the nitrogen atom to which $R^1$ and $R^2$ are originally attached is selected from the group consisting of optionally substituted phenyl, oxadiazolyl, and benzoxazolyl. Yet another subembodiment of this aspect of the invention is realized when the $R^a$ substituent attached adjacent to the nitrogen atom to which $R^1$ and $R^2$ are originally attached is optionally substitute phenyl. Still a further subembodiment of this aspect of the invention is realized when the $R^a$ substituent attached adjacent to the nitrogen atom to which $R^1$ and $R^2$ are originally attached is optionally substitute oxadiazolyl.

A further subembodiment of this aspect of the invention is realized when $R^1$ and $R^2$ combine together with the nitrogen atom to which they are attached to form a 9-10 membered bicyclic heterocyclic ring optionally interrupted by 1 to 2 heteroatoms selected from N, S, and O, said heterocyclic ring optionally substituted with 1 to 3 groups of $R^a$. Another subembodiment of this aspect of the invention is realized when the 9-10 membered bicyclic heterocyclic ring is optionally substituted with 1 to 3 $R^a$ selected from the group consisting of —$C_{1-6}$alkyl, halo, —$(CH_2)_pC_{6-10}$ aryl; —$(CH_2)_pC_{5-10}$ heterocyclyl, $C(O)OC_{1-6}$alkyl, $C(O)N(R)_2$, $C(O)NH(CH_2)_pC_{6-10}$ aryl, $N(R)_2$, said alkyl, aryl, and heterocyclyl optionally substituted with 1 to 3 groups of $R^b$. A further aspect of this embodiment is realized when $R^a$ is selected from the group consisting of $C(O)OC(CH_3)_3$, $C(O)OCH_2CH_3$, $C(O)NHC(CH_3)_3$, $CH_2OH$, $C(O)NC(CH_3)_2CH_3$, —$C_{1-6}$alkyl, and optionally substituted phenyl, benzoxazolyl, benzimidazolyl, oxadiazolyl, piperidinyl, tetrahydropyranyl, pyridyl, benzythiazolyl, $C(O)NH$phenyl, and $C(O)NH(CH_2)_p$phenyl. A subembodiment of this aspect of the invention is realized when $R^1$ and $R^2$ combine together with the nitrogen atom to which they are attached to form optionally substituted quinolinonyl. A further subembodiment of this aspect of the invention is realized when $R^1$ and $R^2$ combine together with the nitrogen atom to which they are attached to form optionally substituted benzimidazolyl.

Another embodiment of the claimed invention of formula I is realized by structural formula II:

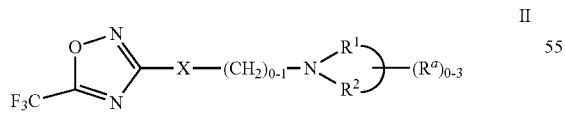

or a pharmaceutically acceptable salt thereof, wherein

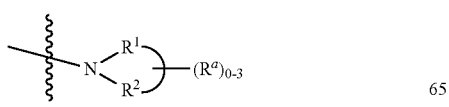

is defined as Q and Q is represented by structural formulas (a), (b), (c), (d), (e), (f), (g), (h), (i), (j), (k), (l), (m), or (n);

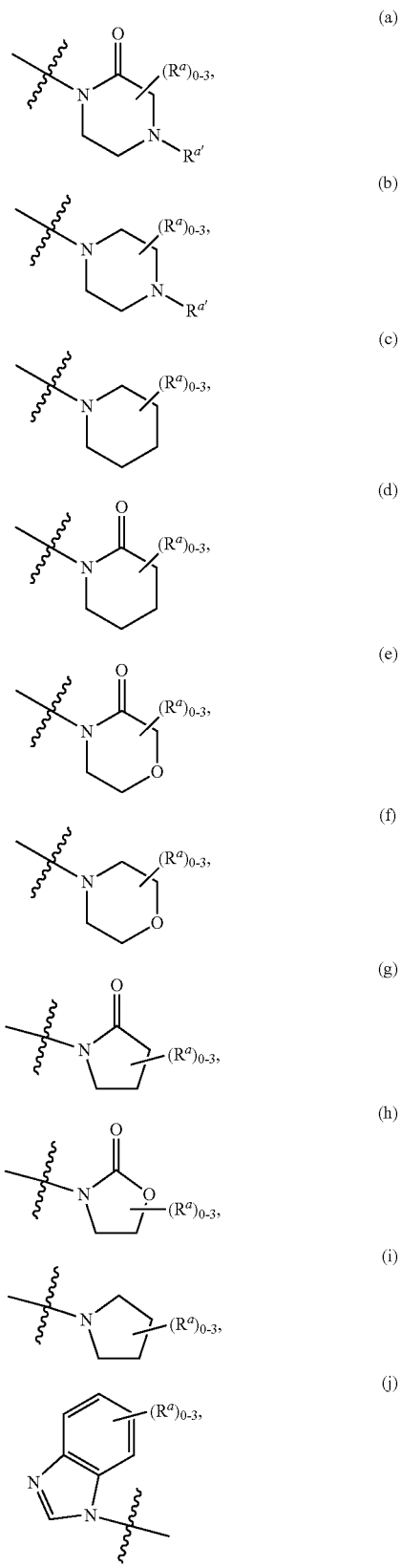

-continued

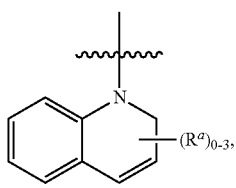
(k)

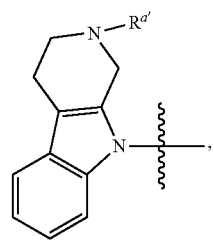
(l)

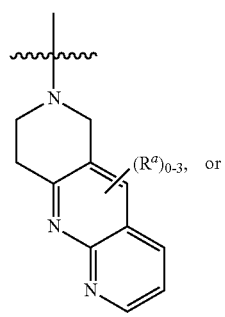
(m)

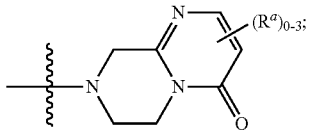
(n)

X is selected from optionally substituted phenyl or pyridyl;

∿∿∿ represents the bond that links the nitrogen to which it is attached to the rest of the molecule;

and $R^{a'}$ is $R^a$ and $R^a$ is as originally described.

A subembodiment of the invention of formula II is realized when X is optionally substituted phenyl and Q is (a) or (b). A further subembodiment is realized when Q is (a). A further subembodiment is realized when Q is (b). Still a further subembodiment of this aspect of the invention is realized when at least one $R^a$ is attached. A further subembodiment of this aspect of the invention is realized when at least one $R^a$ is present and is located on the carbon atom directly adjacent to the linking nitrogen atom. Another subembodiment of this aspect of the invention is realized when $R^a$ selected from the group consisting of C(O)OC(CH$_3$)$_3$, C(O)OCH$_2$CH$_3$, C(O)NHC(CH$_3$)$_3$, CH$_2$OH, C(O)NC(CH$_3$)$_2$CH$_3$, —C$_{1-6}$alkyl, and optionally substituted phenyl, benzoxazolyl, benzimidazolyl, oxadiazolyl, piperidinyl, tetrahydropyranyl, pyridyl, benzythiazolyl, C(O)NHphenyl, and C(O)NH(CH$_2$)$_p$phenyl. Another subembodiment of this aspect of the invention is realized when the $R^a$ is selected from the group consisting of optionally substituted phenyl, oxadiazolyl, and benzoxazolyl. Another subembodiment of this aspect of the invention is realized when the $R^a$ is optionally substituted phenyl. Another subembodiment of this aspect of the invention is realized when the $R^a$ is optionally substituted oxadiazolyl.

A subembodiment of the invention of formula II is realized when X is optionally substituted phenyl and Q is (c) or (d). A further subembodiment is realized when Q is (c). A further subembodiment is realized when Q is (d). Still a further subembodiment of this aspect of the invention is realized when at least one $R^a$ is attached. A further subembodiment of this aspect of the invention is realized when at least one $R^a$ is present and is located on the carbon atom directly adjacent to the linking nitrogen atom. Another subembodiment of this aspect of the invention is realized when $R^a$ selected from the group consisting of C(O)OC(CH$_3$)$_3$, C(O)OCH$_2$CH$_3$, C(O)NHC(CH$_3$)$_3$, CH$_2$OH, C(O)NC(CH$_3$)$_2$CH$_3$, —C$_{1-6}$alkyl, and optionally substituted phenyl, benzoxazolyl, benzimidazolyl, oxadiazolyl, piperidinyl, tetrahydropyranyl, pyridyl, benzythiazolyl, C(O)NHphenyl, and C(O)NH(CH$_2$)$_p$phenyl. Another subembodiment of this aspect of the invention is realized when the $R^a$ is selected from the group consisting of optionally substituted phenyl, oxadiazolyl, and benzoxazolyl. Another subembodiment of this aspect of the invention is realized when the $R^a$ is optionally substituted phenyl. Another subembodiment of this aspect of the invention is realized when the $R^a$ is optionally substituted oxadiazolyl.

A subembodiment of the invention of formula II is realized when X is optionally substituted phenyl and Q is (e) or (f). A further subembodiment is realized when Q is (e). A further subembodiment is realized when Q is (f). Still a further subembodiment of this aspect of the invention is realized when at least one $R^a$ is attached. A further subembodiment of this aspect of the invention is realized when at least one $R^a$ is present and is located on the carbon atom directly adjacent to the linking nitrogen atom. Another subembodiment of this aspect of the invention is realized when $R^a$ selected from the group consisting of C(O)OC(CH$_3$)$_3$, C(O)OCH$_2$CH$_3$, C(O)NHC(CH$_3$)$_3$, CH$_2$OH, C(O)NC(CH$_3$)$_2$CH$_3$, —C$_{1-6}$alkyl, and optionally substituted phenyl, benzoxazolyl, benzimidazolyl, oxadiazolyl, piperidinyl, tetrahydropyranyl, pyridyl, benzythiazolyl, C(O)NHphenyl, and C(O)NH(CH$_2$)$_p$phenyl. Another subembodiment of this aspect of the invention is realized when the $R^a$ is selected from the group consisting of optionally substituted phenyl, oxadiazolyl, and benzoxazolyl. Another subembodiment of this aspect of the invention is realized when the $R^a$ is optionally substituted phenyl. Another subembodiment of this aspect of the invention is realized when the $R^a$ is optionally substituted oxadiazolyl.

A subembodiment of the invention of formula II is realized when X is optionally substituted phenyl and Q is (g), (h), or (i). A further subembodiment is realized when Q is (g). A further subembodiment is realized when Q is (h). A further subembodiment is realized when Q is (i). Still a further subembodiment of this aspect of the invention is realized when at least one $R^a$ is attached. A further subembodiment of this aspect of the invention is realized when at least one $R^a$ is present and is located on the carbon atom directly adjacent to the linking nitrogen atom. Another subembodiment of this aspect of the invention is realized when $R^a$ selected from the group consisting of C(O)OC(CH$_3$)$_3$, C(O)OCH$_2$CH$_3$, C(O)NHC(CH$_3$)$_3$, CH$_2$OH, C(O)NC(CH$_3$)$_2$CH$_3$, —C$_{1-6}$alkyl, and optionally substituted phenyl, benzoxazolyl, benzimidazolyl, oxadiazolyl, piperidinyl, tetrahydropyranyl, pyridyl, benzythiazolyl, C(O)NHphenyl, and C(O)NH(CH$_2$)$_p$phenyl. Another subembodiment of this aspect of the invention is realized when the $R^a$ is selected from the group consisting of optionally substituted phenyl, oxadiazolyl, and benzoxazolyl. Another subembodiment of this aspect of the invention is realized when the $R^a$ is optionally substituted phenyl. Another subembodiment of this aspect of the invention is realized when the $R^a$ is optionally substituted oxadiazolyl.

A subembodiment of the invention of formula II is realized when X is optionally substituted phenyl and Q is (j), (k), (l), (m), or (n). Another subembodiment of this aspect of the invention is realized when $R^a$ selected from the group consisting of $C(O)OC(CH_3)_3$, $C(O)OCH_2CH_3$, $C(O)NHC(CH_3)_3$, $CH_2OH$, $C(O)NC(CH_3)_2CH_3$, —$C_{1-6}$alkyl, and optionally substituted phenyl, benzoxazolyl, benzimidazolyl, oxadiazolyl, piperidinyl, tetrahydropyranyl, pyridyl, benzythiazolyl, C(O)NHphenyl, and $C(O)NH(CH_2)_p$phenyl. Another subembodiment of this aspect of the invention is realized when the $R^a$ is selected from the group consisting of optionally substituted phenyl, oxadiazolyl, and benzoxazolyl. Another subembodiment of this aspect of the invention is realized when the $R^a$ is optionally substituted phenyl. Another subembodiment of this aspect of the invention is realized when the $R^a$ is optionally substituted oxadiazolyl.

A subembodiment of the invention of formula II is realized when X is optionally substituted pyridyl and Q is (a) or (b). A further subembodiment is realized when Q is (a). A further subembodiment is realized when Q is (b). Still a further subembodiment of this aspect of the invention is realized when at least one $R^a$ is attached. A further subembodiment of this aspect of the invention is realized when at least one $R^a$ is present and is located on the carbon atom directly adjacent to the linking nitrogen atom. Another subembodiment of this aspect of the invention is realized when $R^a$ selected from the group consisting of $C(O)OC(CH_3)_3$, $C(O)OCH_2CH_3$, $C(O)NHC(CH_3)_3$, $CH_2OH$, $C(O)NC(CH_3)_2CH_3$, —$C_{1-6}$alkyl, and optionally substituted phenyl, benzoxazolyl, benzimidazolyl, oxadiazolyl, piperidinyl, tetrahydropyranyl, pyridyl, benzythiazolyl, C(O)NHphenyl, and $C(O)NH(CH_2)_p$phenyl. Another subembodiment of this aspect of the invention is realized when the $R^a$ is selected from the group consisting of optionally substituted phenyl, oxadiazolyl, and benzoxazolyl. Another subembodiment of this aspect of the invention is realized when the $R^a$ is optionally substituted phenyl. Another subembodiment of this aspect of the invention is realized when the $R^a$ is optionally substituted oxadiazolyl.

A subembodiment of the invention of formula II is realized when X is optionally substituted pyridyl and Q is (c) or (d). A further subembodiment is realized when Q is (c). A further subembodiment is realized when Q is (d). Still a further subembodiment of this aspect of the invention is realized when at least one $R^a$ is attached. A further subembodiment of this aspect of the invention is realized when at least one $R^a$ is present and is located on the carbon atom directly adjacent to the linking nitrogen atom. Another subembodiment of this aspect of the invention is realized when $R^a$ selected from the group consisting of $C(O)OC(CH_3)_3$, $C(O)OCH_2CH_3$, $C(O)NHC(CH_3)_3$, $CH_2OH$, $C(O)NC(CH_3)_2CH_3$, —$C_{1-6}$alkyl, and optionally substituted phenyl, benzoxazolyl, benzimidazolyl, oxadiazolyl, piperidinyl, tetrahydropyranyl, pyridyl, benzythiazolyl, C(O)NHphenyl, and $C(O)NH(CH_2)_p$phenyl. Another subembodiment of this aspect of the invention is realized when the $R^a$ is selected from the group consisting of optionally substituted phenyl, oxadiazolyl, and benzoxazolyl. Another subembodiment of this aspect of the invention is realized when the $R^a$ is optionally substituted phenyl. Another subembodiment of this aspect of the invention is realized when the $R^a$ is optionally substituted oxadiazolyl.

A subembodiment of the invention of formula II is realized when X is optionally substituted pyridyl and Q is (e) or (f). A further subembodiment is realized when Q is (e). A further subembodiment is realized when Q is (f). Still a further subembodiment of this aspect of the invention is realized when at least one $R^a$ is attached. A further subembodiment of this aspect of the invention is realized when at least one $R^a$ is present and is located on the carbon atom directly adjacent to the linking nitrogen atom. Another subembodiment of this aspect of the invention is realized when $R^a$ selected from the group consisting of $C(O)OC(CH_3)_3$, $C(O)OCH_2CH_3$, $C(O)NHC(CH_3)_3$, $CH_2OH$, $C(O)NC(CH_3)_2CH_3$, —$C_{1-6}$alkyl, and optionally substituted phenyl, benzoxazolyl, benzimidazolyl, oxadiazolyl, piperidinyl, tetrahydropyranyl, pyridyl, benzythiazolyl, C(O)NHphenyl, and $C(O)NH(CH_2)_p$phenyl. Another subembodiment of this aspect of the invention is realized when the $R^a$ is selected from the group consisting of optionally substituted phenyl, oxadiazolyl, and benzoxazolyl. Another subembodiment of this aspect of the invention is realized when the $R^a$ is optionally substituted phenyl. Another subembodiment of this aspect of the invention is realized when the $R^a$ is optionally substituted oxadiazolyl.

A subembodiment of the invention of formula II is realized when X is optionally substituted pyridyl and Q is (g), (h), or (i). A further subembodiment is realized when Q is (g). A further subembodiment is realized when Q is (h). A further subembodiment is realized when Q is (i). Still a further subembodiment of this aspect of the invention is realized when at least one $R^a$ is attached. A further subembodiment of this aspect of the invention is realized when at least one $R^a$ is present and is located on the carbon atom directly adjacent to the linking nitrogen atom. Another subembodiment of this aspect of the invention is realized when $R^a$ selected from the group consisting of $C(O)OC(CH_3)_3$, $C(O)OCH_2CH_3$, $C(O)NHC(CH_3)_3$, $CH_2OH$, $C(O)NC(CH_3)_2CH_3$, —$C_{1-6}$alkyl, and optionally substituted phenyl, benzoxazolyl, benzimidazolyl, oxadiazolyl, piperidinyl, tetrahydropyranyl, pyridyl, benzythiazolyl, C(O)NHphenyl, and $C(O)NH(CH_2)_p$phenyl. Another subembodiment of this aspect of the invention is realized when the $R^a$ is selected from the group consisting of optionally substituted phenyl, oxadiazolyl, and benzoxazolyl. Another subembodiment of this aspect of the invention is realized when the $R^a$ is optionally substituted phenyl. Another subembodiment of this aspect of the invention is realized when the $R^a$ is optionally substituted oxadiazolyl.

A subembodiment of the invention of formula II is realized when X is optionally substituted pyridyl and Q is (j), (k), (l), (m), or (n). Another subembodiment of this aspect of the invention is realized when $R^a$ selected from the group consisting of $C(O)OC(CH_3)_3$, $C(O)OCH_2CH_3$, $C(O)NHC(CH_3)_3$, $CH_2OH$, $C(O)NC(CH_3)_2CH_3$, —$C_{1-6}$alkyl, and optionally substituted phenyl, benzoxazolyl, benzimidazolyl, oxadiazolyl, piperidinyl, tetrahydropyranyl, pyridyl, benzythiazolyl, C(O)NHphenyl, and $C(O)NH(CH_2)_p$phenyl. Another subembodiment of this aspect of the invention is realized when the $R^a$ is selected from the group consisting of optionally substituted phenyl, oxadiazolyl, and benzoxazolyl. Another subembodiment of this aspect of the invention is realized when the $R^a$ is optionally substituted phenyl. Another subembodiment of this aspect of the invention is realized when the $R^a$ is optionally substituted oxadiazolyl.

A subembodiment of the invention of formula II is realized when X is optionally substituted pyridazinyl and Q is (a) or (b). A further subembodiment is realized when Q is (a). A further subembodiment is realized when Q is (b). Still a further subembodiment of this aspect of the invention is realized when at least one $R^a$ is attached. A further subembodiment of this aspect of the invention is realized when at least one $R^a$ is present and is located on the carbon atom directly adjacent to the linking nitrogen atom. Another subembodiment of this aspect of the invention is realized when $R^a$ selected from the group consisting of C(O)OC(CH$_3$)$_3$, C(O)OCH$_2$CH$_3$, C(O)NHC(CH$_3$)$_3$, CH$_2$OH, C(O)NC(CH$_3$)$_2$CH$_3$, —C$_{1-6}$alkyl, and optionally substituted phenyl, benzoxazolyl, benzimidazolyl, oxadiazolyl, piperidinyl, tetrahydropyranyl, pyridyl, benzythiazolyl, C(O)NHphenyl, and C(O)NH(CH$_2$)$_p$phenyl. Another subembodiment of this aspect of the invention is realized when the $R^a$ is selected from the group consisting of optionally substituted phenyl, oxadiazolyl, and benzoxazolyl. Another subembodiment of this aspect of the invention is realized when the $R^a$ is optionally substituted phenyl. Another subembodiment of this aspect of the invention is realized when the $R^a$ is optionally substituted oxadiazolyl.

A subembodiment of the invention of formula II is realized when X is optionally substituted pyridazinyl and Q is (c) or (d). A further subembodiment is realized when Q is (c).

A further subembodiment is realized when Q is (d). Still a further subembodiment of this aspect of the invention is realized when at least one $R^a$ is attached. A further subembodiment of this aspect of the invention is realized when at least one $R^a$ is present and is located on the carbon atom directly adjacent to the linking nitrogen atom. Another subembodiment of this aspect of the invention is realized when $R^a$ selected from the group consisting of C(O)OC(CH$_3$)$_3$, C(O)OCH$_2$CH$_3$, C(O)NHC(CH$_3$)$_3$, CH$_2$OH, C(O)NC(CH$_3$)$_2$CH$_3$, —C$_{1-6}$alkyl, and optionally substituted phenyl, benzoxazolyl, benzimidazolyl, oxadiazolyl, piperidinyl, tetrahydropyranyl, pyridyl, benzythiazolyl, C(O)NHphenyl, and C(O)NH(CH$_2$)$_p$phenyl. Another subembodiment of this aspect of the invention is realized when the $R^a$ is selected from the group consisting of optionally substituted phenyl, oxadiazolyl, and benzoxazolyl. Another subembodiment of this aspect of the invention is realized when the $R^a$ is optionally substituted phenyl. Another subembodiment of this aspect of the invention is realized when the $R^a$ is optionally substituted oxadiazolyl.

A subembodiment of the invention of formula II is realized when X is optionally substituted pyridazinyl and Q is (e) or (f). A further subembodiment is realized when Q is (e). A further subembodiment is realized when Q is (f). Still a further subembodiment of this aspect of the invention is realized when at least one $R^a$ is attached. A further subembodiment of this aspect of the invention is realized when at least one $R^a$ is present and is located on the carbon atom directly adjacent to the linking nitrogen atom. Another subembodiment of this aspect of the invention is realized when $R^a$ selected from the group consisting of C(O)OC(CH$_3$)$_3$, C(O)OCH$_2$CH$_3$, C(O)NHC(CH$_3$)$_3$, CH$_2$OH, C(O)NC(CH$_3$)$_2$CH$_3$, —C$_{1-6}$alkyl, and optionally substituted phenyl, benzoxazolyl, benzimidazolyl, oxadiazolyl, piperidinyl, tetrahydropyranyl, pyridyl, benzythiazolyl, C(O)NHphenyl, and C(O)NH(CH$_2$)$_p$phenyl. Another subembodiment of this aspect of the invention is realized when the $R^a$ is selected from the group consisting of optionally substituted phenyl, oxadiazolyl, and benzoxazolyl. Another subembodiment of this aspect of the invention is realized when the $R^a$ is optionally substituted phenyl. Another subembodiment of this aspect of the invention is realized when the $R^a$ is optionally substituted oxadiazolyl.

A subembodiment of the invention of formula II is realized when X is optionally substituted pyridazinyl and Q is (g), (h), or (i). A further subembodiment is realized when Q is (g). A further subembodiment is realized when Q is (h). A further subembodiment is realized when Q is (i). Still a further subembodiment of this aspect of the invention is realized when at least one $R^a$ is attached. A further subembodiment of this aspect of the invention is realized when at least one $R^a$ is present and is located on the carbon atom directly adjacent to the linking nitrogen atom. Another subembodiment of this aspect of the invention is realized when $R^a$ selected from the group consisting of C(O)OC(CH$_3$)$_3$, C(O)OCH$_2$CH$_3$, C(O)NHC(CH$_3$)$_3$, CH$_2$OH, C(O)NC(CH$_3$)$_2$CH$_3$, —C$_{1-6}$alkyl, and optionally substituted phenyl, benzoxazolyl, benzimidazolyl, oxadiazolyl, piperidinyl, tetrahydropyranyl, pyridyl, benzythiazolyl, C(O)NHphenyl, and C(O)NH(CH$_2$)$_p$phenyl. Another subembodiment of this aspect of the invention is realized when the $R^a$ is selected from the group consisting of optionally substituted phenyl, oxadiazolyl, and benzoxazolyl. Another subembodiment of this aspect of the invention is realized when the $R^a$ is optionally substituted phenyl. Another subembodiment of this aspect of the invention is realized when the $R^a$ is optionally substituted oxadiazolyl.

A subembodiment of the invention of formula II is realized when X is optionally substituted pyridazinyl and Q is (j), (k), (l), (m), or (n). Another subembodiment of this aspect of the invention is realized when $R^a$ selected from the group consisting of C(O)OC(CH$_3$)$_3$, C(O)OCH$_2$CH$_3$, C(O)NHC(CH$_3$)$_3$, CH$_2$OH, C(O)NC(CH$_3$)$_2$CH$_3$, —C$_{1-6}$alkyl, and optionally substituted phenyl, benzoxazolyl, benzimidazolyl, oxadiazolyl, piperidinyl, tetrahydropyranyl, pyridyl, benzythiazolyl, C(O)NHphenyl, and C(O)NH(CH$_2$)$_p$phenyl. Another subembodiment of this aspect of the invention is realized when the $R^a$ is selected from the group consisting of optionally substituted phenyl, oxadiazolyl, and benzoxazolyl. Another subembodiment of this aspect of the invention is realized when the $R^a$ is optionally substituted phenyl. Another subembodiment of this aspect of the invention is realized when the $R^a$ is optionally substituted oxadiazolyl.

A subembodiment of the invention of formula II is realized when X is optionally substituted pyrazinyl and Q is (a) or (b). A further subembodiment is realized when Q is (a). A further subembodiment is realized when Q is (b). Still a further subembodiment of this aspect of the invention is realized when at least one $R^a$ is attached. A further subembodiment of this aspect of the invention is realized when at least one $R^a$ is present and is located on the carbon atom directly adjacent to the linking nitrogen atom. Another subembodiment of this aspect of the invention is realized when $R^a$ is selected from the group consisting of C(O)OC(CH$_3$)$_3$, C(O)OCH$_2$CH$_3$, C(O)NHC(CH$_3$)$_3$, CH$_2$OH, C(O)NC(CH$_3$)$_2$CH$_3$, —C$_{1-6}$alkyl, and optionally substituted phenyl, benzoxazolyl, benzimidazolyl, oxadiazolyl, piperidinyl, tetrahydropyranyl, pyridyl, benzythiazolyl, C(O)NHphenyl, and C(O)NH(CH$_2$)$_p$phenyl. Another subembodiment of this aspect of the invention is realized when the $R^a$ is selected from the group consisting of optionally substituted phenyl, oxadiazolyl, and benzoxazolyl. Another subembodiment of this aspect of the invention is realized when the $R^a$ is optionally substituted phenyl. Another subembodiment of this aspect of the invention is realized when the $R^a$ is optionally substituted oxadiazolyl.

A subembodiment of the invention of formula II is realized when X is optionally substituted pyrazinyl and Q is (c) or (d). A further subembodiment is realized when Q is (c). A further subembodiment is realized when Q is (d). Still a further subembodiment of this aspect of the invention is realized when at least one $R^a$ is attached. A further subembodiment of this aspect of the invention is realized when at least one $R^a$ is present and is located on the carbon atom directly adjacent to the linking nitrogen atom. Another subembodiment of this aspect of the invention is realized when $R^a$ selected from the group consisting of C(O)OC(CH$_3$)$_3$, C(O)OCH$_2$CH$_3$, C(O)NHC(CH$_3$)$_3$, CH$_2$OH, C(O)NC(CH$_3$)$_2$CH$_3$, —C$_{1-6}$alkyl, and optionally substituted phenyl, benzoxazolyl, benzimidazolyl, oxadiazolyl, piperidinyl, tetrahydropyranyl, pyridyl, benzythiazolyl, C(O)NHphenyl, and C(O)NH(CH$_2$)$_p$phenyl. Another subembodiment of this aspect of the invention is realized when the $R^a$ is selected from the group consisting of optionally substituted phenyl, oxadiazolyl, and benzoxazolyl. Another subembodiment of this aspect of the invention is realized when the $R^a$ is optionally substituted phenyl. Another subembodiment of this aspect of the invention is realized when the $R^a$ is optionally substituted oxadiazolyl.

A subembodiment of the invention of formula II is realized when X is optionally substituted pyrazinyl and Q is (e) or (f). A further subembodiment is realized when Q is (e). A further subembodiment is realized when Q is (f). Still a further subembodiment of this aspect of the invention is realized when at least one $R^a$ is attached. A further subembodiment of this aspect of the invention is realized when at least one $R^a$ is present and is located on the carbon atom directly adjacent to the linking nitrogen atom. Another subembodiment of this aspect of the invention is realized when $R^a$ is selected from the group consisting of C(O)OC(CH$_3$)$_3$, C(O)OCH$_2$CH$_3$, C(O)NHC(CH$_3$)$_3$, CH$_2$OH, C(O)NC(CH$_3$)$_2$CH$_3$, —C$_{1-6}$alkyl, and optionally substituted phenyl, benzoxazolyl, benzimidazolyl, oxadiazolyl, piperidinyl, tetrahydropyranyl, pyridyl, benzythiazolyl, C(O)NHphenyl, and C(O)NH(CH$_2$)$_p$phenyl. Another subembodiment of this aspect of the invention is realized when the $R^a$ is selected from the group consisting of optionally substituted phenyl, oxadiazolyl, and benzoxazolyl. Another subembodiment of this aspect of the invention is realized when the $R^a$ is optionally substituted phenyl. Another subembodiment of this aspect of the invention is realized when the $R^a$ is optionally substituted oxadiazolyl.

A subembodiment of the invention of formula II is realized when X is optionally substituted pyrazinyl and Q is (g), (h), or (i). A further subembodiment is realized when Q is (g). A further subembodiment is realized when Q is (h). A further subembodiment is realized when Q is (i). Still a further subembodiment of this aspect of the invention is realized when at least one $R^a$ is attached. A further subembodiment of this aspect of the invention is realized when at least one $R^a$ is present and is located on the carbon atom directly adjacent to the linking nitrogen atom. Another subembodiment of this aspect of the invention is realized when $R^a$ is selected from the group consisting of C(O)OC(CH$_3$)$_3$, C(O)OCH$_2$CH$_3$, C(O)NHC(CH$_3$)$_3$, CH$_2$OH, C(O)NC(CH$_3$)$_2$CH$_3$, —C$_{1-6}$alkyl, and optionally substituted phenyl, benzoxazolyl, benzimidazolyl, oxadiazolyl, piperidinyl, tetrahydropyranyl, pyridyl, benzythiazolyl, C(O)NHphenyl, and C(O)NH(CH$_2$)$_p$phenyl. Another subembodiment of this aspect of the invention is realized when the $R^a$ is selected from the group consisting of optionally substituted phenyl, oxadiazolyl, and benzoxazolyl. Another subembodiment of this aspect of the invention is realized when the $R^a$ is optionally substituted phenyl. Another subembodiment of this aspect of the invention is realized when the $R^a$ is optionally substituted oxadiazolyl.

A subembodiment of the invention of formula II is realized when X is optionally substituted pyrazinyl and Q is (j), (k), (l), (m), or (n). Another subembodiment of this aspect of the invention is realized when $R^a$ is selected from the group consisting of C(O)OC(CH$_3$)$_3$, C(O)OCH$_2$CH$_3$, C(O)NHC(CH$_3$)$_3$, CH$_2$OH, C(O)NC(CH$_3$)$_2$CH$_3$, —C$_{1-6}$alkyl, and optionally substituted phenyl, benzoxazolyl, benzimidazolyl, oxadiazolyl, piperidinyl, tetrahydropyranyl, pyridyl, benzythiazolyl, C(O)NHphenyl, and C(O)NH(CH$_2$)$_p$phenyl. Another subembodiment of this aspect of the invention is realized when the $R^a$ is selected from the group consisting of optionally substituted phenyl, oxadiazolyl, and benzoxazolyl. Another subembodiment of this aspect of the invention is realized when the $R^a$ is optionally substituted phenyl. Another subembodiment of this aspect of the invention is realized when the $R^a$ is optionally substituted oxadiazolyl.

Another embodiment of the claimed invention of formula I is realized by structural formula III:

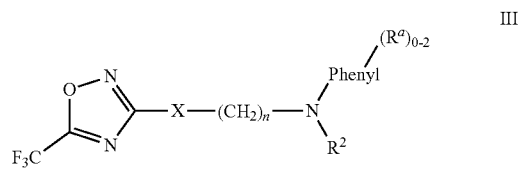

or a pharmaceutically acceptable salt thereof, wherein X is optionally substituted phenyl, pyridyl, pyridazinyl, or pyrazinyl, $R^a$ and $R^2$ are as originally described. An aspect of the invention of formula III is realized when (CH$_2$) is present. An aspect of the invention of formula II is realized when (CH$_2$) is absent.

Another embodiment of the invention of formula III is realized when X is optionally substituted phenyl, one $R^a$ is present on the phenyl, and is selected from the group consisting of halo or CF$_3$, and $R^2$ is selected from the group consisting of —C(O)(C(R$_2$)$_p$C$_{3-6}$heterocyclyl, —C(O)C$_{6-10}$aryl, said aryl and heterocyclyl optionally substituted with 1 to 3 groups of $R^a$. A subembodiment of this aspect of the invention is realized when the aryl and heterocyclyl of $R^2$ is selected from the group consisting of optionally substituted pyridyl, pyrimidinyl, pyrazinyl, piperidinyl, tetrahydropyranyl, oxadiazolyl, morpholinyl, tetrahydrothiopyranyl, dihydropyridazinone, dioxanyl, benzimidazolyl, piperazinyl, oxopyridazinyl, triazolyl, dihydropyrazolyl, isoxazolyl, pyrazolyl, oxetanyl, dioxidothiomorpholinyl. Another subembodiment of this aspect of the invention is realized when $R^2$ is selected from the group consisting of optionally substituted pyridyl, C(O)tetrahydrothiophene, C(O)morpholinyl, C(O)pyrimidinyl, C(O)tetrahydrothiphene, C(O)pyrazine, C(O)piperidinyl, C(O)tetrahydropyranyl, C(O)oxadiazolyl, C(O)dioxanyl, C(O)dihydropyridazinone, C(O)CH$_2$morpholinyl, C(O)CH$_2$dioxidothiomorpholinyl, C(O)CH$_2$oxetanyl, C(O)CH$_2$ isoxazolyl, C(O)CH$_2$dihydropyrazolyl, C(O)CH$_2$piperazinyl, C(O)CH$_2$pyrimidinyl, C(O)CH$_2$pyrazinyl, C(O)CH$_2$benzimidazolyl, C(O)CH(CH$_3$)CH$_2$triazolyl, C(O)(CH$_2$)$_3$triazolyl, C(O)CH$_2$triazolyl, C(O)(CH$_2$)$_2$triazolyl, C(O)CH(CH$_3$)pyrazolyl, and C(O)CH(CH$_3$)triazolyl.

Another embodiment of the invention of formula III is realized when X is optionally substituted phenyl, one $R^a$ is present on the phenyl, and $R^2$ is selected from the group consisting of —C(O)C$_{1-6}$alkyl, C(O)(CH$_2$)$_p$N(R)$_2$, C(O)(CH$_2$)$_p$NHC(O)C$_{1-6}$alkyl, C(O)OR, —C(O)C$_{3-6}$cycloalkyl and C(O)(CH$_2$)$_p$SO$_2$R, said alkyl and cycloalkyl optionally substituted with 1 to 3 groups of $R^a$. Another subembodiment of this aspect of the invention is realized when $R^2$ is selected from the group consisting of —C(O)OC(CH$_3$)$_3$, —C(O)C(CH$_3$)CN, —C(O)CH$_2$CH$_3$, —C(O)CH$_2$SO$_2$CH$_3$, and —C(O)CH$_2$N(CH$_3$)$_2$.

Another embodiment of the invention of formula III is realized when X is optionally substituted pyridyl, one $R^a$ is present on the phenyl, and $R^2$ is selected from the group consisting of —C(O)(CRR)$_p$C$_{3-6}$heterocyclyl, —C(O)C$_{6-10}$aryl, said aryl and heterocyclyl optionally substituted with 1 to 3 groups of $R^a$. A subembodiment of this aspect of the invention is realized when the aryl and heterocyclyl of $R^2$ is selected from the group consisting of optionally substituted pyridyl, pyrimidinyl, pyrazinyl, piperidinyl, tetrahydropyranyl, oxadiazolyl, morpholinyl, tetrahydrothiopyranyl, dihydropyridazinone, dioxanyl, benzimidazolyl, piperazinyl, oxopyridazinyl, triazolyl, dihydropyrazolyl, isoxazolyl, pyrazolyl, oxetanyl, dioxidothiomorpholinyl. Another subembodiment of this aspect of the invention is realized when $R^2$ is selected from the group consisting of optionally substituted pyridyl, C(O)tetrahydrothiophene, C(O)morpholinyl, C(O)pyrimidinyl, C(O)tetrahydrothiphene, C(O)pyrazine, C(O)piperidinyl, C(O)tetrahydropyranyl, C(O)oxadiazolyl, C(O)dioxanyl, C(O)dihydropyridazinone, C(O)CH$_2$morpholinyl, C(O)CH$_2$dioxidothiomorpholinyl, C(O)CH$_2$oxetanyl, C(O)CH$_2$ isoxazolyl, C(O)CH$_2$dihydropyrazolyl, C(O)CH$_2$piperazinyl, C(O)CH$_2$pyrimidinyl, C(O)CH$_2$pyrazinyl, C(O)CH$_2$benzimidazolyl, C(O)CH(CH$_3$)CH$_2$triazolyl, C(O)(CH$_2$)$_3$triazolyl, C(O)CH$_2$triazolyl, C(O)(CH$_2$)$_2$triazolyl, C(O)CH(CH$_3$)pyrazolyl, and C(O)CH(CH$_3$)triazolyl.

Another embodiment of the invention of formula III is realized when X is optionally substituted pyridyl, one $R^a$ is present on the phenyl, and $R^2$ is selected from the group consisting of —C(O)C$_{1-6}$alkyl, C(O)(CH$_2$)$_p$N(R)$_2$, C(O)(CH$_2$)$_p$NHC(O)C$_{1-6}$alkyl, C(O)OR, —C(O)C$_{3-6}$cycloalkyl and C(O)(CH$_2$)$_p$SO$_2$R, said alkyl and cycloalkyl optionally substituted with 1 to 3 groups of $R^a$. Another subembodiment of this aspect of the invention is realized when $R^2$ is selected from the group consisting of —C(O)OC(CH$_3$)$_3$, —C(O)C(CH$_3$)CN, —C(O)CH$_2$CH$_3$, —C(O)CH$_2$SO$_2$CH$_3$, and —C(O)CH$_2$N(CH$_3$)$_2$.

Another embodiment of the invention of formula III is realized when X is optionally substituted pyridazinyl, one $R^a$ is present on the phenyl, and $R^2$ is selected from the group consisting of —C(O)(CRR)$_p$C$_{3-6}$heterocyclyl, —C(O)C$_{6-10}$aryl, said aryl and heterocyclyl optionally substituted with 1 to 3 groups of $R^a$. A subembodiment of this aspect of the invention is realized when the aryl and heterocyclyl of $R^2$ is selected from the group consisting of optionally substituted pyridyl, pyrimidinyl, pyrazinyl, piperidinyl, tetrahydropyranyl, oxadiazolyl, morpholinyl, tetrahydrothiopyranyl, dihydropyridazinone, dioxanyl, benzimidazolyl, piperazinyl, oxopyridazinyl, triazolyl, dihydropyrazolyl, isoxazolyl, pyrazolyl, oxetanyl, dioxidothiomorpholinyl. Another subembodiment of this aspect of the invention is realized when $R^2$ is selected from the group consisting of optionally substituted pyridyl, C(O)tetrahydrothiophene, C(O)morpholinyl, C(O)pyrimidinyl, C(O)tetrahydrothiphene, C(O)pyrazine, C(O)piperidinyl, C(O)tetrahydropyranyl, C(O)oxadiazolyl, C(O)dioxanyl, C(O)dihydropyridazinone, C(O)CH$_2$morpholinyl, C(O)CH$_2$dioxidothiomorpholinyl, C(O)CH$_2$oxetanyl, C(O)CH$_2$ isoxazolyl, C(O)CH$_2$dihydropyrazolyl, C(O)CH$_2$piperazinyl, C(O)CH$_2$pyrimidinyl, C(O)CH$_2$pyrazinyl, C(O)CH$_2$benzimidazolyl, C(O)CH(CH$_3$)CH$_2$triazolyl, C(O)(CH$_2$)$_3$triazolyl, C(O)CH$_2$triazolyl, C(O)(CH$_2$)$_2$triazolyl, C(O)CH(CH$_3$)pyrazolyl, and C(O)CH(CH$_3$)triazolyl.

Another embodiment of the invention of formula III is realized when X is optionally substituted pyridazinyl, one $R^a$ is present on the phenyl, and $R^2$ is selected from the group consisting of —C(O)C$_{1-6}$alkyl, C(O)(CH$_2$)$_p$N(R)$_2$, C(O)(CH$_2$)$_p$NHC(O)C$_{1-6}$alkyl, C(O)OR, —C(O)C$_{3-6}$cycloalkyl and C(O)(CH$_2$)$_p$SO$_2$R, said alkyl and cycloalkyl optionally substituted with 1 to 3 groups of $R^a$. Another subembodiment of this aspect of the invention is realized when $R^2$ is selected from the group consisting of —C(O)OC(CH$_3$)$_3$, —C(O)C(CH$_3$)CN, —C(O)CH$_2$CH$_3$, —C(O)CH$_2$SO$_2$CH$_3$, and —C(O)CH$_2$N(CH$_3$)$_2$.

Another embodiment of the invention of formula III is realized when X is optionally substituted pyrazinyl, one $R^a$ is present on the phenyl, and $R^2$ is selected from the group consisting of —C(O)(CRR)$_p$C$_{3-6}$heterocyclyl, —C(O)C$_{6-10}$aryl, said aryl and heterocyclyl optionally substituted with 1 to 3 groups of $R^a$. A subembodiment of this aspect of the invention is realized when the aryl and heterocyclyl of $R^2$ is selected from the group consisting of optionally substituted pyridyl, pyrimidinyl, pyrazinyl, piperidinyl, tetrahydropyranyl, oxadiazolyl, morpholinyl, tetrahydrothiopyranyl, dihydropyridazinone, dioxanyl, benzimidazolyl, piperazinyl, oxopyridazinyl, triazolyl, dihydropyrazolyl, isoxazolyl, pyrazolyl, oxetanyl, dioxidothiomorpholinyl. Another subembodiment of this aspect of the invention is realized when $R^2$ is selected from the group consisting of optionally substituted pyridyl, C(O)tetrahydrothiophene, C(O)morpholinyl, C(O)pyrimidinyl, C(O)tetrahydrothiphene, C(O)pyrazine, C(O)piperidinyl, C(O)tetrahydropyranyl, C(O)oxadiazolyl, C(O)dioxanyl, C(O)dihydropyridazinone, C(O)CH$_2$morpholinyl, C(O)CH$_2$dioxidothiomorpholinyl, C(O)CH$_2$oxetanyl, C(O)CH$_2$ isoxazolyl, C(O)CH$_2$dihydropyrazolyl, C(O)CH$_2$piperazinyl, C(O)CH$_2$pyrimidinyl, C(O)CH$_2$pyrazinyl, C(O)CH$_2$benzimidazolyl, C(O)CH(CH$_3$)CH$_2$triazolyl, C(O)(CH$_2$)$_3$triazolyl, C(O)CH$_2$triazolyl, C(O)(CH$_2$)$_2$triazolyl, C(O)CH(CH$_3$)pyrazolyl, and C(O)CH(CH$_3$)triazolyl.

Another embodiment of the invention of formula III is realized when X is optionally substituted pyrazinyl, one $R^a$ is present on the phenyl, and $R^2$ is selected from the group consisting of —C(O)C$_{1-6}$alkyl, C(O)(CH$_2$)$_p$N(R)$_2$, C(O)(CH$_2$)$_p$NHC(O)C$_{1-6}$alkyl, C(O)OR, —C(O)C$_{3-6}$cycloalkyl and C(O)(CH$_2$)$_p$SO$_2$R, said alkyl and cycloalkyl optionally substituted with 1 to 3 groups of $R^a$. Another subembodiment of this aspect of the invention is realized when $R^2$ is selected from the group consisting of —C(O)OC(CH$_3$)$_3$, —C(O)C(CH$_3$)CN, —C(O)CH$_2$CH$_3$, —C(O)CH$_2$SO$_2$CH$_3$, and —C(O)CH$_2$N(CH$_3$)$_2$.

Another embodiment of the claimed invention of formula I is realized by structural formula IV:

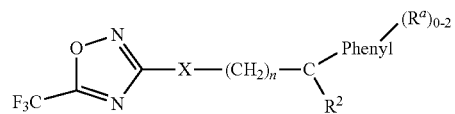

or pharmaceutically acceptable salt thereof wherein,
X is optionally substituted phenyl, pyridyl, pyridazinyl, or pyrazinyl, $R^a$ and $R^2$ are as originally described. An aspect of the invention of formula IV is realized when (CH$_2$) is present. An aspect of the invention of formula II is realized when (CH$_2$) is absent.

Another embodiment of the invention of formula IV is realized when X is optionally substituted phenyl, one $R^a$ is present on the phenyl, and is selected from the group consisting of halo or $CF_3$, and $R^2$ is selected from the group consisting of —$C(O)(C(R_2))_pC_{3-6}$heterocyclyl, —$C(O)C_{6-10}$ aryl, said aryl and heterocyclyl optionally substituted with 1 to 3 groups of $R^a$. A subembodiment of this aspect of the invention is realized when the aryl and heterocyclyl of $R^2$ is selected from the group consisting of optionally substituted pyridyl, pyrimidinyl, pyrazinyl, piperidinyl, tetrahydropyranyl, oxadiazolyl, morpholinyl, tetrahydrothiopyranyl, dihydropyridazinone, dioxanyl, benzimidazolyl, piperazinyl, oxopyridazinyl, triazolyl, dihydropyrazolyl, isoxazolyl, pyrazolyl, oxetanyl, dioxidothiomorpholinyl. Another subembodiment of this aspect of the invention is realized when $R^2$ is selected from the group consisting of optionally substituted pyridyl, C(O)tetrahydrothiophene, C(O)morpholinyl, C(O)pyrimidinyl, C(O)tetrahydrothiphene, C(O)pyrazine, C(O)piperidinyl, C(O)tetrahydropyranyl, C(O)oxadiazolyl, C(O)dioxanyl, C(O)dihydropyridazinone, C(O)CH$_2$morpholinyl, C(O)CH$_2$dioxidothiomorpholinyl, C(O)CH$_2$oxetanyl, C(O)CH$_2$ isoxazolyl, C(O)CH$_2$dihydropyrazolyl, C(O)CH$_2$piperazinyl, C(O)CH$_2$pyrimidinyl, C(O)CH$_2$pyrazinyl, C(O)CH$_2$benzimidazolyl, C(O)CH(CH$_3$)CH$_2$triazolyl, C(O)(CH$_2$)$_3$triazolyl, C(O)CH$_2$triazolyl, C(O)(CH$_2$)$_2$triazolyl, C(O)CH(CH$_3$)pyrazolyl, and C(O)CH(CH$_3$)triazolyl.

Another embodiment of the invention of formula IV is realized when X is optionally substituted phenyl, one $R^a$ is present on the phenyl, and $R^2$ is selected from the group consisting of —$C(O)C_{1-6}$alkyl, $C(O)(CH_2)_pN(R)_2$, $C(O)(CH_2)_pNHC(O)C_{1-6}$alkyl, C(O)OR, —$C(O)C_{3-6}$cycloalkyl and $C(O)(CH_2)_pSO_2R$, said alkyl and cycloalkyl optionally substituted with 1 to 3 groups of $R^a$. Another subembodiment of this aspect of the invention is realized when $R^2$ is selected from the group consisting of —$C(O)OC(CH_3)_3$, —$C(O)C(CH_3)CN$, —$C(O)CH_2CH_3$, —$C(O)CH_2SO_2CH_3$, and —$C(O)CH_2N(CH_3)_2$.

Another embodiment of the invention of formula IV is realized when X is optionally substituted pyridyl, one $R^a$ is present on the phenyl, and $R^2$ is selected from the group consisting of —$C(O)(CRR)_pC_{3-6}$heterocyclyl, —$C(O)C_{6-10}$ aryl, said aryl and heterocyclyl optionally substituted with 1 to 3 groups of $R^a$. A subembodiment of this aspect of the invention is realized when the aryl and heterocyclyl of $R^2$ is selected from the group consisting of optionally substituted pyridyl, pyrimidinyl, pyrazinyl, piperidinyl, tetrahydropyranyl, oxadiazolyl, morpholinyl, tetrahydrothiopyranyl, dihydropyridazinone, dioxanyl, benzimidazolyl, piperazinyl, oxopyridazinyl, triazolyl, dihydropyrazolyl, isoxazolyl, pyrazolyl, oxetanyl, dioxidothiomorpholinyl. Another subembodiment of this aspect of the invention is realized when $R^2$ is selected from the group consisting of optionally substituted pyridyl, C(O)tetrahydrothiophene, C(O)morpholinyl, C(O)pyrimidinyl, C(O)tetrahydrothiphene, C(O)pyrazine, C(O)piperidinyl, C(O)tetrahydropyranyl, C(O)oxadiazolyl, C(O)dioxanyl, C(O)dihydropyridazinone, C(O)CH$_2$morpholinyl, C(O)CH$_2$dioxidothiomorpholinyl, C(O)CH$_2$oxetanyl, C(O)CH$_2$ isoxazolyl, C(O)CH$_2$dihydropyrazolyl, C(O)CH$_2$piperazinyl, C(O)CH$_2$pyrimidinyl, C(O)CH$_2$pyrazinyl, C(O)CH$_2$benzimidazolyl, C(O)CH(CH$_3$)CH$_2$triazolyl, C(O)(CH$_2$)$_3$triazolyl, C(O)CH$_2$triazolyl, C(O)(CH$_2$)$_2$triazolyl, C(O)CH(CH$_3$)pyrazolyl, and C(O)CH(CH$_3$)triazolyl.

Another embodiment of the invention of formula IV is realized when X is optionally substituted pyridyl, one $R^a$ is present on the phenyl, and R is selected from the group consisting of —$C(O)C_{1-6}$alkyl, $C(O)(CH_2)_pN(R)_2$, $C(O)(CH_2)_pNHC(O)C_{1-6}$alkyl, C(O)OR, —$C(O)C_{3-6}$cycloalkyl and $C(O)(CH_2)_pSO_2R$, said alkyl and cycloalkyl optionally substituted with 1 to 3 groups of $R^a$. Another subembodiment of this aspect of the invention is realized when $R^2$ is selected from the group consisting of —$C(O)OC(CH_3)_3$, —$C(O)C(CH_3)CN$, —$C(O)CH_2CH_3$, —$C(O)CH_2SO_2CH_3$, and —$C(O)CH_2N(CH_3)_2$.

Another embodiment of the invention of formula IV is realized when X is optionally substituted pyridazinyl, one $R^a$ is present on the phenyl, and $R^2$ is selected from the group consisting of —$C(O)(CRR)_pC_{3-6}$heterocyclyl, —$C(O)C_{6-10}$ aryl, said aryl and heterocyclyl optionally substituted with 1 to 3 groups of $R^a$. A subembodiment of this aspect of the invention is realized when the aryl and heterocyclyl of $R^2$ is selected from the group consisting of optionally substituted pyridyl, pyrimidinyl, pyrazinyl, piperidinyl, tetrahydropyranyl, oxadiazolyl, morpholinyl, tetrahydrothiopyranyl, dihydropyridazinone, dioxanyl, benzimidazolyl, piperazinyl, oxopyridazinyl, triazolyl, dihydropyrazolyl, isoxazolyl, pyrazolyl, oxetanyl, dioxidothiomorpholinyl. Another subembodiment of this aspect of the invention is realized when $R^2$ is selected from the group consisting of optionally substituted pyridyl, C(O)tetrahydrothiophene, C(O)morpholinyl, C(O)pyrimidinyl, C(O)tetrahydrothiphene, C(O)pyrazine, C(O)piperidinyl, C(O)tetrahydropyranyl, C(O)oxadiazolyl, C(O)dioxanyl, C(O)dihydropyridazinone, C(O)CH$_2$morpholinyl, C(O)CH$_2$dioxidothiomorpholinyl, C(O)CH$_2$oxetanyl, C(O)CH$_2$ isoxazolyl, C(O)CH$_2$dihydropyrazolyl, C(O)CH$_2$piperazinyl, C(O)CH$_2$pyrimidinyl, C(O)CH$_2$pyrazinyl, C(O)CH$_2$benzimidazolyl, C(O)CH(CH$_3$)CH$_2$triazolyl, C(O)(CH$_2$)$_3$triazolyl, C(O)CH$_2$triazolyl, C(O)(CH$_2$)$_2$triazolyl, C(O)CH(CH$_3$)pyrazolyl, and C(O)CH(CH$_3$)triazolyl.

Another embodiment of the invention of formula IV is realized when X is optionally substituted pyridazinyl, one $R^a$ is present on the phenyl, and $R^2$ is selected from the group consisting of —$C(O)C_{1-6}$alkyl, $C(O)(CH_2)_pN(R)_2$, $C(O)(CH_2)_pNHC(O)C_{1-6}$alkyl, C(O)OR, —$C(O)C_{3-6}$cycloalkyl and $C(O)(CH_2)_pSO_2R$, said alkyl and cycloalkyl optionally substituted with 1 to 3 groups of $R^a$. Another subembodiment of this aspect of the invention is realized when $R^2$ is selected from the group consisting of —$C(O)OC(CH_3)_3$, —$C(O)C(CH_3)CN$, —$C(O)CH_2CH_3$, —$C(O)CH_2SO_2CH_3$, and —$C(O)CH_2N(CH_3)_2$.

Another embodiment of the invention of formula IV is realized when X is optionally substituted pyrazinyl, one $R^a$ is present on the phenyl, and $R^2$ is selected from the group consisting of —$C(O)(CRR)_pC_{3-6}$heterocyclyl, —$C(O)C_{6-10}$ aryl, said aryl and heterocyclyl optionally substituted with 1 to 3 groups of $R^a$. A subembodiment of this aspect of the invention is realized when the aryl and heterocyclyl of $R^2$ is selected from the group consisting of optionally substituted pyridyl, pyrimidinyl, pyrazinyl, piperidinyl, tetrahydropyranyl, oxadiazolyl, morpholinyl, tetrahydrothiopyranyl, dihydropyridazinone, dioxanyl, benzimidazolyl, piperazinyl, oxopyridazinyl, triazolyl, dihydropyrazolyl, isoxazolyl, pyrazolyl, oxetanyl, dioxidothiomorpholinyl. Another subembodiment of this aspect of the invention is realized when $R^2$ is selected from the group consisting of optionally substituted pyridyl, C(O)tetrahydrothiophene, C(O)morpholinyl, C(O)pyrimidinyl, C(O)tetrahydrothiphene, C(O)pyrazine, C(O)piperidinyl, C(O)tetrahydropyranyl, C(O)oxadiazolyl, C(O)dioxanyl, C(O)dihydropyridazinone, C(O)CH$_2$morpholinyl, C(O)CH$_2$dioxidothiomorpholinyl, C(O)CH$_2$oxetanyl, C(O)CH$_2$ isoxazolyl, C(O)CH$_2$dihydropyrazolyl, C(O)CH$_2$piperazinyl, C(O)CH$_2$pyrimidinyl, C(O)CH$_2$pyrazinyl, C(O)CH$_2$benzimidazolyl, C(O)CH(CH$_3$)CH$_2$triazolyl, C(O)

$(CH_2)_3$triazolyl, $C(O)CH_2$triazolyl, $C(O)(CH_2)_2$triazolyl, $C(O)CH(CH_3)$pyrazolyl, and $C(O)CH(CH_3)$triazolyl.

Another embodiment of the invention of formula IV is realized when X is optionally substituted pyrazinyl, one $R^a$ is present on the phenyl, and R is selected from the group consisting of —$C(O)C_{1-6}$alkyl, $C(O)(CH_2)_pN(R)_2$, $C(O)(CH_2)_pNHC(O)C_{1-6}$alkyl, $C(O)OR$, —$C(O)C_{3-6}$cycloalkyl and $C(O)(CH_2)_pSO_2R$, said alkyl and cycloalkyl optionally substituted with 1 to 3 groups of $R^a$. Another subembodiment of this aspect of the invention is realized when $R^2$ is selected from the group consisting of —$C(O)OC(CH_3)_3$, —$C(O)C(CH_3)CN$, —$C(O)CH_2CH_3$, —$C(O)CH_2SO_2CH_3$, and —$C(O)CH_2N(CH_3)_2$.

The compounds of the present invention may have asymmetric centers, chiral axes and chiral planes, and occur as racemates, racemic mixtures, and as individual diastereomers, with all possible isomers, including optical isomers, being included in the present invention. (See E. L. Eliel and S. H. Wilen *Stereochemistry of Carbon Compounds* (John Wiley and Sons, New York 1994), in particular pages 1119-1190)

Absolute stereochemistry is illustrated by the use of hashed and solid wedge bonds. As shown in Illus-I and Illus-II. Accordingly, the methyl group of Illus-I is emerging from the page of the paper and the ethyl group in Illus-II is descending into the page, where the cyclohexene ring resides within the plane of the paper. It is assumed that the hydrogen on the same carbon as the methyl group of Illus-I descends into the page and the hydrogen on the same carbon as the ethyl group of Illus-II emerges from the page. The convention is the same where both a hashed and solid rectangle are appended to the same carbon as in Illus-III, the Methyl group is emerging from the plane of the paper and the ethyl group is descending into the plane of the paper with the cyclohexene ring in the plane of the paper.

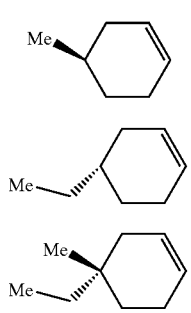

Illus-I

Illus-2

Illus-3

As is conventional, unless otherwise noted in accompanying text, ordinary "stick" bonds or "wavy" bonds indicate that all possible stereochemistry is represented, including, pure compounds, mixtures of isomers, and racemic mixtures.

As described herein, unless otherwise indicated, the use of a compound in treatment means that an amount of the compound, generally presented as a component of a formulation that comprises other excipients, is administered in aliquots of an amount, and at time intervals, which provides and maintains at least a therapeutic serum level of at least one pharmaceutically active form of the compound over the time interval between dose administration.

When any variable (e.g. aryl, heterocycle, $R^1$, $R^2$ etc.) occurs more than one time in any constituent, its definition on each occurrence is independent at every other occurrence.

Also, combinations of substituents/or variables are permissible only if such combinations result in stable compounds, is chemically feasible and/or valency permits.

As used herein, unless otherwise specified, the terms in the paragraphs immediately below have the indicated meanings.

"Alkoxy" means a moiety of the structure: alkyl-O— (i.e., the bond to the substrate moiety is through the oxygen), wherein the alkyl portion of the moiety is as defined below for alkyl; non-limiting examples of suitable alkoxy groups include methoxy, ethoxy, n-propoxy, isopropoxy, n-butoxy and heptoxy.

"Alkyl" is intended to include both branched and straight-chain saturated aliphatic hydrocarbon groups having the specified number of carbon atoms.

"Halogen" or "halo" means fluoro, chloro, bromo and iodo.

"Haloalkyl" means $CF_3$, $CHF_2$, and $CH_2F$.

"Cycloalkyl" is intended to include cyclic saturated aliphatic hydrocarbon groups having the specified number of carbon atoms. Preferably, cycloalkyl is $C_3$-$C_{10}$ cycloalkyl. Examples of such cycloalkyl groups include, but are not limited to, cyclopropyl, cyclobutyl, cyclopentyl, cyclohexyl and cycloheptyl.

"Aryl" is intended to mean any stable monocyclic or bicyclic carbon ring of up to 7 members in each ring, wherein at least one ring is aromatic. Examples of such aryl rings include phenyl, naphthyl, tetrahydronaphthyl, indanyl, biphenyl, phenanthryl, anthryl or acenaphthyl.

The term heterocyclyl, heterocycle or heterocyclic represents a stable 5- to 7-membered monocyclic or stable 8- to 14-membered bicyclic or tricyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. The term heterocyclyl, heterocycle or heterocyclic includes heteroaryl moieties. Examples of such heterocyclic elements include, but are not limited to, azepinyl, benzodioxolyl, benzimidazolyl, benzisoxazolyl, benzofurazanyl, benzopyranyl, benzothiopyranyl, benzofuryl, benzothiazolyl, benzothienyl, benzotriazolyly, benzoxazolyl, chromanyl, cinnolinyl, dihydrobenzofuryl, dihydrobenzothienyl, dihydrobenzothiopyranyl, dihydrobenzothiopyranyl sulfone, 1,3-dioxolanyl, furyl, furopyridinyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyrazolopyridinyl, pyridazinyl, pyrimidinyl, pyrrolidinyl, pyrrolyl, pyrrolopyridinyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, thienyl, and triazolyl.

Preferably, heterocyclyl is selected from furopyridinyl, imidazolyl, indolyl, isoquinolinylisothiazolyl, morpholinyl, naphthyridinyl, oxadiazolyl, piperidyl, piperazinyl, pyridyl, pyrazinyl, pyrazolidinyl, pyrazolyl, pyrazolopyridinyl, pyridazinyl, pyrimidinyl, pyrrolidinyl, pyrrolyl, pyrrolopyridinyl, quinazolinyl, quinolinyl, quinoxalinyl, tetrahydrofuryl, tetrahydroisoquinolinyl, tetrahydroquinolinyl, thiazolyl, thiazolinyl, thienofuryl, thienothienyl, thienyl, and triazolyl.

"Heteroaryl" means any stable monocyclic or bicyclic carbon ring of up to 7 members in each ring, wherein at least one ring is aromatic and wherein from one to four carbon atoms are replaced by heteroatoms selected from the group consisting of N, O, and S. Examples of such heteroaryl rings include, but are not limited to, imidazolyl, indolinyl, indolyl, isochromanyl, isoindolinyl, isoquinolinyl, isothiazolyl, naphthyridinyl, oxadiazolyl, pyridyl, pyrazinyl, pyrazolyl, pyridazinyl, pyrimidinyl, pyrrolyl, quinazolinyl, quinolinyl, tetrahydroisoquinolinyl, tetrahydroquinolinyl, thiazolyl, thienofuryl, thienothienyl, thienyl, triazolyl and the like.

"Effective amount" or "therapeutically effective amount" is meant to describe the provision of an amount of at least one compound of the invention or of a composition comprising at least one compound of the invention which is effective in treating or inhibiting a disease or condition described herein, and thus produce the desired therapeutic, ameliorative, inhibitory or preventative effect. For example, in treating cellular proliferative diseases or central nervous system diseases or disorders with one or more of the compounds described herein "effective amount" (or "therapeutically effective amount") means, for example, providing the amount of at least one compound of Formula I that results in a therapeutic response in a patient afflicted with a central nervous system disease or disorder ("condition"), including a response suitable to manage, alleviate, ameliorate, or treat the condition or alleviate, ameliorate, reduce, or eradicate one or more symptoms attributed to the condition and/or long-term stabilization of the condition, for example, as may be determined by the analysis of pharmacodynamic markers or clinical evaluation of patients afflicted with the condition.

The phrase "at least one" used in reference to the number of components comprising a composition, for example, "at least one pharmaceutical excipient" means that one member of the specified group is present in the composition, and more than one may additionally be present. Components of a composition are typically aliquots of isolated pure material added to the composition, where the purity level of the isolated material added into the composition is the normally accepted purity level for a reagent of the type.

"at least one" used in reference to substituents on a compound or moiety appended to the core structure of a compound means that one substituent of the group of substituents specified is present, and more than one substituent may be bonded to any of the chemically accessible bonding points of the core.

Whether used in reference to a substituent on a compound or a component of a pharmaceutical composition the phrase "one or more", means the same as "at least one".

As used herein, the term "patient" and "subject" means an animal, such as a mammal (e.g., a human being) and is preferably a human being.

"prodrug" means compounds that are rapidly transformed, for example, by hydrolysis in blood, in vivo to the parent compound, e.g., conversion of a prodrug of Formula A to a compound of Formula A, or to a salt thereof; a thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference; the scope of this invention includes prodrugs of the novel compounds of this invention.

Unsatisfied valences in the text, schemes, examples, structural formulae, and any Tables herein is assumed to have a hydrogen atom or atoms of sufficient number to satisfy the valences.

One or more compounds of the invention may also exist as, or optionally be converted to, a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, and hemisolvate, including hydrates (where the solvent is water or aqueous-based) and the like are described by E. C. van Tonder et al, *AAPS PharmSciTech.*, 51), article 12 (2004); and A. L. Bingham et al, *Chem. Commun.*, 603-604 (2001). A typical, non-limiting, process involves dissolving the inventive compound in desired amounts of the desired solvent (for example, an organic solvent, an aqueous solvent, water or mixtures of two or more thereof) at a higher than ambient temperature, and cooling the solution, with or without an antisolvent present, at a rate sufficient to form crystals which are then isolated by standard methods. Analytical techniques such as, for example I.R. spectroscopy, show the presence of the solvent (including water) in the crystals as a solvate (or hydrate in the case where water is incorporated into the crystalline form).

The term "substituted" means that one or more of the enumerated substituents can occupy one or more of the bonding positions on the substrate typically occupied by "—H", provided that such substitution does not exceed the normal valency rules for the atom in the bonding configuration presented in the substrate, and that the substitution ultimate provides a stable compound, which is to say that such substitution does not provide compounds with mutually reactive substituents located geminal or vicinal to each other; and wherein the substitution provides a compound sufficiently robust to survive isolation to a useful degree of purity from a reaction mixture.

Where optional substitution of a moiety is described (e.g. "optionally substituted") the term means that if substituents are present, one or more of the enumerated (or default substituents for the specified substrate, for example, hydrogen on an alkyl or aromatic moiety) can be present on the substrate in a bonding position normally occupied by the default substituent, for example, a hydrogen atom, in accordance with the definition of "substituted" presented herein.

As used herein, unless otherwise specified, the preceding terms used to describe moieties, whether comprising the entire definition of a variable portion of a structural representation of a compound of the invention or a substituent appended to a variable portion of a structural representation of a group of compounds of the invention have the following meanings, and unless otherwise specified, the definitions of each term (i.e., moiety or substituent) apply when that term is used individually or as a component of another term (e.g., the definition of aryl is the same for aryl and for the aryl portion of arylalkyl, alkylaryl, arylalkynyl moieties, and the like); moieties are equivalently described herein by structure, typographical representation or chemical terminology without intending any differentiation in meaning, for example, the chemical term "acyl", defined below, is equivalently described herein by the term itself, or by typographical representations "R'—(C=O)—" or "R'—C(O)—", or by the structural representation:

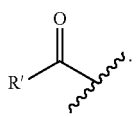

The term "pharmaceutical composition" as used herein encompasses both the bulk composition and individual dosage units comprised of more than one (e.g., two) pharmaceutically active agents such as, for example, a compound of the present invention and an additional agent as described herein, along with any pharmaceutically inactive excipients. As will be appreciated by the ordinarily skilled artisan, excipients are any constituent which adapts the composition to a particular route of administration or aids the processing of a composition into a dosage form without itself exerting an active pharmaceutical effect. The bulk composition and each individual dosage unit can contain fixed amounts of the afore-said "more than one pharmaceutically active agents". The bulk composition is material that has not yet been formed into individual dosage units.

This invention also includes the compounds of this invention in isolated and purified form obtained by routine techniques.

Polymorphic forms of the compounds of Formula I, and of the salts, solvates and prodrugs of the compounds of Formula I, are intended to be included in the present invention. Certain compounds of the invention may exist in different isomeric forms (e.g., enantiomers, diastereoisomers, atropisomers). The inventive compounds include all isomeric forms thereof, both in pure form and admixtures of two or more, including racemic mixtures.

In the same manner, unless indicated otherwise, presenting a structural representation of any tautomeric form of a compound which exhibits tautomerism is meant to include all such tautomeric forms of the compound. Accordingly, where compounds of the invention, their salts, and solvates and prodrugs thereof, may exist in different tautomeric forms or in equilibrium among such forms, all such forms of the compound are embraced by, and included within the scope of the invention. Examples of such tautomers include, but are not limited to, ketone/enol tautomeric forms, imine-enamine tautomeric forms, and for example heteroaromatic forms such as the following moieties:

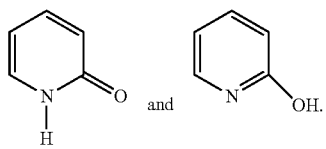 [SMILES: O=c1cccc[nH]1 ; Oc1ccccn1]

All stereoisomers of the compounds of the invention (including salts and solvates of the inventive compounds and their prodrugs), such as those which may exist due to asymmetric carbons present in a compound of the invention, and including enantiomeric forms (which may exist even in the absence of asymmetric carbons), rotameric forms, atropisomers, and diastereomeric forms, are contemplated within the scope of this invention. Individual stereoisomers of the compounds of the invention may be isolated in a pure form, for example, substantially free of other isomers, or may be isolated as an admixture of two or more stereoisomers or as a racemate. The chiral centers of the present invention can have the S or R configuration as defined by the IUPAC 1974 Recommendations. The use of the terms "salt", "solvate" "prodrug" and the like, is intended to equally apply to salts, solvates and prodrugs of isolated enantiomers, stereoisomer pairs or groups, rotamers, tautomers, or racemates of the inventive compounds.

Where diastereomeric mixtures can be separated into their individual diastereomers on the basis of their physical chemical differences by known methods, for example, by chiral chromatography and/or fractional crystallization, simple structural representation of the compound contemplates all diastereomers of the compound. As is known, enantiomers may also be separated by converting the enantiomeric mixture into a diasteromeric mixture by reaction with an appropriate optically active compound (e.g., chiral auxiliary such as a chiral alcohol or Mosher's acid chloride), separating the diastereomers and converting (e.g., hydrolyzing) the individually isolated diastereomers to the corresponding purified enantiomers.

Included in the instant invention is the free base of compounds of Formula I, as well as the pharmaceutically acceptable salts and stereoisomers thereof. The formation of pharmaceutically useful salts from basic (or acidic) pharmaceutical compounds are discussed, for example, by S. Berge et al., Journal of Pharmaceutical Sciences (1977) 66(1) 1-19; P. Gould, International J. of Pharmaceutics (1986) 33 201-217; Anderson et al, The Practice of Medicinal Chemistry (1996), Academic Press, New York; in The Orange Book (Food & Drug Administration, Washington, D.C. on their website); and P. Heinrich Stahl, Camille G. Wermuth (Eds.), Handbook of Pharmaceutical Salts: Properties, Selection, and Use, (2002) Int'l. Union of Pure and Applied Chemistry, pp. 330-331. These disclosures are incorporated herein by reference.

The present invention contemplates all available salts, including salts which are generally recognized as safe for use in preparing pharmaceutical formulations and those which may be formed presently within the ordinary skill in the art and are later classified as being "generally recognized as safe" for use in the preparation of pharmaceutical formulations, termed herein as "pharmaceutically acceptable salts".

Some of the specific compounds exemplified herein are the protonated salts of amine compounds. Compounds of Formula I with a heterocycle ring containing 2 or more N atoms may be protonated on any one, some or all of the N atoms. The term "free base" refers to the amine compounds in non-salt form. The encompassed pharmaceutically acceptable salts not only include the salts exemplified for the specific compounds described herein, but also all the typical pharmaceutically acceptable salts of the free form of compounds of Formula I. The free form of the specific salt compounds described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the instant compounds can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the compounds of this invention include the conventional non-toxic salts of the compounds of this invention as formed by reacting a basic instant compound with an inorganic or organic acid. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, trifluoroacetic and the like. Preferably, a pharmaceutically acceptable salt of this invention contains 1 equivalent of a compound of formula (I) and 1, 2 or 3 equivalent of an inorganic or organic acid. More particularly, pharmaceutically acceptable salts of this invention are the trifluoroacetate or the chloride salts, especially the trifluoroacetate salts.

When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N,N'-dibenzylethylenediamine, diethylamin, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

It will also be noted that the compounds of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

The present invention also embraces isotopically-labeled compounds of the present invention which are structurally identical to those recited herein, but for the fact that a statistically significant percentage of one or more atoms in that form of the compound are replaced by an atom having an atomic mass or mass number different from the atomic mass or mass number of the most abundant isotope usually found in nature, thus altering the naturally occurring abundance of that isotope present in a compound of the invention. Examples of isotopes that can be preferentially incorporated into compounds of the invention include isotopes of hydrogen, carbon, nitrogen, oxygen, phosphorus, iodine, fluorine and chlorine, for example, but not limited to: $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, and $^{36}Cl$, $^{123}I$ and $^{125}I$. It will be appreciated that other isotopes may be incorporated by known means also.

Certain isotopically-labeled compounds of the invention (e.g., those labeled with $^3H$, $^{11}C$ and $^{14}C$) are recognized as being particularly useful in compound and/or substrate tissue distribution assays using a variety of known techniques. Tritiated (i.e., $^3H$) and carbon-14 (i.e., $^{14}C$) isotopes are particularly preferred for their ease of preparation and detection. Further, substitution of a naturally abundant isotope with a heavier isotope, for example, substitution of protium with deuterium (i.e., $^2H$) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in the reaction Schemes and/or in the Examples herein below, by substituting an appropriate isotopically labeled reagent for a non-isotopically labeled reagent, or by well-known reactions of an appropriately prepared precursor to the compound of the invention which is specifically prepared for such a "labeling" reaction. Such compounds are included also in the present invention.

The compounds of the invention can be used in a method of treatment of the human or animal body by therapy.

The compounds of the invention find use in a variety of applications for human and animal health. The compounds of the invention are histone deacetylase (HDAC) inhibitors useful in the treatment of cancer among other diseases. HDACs catalyse the removal of acetyl groups from lysine residues on proteins, including histones and HDAC inhibitors show diverse biological functions including affecting gene expression, cell differentiation, cell cycle progression, growth arrest, and/or apoptosis. See *J. Med. Chem.* (2003) 46:5097 and *Curr. Med. Chem.* (2003) 10:2343.

The compounds of the invention are used to treat cellular proliferation diseases. Disease states which can be treated by the methods and compositions provided herein include, but are not limited to, cancer (further discussed below), neurodegenerative diseases, schizophrenia and stroke.

The compounds, compositions and methods provided herein are particularly deemed useful for the treatment of cancer including solid tumors such as skin, breast, brain, cervical carcinomas, testicular carcinomas, etc. In particular, cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomy oma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botry oid sarcoma (embryonal rhabdomyosarcoma), fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

Thus, the present invention provides a compound of formula I for use in the manufacture of a medicament for treating cellular proliferation diseases.

The present invention also provides a method for the treatment of cellular proliferation diseases, which method comprises administration to a patient in need thereof of an effective amount of a compound of formula I or a composition comprising a compound of formula I.

The compounds of the instant invention may also be useful in the treatment or prevention of neurodegenerative diseases, including, but not limited to, polyglutamine-expansion-related neurodegeneration, Huntington's disease, Kennedy's disease, spinocerebellar ataxia, dentatorubral-pallidoluysian atrophy (DRPLA), protein-aggregation-related neurodegeneration, Machado-Joseph's disease, Alzheimer's disease, Parkinson's disease, amyotrophic lateral sclerosis, spongiform encephalopathy, a prion-related disease and multiple sclerosis (MS).

Thus, the present invention provides a compound of formula I for use in the manufacture of a medicament for treating or preventing neurodegenerative diseases.

The present invention also provides a method for treating or preventing neurodegenerative diseases, which method comprises administration to a patient in need thereof of an effective amount of a compound of formula I or a composition comprising a compound of formula I.

The compounds of the invention may also be useful in the treatment or prevention of mental retardation, in particular "X chromosome-linked mental retardation" and "Rubinstein-Taybi syndrome".

Thus, the present invention provides a compound of formula I for the manufacture of a medicament for treating or preventing mental retardation.

The present invention also provides a method for treating or preventing mental retardation, which method comprises administration to a patient in need thereof of an effective amount of a compound of formula I or a composition comprising a compound of formula I.

The compounds of the invention may also be useful in the treatment or prevention of schizophrenia.

Thus, the present invention provides a compound of formula I for the manufacture of a medicament for treating or preventing schizophrenia.

The present invention also provides a method for treating or preventing schizophrenia, which method comprises administration to a patient in need thereof of an effective amount of a compound of formula I or a composition comprising a compound of formula I.

The compounds of the invention may also be useful in the treatment or prevention of inflammatory diseases, including, but not limited to stroke, rheumatoid arthritis, lupus erythematosus, ulcerative colitis and traumatic brain injuries. See Leoni et al (2002), *PNAS*, 99(5):2995-3000, Suuronen et al (2003) *J. Neurochem*, 87:407-416 and *Drug Discovery Today* (2005), 10:197-204.

Thus, the present invention provides a compound of formula I for the manufacture of a medicament for treating or preventing inflammatory diseases.

The present invention also provides a method for treating or preventing inflammatory diseases, which method comprises administration to a patient in need thereof of an effective amount of a compound of formula I or a composition comprising a compound of formula I.

The compounds of the present invention are also useful in the inhibition of smooth muscle cell proliferation and/or migration and are thus useful in the prevention and/or treatment of restenosis, for example after angioplasty and/or stent implantation.

Thus, the present invention provides a compound of formula I for the manufacture of a medicament for treating or preventing restenosis.

The present invention also provides a method for treating or prevention restenosis, which method comprises administration to a patient in need thereof of an effective amount of a compound of formula I or a composition comprising a compound of formula I.

In one embodiment, smooth muscle cell proliferation and/or migration is inhibited and restenosis is prevented and/or treated by providing a stent device having one or more of the compounds of the instant invention in or on the stent device, e.g. coated onto the stent device.

The stent device is designed to controllably release the compounds of the invention, thereby inhibiting smooth miscle cell proliferation and/or migration and preventing and/or treating restenosis.

Stenosis and restenosis are conditions associated with a narrowing of blood vessels. Stenosis of blood vessels generally occurs gradually over time. Restenosis, in contrast, relates to a narrowing of blood vessels following an endovascular procedure, such as balloon angioplasty and/or stent implantation, or a vascular injury.

Balloon angioplasty is typically performed to open a stenotic blood vessel; stenting is usually performed to maintain the patency of a blood vessel after, or in combination with, balloon angioplasty. A stenotic blood vessel is opened with balloon angioplasty by navigating a balloon-tipped catheter to the site of stenosis, and expanding the balloon tip effectively to dilate the occluded blood vessel. In an effort to maintain the patency of the dilated blood vessel, a stent may be implanted in the blood vessel to provide intravascular support to the opened section of the blood vessel, thereby limiting the extent to which the blood vessel will return to its occluded state after release of the balloon catheter. Restenosis is typically caused by trauma inflicted during angioplasty, effected by, for example, ballon dilation, atherectomy or laser ablation treatment of the artery. For these procedures, restenosis occurs at a rate of about 30% to about 60% depending on the vessel location, lesion length and a number of other variables. This reduces the overall success of the relatively non-invasive balloon angioplasty and stenting procedures.

Restenosis is attributed to many factors, including proliferation of smooth muscle cells (SMC). SMC proliferation is triggered by the initial mechanical injury to the intima that is sustained at the time of balloon angioplasty and stent implantation. The process is characterized by early platelet activation and thrombus formation, followed by SMC recruitment and migration, and, finally, cellular proliferation and extracellular matrix accumulation. Damaged endothelial cells, SMCs, platelets, and macrophages secrete cytokines and growth factors which promote restenosis. SMC proliferation represents the final common pathway leading to neointimal hyperplasia. Therefore, anti-proliferative therapies aimed at inhibiting specific regulatory events in the cell cycle may constitute the most reasonable approach to restenosis after angioplasty.

The compounds of the invention may also be used as immunosuppressants or immunomodulators and can accordingly be used in the treatment or prevention of immune response or immune-mediated responses and diseases such as systemic lupus erythematosus (SLE) and acute or chronic transplant rejection in a recipient of an organ, tissue or cell transplant, (see WO 05/013958).

Examples of autoimmune diseases for which the compounds of the invention may be employed include autoimmune hematological disorders (including hemolytic anaemia, aplastic anaemia, pure red cell anaemia and idiopathic thrombocytopenia), systemic lupus erythematosus, thyroiditis, Hashimoto's thyroiditis, polychondritis, sclerodoma, Wegener granulamatosis, dermatomyositis, chronic active hepatitis, myasthenia gravis, psoriasis, atopic dermatitis, vasculitis, Steven-Johnson syndrome, idiopathic sprue, autoimmune inflammatory bowel disease (including ulcerative colitis and Crohn's disease) endocrine ophthalmopathy, Graves disease, sarcoidosis, multiple sclerosis, primary billiary cirrhosis, juvenile diabetes (diabetes mellitus type I), diabetes type II and the disorders associated therewith, uveitis (anterior and posterior), keratoconjunctivitis sicca and vernal keratoconjunctivitis, interstitial lung fibrosis, psoriatic arthritis, glomerulonephritis (with and without nephrotic syndrome, including idiopathic nephrotic syndrome or minimal change nephropathy), juvenile dermatomyositisinfectious, auto-antibody mediated diseases, aplastic anemia, Evan's syndrome, autoimmune hemolytic anemia, infectious diseases causing aberrant immune response and/or activation, such as traumatic or pathogen induced immune disregulation, including for example, that which are caused by hepatitis B and C infections, *Staphylococcus aureus* infection, viral encephalitis, sepsis, parasitic diseases wherein damage is induced by inflammatory response (e.g. leprosy); and circulatory diseases, such as arteriosclerosis, atherosclerosis, polyarteritis *nodosa* and myocarditis.

Thus, the present invention provides a compound of formula I for the manufacture of a medicament for the treatment or prevention of immune disorders.

The present invention also provides a method for treating or preventing immune disorders, which method comprises administration to a patent in need thereof of an effective amount of a compound of formula I or a composition comprising a compound of formula I.

The compounds of the invention may also be useful in the treatment or prevention of other diseases such as diabetes, cardiovascular disorders, asthma, cardiac hypertrophy and heart failure, (see *Cell* (2002), 110:479-488).

The compounds of this invention may be administered to mammals, preferably humans, either alone or in combination with pharmaceutically acceptable carriers, excipients or diluents, in a pharmaceutical composition, according to standard pharmaceutical practice. In one embodiment, the compounds of this invention may be administered to animals. The compounds can be administered orally or parenterally, including the intravenous, intramuscular, intraperitoneal, subcutaneous, rectal and topical routes of administration.

The invention also provides pharmaceutical compositions comprising one or more compounds of this invention and a pharmaceutically acceptable carrier. The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropylcellulose, or a time delay material such as ethyl cellulose, cellulose acetate butyrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or *arachis* oil, or a mineral oil, for example liquid paraffin or mixtures of these. Suitable emulsifying agents may be naturally occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulsion.

The injectable solutions or microemulsions may be introduced into a patient's blood stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula I are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

When a compound according to this invention is administered into a human subject, the daily dosage will normally be determined by the prescribing physician with the dosage generally varying according to the age, weight, sex and response of the individual patient, as well as the severity of the patient's symptoms.

In one exemplary application, a suitable amount of compound is administered to a mammal undergoing treatment for cancer. Administration generally occurs in an amount between about 0.1 mg/kg of body weight to about 60 mg/kg of body weight per day, preferably of between 0.5 mg/kg of body weight to about 40 mg/kg of body weight per day.

The instant compounds are also useful in combination with known therapeutic agents and anti-cancer agents. Thus, this invention provides combinations of compounds of formula (I) and known therapeutic agents and/or anti-cancer agents for simultaneous, separate or sequential administration. For example, instant compounds are useful in combination with known anti-cancer agents. Combinations of the presently disclosed compounds with other anti-cancer or chemotherapeutic agents are within the scope of the invention. Examples of such agents can be found in *Cancer*

*Principles and Practice of Oncology* by V. T. Devita and S. Hellman (editors), 6th edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: other HDAC inhibitors, estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, inhibitors of cell proliferation and survival signaling, apoptosis inducing agents and agents that interfere with cell cycle checkpoints. The instant compounds are particularly useful when co-administered with radiation therapy.

In an embodiment, the instant compounds are also useful in combination with known anti-cancer agents including the following: other HDAC inhibitors, estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, and other angiogenesis inhibitors.

Examples of "other HDAC inhibitors" include suberoylanilide hydroxamic acid (SAHA), LAQ824, LBH589, PXD101, MS275, FK228, valproic acid, butyric acid and CI-994.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of kinases involved in mitotic progression, antimetabolites; biological response modifiers; hormonal/anti-hormonal therapeutic agents, haematopoietic growth factors, monoclonal antibody targeted therapeutic agents, topoisomerase inhibitors, proteasome inhibitors and ubiquitin ligase inhibitors.

Examples of cytotoxic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum (II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, and 4-demethoxy-3-deamino-3-aziridinyl-4-methylsulphonyl-daunorubicin (see WO 00/50032).

An example of a hypoxia activatable compound is tirapazamine.

Examples of proteasome inhibitors include but are not limited to lactacystin, bortezomib, epoxomicin and peptide aldehydes such as MG 132, MG 115 and PSI.

In an embodiment, the compounds of the present invention may be used in combination with other HDAC inhibitors such as SAHA and proteasome inhibitors.

Examples of microtubule inhibitors/microtubule-stabilising agents include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP 1350, BNPI1100, BN80915, BN80942, etoposide phosphate, teniposide, sobuzoxane, 2'-dimethylamino-2'-deoxyetoposide, GL331, N-[2-(dimethylamino)ethyl]-9-hydroxy-5,6-dimethyl-6H-pyrido[4,3-b]carbazole-1-carboxamide, asulacrine, (5a, 5aB, 8aa,9b)-9-[2-[N-[2-(dimethylamino)ethyl]-N-methylamino]ethyl]-5-[4-hydroxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxybenzo[c]-phenanthridinium, 6,9-bis[(2-aminoethyl)amino]benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins, and in particular the human mitotic kinesin KSP, are described in the prior art.

"Inhibitors of kinases involved in mitotic progression" include, but are not limited to, inhibitors of aurora kinase, inhibitors of Polo-like kinases (PLK) (in particular inhibitors of PLK-1), inhibitors of bub-1 and inhibitors of bub-R1.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-flurouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine and 3-aminopyridine-2-carboxaldehyde thiosemicarbazone.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®), simvastatin (ZOCOR®), pravastatin (PRAVACHOL®), fluvastatin (LESCOL®) and atorvastatin (LIPITOR®). The structural formulas of these and additional HMG-CoA reductase inhibitors that may be used in the instant methods are described at page 87 of M. Yalpani, "Cholesterol Lowering Drugs", Chemistry & Industry, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefore the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase). For an example of the role of a prenyl-protein transferase inhibitor on angiogenesis see European J. of Cancer (1999), 35(9): 1394-1401.

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (PNAS (1992) 89:7384; JNCI (1982) 69:475; Arch. Opthalmol. (1990) 108:573; Anat. Rec. (1994) 238:68; FEBS Letters (1995) 372:83; Clin, Orthop. (1995) 313:76; J. Mol. Endocrinol. (1996) 16:107; Jpn. J. Pharmacol. (1997) 75:105; Cancer Res. (1997) 57:1625 (1997); Cell (1998) 93:705; Intl. J Mol. Med. (1998) 2:715; J. Biol. Chem. (1999) 274:9116)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al (1985) J Lab. Clin. Med. 105:141-145), and antibodies to VEGF (see, Nature Biotechnology (1999) 17:963-968; Kim et al (1993) Nature 362:841-844; WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in Clin. Chem. La. Med. (2000) 38:679-692). Examples of such agents that modulate or inhibit the coagulation and fibrinolysis pathways include, but are not limited to, heparin (see Thromb. Haemost. (1998) 80:10-23), low molecular weight heparins and carboxypeptidase U inhibitors (also known as inhibitors of active thrombin activatable fibrinolysis inhibitor [TAFIa]) (see Thrombosis Res. (2001) 101:329-354).

TAFIa inhibitors have been described in PCT Publication WO 03/013,526 and U.S. Ser. No. 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032.

"Inhibitors of cell proliferation and survival signaling pathway" refer to pharmaceutical agents that inhibit cell surface receptors and signal transduction cascades downstream of those surface receptors. Such agents include inhibitors of inhibitors of EGFR (for example gefitinib and erlotinib), inhibitors of ERB-2 (for example trastuzumab), inhibitors of IGFR (for example those disclosed in WO 03/059951), inhibitors of cytokine receptors, inhibitors of MET, inhibitors of PI3K (for example LY294002), serine/threonine kinases, inhibitors of Raf kinase (for example BAY-43-9006), inhibitors of MEK (for example CI-1040 and PD-098059) and inhibitors of mTOR (for example Wyeth CCI-779 and Ariad AP23573). Such agents include small molecule inhibitor compounds and antibody antagonists.

"Apoptosis inducing agents" include activators of TNF receptor family members (including the TRAIL receptors).

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays.

Inhibitors of COX-2 that are particularly useful in the instant method of treatment are 5-chloro-3-(4-methylsulfonyl)phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to: parecoxib, CELEBREX® and BEXTRA® or a pharmaceutically acceptable salt thereof.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis [imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha_v\beta_5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\square\alpha_v\beta_6$, $\alpha_v\beta_8$, $\alpha_1\beta_1$, $\alpha_2\beta_1$, $\beta_5\alpha_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl]indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malingnancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* (1998) 31:909-913; *J. Biol. Chem.* (1999) 274:9116-9121; *Invest. Ophthalmol Vis. Sci.* (2000) 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* (2001) 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid, and 2(R)-7-(3-(2-chloro-4-(4-fluorophenoxy) phenoxy) propoxy)-2-ethylchromane-2-carboxylic acid.

Another embodiment of the instant invention is the use of the presently disclosed compounds in combination with anti-viral agents (such as nucleoside analogs including ganciclovir for the treatment of cancer.

Another embodiment of the instant invention is the use of the presently disclosed compounds in combination with gene therapy for the treatment of cancer. For an overview of genetic strategies to treating cancer see Hall et al (*Am J Hum Genet* (1997) 61:785-789) and Kufe et al (*Cancer Medicine*, 5th Ed, pp 876-889, BC Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," *Gene Therapy*, August (1998) 5(8):1105-13), and interferon gamma (*J Immunol* (2000) 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, $GABA_B$ receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In an embodiment, an anti-emesis agent selected from a neurokinin-1 receptor antagonist, a 5HT3 receptor antagonist and a corticosteroid is administered as an adjuvant for the treatment or prevention of emesis that may result upon administration of the instant compounds.

In an embodiment, the neurokinin-1 receptor antagonist for use in conjunction with the compounds of the present invention is selected from: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous eythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, isoprinosine and Zadaxin.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

Thus, the scope of the instant invention encompasses the use of the instantly claimed compounds in combination with a second compound selected from: other HDAC inhibitors, an estrogen receptor modulator, an androgen receptor modulator, retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an anti-viral agent, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, an agent that interfers with a cell cycle checkpoint, an apoptosis inducing agent and a bisphosphonate.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

In an embodiment, the angiogenesis inhibitor to be used as the second compound is selected from a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-α, interleukin-12, pentosan polysulfate, a cyclooxygenase inhibitor, carboxyamidotriazole, combretastatin A-4, squalamine, 6-O-chloroacetyl-carbonyl)-fumagillol, thalidomide, angiostatin, troponin-1, or an antibody to VEGF. In an embodiment, the estrogen receptor modulator is tamoxifen or raloxifene.

Also included in the scope of the claims is a method of treating cancer that comprises administering a therapeutically effective amount of a compound of Formula I in combination with radiation therapy and/or in combination with a compound selected from: other HDAC inhibitors, an estrogen receptor modulator, an androgen receptor modulator, retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an anti-viral agent, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, an agent that interfers with a cell cycle checkpoint, an apoptosis inducing agent and a bisphosphonate.

And yet another embodiment of the invention is a method of treating cancer that comprises administering a therapeutically effective amount of a compound of Formula I in combination with paclitaxel or trastuzumab.

The invention further encompasses a method of treating or preventing cancer that comprises administering a therapeutically effective amount of a compound of Formula I in combination with a COX-2 inhibitor.

The instant invention also includes a pharmaceutical composition useful for treating or preventing cancer that comprises a therapeutically effective amount of a compound of Formula I and a compound selected from: other HDAC inhibitors, an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an anti-viral agent, an inhibitor of cell proliferation and survival signaling, an agent that interfers with a cell cycle checkpoint, an apoptosis inducing agent and a bisphosphonate.

These and other aspects of the invention will be apparent from the teachings contained herein.

LIST OF ABBREVIATIONS

AcOH=acetic acid
ACN=acetonitrile
Anal.=analytical
aq=aqueous
n-BuLi=n-butyl lithium
br=broad
calc.=calculated
m-CPBA=3-chloroperoxybenzoic acid
d=doublet
DBU=1,8-diazabicyclo[5.4.0]undec-7-ene
DCE=dichloroethane
DCM=dichloromethane
DEA=diethylamine
DIEA=N,N-diisopropylethylamine
DIPEA=N,N-diisopropylethylamine
DMA=N,N-dimethylacetamide
DMF=N,N-dimethylformamide
DMSO=dimethyl sulfoxide
ESI=electrospray ionization EtOAc=ethyl acetate
EtOH=ethanol
HATU=1-[Bis(dimethylamino)methylene]-1H-1,2,3-triazolo[4,5-b]pyridinium3-oxid hexafluorophosphate
Hex=hexanes
HPLC=high-pressure liquid chromatography
IPA=iso-propyl alcohol
IPAc=iso-propyl acetate
KF=Karl-Fischer titration (to determine water content)
KOt-Bu=potassium tert-butoxide
LCMS=liquid chromatography-mass spectrometry
LiHMDS=lithium hexamethyl silazane
m=multiplet
MeCN=acetonitrile
MeOH=methyl alcohol
MPa=milipascal
MS=mass spectroscopy
MTBE=methyl tert-butyl ether
NHS=normal human serum
NMR=nuclear magnetic resonance spectroscopy
PE=petroleum ether
Piv=pivalate, 2,2-dimethylpropanoyl
Pd/C=palladium on carbon
q=quartet
rt=room temperature
s=singlet
sat. aq.=saturated aqueous
SEM-Cl=2-(trimethylsilyl)ethoxymethyl chlorideSFC=supercritical fluid chromatography
t=triplet
THF=THF
TFA=trifluoroacetic acid
TFAA=trifluoroacetic anhydride
TLC=thin-layer chromatography
p-TsOH=para-toluene sulfonic acid
wt %=percentage by weight
Xantphos=4,5-bis(diphenylphosphino)-9,9-dimethylxanthene The present invention also provides a method for the synthesis of compounds useful as intermediates in the preparation of compounds of the invention.

Reaction Schemes

The compounds of the present invention can be prepared readily according to the following Schemes and specific examples, or modifications thereof, using readily available starting materials, reagents and conventional synthetic procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following Schemes.

Scheme 1 illustrates a general strategy for preparing the 5-(trifluoromethyl)-1,2,4-oxadiazol-3-yl compounds of the present invention in which a nitrile intermediate (1.1) is heated with hydroxylamine to give the hydroxyamidine product 1.2. Cyclization of 1.2 with TFAA in the presence of a base, such as potassium carbonate, pyridine, or triethylamine, then provides the 5-(trifluoromethyl)-1,2,4-oxadiazol-3-yl product 1.3.

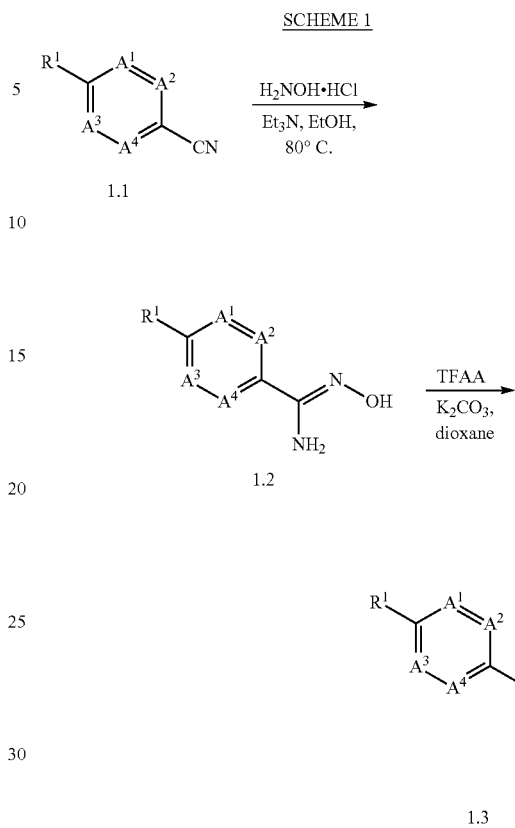

Scheme 2 depicts methods of preparing nitrile intermediates of the present invention. Nitrile intermediate 2.3 is prepared by a cross-coupling reaction of halide 2.1 with lactam 2.2 using copper or a palladium catalyst and a suitable base. Alternatively, nitrile intermediate 2.3 is prepared by a cross-coupling reaction of boronic acid 2.4 with lactam 2.2 using copper catalyst and a suitable base. For the preparation of nitrile intermediate 2.7, heating amine 2.6 with halide 2.5 in the presence of base, such as sodium carbonate, N,N-diisopropyl-N-ethylamine, or sodium hydride, in the absence of cataylst is sufficient to effect the cross-coupling reaction.

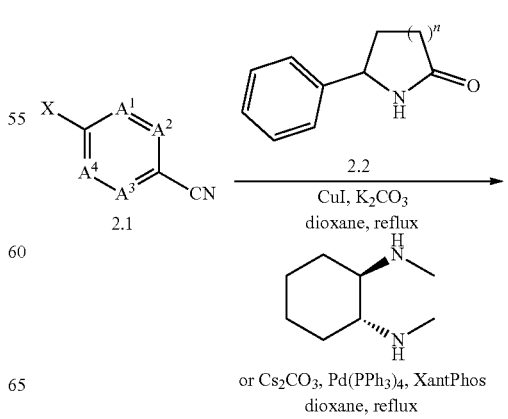

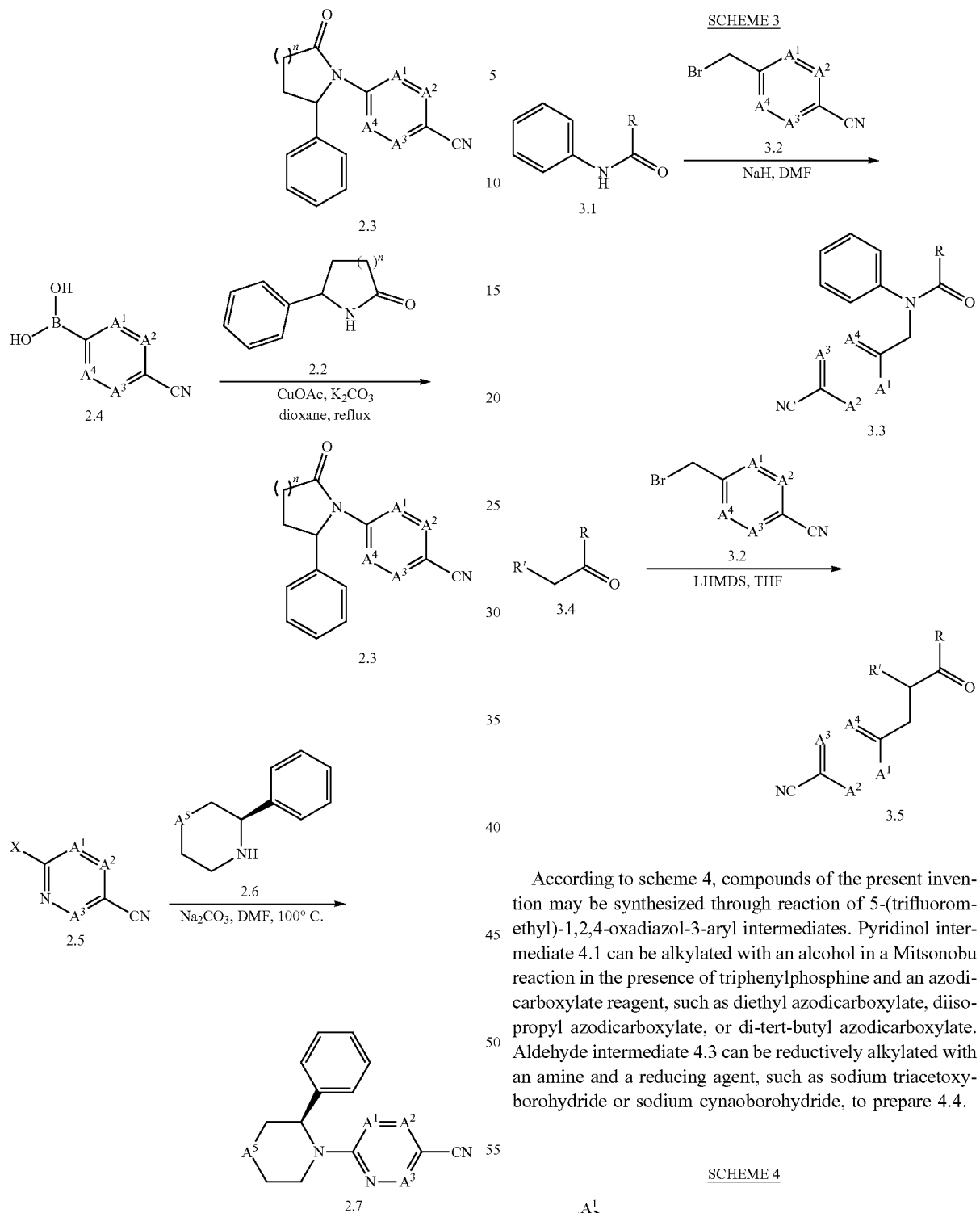

Scheme 3 depicts additional methods of preparing nitrile intermediates of the present invention. Amide intermediate 3.1 can be alkylated with bromide 3.2 in the presence of a base, such as sodium hydride or potassium carbonate to generate nitrile 3.3. Intermediate 3.4 may also be alkylated with bromide 3.2 using a stronger base, such as LHMDS, in the preparation of nitrile intermediate 3.5.

According to scheme 4, compounds of the present invention may be synthesized through reaction of 5-(trifluoromethyl)-1,2,4-oxadiazol-3-aryl intermediates. Pyridinol intermediate 4.1 can be alkylated with an alcohol in a Mitsonobu reaction in the presence of triphenylphosphine and an azodicarboxylate reagent, such as diethyl azodicarboxylate, diisopropyl azodicarboxylate, or di-tert-butyl azodicarboxylate. Aldehyde intermediate 4.3 can be reductively alkylated with an amine and a reducing agent, such as sodium triacetoxyborohydride or sodium cynaoborohydride, to prepare 4.4.

SCHEME 4

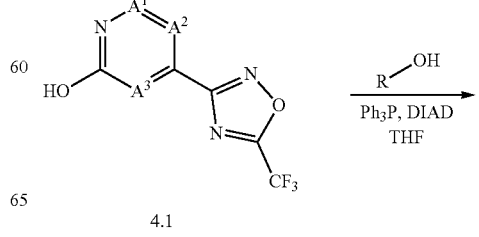

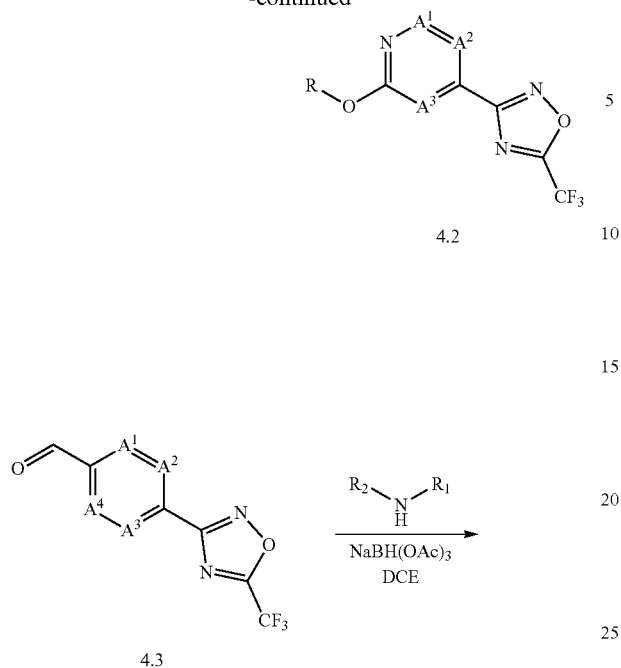

Example 1

(R)-5-Phenyl-4-(4-(5-(trifluoromethyl)-1,2,4-oxadiazol-3-yl)phenyl)morpholin-3-one In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

The following examples are presented to further illustrate compounds of the invention, but, with reference to the general formula presented above, they are not presented as limiting the invention to these specifically exemplified compounds. With appropriate modifications known to those skilled in the art, the compounds illustrated in the present application can be made in accordance with methods described herein.

All temperatures are degrees Celsius unless otherwise noted. Mass spectra (MS) were measured by electrospray ion-mass spectroscopy (ESI). $^1$H NMR spectra were recorded at 400-600 MHz. Compounds described herein were synthesized as a racemic mixture unless otherwise stated in the experimental procedures.

Step A:
(R)-4-(3-Oxo-5-phenylmorpholino)benzonitrile

To a stirred suspension of (R)-5-phenylmorpholin-3-one (500 mg, 2.82 mmol) in anhydrous 1,4-dioxane (14 mL) under an atmosphere of nitrogen was sequentially added 4-bromobenzonitrile (514 mg, 2.82 mmol), cesium carbonate (2.75 g, 8.47 mmol), tris(dibenzylideneacetone)dipalladium(0) (233 mg, 0.254 mmol) and 4,5-bis(diphenylphosphino)-9,9-dimethylxanthene (163 mg, 0.282 mmol). The resulting mixture was heated at 90° C. for 20 h, cooled to ambient temperature, quenched with water (10 mL) and extracted with ethyl acetate (15 mL×3). The combined ethyl acetate extracts were washed with water (5 mL), then brine (5 mL), dried over anhydrous magnesium sulfate, filtered and evaporated to dryness in vacuo. The residue was purified by flash silica gel chromatography (ISCO CombiFlash Rf Purification System®; 40 g SepaFlash® Silica Flash Column, eluting with a 0-75% ethyl acetate in hexanes gradient) to afford the title compound as an oil. MS (ESI) m/z [M+H]$^+$: 279.3.

Step B: (R,Z)—N'-Hydroxy-4-(3-oxo-5-phenylmorpholino)benzimidamide

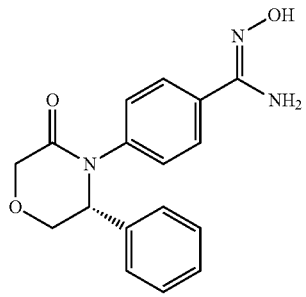 [SMILES: N/C(=N\O)c1ccc(N2C(=O)COC[C@H]2c2ccccc2)cc1]

To a stirred suspension of (R)-4-(3-oxo-5-phenylmorpholino)benzonitrile (552 mg, 1.98 mmol) from Step A above in an ethanol (6 mL) and water (3 mL) mixture was added a 50% aqueous hydroxylamine solution (0.60 mL, 9.9 mmol). The resulting homogeneous solution was heated at 50° C. for 15 h, cooled to ambient temperature and extracted with ethyl acetate (10 mL×3). The combined ethyl acetate extracts were washed with brine (5 mL), dried over anhydrous magnesium sulfate, filtered and evaporated to dryness in vacuo to afford the title compound as a solid. MS (ESI) m/z [M+H]$^+$: 312.3.

Step C: (R)-5-Phenyl-4-(4-(5-(trifluoromethyl)-1,2,4-oxadiazol-3-yl)phenyl)morpholin-3-one

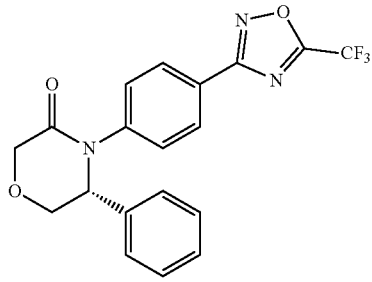 [SMILES: O=C1COC[C@@H](c2ccccc2)N1c1ccc(-c2noc(C(F)(F)F)n2)cc1]

To a stirred suspension of (R,Z)—N'-hydroxy-4-(3-oxo-5-phenylmorpholino)benzimidamide (618 mg, 1.98 mmol) from step B above in dichloromethane (10 mL) cooled to 0° C. under an atmosphere of nitrogen was added neat trifluoroacetic anhydride (0.42 mL, 3.0 mmol) in one portion. The cooling bath was removed and the resulting homogeneous solution was stirred for 2 h with gradual warming to ambient temperature. Neat triethylamine (0.83 mL, 6.0 mmol) was then added in one portion and the resulting solution was allowed to stir for an additional 1 h. The reaction mixture was evaporated to dryness in vacuo and the crude residue was purified by flash silica gel chromatography (ISCO CombiFlash Rf Purification System®; 40 g SepaFlash® Silica Flash Column, eluting with a 0-40% ethyl acetate in hexanes gradient) to afford the title compound as a solid. $^1$H NMR (600 MHz, CDCl$_3$): δ8.01 (d, J=9.0 Hz, 2H), 7.35 (d, J=9.0 Hz, 2H), 7.31-7.25 (m, 5H), 5.05-5.04 (m, 1H), 4.57 (d, J=16.8 Hz, 1H), 4.47 (d, J=16.8 Hz, 1H), 4.27 (dd, J=12, 4.2 Hz, 2H), 4.00 (dd, J=12.0, 4.8 Hz, 2H); MS (ESI) m/z [M+H]$^+$: 390.3.

Example 2

(R)-4-(3-Fluoro-4-(5-(trifluoromethyl)-1,2,4-oxadiazol-3-yl)phenyl)-5-phenylmorpholin-3-one

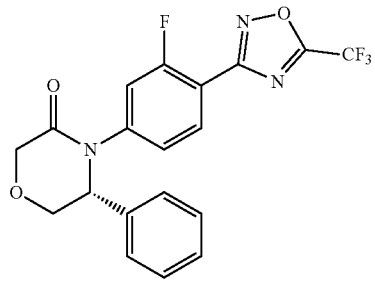 [SMILES: O=C1COC[C@@H](c2ccccc2)N1c1ccc(-c2noc(C(F)(F)F)n2)c(F)c1]

Step A: (R)-2-Fluoro-4-(3-oxo-5-phenylmorpholino)benzonitrile

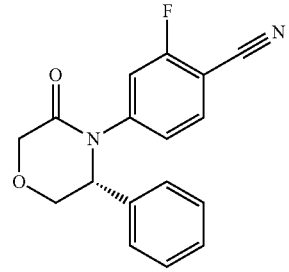 [SMILES: N#Cc1ccc(N2C(=O)COC[C@H]2c2ccccc2)cc1F]

To a stirred suspension of (R)-5-phenylmorpholin-3-one (6.00 g, 33.9 mmol) in anhydrous 1,4-dioxane (170 mL) under an atmosphere of nitrogen was added 4-bromo-2-fluorobenzonitrile (7.45 g, 37.2 mmol) and cesium carbonate (2.75 g, 8.47 mmol). Nitrogen was vigorously bubbled through the mixture for 10 min followed by the addition of tris(dibenzylideneacetone)dipalladium(0) (3.10 g, 3.39 mmol) and 4,5-bis(diphenylphosphino)-9,9-dimethylxanthene (3.92 g, 6.77 mmol). The resulting mixture was heated at 90° C. for 20 h, cooled to ambient temperature and filtered through a pad of Celite®. The filtered solids were washed with ethyl acetate (200 mL) and the combined filtrates were evaporated to dryness in vacuo. The crude residue was purified by flash silica gel chromatography (ISCO CombiFlash Rf Purification System®; 330 g SepaFlash® Silica Flash Column, eluting with a 0-75% ethyl acetate in hexanes gradient) to afford the title compound as an oil. MS (ESI) m/z [M+H]$^+$: 297.3, (M+H$^+$+CH$_3$CN): 338.3.

Step B: (R,Z)-2-Fluoro-N'-hydroxy-4-(3-oxo-5-phenylmorpholino)benzimidamide

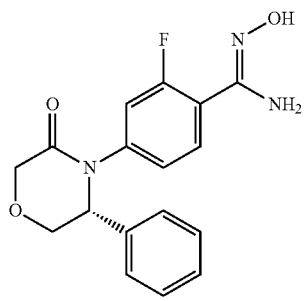 [SMILES: N/C(=N\O)c1ccc(N2C(=O)COC[C@H]2c2ccccc2)cc1F]

To a stirred suspension of (R)-2-fluoro-4-(3-oxo-5-phenylmorpholino)benzonitrile (7.10 g, 24.0 mmol) from Step A above in an ethanol (107 mL) and water (53 mL) mixture was added a 50% aqueous hydroxylamine solution (7.3 mL, 120 mmol). The resulting homogeneous solution was heated at 50° C. for 4 h, cooled to ambient temperature and evaporated in vacuo to remove the ethanol. The remaining aqueous phase was extracted with ethyl acetate (100 mL×3) and the combined extracts were washed with brine (20 mL), dried over anhydrous magnesium sulfate, filtered and evaporated to dryness in vacuo to afford the title compound as a solid. MS (ESI) m/z [M+H]⁺: 330.3.

Step C: (R)-4-(3-Fluoro-4-(5-(trifluoromethyl)-1,2,4-oxadiazol-3-yl)phenyl)-5-phenylmorpholin-3-one

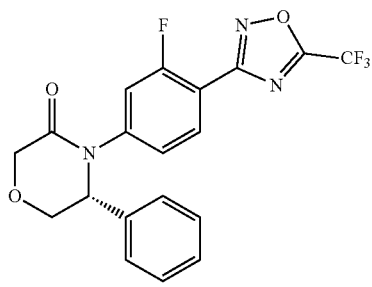

To a stirred suspension of (R,Z)-2-fluoro-N'-hydroxy-4-(3-oxo-5-phenylmorpholino)benzimidamide (7.89 g, 23.96 mmol) from step B above in dichloromethane (160 mL) cooled to 0° C. under an atmosphere of nitrogen was added neat trifluoroacetic anhydride (10 mL, 72 mmol) slowly over 1 min. The cooling bath was removed and the resulting homogeneous solution was stirred for 2 h with gradual warming to ambient temperature. Neat triethylamine (16 mL, 120 mmol) was next added in one portion and the resulting solution was allowed to stir for an additional 3 h. The reaction mixture was diluted with a saturated aqueous sodium bicarbonate solution (100 mL) and the layers were separated. The aqueous phase was extracted with dichloromethane (100 mL×2) and the combined extracts were dried over anhydrous magnesium sulfate, filtered and evaporated to dryness in vacuo. The crude residue was purified by flash silica gel chromatography (ISCO CombiFlash Rf Purification System®; 330 g SepaFlash® Silica Flash Column, eluting with a 0-50% ethyl acetate in hexanes gradient) to afford the title compound as a solid. ¹H NMR (500 MHz, CDCl₃): δ7.97 (t, J=8.0 Hz, 1H), 7.34-7.18 (m, 7H), 5.07 (br s, 1H), 4.56 (d, J=17 Hz, 1H), 4.47 (d, J=17 Hz, 1H), 4.27 (dd, J=12, 3.3 Hz, 2H), 4.00 (dd, J=12, 5.0 Hz, 2H); MS (ESI) m/z [M+H]⁺: 408.3.

Example 3 tert-Butyl(S)-3-phenyl-4-(5-(5-(trifluoromethyl)-1,2,4-oxadiazol-3-yl)pyridin-2-yl)piperazine-1-carboxylate

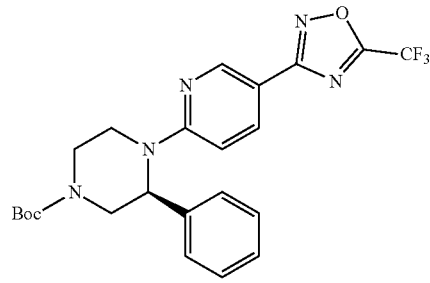 [SMILES: CC(C)(C)OC(=O)N1CCN(c2ccc(-c3noc(C(F)(F)F)n3)cn2)[C@@H](c2ccccc2)C1]

Step A: tert-Butyl(S)-4-(5-cyanopyridin-2-yl)-3-phenylpiperazine-1-carboxylate

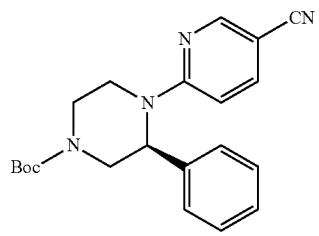 [SMILES: CC(C)(C)OC(=O)N1CCN(c2ccc(C#N)cn2)[C@@H](c2ccccc2)C1]

To a stirred solution of (S)-tert-butyl 3-phenylpiperazine-1-carboxylate (4.73 g, 18.0 mmol) in N,N-dimethylformamide (41 mL) under an atmosphere of nitrogen was added N,N-diisopropyl-N-ethylamine (9.0 mL, 49 mmol), followed by 6-fluoronicotinonitrile (2.0 g, 16 mmol). The resulting mixture was heated at 105° C. for 48 h, cooled to ambient temperature and quenched with water (300 mL). The mixture was then extracted with ethyl acetate (75 mL×3) and the combined extracts were washed with water (25 mL×3), then brine (25 mL), dried over anhydrous magnesium sulfate, filtered and evaporated to dryness in vacuo. The crude residue was purified by flash silica gel chromatography (ISCO CombiFlash Rf Purification System®; 80 g SepaFlash® Silica Flash Column, eluting with a 0-50% ethyl acetate in hexanes gradient) to afford the title compound as a solid. MS (ESI) m/z [M+H]⁺: 365.4.

Step B: tert-Butyl(S,Z)-4-(5-(N'-hydroxycarbamimidoyl)pyridin-2-yl)-3-phenylpiperazine-1-carboxylate

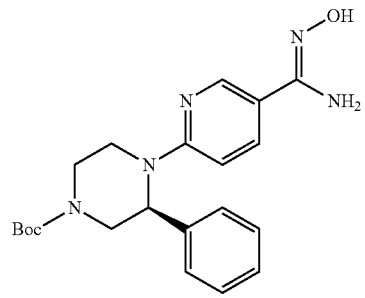 [SMILES: CC(C)(C)OC(=O)N1CCN(c2ccc(/C(N)=N/O)cn2)[C@@H](c2ccccc2)C1]

The title compound was prepared from the product of step A above, tert-butyl(S)-4-(5-cyanopyridin-2-yl)-3-phenylpiperazine-1-carboxylate (1.6 g, 4.4 mmol), according to the procedure outlined in Example 2, step B. The title compound was obtained as a solid. MS (ESI) m/z [M+H]$^+$: 398.4.

Step C: tert-Butyl(S)-3-phenyl-4-(5-(5-(trifluoromethyl)-1,2,4-oxadiazol-3-yl)pyridin-2-yl)piperazine-1-carboxylate

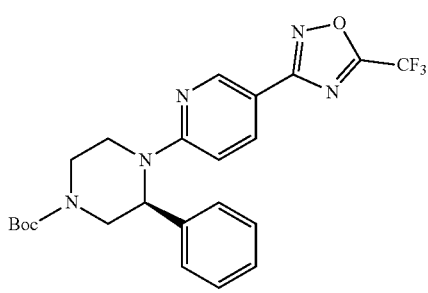 [SMILES: CC(C)(C)OC(=O)N1CCN(c2ccc(-c3noc(C(F)(F)F)n3)cn2)[C@@H](c2ccccc2)C1]

The title compound was prepared from the product of step B above, tert-butyl(S,Z)-4-(5-(N'-hydroxycarbamimidoyl)pyridin-2-yl)-3-phenylpiperazine-1-carboxylate (1.1 g, 2.8 mmol), according to the procedure outlined in Example 2, step C. The crude residue was purified by flash silica gel chromatography (ISCO CombiFlash Rf Purification System®; 40 g SepaFlash® Silica Flash Column, eluting with a 0-40% ethyl acetate in hexanes gradient) to afford the title compound as an oil. $^1$H NMR (500 MHz, CDCl$_3$): δ8.89 (d, J=2.1 Hz, 1H), 8.03 (br s, 1H), 7.35-7.26 (m, 5H), 6.59-6.49 (m, 1H), 5.49-5.35 (m, 1H), 4.59-4.14 (m, 2H), 3.95-3.86 (m, 1H), 3.68 (br s, 2H), 3.44-3.18 (m, 1H), 1.57-1.39 (m, 9H). MS (ESI) m/z [M+H]$^+$: 476.4.

Example 4

(S)-3-(6-(2-Phenylpiperazin-1-yl)pyridin-3-yl)-5-(trifluoromethyl)-1,2,4-oxadiazole trifluoroacetate

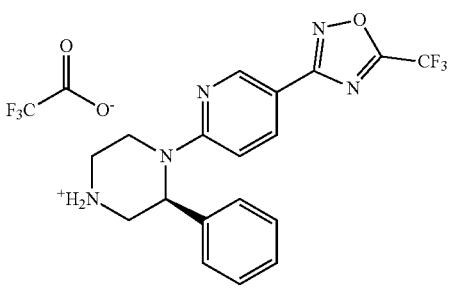 [SMILES: O=C([O-])C(F)(F)F ; FC(F)(F)c1nc(-c2ccc(N3CC[NH2+]C[C@@H]3c3ccccc3)nc2)no1]

To a stirred solution of Example 3, tert-butyl(S)-3-phenyl-4-(5-(5-(trifluoromethyl)-1,2,4-oxadiazol-3-yl)pyridin-2-yl)piperazine-1-carboxylate (69 mg, 0.15 mmol), in dichloromethane (3 mL) was added trifluoroacetic acid (3.0 mL, 39 mmol) and the resulting mixture was stirred at ambient temperature for 1 h. All volatiles were removed in vacuo and the residue was triturated with hexanes (5 mL). After removal of the hexanes in vacuo the residue was dried under high vacuum for 24 h to afford the title compound as an oil. $^1$H NMR (500 MHz, CDCl$_3$): δ8.87 (d, J=2.1 Hz, 1H), 8.21 (dd, J=9.1, 2.1 Hz, 1H), 7.45-7.29 (m, 5H), 6.95 (d, J=9.2 Hz, 1H), 6.00 (br s, 1H), 4.93-4.79 (m, 2H), 4.08 (dd, J=13.4, 3.0 Hz, 1H), 3.68-3.62 (m, 2H), 3.42-3.30 (m, 1H). MS (ESI) m/z [M+H]$^+$: 376.3.

Example 5

1-(3-Fluoro-5-(5-(trifluoromethyl)-1,2,4-oxadiazol-3-yl)pyridin-2-yl)-5-phenylpyrrolidin-2-one Step A: 5-Fluoro-6-(2-oxo-5-phenylpyrrolidin-1-yl)nicotinonitrile

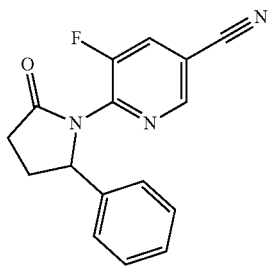 [SMILES: N#Cc1cnc(N2C(=O)CCC2c2ccccc2)c(F)c1]

To a stirred solution of 5-phenylpyrrolidin-2-one (100 mg, 0.620 mmol) in N,N-dimethylformamide (4 mL) cooled to 0° C. under an atmosphere of nitrogen was added 60% sodium hydride suspended in mineral oil (37 mg, 0.93 mmol). After stirring for 20 min, 5,6-difluoronicotinonitrile (130 mg, 0.931 mmol) was added and the resulting mixture was gradually allowed to warm to ambient temperature over 2 h. The mixture was quenched with water (5 mL) and extracted with ethyl acetate (10 mL×3). The combined extracts were washed with water (5 mL×3), then brine (5 mL), dried over anhydrous magnesium sulfate, filtered and evaporated to dryness in vacuo. The crude residue was purified by flash silica gel chromatography (ISCO Combi-Flash Rf Purification System®; 12 g SepaFlash® Silica Flash Column, eluting with a 0-50% ethyl acetate in hexanes gradient) to afford the title compound as a solid. MS (ESI) m/z [M+H]$^+$: 282.2.

Step B: (Z)-5-Fluoro-N'-hydroxy-6-(2-oxo-5-phenylpyrrolidin-1-yl)nicotinimidamide

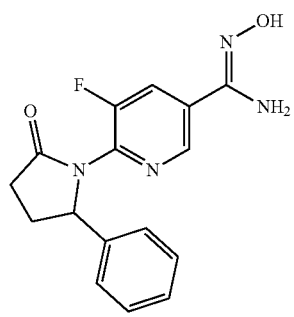 [SMILES: N/C(=N\O)c1cnc(N2C(=O)CCC2c2ccccc2)c(F)c1]

The title compound was prepared from the product of step A above, 5-fluoro-6-(2-oxo-5-phenylpyrrolidin-1-yl)nicotinonitrile (174 mg, 0.620 mmol), according to the procedure outlined in Example 2, step B. The title compound was obtained a solid. MS (ESI) m/z [M+H]$^+$: 315.3.

Step C: 1-(3-Fluoro-5-(5-(trifluoromethyl)-1,2,4-oxadiazol-3-yl)pyridin-2-yl)-5-phenylpyrrolidin-2-one

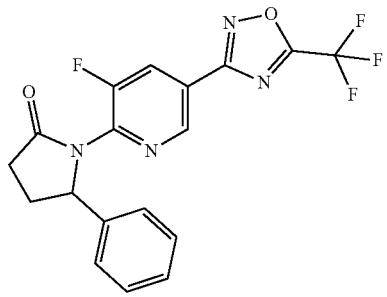 [SMILES: O=C1CCC(c2ccccc2)N1c1ncc(-c2noc(C(F)(F)F)n2)cc1F]

The title compound was prepared from the product of step B above, (Z)-5-fluoro-N'-hydroxy-6-(2-oxo-5-phenylpyrrolidin-1-yl)nicotinimidamide (180 mg, 0.573 mmol), according to the procedure outlined in Example 2, step C. The crude residue was purified by flash silica gel chromatography (ISCO CombiFlash Rf Purification System®; 12 g SepaFlash® Silica Flash Column, eluting with a 0-50% ethyl acetate in hexanes gradient) to afford the title compound as a solid. $^1$H NMR (600 MHz, Chloroform-d) δ 8.84 (d, J=1.8 Hz, 1H), 8.10 (dd, J=9.5, 1.9 Hz, 1H), 7.31-7.23 (m, 5H), 7.20 (t, J=7.1 Hz, 1H), 5.65 (t, J=7.3 Hz, 1H), 2.94-2.79 (m, 1H), 2.78-2.65 (m, 2H), 2.23-2.11 (m, 1H); MS (ESI) m/z [M+H]$^+$: 393.3.

Examples 6 and 7

(R)-5-Phenyl-1-(5-(5-(trifluoromethyl)-1,2,4-oxadiazol-3-yl)pyridin-2-yl)pyrrolidin-2-one and (S)-5-Phenyl-1-(5-(5-(trifluoromethyl)-1,2,4-oxadiazol-3-yl)pyridin-2-yl)pyrrolidin-2-one

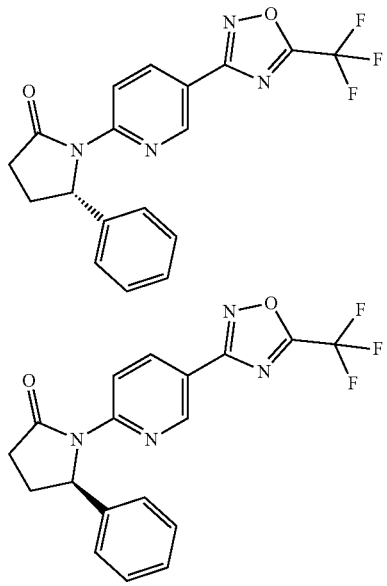

Steps A-C: 5-Phenyl-1-(5-(5-(trifluoromethyl)-1,2,4-oxadiazol-3-yl)pyridin-2-yl)pyrrolidin-2-one

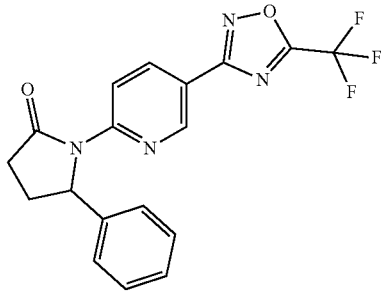 [SMILES: O=C1CCC(c2ccccc2)N1c1ccc(-c2noc(C(F)(F)F)n2)cn1]

The title compound was prepared from 5-phenylpyrrolidin-2-one and 6-chloronicotinonitrile according to the 3 step procedure outlined for the preparation of Example 5. MS (ESI) m/z [M+H]⁺: 375.3

Step D: (R)-5-Phenyl-1-(5-(5-(trifluoromethyl)-1,2,4-oxadiazol-3-yl)pyridin-2-yl)pyrrolidin-2-one and (S)-5-Phenyl-1-(5-(5-(trifluoromethyl)-1,2,4-oxadiazol-3-yl)pyridin-2-yl)pyrrolidin-2-one

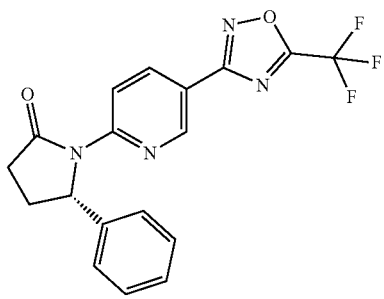

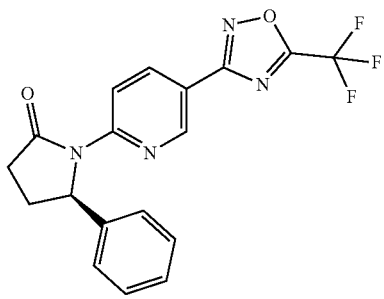

The enantiomers of 5-phenyl-1-(5-(5-(trifluoromethyl)-1,2,4-oxadiazol-3-yl)pyridin-2-yl)pyrrolidin-2-one, obtained from steps A-C above, were separated by supercritical fluid chromatography employing a Berger Multigram SFC equipped with a CHIRALPAK® IA column (2×25 cm) eluting with a 15% methanol in $CO_2$ mixture at 70 mL/min and 100 bar pressure. The first enantiomer to elute was assigned Example 6 and the second enantiomer to elute was assigned Example 7. The absolute stereochemistry was not determined for either Example 6 or Example 7.

Example 6: (R or S)-5-Phenyl-1-(5-(5-(trifluoromethyl)-1,2,4-oxadiazol-3-yl)pyridin-2-yl)pyrrolidin-2-one Chiral analytical analysis was performed using a CHIRALPAK® IA column (25×0.46 cm) eluting with a 40% methanol containing a diethylamine modifier in $CO_2$ mixture at 3 mL/min and 100 bar pressure. Elution time was 1.3 min. Enantiomeric excess determined to be >99%. ¹H NMR (500 MHz, $CDCl_3$): δ8.90 (s, 1H), 8.61 (d, J=8.5 Hz, 1H), 8.35 (dd, J=8.5, 1.8 Hz, 1H), 7.31-7.20 (m, 5H), 5.94 (d, J=5.8 Hz, 1H), 2.89-2.82 (m, 1H), 2.70-2.61 (m, 2H), 2.10-2.06 (m, 1H). MS (ESI) m/z [M+H]⁺: 375.3

Example 7: (R or S)-5-Phenyl-1-(5-(5-(trifluoromethyl)-1,2,4-oxadiazol-3-yl)pyridin-2-yl)pyrrolidin-2-one Chiral analytical analysis was performed using a CHIRALPAK® IA column (25×0.46 cm) eluting with a 40% methanol containing a diethylamine modifier in $CO_2$ mixture at 3 mL/min and 100 bar pressure. Elution time was 1.6 min. Enantiomeric excess determined to be >99%. ¹H NMR (500 MHz, $CDCl_3$): δ8.90 (s, 1H), 8.61 (d, J=8.5 Hz, 1H), 8.35 (dd, J=8.5, 1.8 Hz, 1H), 7.31-7.20 (m, 5H), 5.94 (d, J=5.8 Hz, 1H), 2.89-2.82 (m, 1H), 2.70-2.61 (m, 2H), 2.10-2.06 (m, 1H). MS (ESI) m/z [M+H]⁺: 375.3

Example 8 tert-Butyl(S)-1-(2,5-difluoro-4-(5-(trifluoromethyl)-1,2,4-oxadiazol-3-yl)phenyl)-5-oxopyrrolidine-2-carboxylate

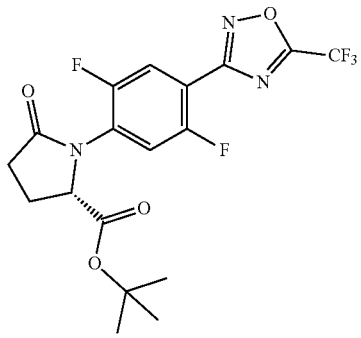 [SMILES: CC(C)(C)OC(=O)[C@@H]1CCC(=O)N1c1cc(F)c(-c2noc(C(F)(F)F)n2)cc1F]

The title compound was prepared from tert-butyl(S)-5-oxopyrrolidine-2-carboxylate and 4-bromo-2,5-difluorobenzonitrile according to the 3 step procedure outlined for the preparation of Example 2. ¹H NMR (600 MHz, Chloroform-d) δ 7.86 (dd, J=11.1, 6.0 Hz, 1H), 7.65 (dd, J=10.8, 6.0 Hz, 1H), 4.76 (dd, J=7.7, 4.1 Hz, 1H), 2.73-2.64 (m, 1H), 2.62-2.51 (m, 2H), 2.27-2.19 (m, 1H), 1.38 (s, 9H); MS (ESI) m/z [M+H]⁺: 434.3; (M+H⁺+$CH_3CN$): 475.3.

Example 9

(S)-1-(2,5-Difluoro-4-(5-(trifluoromethyl)-1,2,4-oxadiazol-3-yl)phenyl)-5-(3-methyl-1,2,4-oxadiazol-5-yl)pyrrolidin-2-one

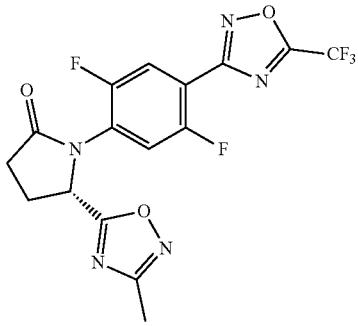

Step A: (S)-1-(2,5-Difluoro-4-(5-(trifluoromethyl)-1,2,4-oxadiazol-3-yl)phenyl)-5-oxopyrrolidine-2-carboxylic acid

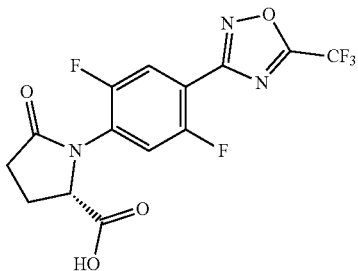 [SMILES: O=C(O)[C@@H]1CCC(=O)N1c1cc(F)c(-c2noc(C(F)(F)F)n2)cc1F]

To a stirred solution of Example 8, tert-butyl(S)-1-(2,5-difluoro-4-(5-(trifluoromethyl)-1,2,4-oxadiazol-3-yl)phenyl) 5-oxopyrrolidine-2-carboxylate (533 mg, 1.23 mmol), in dichloromethane (6 mL) was added trifluoroacetic acid (1.5 mL, 19 mmol) and the resulting solution was stirred at ambient temperature for 12 h. The reaction was quenched with water (5 mL) and extracted with dichloromethane (10 mL×2). The combined extracts were dried over anhydrous magnesium sulfate, filtered and evaporated to dryness in vacuo to afford the title compound as a solid. MS (ESI) m/z [M+H]$^+$: 378.2; (M+H$^+$+CH$_3$CN): 419.3.

Step B: (S)-1-(2,5-Difluoro-4-(5-(trifluoromethyl)-1,2,4-oxadiazol-3-yl)phenyl)-5-(3-methyl-1,2,4-oxadiazol-5-yl)pyrrolidin-2-one

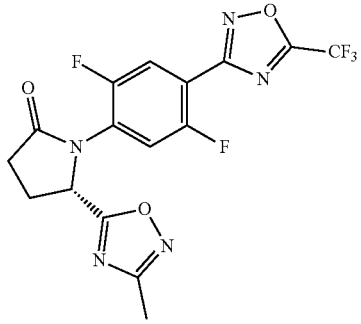 [SMILES: Cc1noc([C@@H]2CCC(=O)N2c2cc(F)c(-c3noc(C(F)(F)F)n3)cc2F)n1]

To a stirred solution of the product of step A above, (S)-1-(2,5-difluoro-4-(5-(trifluoromethyl)-1,2,4-oxadiazol-3-yl)phenyl)-5-oxopyrrolidine-2-carboxylic acid (41 mg, 0.11 mmol), in N,N-dimethylformamide (0.800 mL) was added N,N-carbonyl diimidazole (22 mg, 0.14 mmol). After stirring for 30 min at ambient temperature, (Z)—N'-hydroxyacetimidamide (11 mg, 0.14 mmol) was added and the resulting mixture was heated at 100° C. for 1 h. The reaction mixture was cooled and purified directly via reverse-phase HPLC (Gilson GX-281 Purification System®, employing a Sunfire Prep C18 OBD® 10 micron (20×150 mm) column eluting with a 20-80% acetonitrile (containing 0.01% trifluoroacetic acid modifier) in water (containing 0.01% trifluoroacetic acid modifier) gradient and lyophilized to obtain a solid. $^1$H NMR (500 MHz, DMSO-d$_6$) δ 7.95 (dd, J=11.3, 6.6 Hz, 1H), 7.80 (dd, J=11.6, 6.3 Hz, 1H), 5.86-5.80 (m, 1H), 2.75 (s, 1H), 2.73-2.57 (m, 2H), 2.38 (d, J=5.7 Hz, 1H), 2.31-2.27 (m, 4H); MS (ESI) m/z [M+H]$^+$: 416.3.

Example 10

(R)-5-(1-(3-Chloro-5-(5-(trifluoromethyl)-1,2,4-oxadiazol-3-yl)pyridin-2-yl)piperidin-2-yl)-3-methyl-1,2,4-oxadiazole

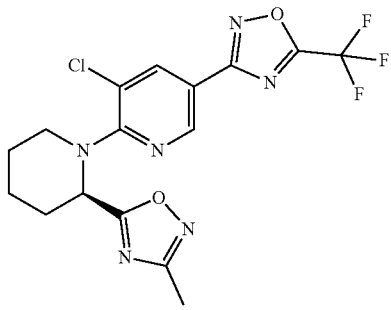 [SMILES: Cc1noc([C@H]2CCCCN2c2ncc(-c3noc(C(F)(F)F)n3)cc2Cl)n1]

Step A: (R)-5-Chloro-6-(2-(3-methyl-1,2,4-oxadi-azol-5-yl)piperidin-1-yl)nicotinonitrile

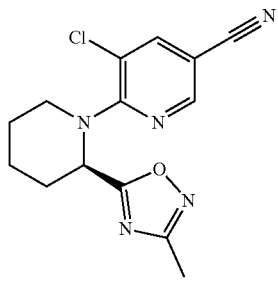 [SMILES: Cc1noc([C@H]2CCCCN2c2ncc(C#N)cc2Cl)n1]

To a stirred solution of 5,6-dichloronicotinonitrile (75 mg, 0.43 mmol) in N,N-dimethylformamide (0.70 mL) under an atmosphere of nitrogen was added sodium carbonate (138 mg, 1.30 mmol) followed by (R)-3-methyl-5-(piperidin-2-yl)-1,2,4-oxadiazole hydrochloride (88 mg, 0.43 mmol) and the resulting mixture was heated at 100° C. for 15 h. After cooling to ambient temperature, the mixture was quenched with a saturated aqueous sodium bicarbonate solution (10 mL) and extracted with ethyl acetate (15 mL×3). The combined extracts were washed with water (5 mL), then brine (5 mL), dried over anhydrous magnesium sulfate, filtered and evaporated to dryness in vacuo. The crude residue was purified by flash silica gel chromatography (ISCO CombiFlash Rf Purification System®; 4 g Sepa-Flash® Silica Flash Column, eluting with a 0-100% ethyl acetate in hexanes gradient) to afford the title compound as a solid. MS (ESI) m/z [M+H]⁺: 304.2 and 306.2.

Steps B and C: (R)-5-(1-(3-Chloro-5-(5-(trifluorom-ethyl)-1,2,4-oxadiazol-3-yl)pyridin-2-yl)piperidin-2-yl)-3-methyl-1,2,4-oxadiazole

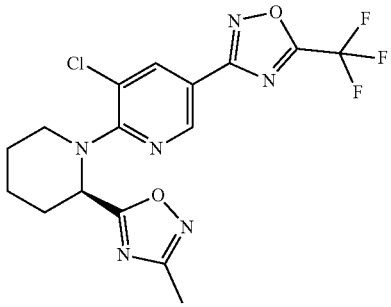 [SMILES: Cc1noc([C@H]2CCCCN2c2ncc(-c3noc(C(F)(F)F)n3)cc2Cl)n1]

The title compound was prepared from the product of step A above, (R)-5-chloro-6-(2-(3-methyl-1,2,4-oxadiazol-5-yl)piperidin-1-yl)nicotinonitrile, according to the procedure outlined in Example 2, steps B and C. ¹H NMR (500 MHz, CDCl₃): δ8.76 (t, J=1.9 Hz, 1H), 8.25 (t, J=1.8 Hz, 1H), 5.54 (m, 1H), 4.02 (dtd, J=13.3, 4.0, 2.1 Hz, 1H), 3.57 (dt, J=15.1, 6.7 Hz, 1H), 2.39 (s, 3H), 2.28 (m, 1H), 2.15 (m, 1H), 1.85-1.75 (m, 3H), 1.70-1.60 (m, 1H) MS (ESI) m/z [M+H]⁺: 415.2 and 417.2

Example 11

(R)-3-Methyl-5-(1-(5-(5-(trifluoromethyl)-1,2,4-oxadiazol-3-yl)pyrimidin-2-yl)piperidin-2-yl)-1,2,4-oxadiazole

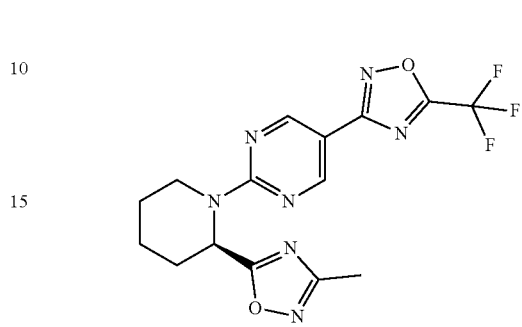

The title compound was prepared from 2-chloropyrimi-dine-5-carbonitrile and (R)-3-methyl-5-(piperidin-2-yl)-1,2,4-oxadiazole hydrochloride according to the procedure outlined for the preparation of example 10. ¹H NMR (500 MHz, Chloroform-d) δ 8.99 (s, 1H), 6.45 (dd, J=6.1, 2.1 Hz, 1H), 4.94 (dd, J=13.2, 4.0 Hz, 1H), 3.22-3.12 (m, 1H), 2.52-2.43 (m, 1H), 2.38 (s, 3H), 2.01 (tdd, J=13.6, 5.7, 3.5 Hz, 1H), 1.68-1.46 (m, 5H); MS (ESI) m/z [M+H]⁺: 382.3.

Example 12

(S)-1-(2,3-Difluoro-4-(5-(trifluoromethyl)-1,2,4-oxadiazol-3-yl)phenyl)-5-(3-methyl-1,2,4-oxadiazol-5-yl)pyrrolidin-2-one

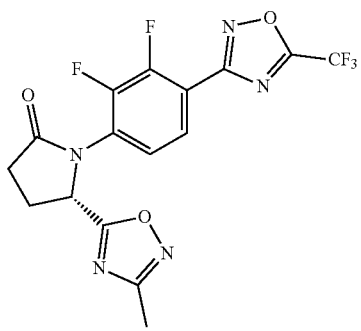 [SMILES: Cc1noc([C@@H]2CCC(=O)N2c2ccc(-c3noc(C(F)(F)F)n3)c(F)c2F)n1]

The title compound was prepared from tert-butyl(S)-5-oxopyrrolidine-2-carboxylate and 4-bromo-2,3-difluoroben-zonitrile according to the procedures outlined for the preparation of Examples 8, followed by the procedures outlined for the preparation of Example 9. ¹H NMR (600 MHz, Chloroform-d) δ 7.86 (t, J=7.2 Hz, 1H), 7.41 (t, J=7.0 Hz, 1H), 5.56 (dd, J=8.4, 3.4 Hz, 1H), 2.89 (dt, J=17.0, 8.8 Hz, 1H), 2.81 (dq, J=12.8, 8.6 Hz, 1H), 2.71 (ddd, J=16.5, 9.1, 4.2 Hz, 1H), 2.48 (ddt, J=12.9, 8.5, 3.8 Hz, 1H), 2.36 (s, 3H); MS (ESI) m/z [M+H]⁺: 416.3.

Example 13 tert-Butyl(S)-4-(2,6-difluoro-4-(5-(trifluoromethyl)-1,2,4-oxadiazol-3-yl)phenyl)-3-phenylpiperazine-1-carboxylate

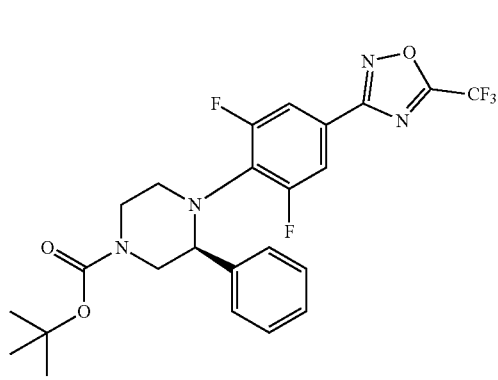 [SMILES: CC(C)(C)OC(=O)N1CCN(c2c(F)cc(-c3noc(C(F)(F)F)n3)cc2F)[C@@H](c2ccccc2)C1]

The title compound was prepared from tert-butyl(S)-3-phenylpiperazine-1-carboxylate and 3,4,5-trifluorobenzonitrile according to the procedure outlined for the preparation of Example 3. $^1$H NMR (500 MHz, CDCl$_3$): δ7.46-7.41 (m, 2H), 7.36-7.30 (m, 2H), 7.20-7.11 (m, 3H), 4.47-4.42 (m, 1H), 4.21-4.20 (br s, 2H), 3.38-3.14 (m, 3H), 3.07-2.95 (m, 1H), 1.57-1.39 (m, 9H). MS (ESI) m/z [M+H]$^+$: 434.3; [M+H]$^+$: 511.2.

Example 14

5-(2-Chlorophenyl)-1-(3,5-difluoro-4-(5-(trifluoromethyl)-1,2,4-oxadiazol-3-yl)phenyl)pyrrolidin-2-one

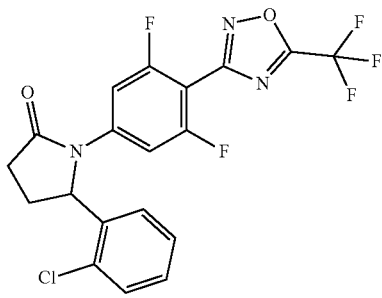 [SMILES: O=C1CCC(c2ccccc2Cl)N1c1cc(F)c(-c2noc(C(F)(F)F)n2)c(F)c1]

The title compound was prepared from 5-(2-chlorophenyl)pyrrolidin-2-one and 4-bromo-2,6-difluorobenzonitrile according to the procedure outlined for the preparation of Example 2. $^1$H NMR (600 MHz, CDCl$_3$): δ 7.48 (d, J=7.8 Hz, 1H), 7.36 (d, J=11.2 Hz, 2H), 7.28 (dd, J=8.1, 6.7 Hz, 1H), 7.22 (t, J=7.6 Hz, 1H), 7.01 (d, J=7.7 Hz, 1H), 5.65 (d, J=7.5 Hz, 1H), 2.73 (td, J=12.2, 11.6, 8.0 Hz, 2H), 2.71-2.64 (m, 1H), 2.08 (m, 1H). MS (ESI) m/z [M+H]$^+$: 444.10 (M+1).

Example 15

(R)-5-Phenyl-4-(6-(5-(trifluoromethyl)-1,2,4-oxadiazol-3-yl)pyridin-3-yl)morpholin-3-one

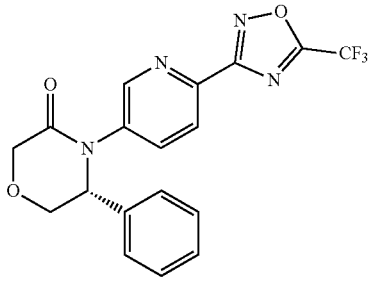 [SMILES: O=C1COC[C@@H](c2ccccc2)N1c1ccc(-c2noc(C(F)(F)F)n2)nc1]

The title compound was prepared from (R)-5-phenylmorpholin-3-one and 5-bromopicolinonitrile according to the procedure outlined for the preparation of Example 1. $^1$H NMR (600 MHz, DMSO): δ 8.78 (dd, J=2.4, 0.9 Hz, 1H), 8.11-7.95 (m, 2H), 7.43-7.33 (m, 2H) 7.27 (dd, J=8.5, 6.9 Hz, 2H), 7.23-7.13 (m, 1H), 5.50 (t, J=4.5 Hz, 1H), 4.53 (d, J=16.7 Hz, 1H), 4.37 (d, J=16.7 Hz, 1H), 4.27 (dd, J=12.0, 3.9 Hz, 1H), 3.93 (dd, J=12.0, 5.2 Hz, 1H). MS (ESI) m/z [M+H]$^+$: 434.3; (M+H$^+$+CH$_3$CN): 391.2

Example 16

(R)-3-(2,5-Difluoro-4-(5-(trifluoromethyl)-1,2,4-oxadiazol-3-yl)phenyl)-4-phenyloxazolidin-2-one

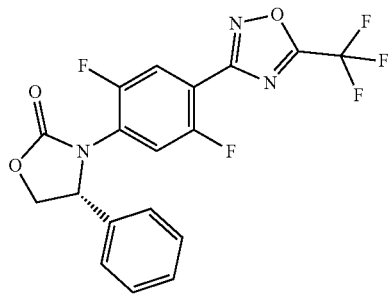 [SMILES: O=C1OC[C@@H](c2ccccc2)N1c1cc(F)c(-c2noc(C(F)(F)F)n2)cc1F]

Step A: (R)-2,5-Difluoro-4-(2-oxo-4-phenyloxazolidin-3-yl)benzonitrile

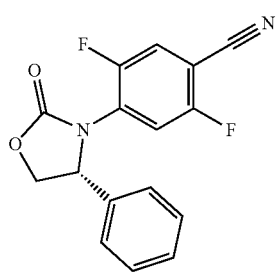 [SMILES: N#Cc1cc(F)c(N2C(=O)OC[C@H]2c2ccccc2)cc1F]

To a stirred suspension of (R)-4-phenyloxazolidin-2-one (100 mg, 0.613 mmol), 4-bromo-2,5-difluorobenzonitrile (134 mg, 0.613 mmol), copper(I) iodide (175 mg, 0.919 mmol), and potassium carbonate (254 mg, 1.84 mmol) in anhydrous 1,4-dioxane (3.0 mL) under an atmosphere of nitrogen was added (1S,2S)-(+)—N,N'-dimethylcyclohexane-1,2-diamine (0.29 mL, 1.8 mmol) and the resulting mixture was heated at 90° C. for 20 h. After cooling to ambient temperature the mixture was filtered through a pad of Celite® and the filtered solids were washed with ethyl acetate (30 mL). The combined filtrates were evaporated to dryness in vacuo and the crude residue was purified by flash silica gel chromatography (ISCO CombiFlash Rf Purification System®; 12 g SepaFlash® Silica Flash Column, eluting with a 0-50% ethyl acetate in hexanes gradient) to afford the title compound as an oil. MS (ESI) m/z [M+H+ CH$_3$CN]$^+$: 342.2.

Steps B and C: (R)-3-(2,5-Difluoro-4-(5-(trifluoromethyl)-1,2,4-oxadiazol-3-yl)phenyl)-4-phenyloxazolidin-2-one

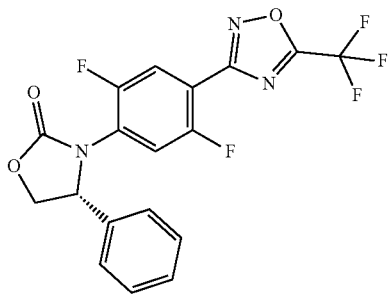 [SMILES: O=C1OC[C@@H](c2ccccc2)N1c1cc(F)c(-c2noc(C(F)(F)F)n2)cc1F]

The title compound was prepared from the product of step A above, (R)-2,5-difluoro-4-(2-oxo-4-phenyloxazolidin-3-yl)benzonitrile, according to the procedure outlined in Example 2, steps B and C. $^1$H NMR (500 MHz, DMSO-d$_6$) δ 7.87 (dd, J=10.5, 6.2 Hz, 1H), 7.80 (dd, J=11.2, 5.9 Hz, 1H), 7.44 (d, J=7.6 Hz, 2H), 7.35 (t, J=7.5 Hz, 2H), 7.30 (t, J=7.4 Hz, 1H), 5.76 (t, J=8.4 Hz, 1H), 4.95 (t, J=8.7 Hz, 1H), 4.31 (t, J=8.4 Hz, 1H); MS (ESI) m/z [M+H]$^+$: 412.1.

Example 17

(S)-5-(3-(Pyridin-2-yl)-1,2,4-oxadiazol-5-yl)-1-(4-(5-(trifluoromethyl)-1,2,4-oxadiazol-3-yl)phenyl)pyrrolidin-2-one

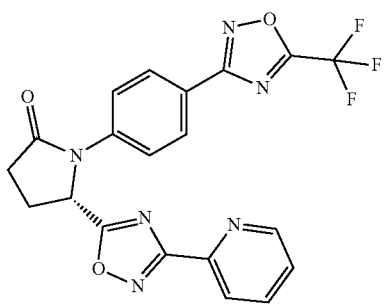 [SMILES: O=C1CC[C@@H](c2nc(-c3ccccn3)no2)N1c1ccc(-c2noc(C(F)(F)F)n2)cc1]

Steps A-C: tert-Butyl(S)-5-oxo-1-(4-(5-(trifluoromethyl)-1,2,4-oxadiazol-3-yl)phenyl)pyrrolidine-2-carboxylate

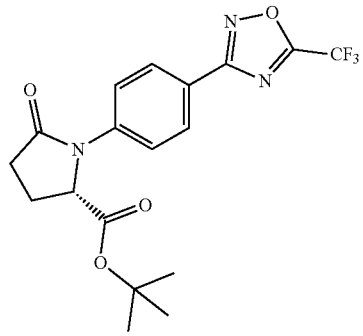 [SMILES: CC(C)(C)OC(=O)[C@@H]1CCC(=O)N1c1ccc(-c2noc(C(F)(F)F)n2)cc1]

The title compound was prepared from tert-butyl(S)-5-oxopyrrolidine-2-carboxylate and 4-bromobenzonitrile according to the procedures outlined for the preparation of Example 1. MS (ESI) m/z [M+H]$^+$: 287.

Step D: (S)-5-Oxo-1-(4-(5-(trifluoromethyl)-1,2,4-oxadiazol-3-yl)phenyl)pyrrolidine-2-carboxylic acid

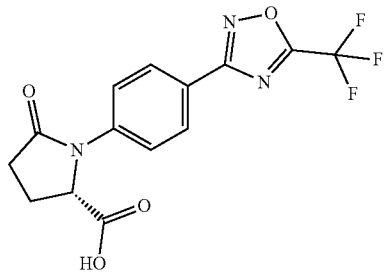 [SMILES: O=C(O)[C@@H]1CCC(=O)N1c1ccc(-c2noc(C(F)(F)F)n2)cc1]

The title compound was prepared from the product of steps A-C above, tert-butyl(S)-5-oxo-1-(4-(5-(trifluoromethyl)-1,2,4-oxadiazol-3-yl)phenyl)pyrrolidine-2-carboxylate, according to the procedure outlined in Example 9, Step A. MS (ESI) m/z [M+H]$^+$: 342.2; [M+H+CH$_3$CN]$^+$: 383.2.

Step E: (S)-5-(3-(Pyridin-2-yl)-1,2,4-oxadiazol-5-yl)-1-(4-(5-(trifluoromethyl)-1,2,4-oxadiazol-3-yl)phenyl)pyrrolidin-2-one

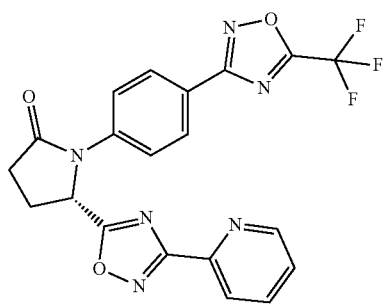 [SMILES: O=C1CC[C@@H](c2nc(-c3ccccn3)no2)N1c1ccc(-c2noc(C(F)(F)F)n2)cc1]

The title compound was prepared from the product of Step D above, (S)-5-oxo-1-(4-(5-(trifluoromethyl)-1,2,4-oxadiazol-3-yl)phenyl)pyrrolidine-2-carboxylic acid, according to the procedure outlined in Example 9, Step B using (Z)—N'-hydroxypicolinimidamide in place of (Z)—N'-hydroxyacetimidamide. $^1$H NMR (500 MHz, DMSO-d$_6$) δ 8.72 (d, J=4.7 Hz, 1H), 8.09-8.04 (m, 3H), 8.04-7.95 (m, 3H), 7.85 (d, J=8.8 Hz, 3H), 7.59 (s, 1H), 6.17 (dd, J=8.3, 2.8 Hz, 1H), 2.89-2.71 (m, 1H), 2.71-2.62 (m, 2H), 2.39 (s, 1H); MS (ESI) m/z [M+H]$^+$: 443.1.

Example 18

(R)-3-(2-Chloro-4-(2-(3-methyl-1,2,4-oxadiazol-5-yl)piperidin-1-yl)phenyl)-5-(trifluoromethyl)-1,2,4-oxadiazole

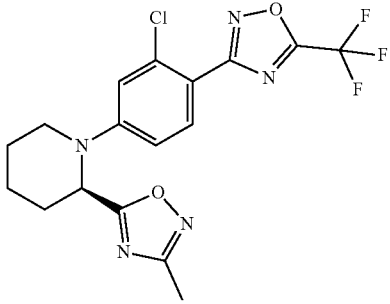 [SMILES: Cc1noc([C@H]2CCCCN2c2ccc(-c3noc(C(F)(F)F)n3)c(Cl)c2)n1]

Step A: (R)-2-Chloro-4-(2-(3-methyl-1,2,4-oxadiazol-5-yl)piperidin-1-yl)benzonitrile

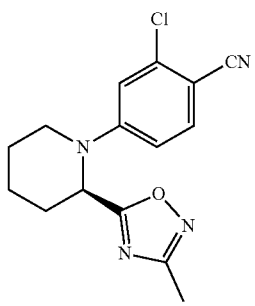 [SMILES: Cc1noc([C@H]2CCCCN2c2ccc(C#N)c(Cl)c2)n1]

To a stirred suspension of (R)-3-methyl-5-(piperidin-2-yl)-1,2,4-oxadiazole dihydrochloride (122 mg, 0.508 mmol), 4-bromo-2-chlorobenzonitrile (100 mg, 0.462 mmol), (2-dicyclohexylphosphino-2',6'-diisopropoxy-1,1'-biphenyl)[2-(2'-amino-1,1'-biphenyl)]palladium(II) methansulfonate (39 mg, 0.046 mmol) and 2-dicyclohexylphosphino-2',6'-diisopropoxy-1,1'-biphenyl (22 mg, 0.046 mmol) in anhydrous 1,4-dioxane (2.0 mL) under an atmosphere of nitrogen was added sodium tert-butoxide (133 mg, 1.39 mmol). The resulting mixture was heated at 90° C. for 20 h, cooled to ambient temperature, diluted with ethyl acetate (15 mL) and washed with water (5 mL×3). The ethyl acetate layer was washed with brine (5 mL), dried over anhydrous magnesium sulfate, filtered and evaporated to dryness in vacuo. The crude residue was purified by flash silica gel chromatography (ISCO CombiFlash Rf Purification System®; 12 g SepaFlash® Silica Flash Column, eluting with a 0-50% ethyl acetate in hexanes gradient) to afford the title compound as an oil. MS (ESI) m/z [M+H]$^+$: 303.2; [M+H+CH$_3$CN]$^+$: 344.3.

Steps B and C: (R)-3-(2-Chloro-4-(2-(3-methyl-1,2,4-oxadiazol-5-yl)piperidin-1-yl)phenyl)-5-(trifluoromethyl)-1,2,4-oxadiazole

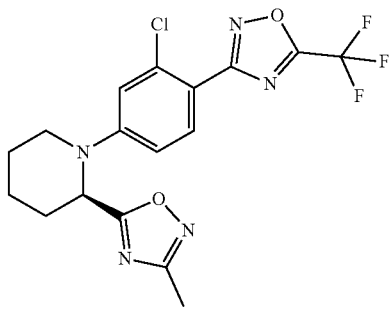 [SMILES: Cc1noc([C@H]2CCCCN2c2ccc(-c3noc(C(F)(F)F)n3)c(Cl)c2)n1]

The title compound was prepared from the product of step A above and (R)-2-chloro-4-(2-(3-methyl-1,2,4-oxadiazol-5-yl)piperidin-1-yl)benzonitrile, according to the procedure outlined in Example 1, steps B and C. $^1$H NMR (500 MHz, Chloroform-d) δ 7.92-7.86 (m, 1H), 7.04 (d, J=2.6 Hz, 1H), 6.88 (dd, J=8.9, 2.6 Hz, 1H), 5.35 (dd, J=5.8, 2.4 Hz, 1H), 3.77 (d, J=13.0 Hz, 1H), 3.37 (td, J=12.5, 3.3 Hz, 1H), 2.37 (s, 4H), 2.18-2.07 (m, 1H), 1.90 (d, J=13.4 Hz, 1H), 1.75 (dtt, J=38.1, 12.8, 3.9 Hz, 2H), 1.57-1.48 (m, 1H); MS (ESI) m/z [M+H]$^+$: 414.3.

Example 19

(S)—N-(tert-Butyl)-1-(2,5-difluoro-4-(5-(trifluoromethyl)-1,2,4-oxadiazol-3-yl)phenyl)-N-methyl-5-oxopyrrolidine-2-carboxamide

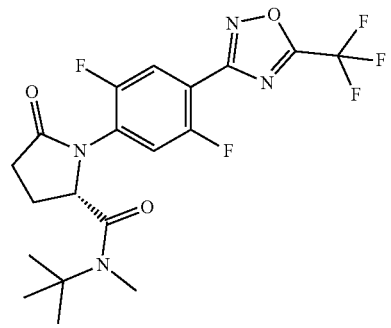 [SMILES: CN(C(=O)[C@@H]1CCC(=O)N1c1cc(F)c(-c2noc(C(F)(F)F)n2)cc1F)C(C)(C)C]

To a stirred solution of the product of Example 9, Step A, (S)-1-(2,5-difluoro-4-(5-(trifluoromethyl)-1,2,4-oxadiazol-3-yl)phenyl)-5-oxopyrrolidine-2-carboxylic acid (20 mg, 0.053 mmol), in N,N-dimethylformamide (1 mL) under an atmosphere of nitrogen was added 2-(3H-[1,2,3]triazolo[4,5-b]pyridin-3-yl)-1,1,3,3-tetramethylisouronium hexafluorophosphate(V) (40 mg, 0.11 mmol) followed by tert-butylmethylamine (8.0 mg, 0.11 mmol) and triethylamine (0.022 mL, 0.16 mmol). The resulting mixture was stirred at ambient temperature overnight and then purified directly via reverse-phase HPLC (Gilson GX-281 Purification System®, employing a Sunfire Prep C18 OBD® 10 micron (20×150 mm) column eluting with a 40-85% acetonitrile (containing 0.01% trifluoroacetic acid modifier) in water (containing 0.01% trifluoroacetic acid modifier) gradient) and lyophilized to obtain a solid. ¹H NMR (500 MHz, DMSO-d₆) δ 7.89 (dd, J=11.1, 6.3 Hz, 1H), 7.68 (dd, J=11.7, 5.7 Hz, 1H), 5.33 (s, 1H), 2.92 (s, 3H), 2.54 (s, 3H), 1.92 (s, 1H), 1.28 (s, 9H); MS (ESI) m/z [M+H]⁺: 447.2.

Example 20

(S)—N-(2-Aminophenyl)-5-oxo-1-(4-(5-(trifluoromethyl)-1,2,4-oxadiazol-3-yl)phenyl)pyrrolidine-2-carboxamide

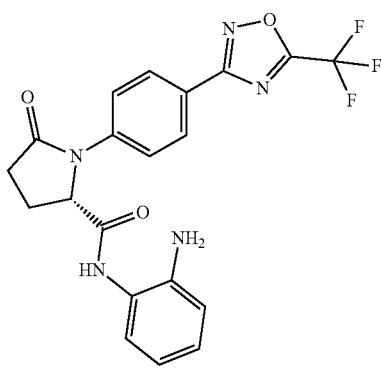 [SMILES: Nc1ccccc1NC(=O)[C@@H]1CCC(=O)N1c1ccc(-c2noc(C(F)(F)F)n2)cc1]

To a stirred solution of the product of Example 17, Step D, (S)-5-oxo-1-(4-(5-(trifluoromethyl)-1,2,4-oxadiazol-3-yl)phenyl)pyrrolidine-2-carboxylic acid (100 mg, 0.293 mmol), in dichloromethane (1.5 mL) under an atmosphere of nitrogen was added benzene-1,2-diamine (48 mg, 0.44 mmol), 2-(3H-[1,2,3]triazolo[4,5-b]pyridin-3-yl)-1,1,3,3-tetramethylisouronium hexafluorophosphate(V) (167 mg, 0.440 mmol) and triethylamine (123 mL, 0.879 mmol). The resulting mixture was stirred at ambient temperature for 20 h and purified by flash silica gel chromatography (ISCO CombiFlash Rf Purification System®; 12 g SepaFlash® Silica Flash Column, eluting with a 0-100% ethyl acetate in hexanes gradient) to afford the title compound as a solid. ¹H NMR (600 MHz, Chloroform-d) δ 8.17 (d, J=8.5 Hz, 2H), 7.84 (d, J=8.6 Hz, 2H), 7.45 (s, 1H), 7.04 (t, J=7.7 Hz, 1H), 6.79 (t, J=7.6 Hz, 1H), 6.74 (d, J=8.0 Hz, 1H), 4.90 (dd, J=8.6, 4.3 Hz, 1H), 3.35 (s, 2H), 2.87 (t, J=9.8 Hz, 1H), 2.72 (d, J=13.8 Hz, 2H), 2.40 (m, 1H); MS (ESI) m/z [M+H]⁺: 432.3.

Example 21

(S)-5-(1H-Benzo[d]imidazol-2-yl)-1-(4-(5-(trifluoromethyl)-1,2,4-oxadiazol-3-yl)phenyl)pyrrolidin-2-one

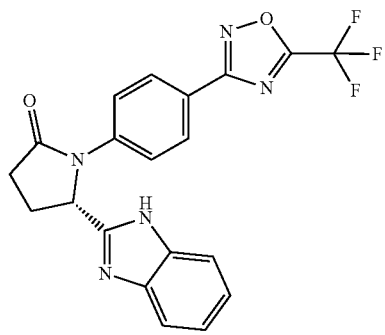 [SMILES: O=C1CC[C@@H](c2nc3ccccc3[nH]2)N1c1ccc(-c2noc(C(F)(F)F)n2)cc1]

The product of Step A above and (S)—N-(2-aminophenyl)-5-oxo-1-(4-(5-(trifluoromethyl)-1,2,4-oxadiazol-3-yl)phenyl)pyrrolidine-2-carboxamide (63 mg, 0.15 mmol) were suspended in acetic acid (0.600 mL) and heated at 90° C. for 1.5 h. The reaction mixture was cooled to ambient temperature and purified by reverse-phase HPLC (Gilson GX-281 Purification System®, employing a Sunfire Prep C18 OBD® 10 micron (20×150 mm) column eluting with a 30-100% acetonitrile (containing 0.01% trifluoroacetic acid modifier) in water (containing 0.01% trifluoroacetic acid modifier) gradient. The fractions containing the desired product were combined and evaporated in vacuo to remove the acetonitrile. The aqueous phase was made basic with a saturated aqueous sodium bicarbonate solution and then extracted with ethyl acetate (10×3 mL). The combined ethyl acetate layers were dried over anhydrous magnesium sulfate, filtered, and evaporated to dryness in vacuo to afford the title compound as a solid. ¹H NMR (600 MHz, Methanol-d₄) δ 8.05-7.99 (m, 2H), 7.76-7.71 (m, 2H), 7.57 (s, 1H), 7.40 (s, 1H), 7.22-7.17 (m, 2H), 5.77 (dd, J=8.4, 5.3 Hz, 1H), 2.96-2.88 (m, 1H), 2.85-2.72 (m, 2H), 2.36-2.26 (m, 1H); MS (ESI) m/z [M+H]⁺: 414.3.

Example 22

(S)-5-(Benzo[d]oxazol-2-yl)-1-(2-fluoro-4-(5-(trifluoromethyl)-1,2,4-oxadiazol-3-yl)phenyl)pyrrolidin-2-one

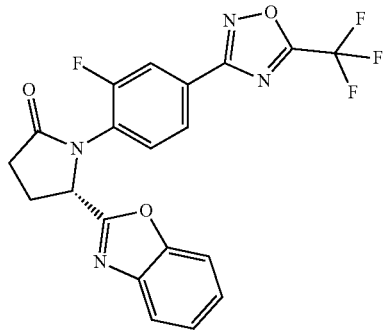 [SMILES: O=C1CC[C@@H](c2nc3ccccc3o2)N1c1ccc(-c2noc(C(F)(F)F)n2)cc1F]

Steps A-D: (S)-1-(2-Fluoro-4-(5-(trifluoromethyl)-1,2,4-oxadiazol-3-yl)phenyl)-5-oxopyrrolidine-2-carboxylic acid

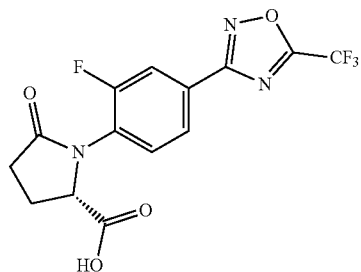 [SMILES: O=C(O)[C@@H]1CCC(=O)N1c1ccc(-c2noc(C(F)(F)F)n2)cc1F]

The title compound was prepared from tert-butyl(S)-5-oxopyrrolidine-2-carboxylate and 3-fluoro-4-iodobenzonitrile according to the 3 step procedure outlined for the preparation of Example 2, followed by the procedure outlined in Example 9, Step A. MS (ESI) m/z [M+H]$^+$: 360.1.

Step E: (S)-1-(2-Fluoro-4-(5-(trifluoromethyl)-1,2,4-oxadiazol-3-yl)phenyl)-N-(2-hydroxyphenyl)-5-oxopyrrolidine-2-carboxamide

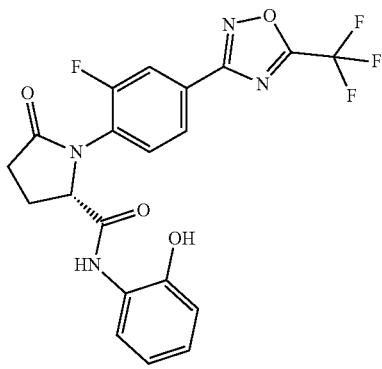 [SMILES: O=C(Nc1ccccc1O)[C@@H]1CCC(=O)N1c1ccc(-c2noc(C(F)(F)F)n2)cc1F]

The title compound was prepared from the product from steps A-D above, (S)-1-(2-fluoro-4-(5-(trifluoromethyl)-1,2,4-oxadiazol-3-yl)phenyl)-5-oxopyrrolidine-2-carboxylic acid (47 mg, 0.13 mmol) and 2-aminophenol (21 mg, 0.20 mmol) according to procedure outlined for the preparation of Example 20. MS (ESI) m/z [M+H]$^+$: 451.3.

Step F: (S)-5-(Benzo[d]oxazol-2-yl)-1-(2-fluoro-4-(5-(trifluoromethyl)-1,2,4-oxadiazol-3-yl)phenyl)pyrrolidin-2-one

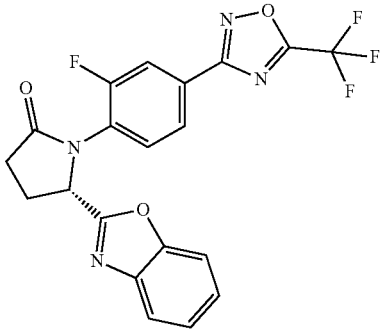 [SMILES: O=C1CC[C@@H](c2nc3ccccc3o2)N1c1ccc(-c2noc(C(F)(F)F)n2)cc1F]

To a stirred solution of the product of Step E above, (S)-1-(2-fluoro-4-(5-(trifluoromethyl)-1,2,4-oxadiazol-3-yl)phenyl)-N-(2-hydroxyphenyl)-5-oxopyrrolidine-2-carboxamide (45 mg, 0.10 mmol), in tetrahydrofuran (0.5 mL) cooled to 0° C. under an atmosphere of nitrogen was added resin supported triphenyl phosphine (1.8 mmol/g: 26 mg, 0.10 mmol). After stirring for 30 min, diisopropyl(E)-diazene-1,2-dicarboxylate (42 µl, 0.22 mmol) was added and the resulting mixture was warmed to ambient temperature over 2 h. The reaction mixture was filtered through Celite® and the filter cake washed with methanol (10 mL). The combined filtrates were evaporated to dryness in vacuo and the crude residue was purified by flash silica gel chromatography (ISCO CombiFlash Rf Purification System®; 12 g SepaFlash® Silica Flash Column, eluting with a 0-50% ethyl acetate in hexanes gradient) to afford the title compound as an oil. $^1$H NMR (600 MHz, Chloroform-d) δ 7.87 (dd, J=9.7, 1.3 Hz, 2H), 7.68-7.63 (m, 1H), 7.58 (t, J=7.8 Hz, 1H), 7.51-7.46 (m, 1H), 7.37-7.29 (m, 2H), 5.59 (dd, J=8.4, 3.9 Hz, 1H), 2.98 (ddd, J=17.2, 9.5, 7.7 Hz, 1H), 2.86-2.77 (m, 1H), 2.74 (ddd, J=16.9, 9.5, 4.4 Hz, 1H), 2.58 (ddt, J=16.5, 8.4, 4.1 Hz, 1H); MS (ESI) m/z [M+H]$^+$: 433.3.

Example 23

(R)-4-Phenyl-3-(5-(5-(trifluoromethyl)-1,2,4-oxadiazol-3-yl)pyridin-2-yl)oxazolidin-2-one

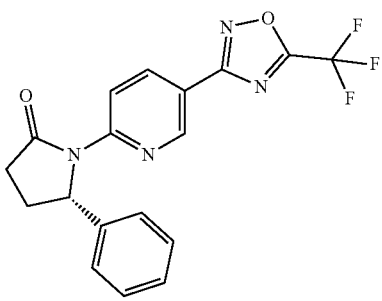 [SMILES: O=C1CC[C@@H](c2ccccc2)N1c1ccc(-c2noc(C(F)(F)F)n2)cn1]

Step A: (R)-6-((2-Hydroxy-1-phenylethyl)amino)nicotinonitrile

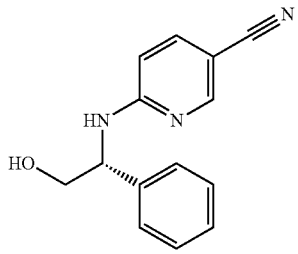 [SMILES: N#Cc1ccc(N[C@@H](CO)c2ccccc2)nc1]

To a stirred solution of (R)-2-amino-2-phenylethanol (500 mg, 3.64 mmol) in N,N-dimethylformamide (8.0 mL) under an atmosphere of nitrogen was added N,N-diisopropyl-N-ethylamine (9.0 mL, 49 mmol) followed by 6-fluoronicotinonitrile (445 mg, 3.64 mmol). The resulting mixture was heated at 105° C. for 20 h, cooled to ambient temperature, diluted with ethyl acetate (40 mL) and washed with water (10 mL×3). The ethyl acetate layer was washed with brine (5 mL), dried over anhydrous magnesium sulfate, filtered and evaporated to dryness in vacuo. The crude residue was purified by flash silica gel chromatography (ISCO CombiFlash Rf Purification System®; 40 g SepaFlash® Silica Flash Column, eluting with a 0-100% ethyl acetate in hexanes gradient) to afford the title compound as a foam. MS (ESI) m/z [M+H]$^+$: 240.2.

Step B: (R,Z)—N'-Hydroxy-6-((2-hydroxy-1-phenylethyl)amino)nicotinimidamide

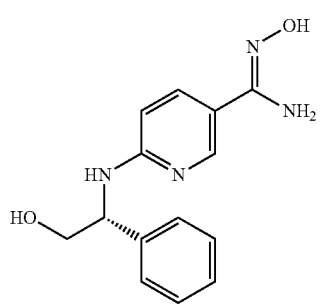 [SMILES: N/C(=N\O)c1ccc(N[C@@H](CO)c2ccccc2)nc1]

To a stirred suspension of (R)-6-((2-hydroxy-1-phenylethyl)amino)nicotinonitrile (722 mg, 3.02 mmol) from Step A above in an ethanol (7.0 mL) and water (3.5 mL) mixture was added a 50% aqueous hydroxylamine solution (0.350 mL, 57.1 mmol). The resulting homogeneous solution was heated at 50° C. for 15 h, cooled to ambient temperature and extracted with ethyl acetate (10 mL×3). The combined ethyl acetate extracts were washed with brine (5 mL), dried over anhydrous magnesium sulfate, filtered and evaporated to dryness in vacuo to afford the title compound as a solid. MS (ESI) m/z [M+H]$^+$: 273.3.

Step C: (R)-2-Phenyl-2-((5-(5-(trifluoromethyl)-1,2,4-oxadiazol-3-yl)pyridin-2-yl)amino)ethan-1-ol

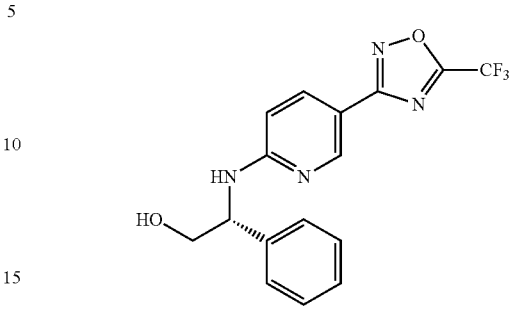

To a stirred suspension of (R,Z)—N'-hydroxy-6-((2-hydroxy-1-phenylethyl)amino)nicotinimidamide (776 mg, 2.85 mmol) from step B above in dichloromethane (15 mL) cooled to 0° C. under an atmosphere of nitrogen was added neat trifluoroacetic anhydride (1.2 mL, 8.6 mmol). The cooling bath was removed and the resulting homogeneous solution was stirred for 20 h with gradual warming to ambient temperature. Neat triethylamine (1.2 mL, 8.6 mmol) was next added in one portion and the resulting solution was allowed to stir for an additional 1 h. The reaction mixture was diluted with a saturated aqueous sodium bicarbonate solution (5 mL) and the layers were separated. The aqueous phase was extracted with dichloromethane (100 mL×2) and the combined extracts were dried over anhydrous magnesium sulfate, filtered and evaporated to dryness in vacuo. The crude residue was purified by flash silica gel chromatography (ISCO CombiFlash Rf Purification System®; 40 g SepaFlash® Silica Flash Column, eluting with a 0-50% ethyl acetate in hexanes gradient) to afford the title compound as a solid. MS (ESI) m/z [M+H]$^+$: 351.1.

Step D: (R)-4-Phenyl-3-(5-(5-(trifluoromethyl)-1,2,4-oxadiazol-3-yl)pyridin-2-yl)oxazolidin-2-one

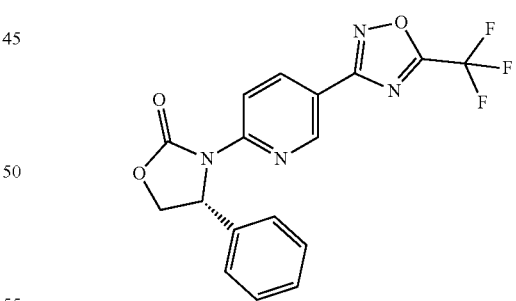

To a stirred suspension of (R)-2-phenyl-2-((5-(5-(trifluoromethyl)-1,2,4-oxadiazol-3-yl)pyridin-2-yl)amino)ethan-1-ol (50 mg, 0.14 mmol) from step C above in dichloromethane (1.0 mL) cooled to 0° C. under an atmosphere of nitrogen was added N,N-carbonyl diimidazole (28 mg, 0.17 mmol), followed by N,N-diisopropyl-N-ethylamine (0.075 mL, 0.43 mmol). The cooling bath was removed and the resulting homogeneous solution was stirred for 3 h with gradual warming to ambient temperature. Neat 1,8-diazabicyclo[5.4.0]undec-7-ene (0.065 mL, 0.43 mmol) was added and the resulting solution was allowed to stir for an additional 1 h then evaporated to dryness in vacuo. The crude residue was purified by flash silica gel chromatography (ISCO CombiFlash Rf Purification System®; 4 g SepaFlash® Silica Flash Column, eluting with a 0-15% ethyl acetate in hexanes gradient) to afford the title compound as a solid. ¹H NMR (600 MHz, Chloroform-d) δ 8.92-8.88 (m, 1H), 8.42 (dd, J=8.9, 0.9 Hz, 1H), 8.35 (dd, J=8.9, 2.3 Hz, 1H), 7.38-7.27 (m, 5H), 5.94 (dd, J=8.8, 4.1 Hz, 1H), 4.84 (t, J=8.7 Hz, 1H), 4.38 (dd, J=8.7, 4.1 Hz, 1H); MS (ESI) m/z [M+H]⁺: 377.2.

Example 24

3-(2-((2-Fluorobenzyl)oxy)pyridin-4-yl)-5-(trifluoromethyl)-1,2,4-oxadiazole

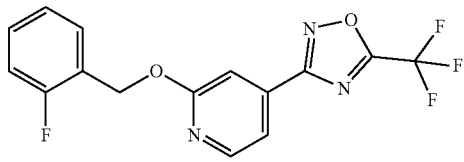 [SMILES: Fc1ccccc1COc1cc(-c2noc(C(F)(F)F)n2)ccn1]

Step A: (Z)—N'-Hydroxy-2-oxo-1,2-dihydropyridine-4-carboximidamide

To a solution of 2-oxo-1,2-dihydropyridine-4-carbonitrile (4.35 g, 36.2 mmol) in EtOH (12 mL) was added 50% hydroxylamine in water (12 mL, 1800 mmol). The reaction was stirred at reflux for 2 h, concentrated and taken on crude.

Step B: 4-(5-(Trifluoromethyl)-1,2,4-oxadiazol-3-yl)pyridin-2(1H)-one

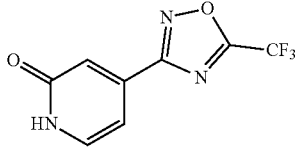 [SMILES: O=c1cc(-c2noc(C(F)(F)F)n2)cc[nH]1]

To a solution of (Z)—N'-hydroxy-2-oxo-1,2-dihydropyridine-4-carboximidamide (5.50 g, 35.9 mmol) in CH₂Cl₂ (180 mL) from step A above was added triethylamine (15 mL, 108 mmol), followed by the dropwise addition of TFAA (15.2 mL, 108 mmol). The reaction was stirred at ambient temperature for 2 h, and then concentrated. The residue was suspended in 5 mL of CH₂Cl₂, filtered, rinsed with CH₂Cl₂, and dried to give the desired product as a powder. MS (ESI) m/z [M+H]⁺: 232.1.

Step C: 3-(2-((2-Fluorobenzyl)oxy)pyridin-4-yl)-5-(trifluoromethyl)-1,2,4-oxadiazole

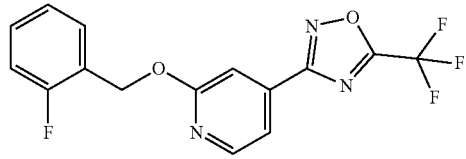 [SMILES: Fc1ccccc1COc1cc(-c2noc(C(F)(F)F)n2)ccn1]

To a suspension of 4-(5-(trifluoromethyl)-1,2,4-oxadiazol-3-yl)pyridin-2(1H)-one (500 mg, 2.16 mmol) from step B above in THF was added (2-fluorophenyl)methanol (546 mg, 4.33 mmol), PS-Ph₃P (1.97 g, 6.49 mmol), and di-tert-butyl azodicarboxylate (747 mg, 3.24 mmol). The reaction was sonicated for 12 h, filtered, concentrated, and chromatographed by prep-HPLC to give the desired product. ¹H NMR (500 MHz, DMSO-d): δ 8.46 (d, J=5.3 Hz, 1H), 7.58-7.62 (m, 2H), 7.43-7.44 (m, 2H), 7.21-7.26 (m, 2H), 5.49 (s, 2H) MS (ESI) m/z [M+H]⁺: 340.1.

Example 25

(S)-6-(Benzo[d]thiazol-2-yl)-1-(4-(5-(trifluoromethyl)-1,2,4-oxadiazol-3-1)phenyl)piperidin-2-one

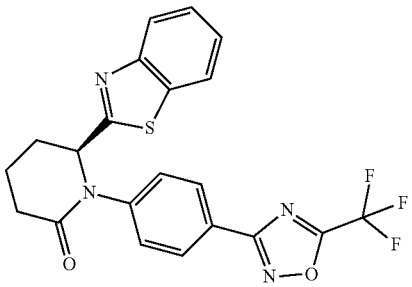 [SMILES: O=C1CCC[C@@H](c2nc3ccccc3s2)N1c1ccc(-c2noc(C(F)(F)F)n2)cc1]

Step B: (S,Z)-1-(4-(N'-Hydroxycarbamimidoyl)phenyl)-6-oxopiperidine-2-carboxylic acid

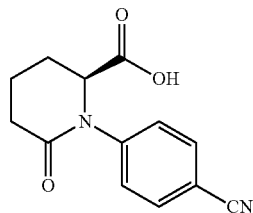 [SMILES: N#Cc1ccc(N2C(=O)CCC[C@H]2C(=O)O)cc1]

Copper (II) acetate (7.61 g, 41.9 mmol) was added to a mixture of (S)-6-oxopiperidine-2-carboxylic acid (3.00 g, 21.0 mmol), (4-cyanophenyl) boronic acid (6.16 g, 41.9 mmol), pyridine (5.09 mL. 62.9 mmol) and triethylamine (8.76 mL, 62.9 mmol) in 1,2-dichlorocthane (100 mL) at 9° C. After the addition was complete, the mixture was stirred at 9° C. for 50 h under O₂ (15 psi) protection. The mixture was concentrated under reduced pressure to give a reside, which was diluted with saturated sodium bicarbonate (300 mL). filtered with diatomaceous earth, and the filtrate was extracted with EtOAc (300 mL×2), the aqueous layer was adjusted to pH 2 with 1N HCl, and then extracted with EtOAc (300 mL×4). The collected organic layers were washed with brine (500 mL) and dried over anhydrous Na₂SO₄. The mixture was filtered and the filtrate was concentrated under reduced pressure to give the title compound as a solid MS (ESI) m/z [M+H]⁺: 245.0.

Step B: (S,Z)-1-(4-(N'-Hydroxycarhamimidoyl)phenyl)-6-oxopiperidine-2-carboxylic acid

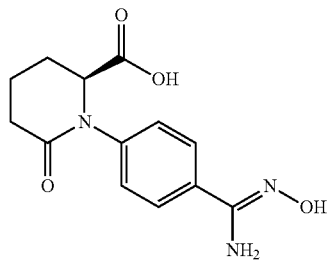 [SMILES: N/C(=N\O)c1ccc(N2C(=O)CCC[C@H]2C(=O)O)cc1]

Hydroxylamine hydrochloride (2.276 g, 32.8 mmol) was added to a mixture of (S)-1-(4-cyanophenyl)-6-oxopiperidine-2-carboxylic acid (4.00 g, 16.4 mmol) and triethylamine (4.57 mL, 32.8 mmol) in ethanol (80 mL) at 10° C. After the addition was complete, the mixture was stirred at 80° C. for 2 h. After cooling to ambient temperature, the mixture was concentrated under reduced pressure to give the title compound as a solid. MS (ESI) m/z [M+H]⁺: 278.0.

Step C: (S)-6-Oxo-1-(4-(5-(trifluoromethyl)-1,2,4-oxadiazol-3-yl)phenyl)piperidine-2-carboxylic acid

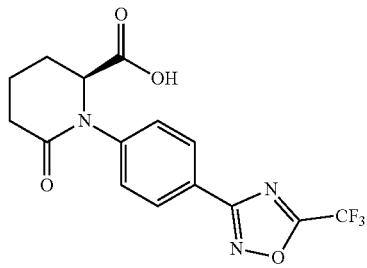 [SMILES: O=C(O)[C@@H]1CCCC(=O)N1c1ccc(-c2noc(C(F)(F)F)n2)cc1]

TFAA (12.53 mL, 89 mmol) was added to a mixture of (S,Z)-1-(4-(N'-hydroxycarbamimidoyl)phenyl)-6-oxopiperidine-2-carboxylic acid (8.2 g, 29.6 mmol) and pyridine (7.18 mL, 89 mmol) in toluene (100 mL) at 10° C. After the addition was complete, the mixture was stirred at 110° C. for 3 h. After cooling to ambient temperature, the mixture was concentrated under reduced pressure to give a residue, which was diluted with EtOAc (100 mL). The organic layer was washed with H₂O (100 mL). The water layer was extracted with EtOAc (100 mL×2). The collected organic layers were washed with brine (100 mL) and dried over anhydrous Na₂SO₄. The mixture was filtered and the filtrate was concentrated under reduced pressure to give a residue. The residue was purified by prep-HPLC (preparative HPLC on a GILSON 281 instrument fitted with a Syneri Polar-RP 100×30 5 um using water and acetonitrile as the eluents. Mobile phase A: water (containing 0.1% TFA, v/v), mobile phase B: acetonitrile. Gradient: 35-65% B, 0-10 min; 100% B, 10.5-12.5 min; 5% B, 13-15 min) to give the title compound as a solid. MS (ESI) m/z [M+H]⁺: 356.0.

Step D: (S)-6-(Benzo[d]thiazol-2-yl)-1-(4-(5-(trifluoromethyl)-1,2,4-oxadiazol-3-yl)phenyl)piperidin-2-one

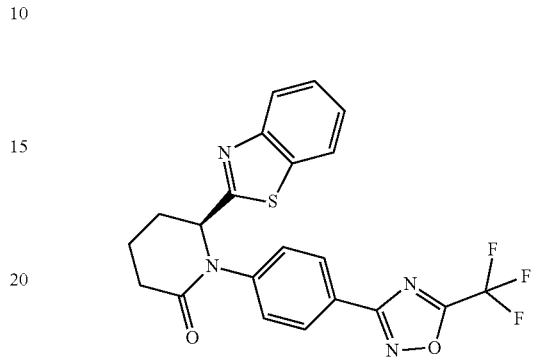

Diisopropylethylamine (157.0 µl, 0.901 mmol) was added to a stirred mixture of (S)-6-oxo-1-(4-(5-(trifluoromethyl)-1,2,4-oxadiazol-3-yl)phenyl)piperidine-2-carboxylic acid (0.16 g, 0.450 mmol), 2-aminobenzenethiol (85.0 mg, 0.676 mmol) and propylphosphonic anhydride solution (0.573 g, 0.901 mmol) (50% in EtOAc). The mixture was heated at 100° C. by microwave for 10 min. The resulting mixture was extracted with ethyl acetate (30 mL×2). The combined organic layers were washed with brine (20 mL), dried over Na₂SO₄, filtered, and concentrated in vacuo. The residue was purified by reverse-phase prep-HPLC (preparative HPLC on a GILSON 281 instrument fitted with a Phenomenex Synergi C18 250×21.2 mm×4 um using water and acetonitrile as the eluents. Mobile phase A: water, mobile phase B: acetonitrile (containing: 0.1% TFA-ACN). Gradient: 34-64%, 0-10 min; 100% B, 10.5-12.5 min; 5% B, 13-15 min) to give the (S)-6-(benzo[d]thiazol-2-yl)-1-(4-(5-(trifluoromethyl)-1,2,4-oxadiazol-3-yl)phenyl)piperidin-2-one as an oil. ¹H NMR (400 MHz, CD₃OD): δ 1.92-2.05 (m, 1H) 2.11 (br s, 1H) 2.33-2.45 (m, 1H) 2.53-2.83 (m, 3H) 5.72 (t, J=5.1 Hz, 1H) 7.37-7.44 (m, 1H) 7.46-7.52 (m, 1H) 7.55 (d, J=8.6 Hz, 2H) 7.94 (t, J=7.7 Hz, 2H) 8.05 (d, J=8.8 Hz, 2H); ESI-MS m/z [M+H⁺]: 445.2.

Example 26

N-((1R,2S)-2-Phenylcyclohexyl)-5-(5-(trifluoromethyl)-1,2,4-oxadiazol-3-yl)pyridin-2-amine

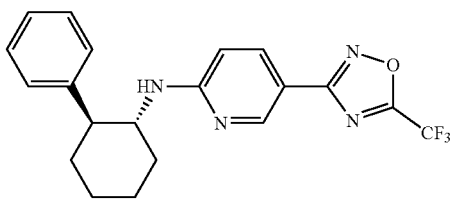 [SMILES: FC(F)(F)c1nc(-c2ccc(N[C@@H]3CCCC[C@H]3c3ccccc3)nc2)no1]

Step A: 6-(((1R,2S)-2-Phenylcyclohexyl)amino)nicotinonitrile

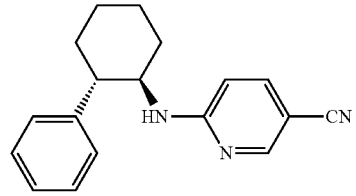 [SMILES: N#Cc1ccc(N[C@@H]2CCCC[C@H]2c2ccccc2)nc1]

A mixture of (1R,2S)-2-phenylcyclohexanamine (300 mg, 1.71 mmol), 6-fluoronicotinonitrile (230 mg, 1.88 mmol) and diisopropylethylamine (0.598 mL, 3.42 mmol) in DMSO (7 mL) was stirred at 120° C. for 16 h. The mixture was cooled to ambient temperature and ACN (3 mL) was added and the mixture was purified by reverse-phase prep-HPLC (preparative HPLC on a GILSON 281 instrument fitted with a Waters XSELECT C18 150×30 mm×5 um using water and acetonitrile as the eluents. Mobile phase A: water (0.1% TFA)-ACN, mobile phase B: acetonitrile. Gradient: 40-60%, 0-10 min; 100% B, 10.5-12.5 min; 5% B, 13-15 min) to give 6-(((1R,2S)-2-phenylcyclohexyl)amino)nicotinonitrile as a solid. MS (ESI) m/z [M+H]$^+$: 278.1.

Step B: N-Hydroxy-6-(((1R,2S)-2-phenylcyclohexyl)amino)nicotinimidamide

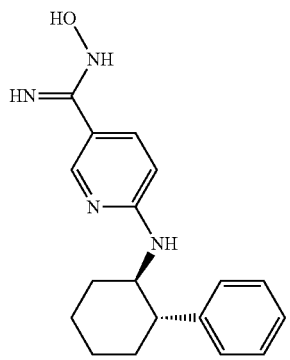 [SMILES: N=C(NO)c1ccc(N[C@@H]2CCCC[C@H]2c2ccccc2)nc1]

A mixture of 6-(((1R,2S)-2-phenylcyclohexyl)amino)nicotinonitrile (400 mg, 1.44 mmol), hydroxylamine hydrochloride (251 mg, 3.61 mmol) and triethylamine (0.704 mL, 5.05 mmol) in EtOH (10 mL) was stirred at 80° C. for 3 h. After cooling to ambient temperature, the mixture was concentrated under reduced pressure to give a residue, which was diluted with H$_2$O (20 mL). The water layer was extracted with EtOAc (30 mL×3). The collected organic layers were washed with brine (25 mL) and dried over anhydrous Na$_2$SO$_4$. The mixture was filtered and the filtrate was concentrated under reduced pressure to give N-hydroxy-6-(((1R,2S)-2-phenylcyclohexyl)amino)nicotinimidamide as a solid. MS (ESI) m/z [M+H]$^+$: 310.9.

Step C: 2,2,2-Trifluoro-N-((1R,2S)-2-phenylcyclohexyl)-N-(5-(5-(trifluoromethyl)-1,2,4-oxadiazol-3-yl)pyridin-2-yl)acetamide

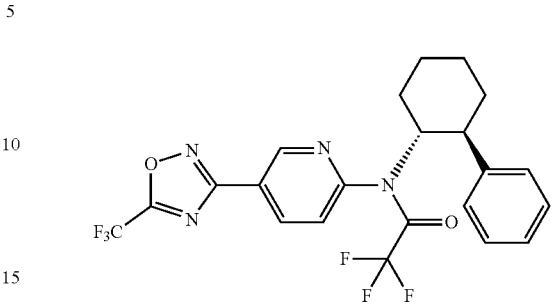

A mixture of TFAA (0.137 mL, 0.967 mmol), pyridine (0.078 mL, 0.967 mmol) and N-hydroxy-6-(((1R,2S)-2-phenylcyclohexyl)amino)nicotinimidamide (100 mg, 0.322 mmol) in toluene (3 mL) was stirred at 7° C. for 1 h and stirred at 120° C. for 3 h. After cooling to ambient temperature, the mixture was concentrated under reduced pressure. The residue was purified by reverse-phase prep-HPLC (preparative HPLC on a GILSON 281 instrument fitted with a Phenomenex Synergi C18 250×21.2 mm×4 um using water and acetonitrile as the eluents. Mobile phase A: water (containing water (0.1% TFA)-ACN, v/v), mobile phase B: acetonitrile. Gradient: 61-91% B, 0-10 min; 100% B, 10.5-12.5 min; 5% B, 13-15 min) to give 2,2,2-trifluoro-N-((1R,2S)-2-phenylcyclohexyl)-N-(5-(5-(trifluoromethyl)-1,2,4-oxadiazol-3-yl)pyridin-2-yl)acetamide as an oil. MS (ESI) m/z [M+H]$^+$: 485.2.

Step D: N-((1R,2S)-2-Phenylcyclohexyl)-5-(5-(trifluoromethyl)-1,2,4-oxadiazol-3-yl)pyridin-2-amine

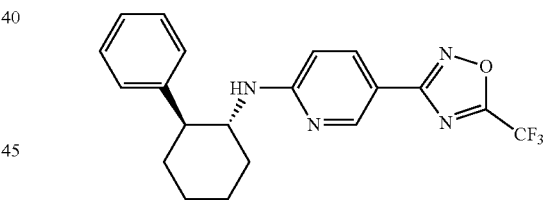

A solution of 2,2,2-trifluoro-N-((1R,2S)-2-phenylcyclohexyl)-N-(5-(5-(trifluoromethyl)-1,2,4-oxadiazol-3-yl)pyridin-2-yl)acetamide (165 mg, 0.341 mmol) and potassium carbonate (141 mg, 1.022 mmol) in ACN (2 mL) and MeOH (0.5 mL) was stirred at 15° C. for 2 h. To the residue was added ACN (3 mL) and the mixture was filtered and purified by reverse-phase prep-HPLC (preparative HPLC on a GILSON 281 instrument fitted with a Phenomenex Synergi C18 250×21.2 mm×4 um using water and acetonitrile as the eluents. Mobile phase A: water (0.1% TFA)-ACN, mobile phase B: acetonitrile. Gradient: 35-65%, 0-10 min; 100% B, 10.5-12.5 min; 5% B, 13-15 min) to give N-((1R,2S)-2-phenylcyclohexyl)-5-(5-(trifluoromethyl)-1,2,4-oxadiazol-3-yl)pyridin-2-amine as a solid. $^1$H NMR (400 MHz, CD$_3$OD) δ ppm 1.41-1.69 (m, 3H) 1.76 (q, J=12.8 Hz, 1H) 1.85-2.04 (m, 3H) 2.21 (br d, J=14.11 Hz, 1H) 2.63-2.73 (m, 1H) 3.96-4.05 (m, 1H) 6.83 (br d, J=9.0 Hz, 1H) 7.03-7.14 (m, 1H) 7.18-7.25 (m, 2H) 7.25-7.31 (m, 2H) 8.13 (br d, J=9.5 Hz, 1H) 8.32 (s, 1H); MS (ESI) m/z [M+H]$^+$: 389.2.

Example 27

N-(Pyridin-2-yl)-N-(4-(5-(trifluoromethyl)-1,2,4-oxadiazol-3-yl)benzyl)pyridin-2-amine

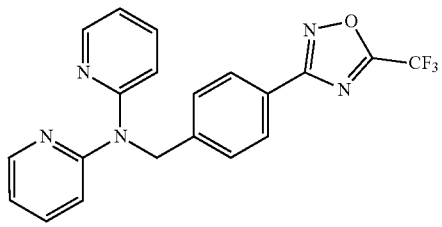 [SMILES: FC(F)(F)c1nc(-c2ccc(CN(c3ccccn3)c3ccccn3)cc2)no1]

Step A:
4-((Di(pyridin-2-yl)amino)methyl)benzonitrile

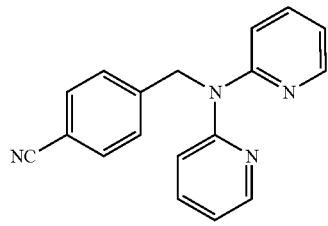 [SMILES: N#Cc1ccc(CN(c2ccccn2)c2ccccn2)cc1]

A mixture of sodium 2-methylpropan-2-olate (291 mg, 3.03 mmol), 2,2'-bis(diphenylphosphino)-1,1'-binaphthyl (188 mg, 0.303 mmol), 4-(aminomethyl)benzonitrile (200 mg, 1.513 mmol), 2-bromopyridine (956 mg, 6.05 mmol) and $Pd_2(dba)_3$ (139 mg, 0.151 mmol) in toluene (10 mL) was stirred at 110° C. for 16 h. After cooling to ambient temperature, the mixture was concentrated under reduced pressure to give a residue, which was diluted with $H_2O$ (50 mL). The water layer was extracted with EtOAc (30 mL×2). The collected organic layers were washed with brine (30 mL) and dried over anhydrous $Na_2SO_4$. The mixture was filtered and the filtrate was concentrated under reduced pressure. The residue was purified by reverse-phase prep-HPLC (preparative HPLC on a GILSON 281 instrument fitted with Phenomenex Synergi C18 250×21.2 mm×4 um using water and acetonitrile as the eluents. Mobile phase A: water, mobile phase B: acetonitrile (containing: 0.1% TFA-ACN). Gradient: 28-58%, 0-min; 100% B, 10.5-12.5 min; 5% B, 13-15 min) to give 4-((di(pyridin-2-yl)amino)methyl)benzonitrile as an oil. ESI-MS m/z [M+H]⁺: 287.1.

Step B: (Z)-4-((Di(pyridin-2-yl)amino)methyl)-N'-hydroxybenzimidamide

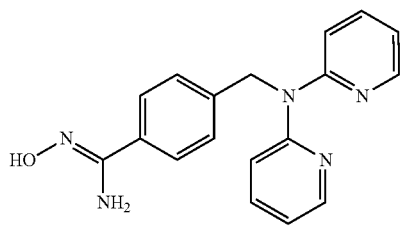 [SMILES: N/C(=N\O)c1ccc(CN(c2ccccn2)c2ccccn2)cc1]

A mixture of 4-((di(pyridin-2-yl)amino)methyl)benzonitrile (120 mg, 0.419 mmol), hydroxylamine hydrochloride (58.2 mg, 0.838 mmol) and triethylamine (0.117 mL, 0.838 mmol) in EtOH (5 mL) was stirred at 80° C. for 16 h. After cooling to ambient temperature, the mixture was concentrated under reduced pressure to give a residue, which was diluted with $H_2O$ (30 mL). The water layer was extracted with EtOAc (20 mL×2). The collected organic layers were washed with brine (20 mL) and dried over anhydrous $Na_2SO_4$. The mixture was filtered and the filtrate was concentrated under reduced pressure to give (Z)-4-((di(pyridin-2-yl)amino)methyl)-N'-hydroxybenzimidamide as an oil. ESI-MS m/z [M+H]⁺: 320.1.

Step C: N-(Pyridin-2-yl)-N-(4-(5-(trifluoromethyl)-1,2,4-oxadiazol-3-yl)benzyl)pyridin-2-amine A mixture of TFAA (0.761 mL, 5.39 mmol), pyridine (0.087 mL, 1.077 mmol) and (Z)-4-((di(pyridin-2-yl)amino)methyl)-N'-hydroxybenzimidamide (172 mg, 0.539 mmol) in toluene (5 mL) was stirred at 110° C. for 16 h. After cooling to ambient temperature, the mixture was concentrated under reduced pressure to give a residue, which was diluted with $H_2O$ (30 mL). The water layer was extracted with EtOAc (20 mL×2). The collected organic layers were washed with brine (20 mL) and dried over anhydrous $Na_2SO_4$. The mixture was filtered and the filtrate was concentrated under reduced pressure. The residue was purified by reverse-phase prep-HPLC (preparative HPLC on a GILSON 281 instrument fitted with Phenomenex Synergi C18 250×21.2 mm×4 um using water and acetonitrile as the eluents. Mobile phase A: water, mobile phase B: acetonitrile (containing: 0.1% TFA-ACN). Gradient: 32-62%, 0-10 min; 100% B, 10.5-12.5 min; 5% B, 13-15 min) to give N-(pyridin-2-yl)-N-(4-(5-(trifluoromethyl)-1,2,4-oxadiazol-3-yl)benzyl)pyridin-2-amine as an oil. ¹H NMR (400 MHz, $CD_3OD$): δ ppm 8.44 (br d, J=4.3 Hz, 2H), 8.10 (br d, J=8.6 Hz, 2H), 7.96-8.06 (m, 2H), 7.57 (br d, J=8.22 Hz, 2H), 7.38 (br d, J=8.6 Hz, 2H), 7.23-7.33 (m, 2H), 5.57 (s, 2H); ESI-MS m/z [M+H]⁺: 398.1.

Example 28

1-(4-(5-(Trifluoromethyl)-1,2,4-oxadiazol-3-yl)benzyl)quinolin-2(1H)-one

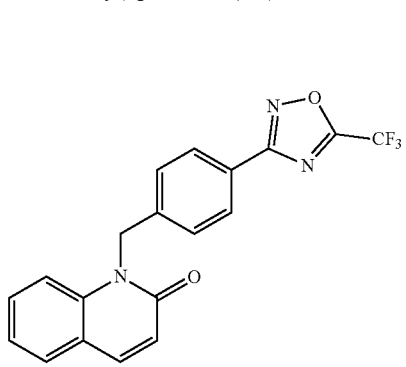

Step A: 4-((2-Oxoquinolin-1(2H)-yl)methyl)benzonitrile

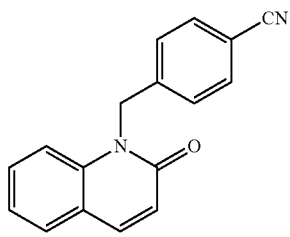 [SMILES: N#Cc1ccc(Cn2c(=O)ccc3ccccc32)cc1]

Sodium hydride (124 mg, 3.10 mmol) (60% in mineral oil) was added to a mixture of quinolin-2-ol (300 mg, 2.067 mmol) in DMF (10 mL) at 0° C., and the mixture was stirred at 0° C. for 30 min. 4-(Bromomethyl)benzonitrile (405 mg, 2.067 mmol) was added thereto all at once, and the resulting mixture was stirred at 0° C. for 3 h. The mixture was quenched with saturated aqueous ammonium chloride (50 mL) and extracted with EtOAc (50 mL×3). The combined organic layers were washed with brine (50 mL×3) and dried over anhydrous Na$_2$SO$_4$. The mixture was filtered and the filtrate was concentrated under reduced pressure to give a residue. The residue was purified by pre-HPLC (preparative HPLC on a GILSON 281 instrument fitted with a Waters XSELECT C18 150×30 mm×5 um using water and acetonitrile as the eluents. Mobile phase A: water (containing 0.1% TFA, v/v), mobile phase B: acetonitrile. Gradient: 43-63% B, 0-10 min; 100% B, 10.5-12.5 min; 5% B, 13-15 min) to give 4-((2-oxoquinolin-1(2H)-yl)methyl)benzonitrile and 4-((quinolin-2-yloxy)methyl)benzonitrile as solids. MS (ESI) m/z [M+H]$^+$: 261.0.

Step B: (Z)—N'-Hydroxy-4-((2-oxoquinolin-1(2H)-yl)methyl)benzimidamide

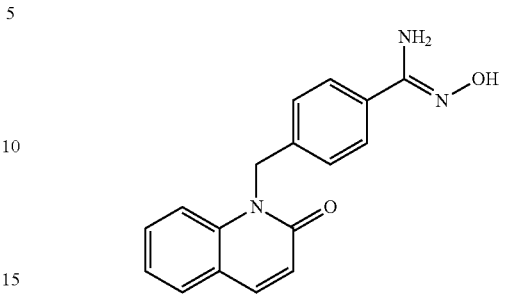

Hydroxylamine hydrochloride (107 mg, 1.537 mmol) was added to a mixture of 4-((2-oxoquinolin-1(2H)-yl)methyl)benzonitrile (200 mg, 0.768 mmol) and triethylamine (0.214 mL, 1.537 mmol) in EtOH (8 mL) at 8° C. After the addition was complete, the mixture was stirred at 80° C. for 2 h. The reaction mixture was cooled to ambient temperature and concentrated under reduced pressure to give a residue, which was diluted with H$_2$O (20 mL). The water layer was extracted with EtOAc (20 mL×3), the combined organic layers were washed with brine (20 mL) and dried over anhydrous Na$_2$SO$_4$. The mixture was filtered and the filtrate was concentrated under reduced pressure to give (Z)—N'-hydroxy-4-((2-oxoquinolin-1(2H)-yl)methyl)benzimidamide as a solid. MS (ESI) m/z [M+H]$^+$: 293.9.

Step C: 1-(4-(5-(Trifluoromethyl)-1,2,4-oxadiazol-3-yl)benzyl)quinolin-2(1H)-one

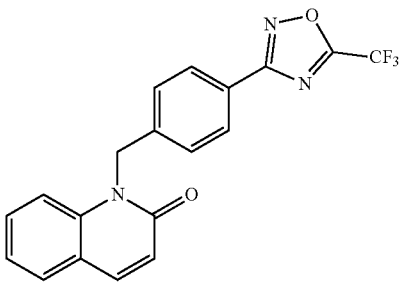 [SMILES: O=c1ccc2ccccc2n1Cc1ccc(-c2noc(C(F)(F)F)n2)cc1]

To a mixture of (Z)—N'-hydroxy-4-((2-oxoquinolin-1(2H)-yl)methyl)benzimidamide (236 mg, 0.805 mmol) and pyridine (0.195 mL, 2.41 mmol) in anhydrous toluene (10 mL) was added TFAA (0.341 mL, 2.41 mmol) at 0° C., and the resulting mixture was stirred at 110° C. for 2 h. After the starting material was consumed completely, the mixture was concentrated under reduced pressure to give a residue, which was diluted with H$_2$O (20 mL). The water layer was extracted with EtOAc (20 mL×2). The combined organic layers were washed with brine (20 mL) and dried over anhydrous Na$_2$SO$_4$. The mixture was filtered and the filtrate was concentrated under reduced pressure. The residue was purified by pre-HPLC (preparative HPLC on a GILSON 281 instrument fitted with a Phenomenex Synergi C18 250×21.2 mm×4 um using water and acetonitrile as the eluents. Mobile phase A: water (containing 0.1% TFA, v/v), mobile phase B: acetonitrile. Gradient: 45-75% B, 0-10 min; 100% B, 10.5-12.5 min; 5% B, 13-15 min) to give 1-(4-(5-

(trifluoromethyl)-1,2,4-oxadiazol-3-yl)benzyl)quinolin-2 (1H)-one as a solid. $^1$H NMR (400 MHz, CD$_3$OD): δ ppm 8.00-8.09 (m, 3H) 7.74 (br d, J=7.7 Hz, 1H) 7.50-7.56 (m, 1H) 7.38-7.44 (m, 3H) 7.29 (br t, J=7.4 Hz, 1H) 6.80 (d, J=9.5 Hz, 1H) 5.71 (br s, 2H) MS (ESI) m/z [M+H]$^+$: 372.0.

Example 29

3-(3-Fluoro-4-((5-fluoro-2-methyl-1H-benzo[d]imidazol-1-yl)methyl)phenyl)-5-(trifluoromethyl)-1,2,4-oxadiazole

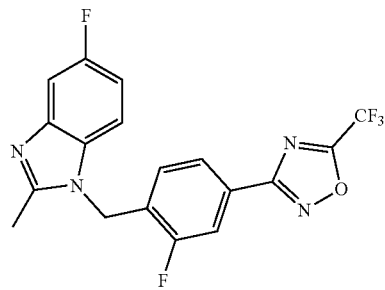 [SMILES: Cc1nc2cc(F)ccc2n1Cc1ccc(-c2noc(C(F)(F)F)n2)cc1F]

Step A: 5-Fluoro-2-methyl-1H-benzo[d]imidazole

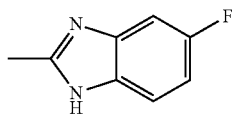

A mixture of 1,1,1-trimethoxyethane (19.0 g, 159 mmol) and 4-fluorobenzene-1,2-diamine (2.00 g, 15.9 mmol) in MeOH (10 mL) was stirred at 60° C. for 12 h. After cooling to ambient temperature, the mixture was concentrated. The residue was purified by flash silica gel chromatography (ISCO®; 40 g SepaFlash® Silica Flash Column, Eluent of 50-100% EA/PE gradient @ 40 mL/min) to give 5-fluoro-2-methyl-1H-benzo[d]imidazole as a solid.

Step B: 3-Fluoro-4-((5-fluoro-2-methyl-1H-benzo[d]imidazol-1-yl)methyl)benzonitrile

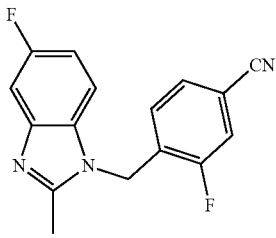 [SMILES: Cc1nc2cc(F)ccc2n1Cc1ccc(C#N)cc1F]

A mixture of 4-(bromomethyl)-3-fluorobenzonitrile (499 mg, 2.33 mmol) and 5-fluoro-2-methyl-1H-benzo[d]imidazole (350 mg, 2.33 mmol) in DMF (15 mL) was stirred at 16° C. for 16 h. The mixture was washed with water (50 mL) and extracted with EtOAc (3×30 mL). The collected organic layers were washed with brine (30 mL) and dried over anhydrous Na$_2$SO$_4$. The mixture was filtered and the filtrate was concentrated to get the crude product. The crude product was purified by reverse-phase Prep-HPLC (preparative HPLC on a GILSON 281 instrument fitted with Phenomenex Synergi C18 250×21.2 mm×4 um using water and acetonitrile as the eluents. Mobile phase A: water, mobile phase B: acetonitrile (containing: 0.1% TFA-ACN). Gradient: 35-65%, 0-10 min; 100% B, 10.5-12.5 min; 5% B, 13-15 min) to give 3-fluoro-4-((5-fluoro-2-methyl-1H-benzo[d]imidazol-1-yl)methyl)benzonitrile as an oil. ESI-MS m/z [M+H]$^+$: 284.0.

Step C: (Z)-3-Fluoro-4-((5-fluoro-2-methyl-1H-benzo[d]imidazol-1-yl)methyl)-N'-hydroxybenzimidamide

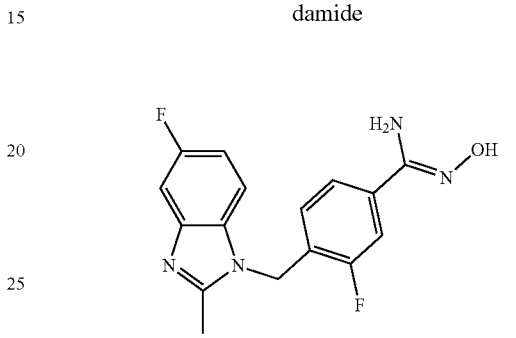

A mixture of 3-fluoro-4-((5-fluoro-2-methyl-1H-benzo[d]imidazol-1-yl)methyl)benzonitrile (260 mg, 0.918 mmol), hydroxylamine hydrochloride (128 mg, 1.84 mmol) and triethylamine (0.256 mL, 1.84 mmol) in EtOH (10 mL) was stirred at 80° C. for 2 h. After cooling to ambient temperature, the mixture was concentrated under reduced pressure to give a residue, which was diluted with H$_2$O (50 mL). The water layer was extracted with EtOAc (30 mL×2). The collected organic layers were washed with brine (20 mL) and dried over anhydrous Na$_2$SO$_4$. The mixture was filtered and the filtrate was concentrated under reduced pressure to give (Z)-3-fluoro-4-((5-fluoro-2-methyl-1H-benzo[d]imidazol-1-yl)methyl)-N'-hydroxybenzimidamide as an oil. ESI-MS m/z [M+H]$^+$: 317.1.

Step D: 3-(3-Fluoro-4-((5-fluoro-2-methyl-1H-benzo[d]imidazol-1-yl)methyl)phenyl)-5-(trifluoromethyl)-1,2,4-oxadiazole

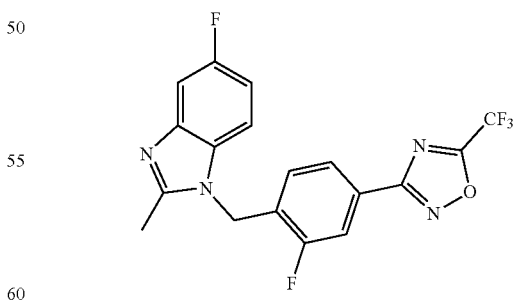

A mixture of potassium carbonate (135 mg, 0.979 mmol), (Z)-3-fluoro-4-((5-fluoro-2-methyl-1H-benzo[d]imidazol-1-yl)methyl)-N'-hydroxybenzimidamide (258 mg, 0.816 mmol) and methyl 2,2,2-trifluoroacetate (209 mg, 1.631 mmol) in toluene (5 mL) and DMF (0.5 mL) was stirred at 80° C. for 16 h. After cooling to ambient temperature, the mixture was concentrated. The residue was purified by reverse-phase Prep-HPLC (preparative HPLC on a GILSON 281 instrument fitted with Phenomenex Synergi C18 250× 21.2 mm×4 um using water and acetonitrile as the eluents. Mobile phase A: water, mobile phase B: acetonitrile (containing: 0.1% TFA-ACN). Gradient: 25-55%, 0-10 min; 100% B, 10.5-12.5 min; 5% B, 13-15 min) to give crude product. Further purification was done via chiral HPLC separation (Column: OD(250 mm×30 mm, 5 um), Condition: Base-EtOH, Begin B: 20%, End B: 20%, FlowRate (mL/min): 60) to give 3-(3-fluoro-4-((5-fluoro-2-methyl-1H-benzo[d]imidazol-1-yl)methyl)phenyl)-5-(trifluoromethyl)-1,2,4-oxadiazole as an oil. $^1$H NMR (400 MHz, CD$_3$OD): δ ppm 7.85-7.95 (m, 2H), 7.39-7.47 (m, 1H), 7.28-7.35 (m, 1H), 7.11-7.24 (m, 1H), 6.96-7.10 (m, 1H), 5.65 (s, 2H), 2.65 (s, 3H); ESI-MS m/z [M+H]$^+$: 395.0.

Example 30

N-(4-(5-(Trifluoromethyl)-1,2,4-oxadiazol-3-yl)benzyl)-N-(3-(trifluoromethyl)phenyl)tetrahydro-2H-thiopyran-4-carboxamide 1,1-dioxide

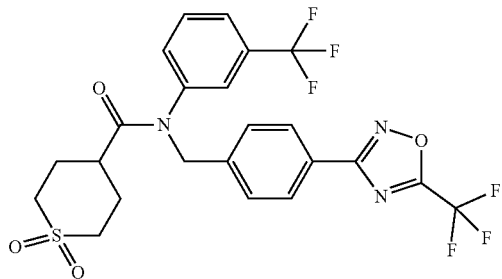 [SMILES: O=C(C1CCS(=O)(=O)CC1)N(Cc1ccc(-c2noc(C(F)(F)F)n2)cc1)c1cccc(C(F)(F)F)c1]

Step A: tert-Butyl 4-cyanobenzyl(3-(trifluoromethyl)phenyl)carbamate

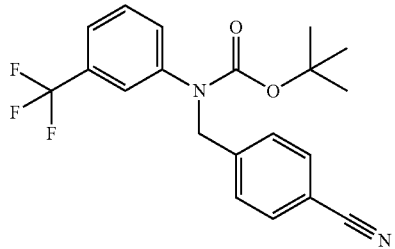 [SMILES: CC(C)(C)OC(=O)N(Cc1ccc(C#N)cc1)c1cccc(C(F)(F)F)c1]

To a stirred solution of tert-butyl(3-(trifluoromethyl)phenyl)carbamate (2.00 g, 7.66 mmol) in anhydrous DMF (15 mL) at 0° C. under an atmosphere of nitrogen was added sodium hydride (60 wt %, 398 mg, 9.95 mmol). The resulting mixture was stirred at 0° C. for 0.5 h, then 4-cyanobenzyl bromide was added slowly and the solution warmed to ambient temperature for 18 h. The reaction mixture was quenched with water (100 mL) and extracted with diethyl ether (50 mL×3). The combined diethyl ether extracts were dried over anhydrous sodium sulfate, filtered and evaporated to dryness in vacuo. The residue was purified by flash silica gel chromatography (ISCO CombiFlash Rf Purification System®; 120 g SepaFlash® Silica Flash Column, eluting with a 0-50% ethyl acetate in hexanes gradient) to afford the title compound as a solid.

Step B: tert-Butyl(Z)-(4-(N'-hydroxycarbamimidoyl)benzyl)(3-(trifluoromethyl)phenyl)carbamate

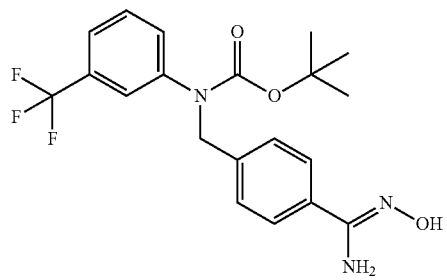

To a stirred suspension of tert-butyl 4-cyanobenzyl(3-(trifluoromethyl)phenyl)carbamate (2.43 g, 6.46 mmol) from Step A above in ethanol (15 mL) was added a 50% aqueous hydroxylamine solution (14.6 mL, 239 mmol). The resulting solution was heated at 50° C. for 3 h, cooled to ambient temperature, poured onto water (100 mL), and extracted with ethyl acetate (50 mL×3). The combined ethyl acetate extracts were dried over anhydrous sodium sulfate, filtered and evaporated to dryness in vacuo to afford the title compound as an oil. MS (ESI) m/z [M+H]$^+$: 410.4.

Step C: tert-Butyl-4-(5-(trifluoromethyl)-1,2,4-oxadiazol-3-yl)benzyl(3-(trifluoromethyl)phenyl)carbamate

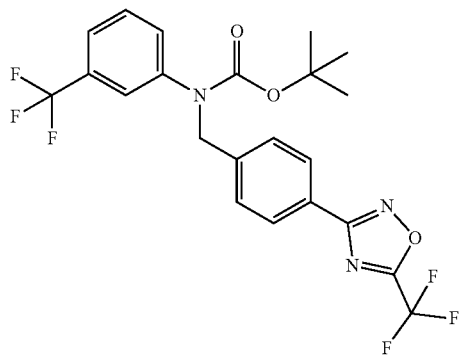 [SMILES: CC(C)(C)OC(=O)N(Cc1ccc(-c2noc(C(F)(F)F)n2)cc1)c1cccc(C(F)(F)F)c1]

To a stirred suspension of tert-butyl(Z)-(4-(N'-hydroxycarbamimidoyl)benzyl)(3-(trifluoromethyl)phenyl)carbamate (2.64 g, 6.45 mmol) from step B above and triethylamine (2.70 mL, 19.4 mmol) in dichloromethane (25 mL) cooled to 0° C. was added neat trifluoroacetic anhydride (1.37 mL, 9.67 mmol) dropwise. The cooling bath was removed and the resulting solution was stirred for 3 h. Additional triethylamine (2.70 mL, 19.4 mmol) and trifluoroacetic anhydride (1.37 mL, 9.67 mmol) were added and the resulting solution stirred for an additional 21 h. Additional trifluoroacetic anhydride (0.195 mL, 0.846 mmol) was added in one portion and the resulting solution was stirred for an additional 1 h. The reaction mixture was evaporated to dryness in vacuo and the crude residue purified by flash silica gel chromatography (ISCO CombiFlash Rf Purification System®; 120 g SepaFlash® Silica Flash Column, eluting with a 0-60% ethyl acetate in hexanes gradient) to afford the title compound as an oil.

Step D: 3-(Trifluoromethyl)-N-(4-(5-(trifluoromethyl)-1,2,4-oxadiazol-3-yl)benzyl)aniline hydrochloride

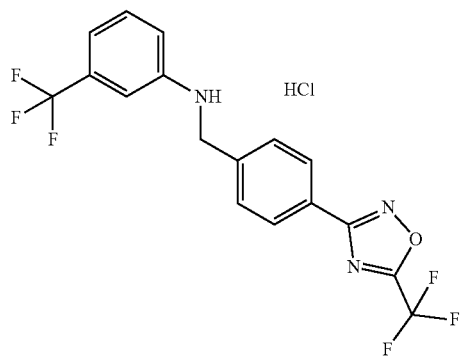 [SMILES: FC(F)(F)c1cccc(NCc2ccc(-c3noc(C(F)(F)F)n3)cc2)c1 ; Cl]

A suspension of tert-butyl 4-(5-(trifluoromethyl)-1,2,4-oxadiazol-3-yl)benzyl(3-(trifluoromethyl)phenyl)carbamate (2.24 g, 4.60 mmol) from step C above and 4M HCl in dioxane (11.5 mL, 46.0 mmol) was stirred for 3 h. The suspension was evaporated to dryness in vacuo to afford the title compound as a solid. MS (ESI) m/z [M+H]$^+$: 388.3.

Step E: N-(4-(5-(Trifluoromethyl)-1,2,4-oxadiazol-3-yl)benzyl)-N-(3-(trifluoromethyl)phenyl)tetrahydro-2H-thiopyran-4-carboxamide 1,1-dioxide

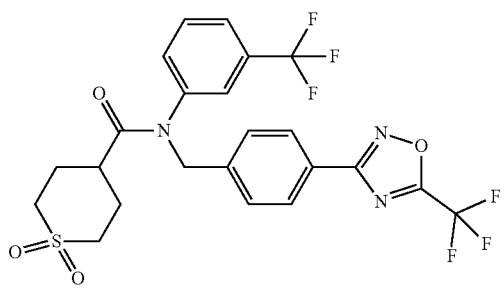 [SMILES: O=C(C1CCS(=O)(=O)CC1)N(Cc1ccc(-c2noc(C(F)(F)F)n2)cc1)c1cccc(C(F)(F)F)c1]

To a solution of 3-(trifluoromethyl)-N-(4-(5-(trifluoromethyl)-1,2,4-oxadiazol-3-yl)benzyl)aniline hydrochloride (65.0 mg, 0.168 mmol) from step D above and tetrahydro-2H-thiopyran-4-carboxylic acid 1,1-dioxide (35.9 mg, 0.201 mmol) in pyridine (1 mL) was added phosphorous oxychloride (47.0 µL, 0.504 mmol) and the mixture was stirred for 1.5 h. Additional phosphorous oxychloride (15.0 µL, 0.161 mmol) was added and stirring continued an additional 1 h. The reaction mixture was diluted with DMF (1 mL) and purified on a Gilson HPLC (YMC Pro C18 column, eluting with a 20-95% acetonitrile in water gradient containing a 0.1% TFA modifier) to afford the title compound as a solid. $^1$H NMR (600 MHz, CDCl$_3$): δ8.06 (d, J=8.3 Hz, 2H), 7.69 (d, J=7.8 Hz, 1H), 7.55 (t, J=8.1 Hz, 1H), 7.31 (d, J=7.8 Hz, 2H), 7.15 (d, J=7.8 Hz, 2H), 4.95 (s, 2H), 4.00-3.65 (m, 1H), 3.34-3.33 (m, 2H), 2.81-2.76 (m, 2H), 2.43-2.39 (m, 2H), 2.13-2.02 (m, 2H); MS (ESI) m/z [M+H]$^+$: 548.3.

Example 31

3-(3-Fluoro-5-(2-fluorobenzyl)pyridin-2-yl)-5-(trifluoromethyl)-1,2,4-oxadiazole

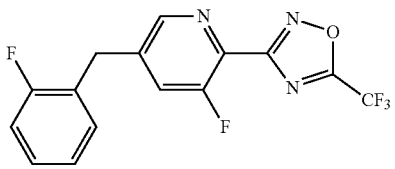 [SMILES: Fc1ccccc1Cc1cnc(-c2noc(C(F)(F)F)n2)c(F)c1]

Step A: (Z)-3-Fluoro-5-(2-fluorobenzyl)-N'-hydroxypicolinimidamide

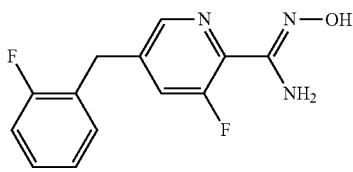

To a solution of 5-bromo-3-fluoropicolinonitrile (25 mg, 0.125 mmol) in THF (0.5 mL) at ambient temperature was added 2-fluorobenzylzinc chloride (0.50 M in THF, 0.50 mL, 0.25 mmol) followed by chloro[(tri-tert-butylphosphine)-2-(2-aminobiphenyl)]palladium(II) (6.4 mg, 0.013 mmol) and potassium acetate (6.1 mg, 0.063 mmol). The mixture was sealed under N$_2$ and heated at 50° C. for 16 h. After cooling to ambient temperature the solution was diluted with hydroxylamine (50% aq., 0.58 mL, 9.4 mmol) and ethanol (0.50 mL) and then heated at 80° C. for 3 h. The resulting mixture was diluted with ethyl acetate (3 mL), filtered through celite (SPE cartridge, 1 g) and concentrated to afford the crude title compound. MS (ESI) m/z [M+H]$^+$: 264.1.

Step B: 3-(3-Fluoro-5-(2-fluorobenzyl)pyridin-2-yl)-5-(trifluoromethyl)-1,2,4-oxadiazole

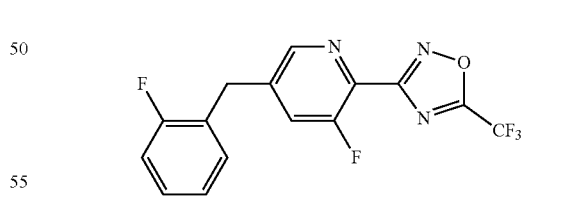

To a solution of (Z)-3-fluoro-5-(2-fluorobenzyl)-N'-hydroxypicolinimidamide (crude, 0.125 mmol) in CH$_2$Cl$_2$ (1 mL) at ambient temperature was added trifluoroacetic anhydride (71 L, 0.50 mmol) and triethylamine (70 µL, 0.50 mmol). The mixture was stirred at ambient temperature overnight and then concentrated. The mixture was then purified by prep-HPLC to give the title compound as a solid. $^1$H NMR (500 MHz, d$^6$-DMSO): δ 8.62 (s, 1H), 7.90 (d, J=11.2 Hz, 1H), 7.43 (m, 1H), 7.34 (m, 1H), 7.25-7.16 (m, 2H), 4.19 (s, 2H). MS (ESI) m/z [M+H]$^+$: 342.1.

Example 32

N-(4-(5-(Trifluoromethyl)-1,2,4-oxadiazol-3-yl)benzyl)-N-(3-(trifluoromethyl)phenyl)morpholine-4-carboxamide

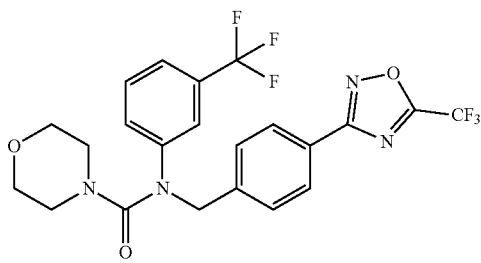 [SMILES: O=C(N1CCOCC1)N(Cc1ccc(-c2noc(C(F)(F)F)n2)cc1)c1cccc(C(F)(F)F)c1]

Step A: N-(3-(Trifluoromethyl)phenyl)morpholine-4-carboxamide

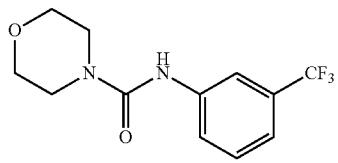 [SMILES: O=C(Nc1cccc(C(F)(F)F)c1)N1CCOCC1]

A mixture of morpholine (236 mg, 2.71 mmol) and 1-isothiocyanato-3-(trifluoromethyl)benzene (500 mg, 2.46 mmol) in EtOAc (15 mL) was stirred at 22° C. for 1.5 h. Hydrogen peroxide (2.16 mL, 24.6 mmol) was added dropwise and the mixture was stirred at 22° C. for 15 h. To the mixture was added H$_2$O (10 mL) and the water layer was extracted with EtOAc (15 mL×2). The collected organic layers were washed with brine (10 mL) and dried over anhydrous Na$_2$SO$_4$. The mixture was filtered and the filtrate was concentrated under reduced pressure to give crude product. The crude product was purified by flash silica gel chromatography (ISCO®; 12 g SepaFlash® Silica Flash Column, Eluent of 0-40% EA/PE gradient @ 30 mL/min) to give the title product as an oil. ESI-MS m/z [M+H]$^+$:274.9.

Step B: N-(4-Cyanobenzyl)-N-(3-(trifluoromethyl)phenyl)morpholine-4-carboxamide

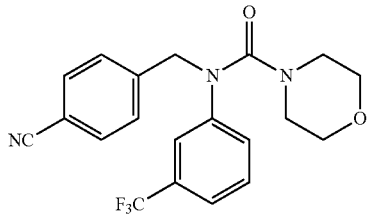 [SMILES: N#Cc1ccc(CN(C(=O)N2CCOCC2)c2cccc(C(F)(F)F)c2)cc1]

To a mixture of N-(3-(trifluoromethyl)phenyl)morpholine-4-carboxamide (260 mg, 0.948 mmol) in DMF (8 mL) was added sodium hydride (114 mg, 2.84 mmol) (60% in mineral oil) at 22° C., and 1 h later 4-(bromomethyl)benzonitrile (279 mg, 1.422 mmol) was added and the mixture was stirred at 80° C. for 15 h. To the mixture was added H$_2$O (10 mL) at 0° C. slowly. The water layer was extracted with EtOAc (15 mL×2). The collected organic layers were washed with brine (10 mL) and dried over anhydrous Na$_2$SO$_4$. The mixture was filtered and the filtrate was concentrated under reduced pressure to give crude product. The residue was purified by pre-HPLC (preparative HPLC on a GILSON 281 instrument fitted with a Waters XSELECT C18 150×30 mm×5 um using water and acetonitrile as the eluents. Mobile phase A: water (containing water (0.1% TFA)-ACN, v/v), mobile phase B: acetonitrile. Gradient: 46-76% B, 0-10 min; 100% B, 10.5-12.5 min; 5% B, 13-15 min) to give the title product as an oil. ESI-MS m/z [M+H]$^+$:390.2.

Step C: (Z)—N'-(4-(N'-Hydroxycarbamimidoyl)benzyl)-N-(3-(trifluoromethyl)phenyl)morpholine-4-carboxamide

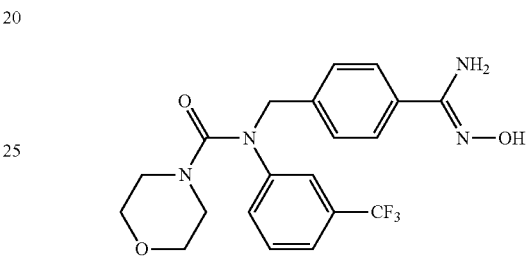

A mixture of N-(4-Cyanobenzyl)-N-(3-(trifluoromethyl)phenyl)morpholine-4-carboxamide (35 mg, 0.090 mmol), hydroxylamine hydrochloride (18.74 mg, 0.270 mmol) and triethylamine (0.050 mL, 0.360 mmol) in EtOH (3 mL) was stirred at 80° C. for 4 h. After cooling to ambient temperature, the mixture was concentrated under reduced pressure to give a residue, which was diluted with H$_2$O (10 mL). The water layer was extracted with DCM (20 mL×2). The collected organic layers were washed with brine (15 mL) and dried over anhydrous Na$_2$SO$_4$. The mixture was filtered and the filtrate was concentrated under reduced pressure to give the title compound as a solid. ESI-MS m/z [M+H]$^+$: 423.0.

Step D: N-(4-(5-(Trifluoromethyl)-1,2,4-oxadiazol-3-yl)benzyl)-N-(3 (trifluoromethyl)phenyl) morpholine-4-carboxamide

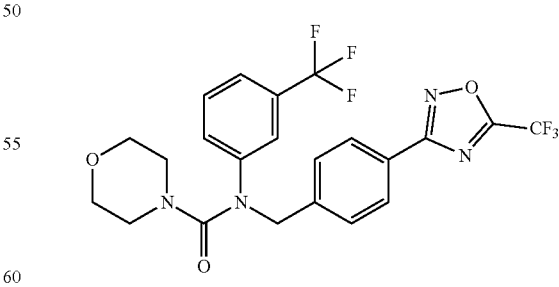

A mixture of 2,2,2-trifluoroacetic anhydride (0.040 mL, 0.284 mmol), pyridine (22.47 mg, 0.284 mmol) and (Z)—N-(4-(N'-hydroxycarbamimidoyl)benzyl)-N-(3-(trifluoromethyl)phenyl)morpholine-4-carboxamide (40 mg, 0.095 mmol) in toluene (2 mL) was stirred at 22° C. for 1 h and at 120° C. for 3 h. After cooling to ambient temperature, the mixture was diluted with H₂O (30 mL) and extracted with EtOAc (30 mL×2). The collected organic layers were washed with brine (30 mL) and dried over anhydrous Na₂SO₄. The mixture was filtered and the filtrate was concentrated under reduced pressure. The residue was purified by prep-HPLC (preparative HPLC on a GILSON 281 instrument fitted with a Phenomenex Synergi C18 250×21.2 mm×4 um using water and acetonitrile as the eluents. Mobile phase A: water (containing water (0.1% TFA)-ACN, v/v), mobile phase B: acetonitrile. Gradient: 49-79% B, 0-10 min; 100% B, 10.5-12.5 min; 5% B, 13-15 min) to give the title compound as an oil. $^1$H NMR (400 MHz, CD₃OD): δ 3.20-3.29 (m, 4H) 3.45-3.53 (m, 4H) 5.02 (s, 2H) 7.38-7.48 (m, 3H) 7.50-7.59 (m, 3H) 8.04 (d, J=8.22 Hz, 2H); ESI-MS m/z [M+H]⁺:501.2.

Example 33

3-(4-(4-Methyl-2-phenylpiperazin-1-yl)phenyl)-5-(trifluoromethyl)-1,2,4-oxadiazole

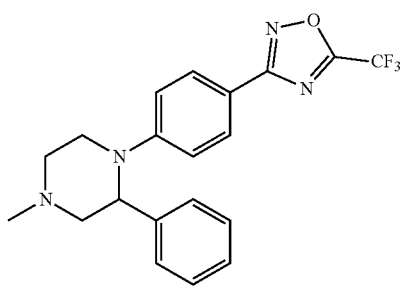 [SMILES: CN1CCN(c2ccc(-c3noc(C(F)(F)F)n3)cc2)C(c2ccccc2)C1]

Step A:
4-(4-Methyl-2-phenylpiperazin-1-yl)benzonitrile

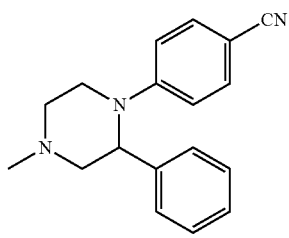 [SMILES: CN1CCN(c2ccc(C#N)cc2)C(c2ccccc2)C1]

A mixture of 4-iodobenzonitrile (300 mg, 1.31 mmol), 1-methyl-3-phenylpiperazine (346 mg, 1.96 mmol), cesium carbonate (1.28 g, 3.93 mmol) and chloro(2-dicyclohexylphosphino-2',6'-dimethoxy-1,1'-biphenyl)[2-(2-aminoethylphenyl)]palladium(II) dichloromethane adduct (176 mg, 0.262 mmol) in tert-amyl alcohol (5 mL) was stirred at 100° C. for 16 h under N₂. After cooling to ambient temperature, the mixture was concentrated under reduced pressure to give a residue, which was diluted with H₂O (10 mL). The water layer was extracted with EtOAc (20 mL×2). The collected organic layers were washed with brine (10 mL) and dried over anhydrous Na₂SO₄. The mixture was filtered and the filtrate was concentrated under reduced pressure. The residue was purified by flash silica gel chromatography (ISCO®; 4 g SepaFlash® Silica Flash Column, Eluent of 0-65% EA/PE gradient @ 40 mL/min) to give 4-(4-methyl-2-phenylpiperazin-1-yl)benzonitrile as an oil. ESI-MS m/z [M+H]⁺: 277.9.

Step B: (Z)—N'-Hydroxy-4-(4-methyl-2-phenylpiperazin-1-yl)benzimidamide

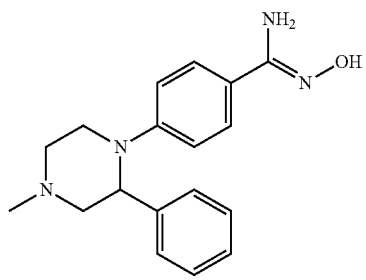 [SMILES: CN1CCN(c2ccc(/C(N)=N/O)cc2)C(c2ccccc2)C1]

A mixture of 4-(4-methyl-2-phenylpiperazin-1-yl)benzonitrile (153 mg, 0.552 mmol), hydroxylamine hydrochloride (77 mg, 1.10 mmol) and triethylamine (0.154 mL, 1.10 mmol) in EtOH (10 mL) was stirred at 80° C. for 3 h. After cooling to ambient temperature, the mixture was concentrated under reduced pressure to give a residue, which was diluted with H₂O (20 mL). The water layer was extracted with EtOAc (30 mL×2). The collected organic layers were washed with brine (15 mL) and dried over anhydrous Na₂SO₄. The mixture was filtered and the filtrate was concentrated under reduced pressure to give (Z)—N'-hydroxy-4-(4-methyl-2-phenylpiperazin-1-yl)benzimidamide. ESI-MS m/z [M+H]⁺: 311.1.

Step C: 3-(4-(4-Methyl-2-phenylpiperazin-1-yl)phenyl)-5-(trifluoromethyl)-1,2,4-oxadiazole

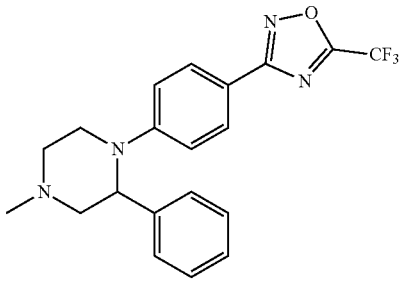 [SMILES: CN1CCN(c2ccc(-c3noc(C(F)(F)F)n3)cc2)C(c2ccccc2)C1]

2,2,2-Trifluoroacetic anhydride (0.182 mL, 1.289 mmol) was added to a stirred mixture of (Z)—N'-hydroxy-4-(4-methyl-2-phenylpiperazin-1-yl)benzimidamide (80 mg, 0.258 mmol) in 1,4-dioxane (5 mL) at 25° C. and the mixture was stirred at 25° C. for 16 h. Water (20 mL) was added and the mixture was extracted with ethyl acetate (30 mL×2). The combined organic layers were washed with brine (20 mL), dried over Na₂SO₄, filtered and concentrated in vacuo. The residue was purified by reverse-phase Prep-HPLC (preparative HPLC on a GILSON 281 instrument fitted with Boston Green ODS 150×30 5 um using water and acetonitrile as the eluents. Mobile phase A: water, mobile phase B: acetonitrile (containing: 0.1% TFA-ACN). Gradient: 30-56%, 0-10 min; 100% B, 10.5-12.5 min; 5% B, 13-15 min) to give 3-(4-(4-methyl-2-phenylpiperazin-1-yl)phenyl)-5-(trifluoromethyl)-1,2,4-oxadiazole as a solid. ¹H NMR (400 MHz, CDCl₃): δ 7.87 (d, J=8.2 Hz, 2H), 7.31-7.18 (m, 5H), 7.05 (d, J=7.7 Hz, 2H), 4.70 (br. s., 1H), 3.87-3.59 (m, 3H), 3.51 (br. s., 1H), 3.26 (br. s., 1H), 2.89 (s, 4H); ESI-MS m/z [M+H]⁺: 389.1.

Example 34

(S)-5-(3-(Pyridin-2-yl)-1,2,4-oxadiazol-5-yl)-4-(4-(5-(trifluoromethyl)-1,2,4-oxadiazol-3-yl)phenyl)morpholin-3-one

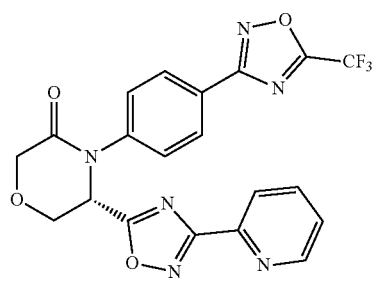 [SMILES: O=C1COC[C@@H](c2nc(-c3ccccn3)no2)N1c1ccc(-c2noc(C(F)(F)F)n2)cc1]

Steps A-C: (S)-5-Oxo-4-(4-(5-(trifluoromethyl)-1,2,4-oxadiazol-3-yl)phenyl)morpholine-3-carboxylic acid

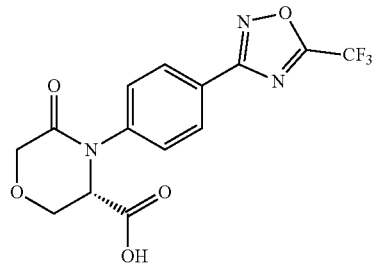 [SMILES: O=C(O)[C@@H]1COCC(=O)N1c1ccc(-c2noc(C(F)(F)F)n2)cc1]

The title compound was prepared from (S)-5-oxomorpholine-3-carboxylic acid and (4-cyanophenyl) boronic acid according to the procedure outlined in Example 25, steps A-C. MS (ESI) m/z [M+H]⁺: 358.0.

Step D: (S)-5-(3-(Pyridin-2-yl)-1,2,4-oxadiazol-5-yl)-4-(4-(5-(trifluoromethyl)-1,2,4-oxadiazol-3-yl)phenyl)morpholin-3-one

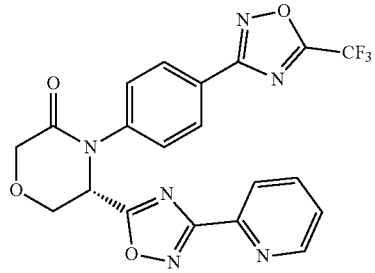 [SMILES: O=C1COC[C@@H](c2nc(-c3ccccn3)no2)N1c1ccc(-c2noc(C(F)(F)F)n2)cc1]

The title compound was prepared from the product of steps A-C above, (S)-5-oxo-4-(4-(5-(trifluoromethyl)-1,2,4-oxadiazol-3-yl)phenyl)morpholine-3-carboxylic acid (25 mg, 0.053 mmol), and (Z)—N'-hydroxypicolinimidamide (7.2 mg, 0.053 mmol) according to the procedure outlined in Example 17, step E. MS (ESI) m/z [M+H]⁺: 459.1.

Example 35

(S)-5-(Benzo[d]oxazol-2-yl)-4-(4-(5-(trifluoromethyl)-1,2,4-oxadiazol-3-yl)phenyl)morpholin-3-one

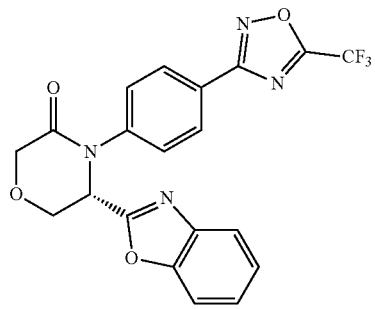 [SMILES: O=C1COC[C@@H](c2nc3ccccc3o2)N1c1ccc(-c2noc(C(F)(F)F)n2)cc1]

The title compound was prepared from the product of Example 34, Steps A-C, (S)-5-oxomorpholine-3-carboxylic acid and 2-aminophenol according to the procedures outlined in Example 22, Steps E-F. MS (ESI) m/z [M+H]⁺: 358.0.

The following examples displayed in TABLE 1 were prepared according to the identified procedures using the appropriate commercially available starting materials.

TABLE 1

| Ex # | Structure | Name | Stereo-chemistry | [M + H]+ | General Procedures |
|---|---|---|---|---|---|
| 36 | 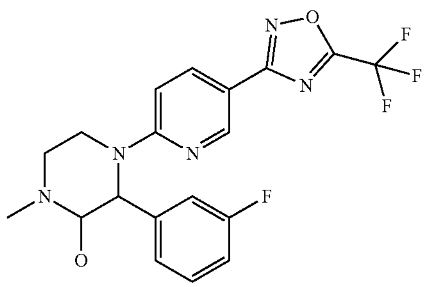 [SMILES: CN1CCN(c2ccc(-c3noc(C(F)(F)F)n3)cn2)C(c2cccc(F)c2)C1O] | 3-(3-fluorophenyl)-1-methyl-4-(5-(5-(trifluoromethyl)-1,2,4-oxadiazol-3-yl)pyridin-2-yl)piperazin-2-one | RACEMIC | 422 | 3 |
| 37 | 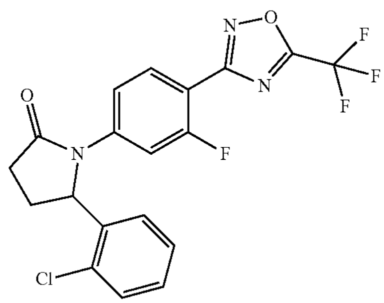 [SMILES: O=C1CCC(c2ccccc2Cl)N1c1ccc(-c2noc(C(F)(F)F)n2)c(F)c1] | 5-(2-chlorophenyl)-1-(3-fluoro-4-(5-(trifluoromethyl)-1,2,4-oxadiazol-3-yl)phenyl)pyrrolidin-2-one | RACEMIC | 426 | 2 |
| 38 | 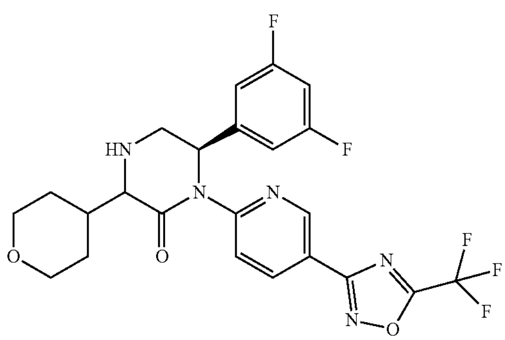 [SMILES: O=C1C(C2CCOCC2)NC[C@@H](c2cc(F)cc(F)c2)N1c1ccc(-c2noc(C(F)(F)F)n2)cn1] | (6R)-6-(3,5-difluorophenyl)-3-(tetrahydro-2H-pyran-4-yl)-1-(5-(5-(trifluoromethyl)-1,2,4-oxadiazol-3-yl)pyridin-2-yl)piperazin-2-one | R, R or S | 510 | 5 and 4 |
| 39 | 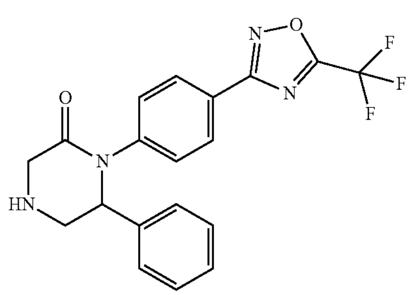 [SMILES: O=C1CNCC(c2ccccc2)N1c1ccc(-c2noc(C(F)(F)F)n2)cc1] | 6-phenyl-1-(4-(5-(trifluoromethyl)-1,2,4-oxadiazol-3-yl)phenyl)piperazin-2-one | R OR S | 389 | 2 and 4 |
| 40 | 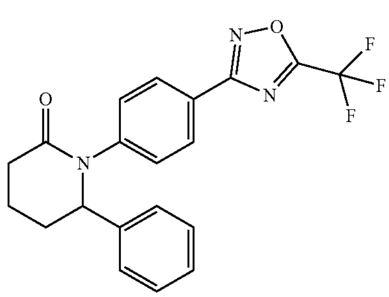 [SMILES: O=C1CCCC(c2ccccc2)N1c1ccc(-c2noc(C(F)(F)F)n2)cc1] | 6-phenyl-1-(4-(5-(trifluoromethyl)-1,2,4-oxadiazol-3-yl)phenyl)piperidin-2-one | R OR S | 388 | 2 and 6,7-step D |

TABLE 1-continued

| Ex # | Structure | Name | Stereo-chemistry | [M + H]+ | General Procedures |
|---|---|---|---|---|---|
| 41 | 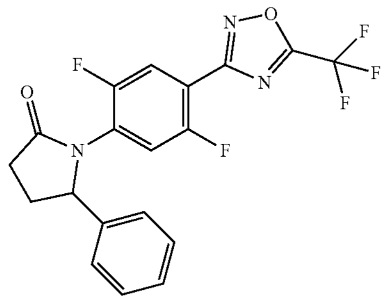 [SMILES: O=C1CCC(c2ccccc2)N1c1cc(F)c(-c2noc(C(F)(F)F)n2)cc1F] | 1-(2,5-difluoro-4-(5-(trifluoromethyl)-1,2,4-oxadiazol-3-yl)phenyl)-5-phenylpyrrolidin-2-one | R OR S | 410 | 14 and 6,7-step D |
| 42 | 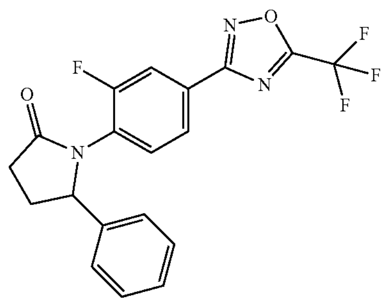 [SMILES: O=C1CCC(c2ccccc2)N1c1ccc(-c2noc(C(F)(F)F)n2)cc1F] | 1-(2-fluoro-4-(5-(trifluoromethyl)-1,2,4-oxadiazol-3-yl)phenyl)-5-phenylpyrrolidin-2-one | R OR S | 392 | 14 and 6, -step D |
| 43 | 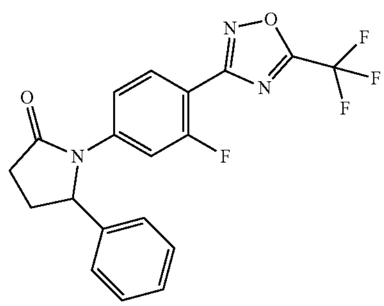 [SMILES: O=C1CCC(c2ccccc2)N1c1ccc(-c2noc(C(F)(F)F)n2)c(F)c1] | 1-(3-fluoro-4-(5-(trifluoromethyl)-1,2,4-oxadiazol-3-yl)phenyl)-5-phenylpyrrolidin-2-one | R OR S | 392 | 14 and 6,7-step D |
| 44 | 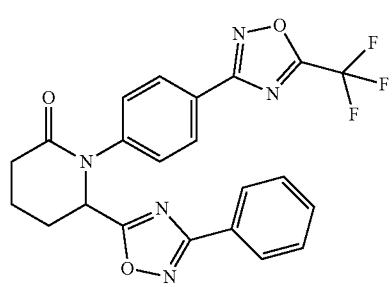 [SMILES: O=C1CCCC(c2nc(-c3ccccc3)no2)N1c1ccc(-c2noc(C(F)(F)F)n2)cc1] | 6-(3-phenyl-1,2,4-oxadiazol-5-yl)-1-(4-(5-(trifluoromethyl)-1,2,4-oxadiazol-3-yl)phenyl)piperidin-2-one | R OR S | 456 | 34 |
| 45 | 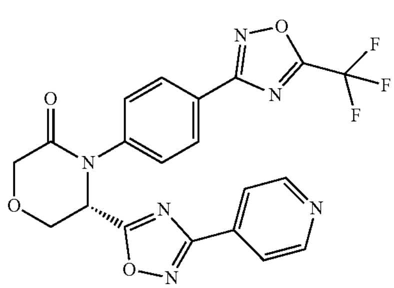 [SMILES: O=C1COC[C@@H](c2nc(-c3ccncc3)no2)N1c1ccc(-c2noc(C(F)(F)F)n2)cc1] | (S)-5-(3-(pyridin-4-yl)-1,2,4-oxadiazol-5-yl)-4-(4-(5-(trifluoromethyl)-1,2,4-oxadiazol-3-yl)phenyl)morpholin-3-one | S | 459 | 34 |

TABLE 1-continued

| Ex # | Structure | Name | Stereo-chemistry | [M + H]+ | General Procedures |
|---|---|---|---|---|---|
| 46 | 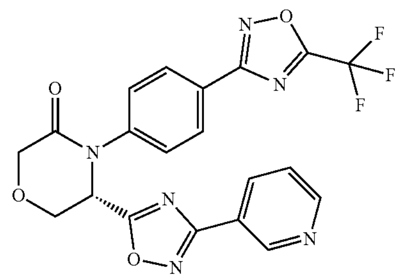 [SMILES: O=C1COC[C@@H](c2nc(-c3cccnc3)no2)N1c1ccc(-c2noc(C(F)(F)F)n2)cc1] | (S)-5-(3-(pyridin-3-yl)-1,2,4-oxadiazol-5-yl)-4-(4-(5-(trifluoromethyl)-1,2,4-oxadiazol-3-yl)phenyl)morpholin-3-one 1,2,4-oxadiazol-5-yl)-4-(4-(5-(trifluoromethyl)-1,2,4-oxadiazol-3-yl)phenyl)morpholin-3-one | S | 458 | 34 |
| 47 | 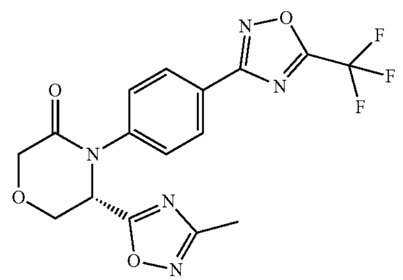 [SMILES: Cc1noc([C@@H]2COCC(=O)N2c2ccc(-c3noc(C(F)(F)F)n3)cc2)n1] | (S)-5-(3-methyl-1,2,4-oxadiazol-5-yl)-4-(4-(5-(trifluoromethyl)-1,2,4-oxadiazol-3-yl)phenyl)morpholin-3-one | S | 396 | 34 |
| 48 | 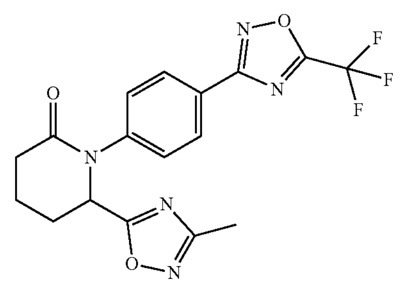 [SMILES: Cc1noc(C2CCCC(=O)N2c2ccc(-c3noc(C(F)(F)F)n3)cc2)n1] | 6-(3-methyl-1,2,4-oxadiazol-5-yl)-1-(4-(5-(trifluoromethyl)-1,2,4-oxadiazol-3-yl)phenyl)piperidin-2-one | RACEMIC | 394 | 34 |
| 49 | 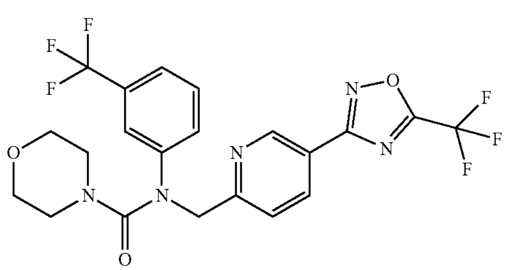 [SMILES: O=C(N1CCOCC1)N(Cc1ccc(-c2noc(C(F)(F)F)n2)cn1)c1cccc(C(F)(F)F)c1] | N-((5-(5-(trifluoromethyl)-1,2,4-oxadiazol-3-yl)pyridin-2-yl)methyl)-N-(3-(trifluoromethyl)phenyl)morpholine-4-carboxamide | | 502 | 32 |
| 50 | 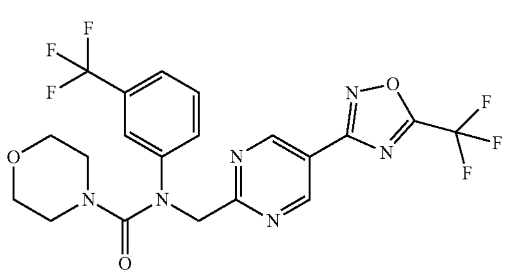 [SMILES: O=C(N1CCOCC1)N(Cc1ncc(-c2noc(C(F)(F)F)n2)cn1)c1cccc(C(F)(F)F)c1] | N-((5-(5-(trifluoromethyl)-1,2,4-oxadiazol-3-yl)pyrimidin-2-yl)methyl)-N-(3-(trifluoromethyl)phenyl)morpholine-4-carboxamide | | 503 | 32 |

TABLE 1-continued

| Ex # | Structure | Name | Stereo-chemistry | [M + H]+ | General Procedures |
|---|---|---|---|---|---|
| 51 | 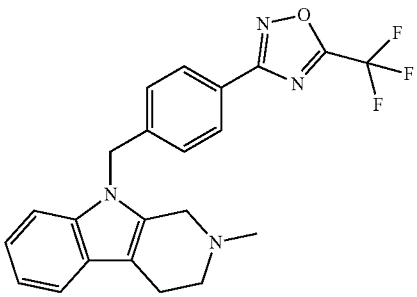 [SMILES: CN1CCc2c(n(Cc3ccc(-c4noc(C(F)(F)F)n4)cc3)c3ccccc23)C1] | 3-(4-((2-methyl-1,2,3,4-tetrahydro-9H-pyrido[3,4-b]indol-9-yl)methyl)phenyl)-5-(trifluoromethyl)-1,2,4-oxadiazole | | 413 | 32 |
| 52 | 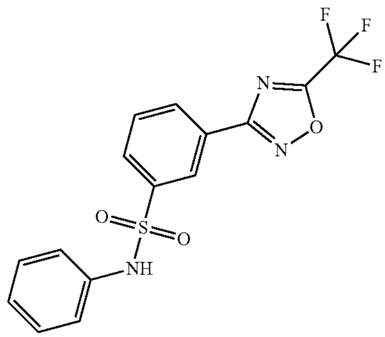 [SMILES: O=S(=O)(Nc1ccccc1)c1cccc(-c2noc(C(F)(F)F)n2)c1] | N-phenyl-3-(5-(trifluoromethyl)-1,2,4-oxadiazol-3-yl)benzenesulfonamide | | 370 | 31 |
| 53 | 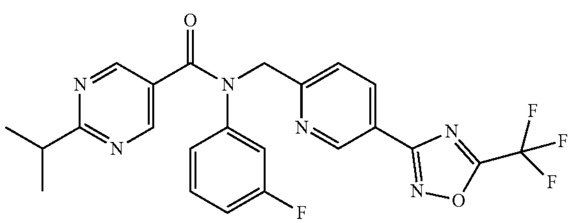 [SMILES: CC(C)c1ncc(C(=O)N(Cc2ccc(-c3noc(C(F)(F)F)n3)cn2)c2cccc(F)c2)cn1] | N-(3-fluorophenyl)-2-isopropyl-N-((5-(5-(trifluoromethyl)-1,2,4-oxadiazol-3-yl)pyridin-2-yl)methyl)pyrimidine-5-carboxamide | | 487 | 30 |
| 54 | 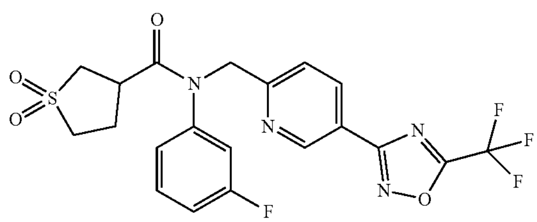 [SMILES: O=C(C1CCS(=O)(=O)C1)N(Cc1ccc(-c2noc(C(F)(F)F)n2)cn1)c1cccc(F)c1] | N-(3-fluorophenyl)-N-((5-(5-(trifluoromethyl)-1,2,4-oxadiazol-3-yl)pyridin-2-yl)methyl)tetrahydrothiophene-3-carboxamide 1,1-dioxide | RACEMIC | 485 | 30 |
| 55 | 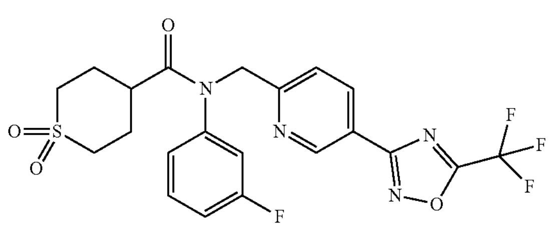 [SMILES: O=C(C1CCS(=O)(=O)CC1)N(Cc1ccc(-c2noc(C(F)(F)F)n2)cn1)c1cccc(F)c1] | N-(3-fluorophenyl)-N-((5-(5-(trifluoromethyl)-1,2,4-oxadiazol-3-yl)pyridin-2-yl)methyl)tetrahydro-2H-thiopyran-4-carboxamide 1,1-dioxide | | 499 | 30 |
| 56 | 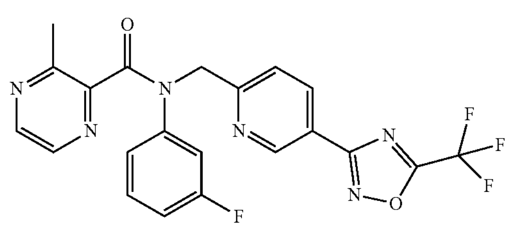 [SMILES: Cc1nccnc1C(=O)N(Cc1ccc(-c2noc(C(F)(F)F)n2)cn1)c1cccc(F)c1] | N-(3-fluorophenyl)-3-methyl-N-((5-(5-(trifluoromethyl)-1,2,4-oxadiazol-3-yl)pyridin-2-yl)methyl)pyrazine-2-carboxamide | | 459 | 30 |

TABLE 1-continued

| Ex # | Structure | Name | Stereo-chemistry | [M + H]+ | General Procedures |
|---|---|---|---|---|---|
| 57 | 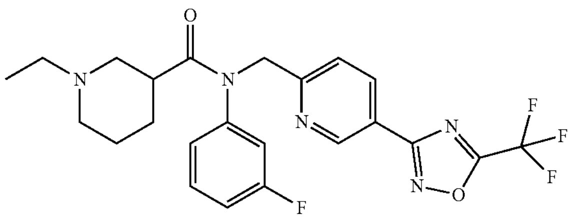 [SMILES: CCN1CCCC(C(=O)N(Cc2ccc(-c3noc(C(F)(F)F)n3)cn2)c2cccc(F)c2)C1] | 1-ethyl-N-(3-fluorophenyl)-N-((5-(5-(trifluoromethyl)-1,2,4-oxadiazol-3-yl)pyridin-2-yl)methyl) piperidine-3-carboxamide | RACEMIC | 478 | 30 |
| 58 | 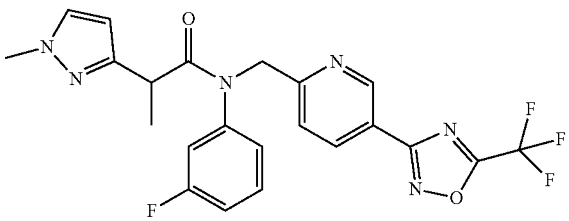 [SMILES: CC(C(=O)N(Cc1ccc(-c2noc(C(F)(F)F)n2)cn1)c1cccc(F)c1)c1ccn(C)n1] | N-(3-fluorophenyl)-2-(1-methyl-1H-pyrazol-3-yl)-N-((5-(5-(trifluoromethyl)-1,2,4-oxadiazol-3-yl)pyridin-2-yl)methyl) propanamide | RACEMIC | 475 | 30 |
| 59 | 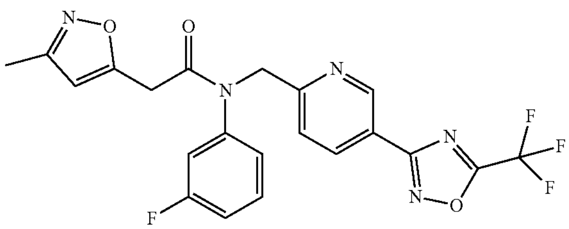 [SMILES: Cc1cc(CC(=O)N(Cc2ccc(-c3noc(C(F)(F)F)n3)cn2)c2cccc(F)c2)on1] | N-(3-fluorophenyl)-2-(3-methylisoxazol-5-yl)-N-((5-(5-(trifluoromethyl)-1,2,4-oxadiazol-3-yl)pyridin-2-yl)methyl) acetamide | | 462 | 30 |
| 60 | 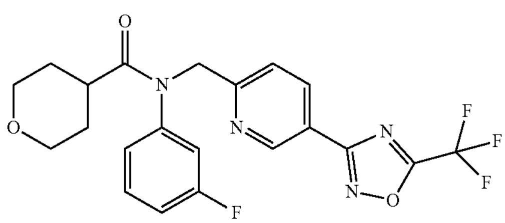 [SMILES: O=C(C1CCOCC1)N(Cc1ccc(-c2noc(C(F)(F)F)n2)cn1)c1cccc(F)c1] | N-(3-fluorophenyl)-N-((5-(5-(trifluoromethyl)-1,2,4-oxadiazol-3-yl)pyridin-2-yl)methyl) tetrahydro-2H-pyran-4-carboxamide | | 451 | 30 |
| 61 | 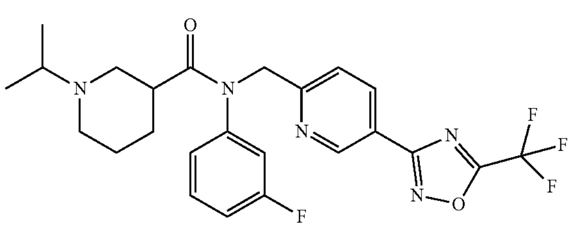 [SMILES: CC(C)N1CCCC(C(=O)N(Cc2ccc(-c3noc(C(F)(F)F)n3)cn2)c2cccc(F)c2)C1] | N-(3-fluorophenyl)-1-isopropyl-N-((5-(5-(trifluoromethyl)-1,2,4-oxadiazol-3-yl)pyridin-2-yl)methyl) piperidine-3-carboxamide | RACEMIC | 492 | 30 |
| 62 | 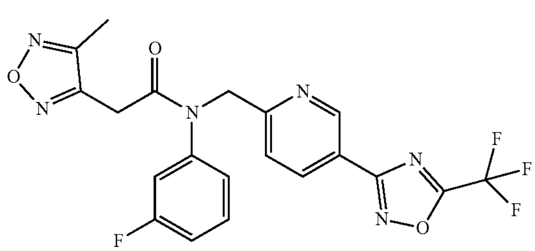 [SMILES: Cc1nonc1CC(=O)N(Cc1ccc(-c2noc(C(F)(F)F)n2)cn1)c1cccc(F)c1] | N-(3-fluorophenyl)-2-(4-methyl-1,2,5-oxadiazol-3-yl)-N-((5-(5-(trifluoromethyl)-1,2,4-oxadiazol-3-yl)pyridin-2-yl)methyl)acetamide | | 463 | 30 |

TABLE 1-continued

| Ex # | Structure | Name | Stereo-chemistry | [M + H]+ | General Procedures |
|---|---|---|---|---|---|
| 63 | 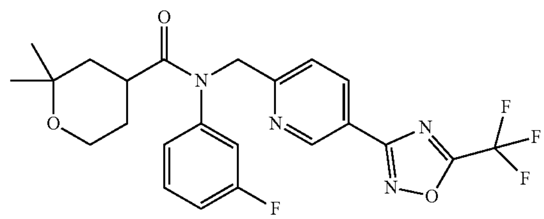 [SMILES: CC1(C)CC(C(=O)N(Cc2ccc(-c3noc(C(F)(F)F)n3)cn2)c2cccc(F)c2)CCO1] | N-(3-fluorophenyl)-2,2-dimethyl-N-((5-(5-(trifluoromethyl)-1,2,4-oxadiazol-3-yl)pyridin-2-yl)methyl) tetrahydro-2H-pyran-4-carboxamide | RACEMIC | 479 | 30 |
| 64 | 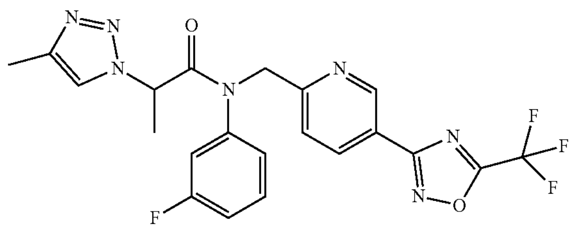 [SMILES: Cc1cn(C(C)C(=O)N(Cc2ccc(-c3noc(C(F)(F)F)n3)cn2)c2cccc(F)c2)nn1] | N-(3-fluorophenyl)-2-(4-methyl-1H-1,2,3-triazol-1-yl)-N-((5-(5-(trifluoromethyl)-1,2,4-oxadiazol-3-yl)pyridin-2-yl)methyl) propanamide | RACEMIC | 476 | 30 |
| 65 | 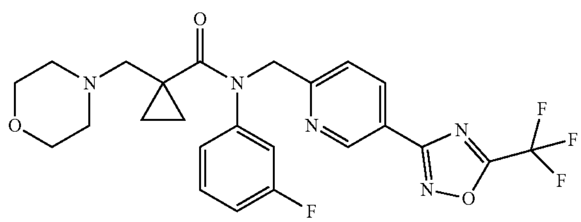 [SMILES: O=C(N(Cc1ccc(-c2noc(C(F)(F)F)n2)cn1)c1cccc(F)c1)C1(CN2CCOCC2)CC1] | N-(3-fluorophenyl)-1-(morpholinomethyl)-N-((5-(5-(trifluoromethyl)-1,2,4-oxadiazol-3-yl)pyridin-2-yl)methyl) cyclopropane-1-carboxamide | | 506 | 30 |
| 66 | 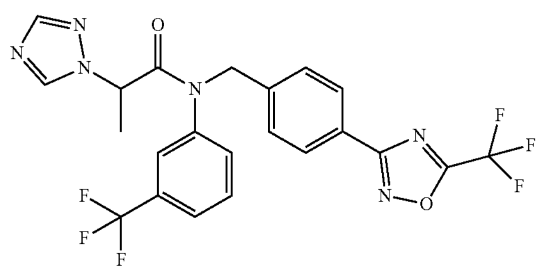 [SMILES: CC(C(=O)N(Cc1ccc(-c2noc(C(F)(F)F)n2)cc1)c1cccc(C(F)(F)F)c1)n1cncn1] | 2-(1H-1,2,4-triazol-1-yl)-N-(4-(5-(trifluoromethyl)-1,2,4-oxadiazol-3-yl)benzyl)-N-(3-(trifluoromethyl) phenyl)propanamide | RACEMIC | 511 | 30 |
| 67 | 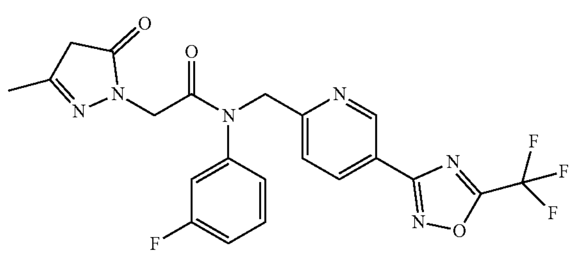 [SMILES: CC1=NN(CC(=O)N(Cc2ccc(-c3noc(C(F)(F)F)n3)cn2)c2cccc(F)c2)C(=O)C1] | N-(3-fluorophenyl)-2-(3-methyl-5-oxo-4,5-dihydro-1H-pyrazol-1-yl)-N-((5-(5-(trifluoromethyl)-1,2,4-oxadiazol-3-yl)pyridin-2-yl)methyl) acetamide | | 477 | 30 |
| 68 | 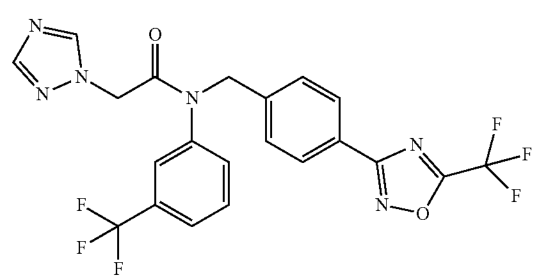 [SMILES: O=C(Cn1cncn1)N(Cc1ccc(-c2noc(C(F)(F)F)n2)cc1)c1cccc(C(F)(F)F)c1] | 2-(1H-1,2,4-triazol-1-yl)-N-(4-(5-(trifluoromethyl)-1,2,4-oxadiazol-3-yl)benzyl)-N-(3-(trifluoromethyl) phenyl)acetamide | | 497 | 30 |

TABLE 1-continued

| Ex # | Structure | Name | Stereo-chemistry | [M + H]+ | General Procedures |
|---|---|---|---|---|---|
| 69 | 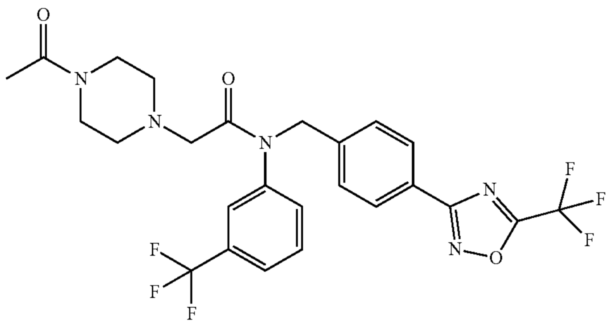 [SMILES: CC(=O)N1CCN(CC(=O)N(Cc2ccc(-c3noc(C(F)(F)F)n3)cc2)c2cccc(C(F)(F)F)c2)CC1] | 2-(4-acetylpiperazin-1-yl)-N-(4-(5-(trifluoromethyl)-1,2,4-oxadiazol-3-yl)benzyl)-N-(3-(trifluoromethyl)phenyl)acetamide | | 556 | 30 |
| 70 | 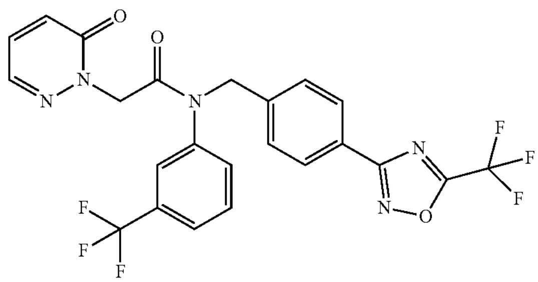 [SMILES: O=C(Cn1ncccc1=O)N(Cc1ccc(-c2noc(C(F)(F)F)n2)cc1)c1cccc(C(F)(F)F)c1] | 2-(6-oxopyridazin-1(6H)-yl)-N-(4-(5-(trifluoromethyl)-1,2,4-oxadiazol-3-yl)benzyl)-N-(3-(trifluoromethyl)phenyl)acetamide | | 524 | 30 |
| 71 | 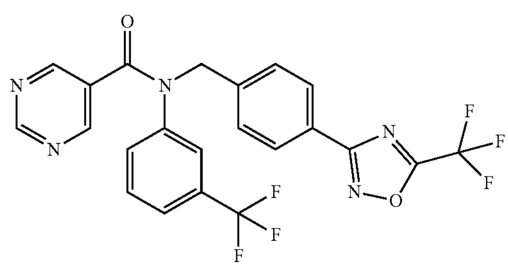 [SMILES: O=C(c1cncnc1)N(Cc1ccc(-c2noc(C(F)(F)F)n2)cc1)c1cccc(C(F)(F)F)c1] | N-(4-(5-(trifluoromethyl)-1,2,4-oxadiazol-3-yl)benzyl)-N-(3-(trifluoromethyl)phenyl)pyrimidine-5-carboxamide | | 494 | 30 |
| 72 | 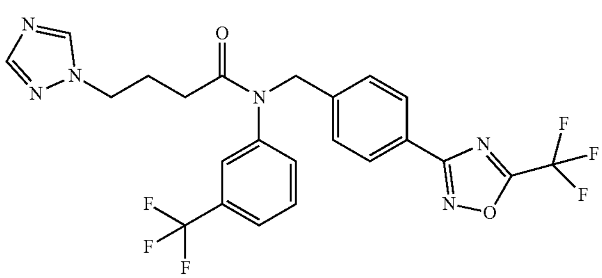 [SMILES: O=C(CCCn1cncn1)N(Cc1ccc(-c2noc(C(F)(F)F)n2)cc1)c1cccc(C(F)(F)F)c1] | 4-(1H-1,2,4-triazol-1-yl)-N-(4-(5-(trifluoromethyl)-1,2,4-oxadiazol-3-yl)benzyl)-N-(3-(trifluoromethyl)phenyl)butanamide | | 525 | 30 |
| 73 | 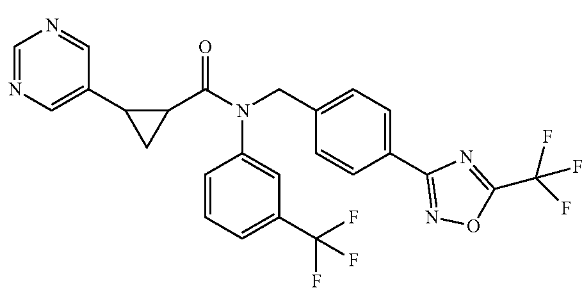 [SMILES: O=C(C1CC1c1cncnc1)N(Cc1ccc(-c2noc(C(F)(F)F)n2)cc1)c1cccc(C(F)(F)F)c1] | 2-(pyrimidin-5-yl)-N-(4-(5-(trifluoromethyl)-1,2,4-oxadiazol-3-yl)benzyl)-N-(3-(trifluoromethyl)phenyl)cyclopropane-1-carboxamide | RACEMIC | 534 | 30 |

TABLE 1-continued

| Ex # | Structure | Name | Stereo-chemistry | [M + H]+ | General Procedures |
|---|---|---|---|---|---|
| 74 | 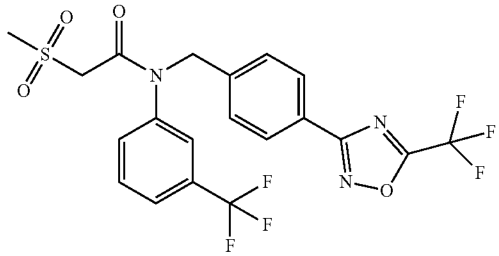 [SMILES: CS(=O)(=O)CC(=O)N(Cc1ccc(-c2noc(C(F)(F)F)n2)cc1)c1cccc(C(F)(F)F)c1] | 2-(methylsulfonyl)-N-(4-(5-(trifluoromethyl)-1,2,4-oxadiazol-3-yl)benzyl)-N-(3-(trifluoromethyl)phenyl)acetamide | | 508 | 30 |
| 75 | 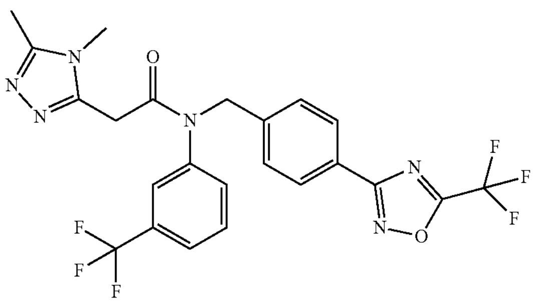 [SMILES: Cc1nnc(CC(=O)N(Cc2ccc(-c3noc(C(F)(F)F)n3)cc2)c2cccc(C(F)(F)F)c2)n1C] | 2-(4,5-dimethyl-4H-1,2,4-triazol-3-yl)-N-(4-(5-(trifluoromethyl)-1,2,4-oxadiazol-3-yl)benzyl)-N-(3-(trifluoromethyl)phenyl)acetamide | | 525 | 30 |
| 76 | 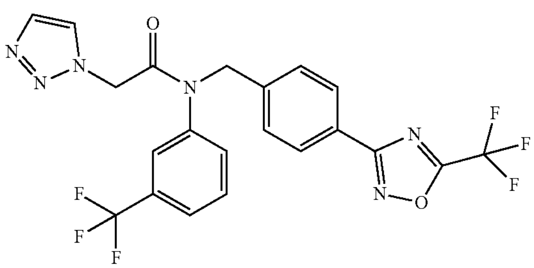 [SMILES: O=C(Cn1ccnn1)N(Cc1ccc(-c2noc(C(F)(F)F)n2)cc1)c1cccc(C(F)(F)F)c1] | 2-(1H-1,2,3-triazol-1-yl)-N-(4-(5-(trifluoromethyl)-1,2,4-oxadiazol-3-yl)benzyl)-N-(3-(trifluoromethyl)phenyl)acetamide | | 497 | 30 |
| 77 | 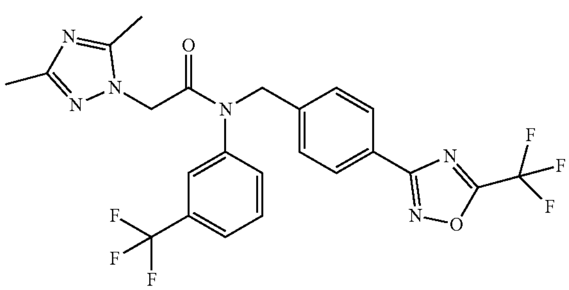 [SMILES: Cc1nc(C)n(CC(=O)N(Cc2ccc(-c3noc(C(F)(F)F)n3)cc2)c2cccc(C(F)(F)F)c2)n1] | 2-(3,5-dimethyl-1H-1,2,4-triazol-1-yl)-N-(4-(5-(trifluoromethyl)-1,2,4-oxadiazol-3-yl)benzyl)-N-(3-(trifluoromethyl)phenyl)acetamide | | 525 | 30 |
| 78 | 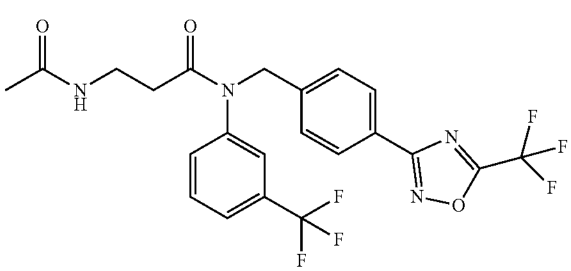 [SMILES: CC(=O)NCCC(=O)N(Cc1ccc(-c2noc(C(F)(F)F)n2)cc1)c1cccc(C(F)(F)F)c1] | 3-acetamido-N-(4-(5-(trifluoromethyl)-1,2,4-oxadiazol-3-yl)benzyl)-N-(3-(trifluoromethyl)phenyl)propanamide | | 501 | 30 |

TABLE 1-continued

| Ex # | Structure | Name | Stereo-chemistry | [M + H]+ | General Procedures |
|---|---|---|---|---|---|
| 79 | 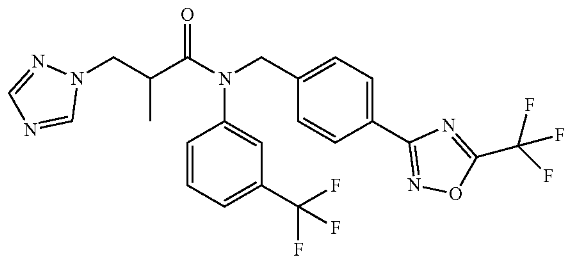 [SMILES: CC(Cn1cncn1)C(=O)N(Cc1ccc(-c2noc(C(F)(F)F)n2)cc1)c1cccc(C(F)(F)F)c1] | 2-methyl-3-(1H-1,2,4-triazol-1-yl)-N-(4-(5-(trifluoromethyl)-1,2,4-oxadiazol-3-yl)benzyl)-N-(3-(trifluoromethyl)phenyl)propanamide | RACEMIC | 525 | 30 |
| 80 | 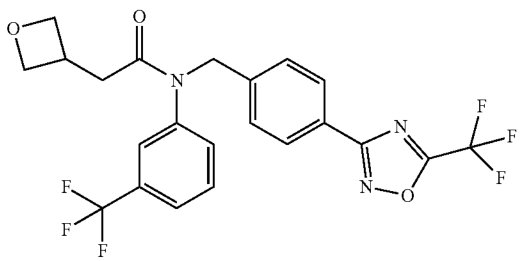 [SMILES: O=C(CC1COC1)N(Cc1ccc(-c2noc(C(F)(F)F)n2)cc1)c1cccc(C(F)(F)F)c1] | 2-(oxetan-3-yl)-N-(4-(5-(trifluoromethyl)-1,2,4-oxadiazol-3-yl)benzyl)-N-(3-(trifluoromethyl)phenyl)acetamide | | 486 | 30 |
| 81 | 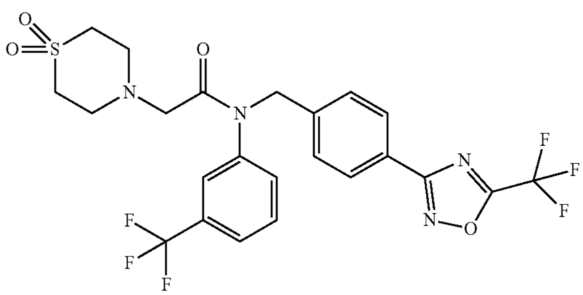 [SMILES: O=C(CN1CCS(=O)(=O)CC1)N(Cc1ccc(-c2noc(C(F)(F)F)n2)cc1)c1cccc(C(F)(F)F)c1] | 2-(1,1-dioxidothio-morpholino)-N-(4-(5-(trifluoromethyl)-1,2,4-oxadiazol-3-yl)benzyl)-N-(3-(trifluoromethyl)phenyl)acetamide | | 563 | 30 |
| 82 | 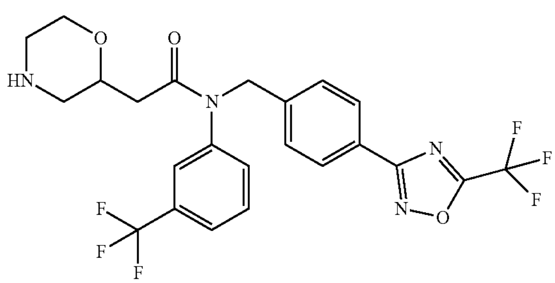 [SMILES: O=C(CC1CNCCO1)N(Cc1ccc(-c2noc(C(F)(F)F)n2)cc1)c1cccc(C(F)(F)F)c1] | 2-(morpholin-2-yl)-N-(4-(5-(trifluoromethyl)-1,2,4-oxadiazol-3-yl)benzyl)-N-(3-(trifluoromethyl)phenyl)acetamide | RACEMIC | 515 | 30 |
| 83 | 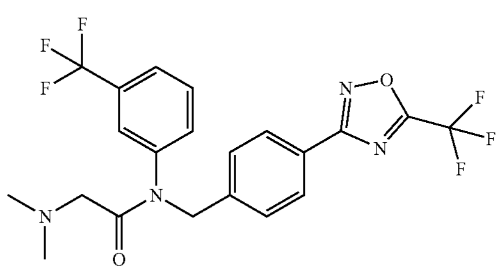 [SMILES: CN(C)CC(=O)N(Cc1ccc(-c2noc(C(F)(F)F)n2)cc1)c1cccc(C(F)(F)F)c1] | 2-(dimethylamino)-N-(4-(5-(trifluoromethyl)-1,2,4-oxadiazol-3-yl)benzyl)-N-(3-(trifluoromethyl)phenyl)acetamide | | 473 | 30 |

TABLE 1-continued

| Ex # | Structure | Name | Stereo-chemistry | [M + H]+ | General Procedures |
|---|---|---|---|---|---|
| 84 | 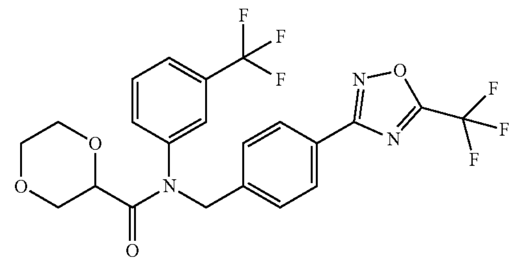 [SMILES: O=C(C1COCCO1)N(Cc1ccc(-c2noc(C(F)(F)F)n2)cc1)c1cccc(C(F)(F)F)c1] | N-(4-(5-(trifluoromethyl)-1,2,4-oxadiazol-3-yl)benzyl)-N-(3-(trifluoromethyl)phenyl)-1,4-dioxane-2-carboxamide | RACEMIC | 502 | 30 |
| 85 | 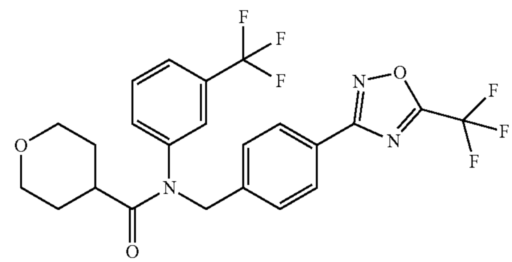 [SMILES: O=C(C1CCOCC1)N(Cc1ccc(-c2noc(C(F)(F)F)n2)cc1)c1cccc(C(F)(F)F)c1] | N-(4-(5-(trifluoromethyl)-1,2,4-oxadiazol-3-yl)benzyl)-N-(3-(trifluoromethyl)phenyl)tetrahydro-2H-pyran-4-carboxamide | | 500 | 30 |
| 86 | 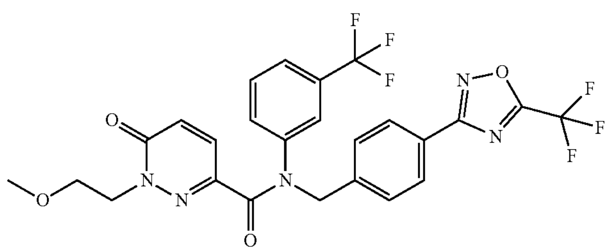 [SMILES: COCCn1nc(C(=O)N(Cc2ccc(-c3noc(C(F)(F)F)n3)cc2)c2cccc(C(F)(F)F)c2)ccc1=O] | 1-(2-methoxyethyl)-6-oxo-N-(4-(5-(trifluoromethyl)-1,2,4-oxadiazol-3-yl)benzyl)-N-(3-(trifluoromethyl)phenyl)-1,6-dihydropyridazine-3-carboxamide | | 568 | 30 |
| 87 | 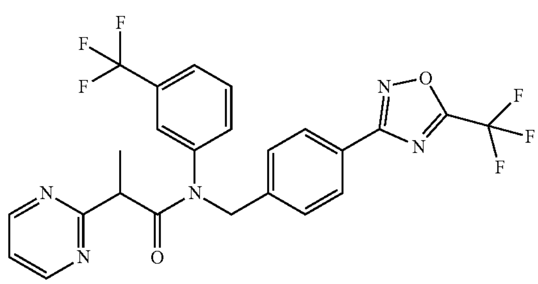 [SMILES: CC(C(=O)N(Cc1ccc(-c2noc(C(F)(F)F)n2)cc1)c1cccc(C(F)(F)F)c1)c1ncccn1] | 2-(pyrimidin-2-yl)-N-(4-(5-(trifluoromethyl)-1,2,4-oxadiazol-3-yl)benzyl)-N-(3-(trifluoromethyl)phenyl)propanamide | RACEMIC | 544 | 30 |
| 88 | 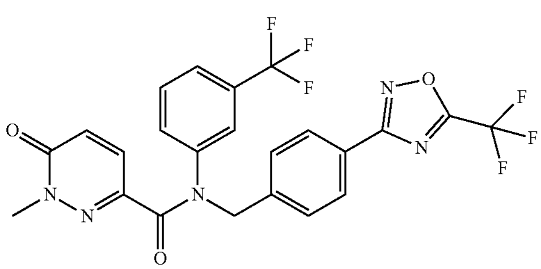 [SMILES: Cn1nc(C(=O)N(Cc2ccc(-c3noc(C(F)(F)F)n3)cc2)c2cccc(C(F)(F)F)c2)ccc1=O] | 1-methyl-6-oxo-N-(4-(5-(trifluoromethyl)-1,2,4-oxadiazol-3-yl)benzyl)-N-(3-(trifluoromethyl)phenyl)-1,6-dihydropyridazine-3-carboxamide | | 524 | 30 |
| 89 | 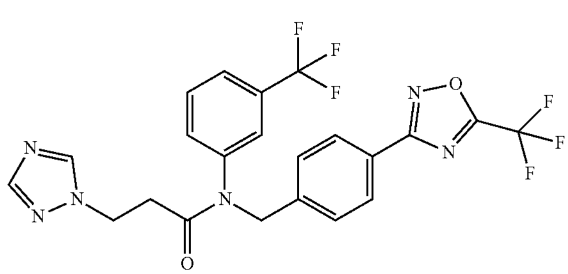 [SMILES: O=C(CCn1cncn1)N(Cc1ccc(-c2noc(C(F)(F)F)n2)cc1)c1cccc(C(F)(F)F)c1] | 3-(1H-1,2,4-triazol-1-yl)-N-(4-(5-(trifluoromethyl)-1,2,4-oxadiazol-3-yl)benzyl)-N-(3-(trifluoromethyl)phenyl)propanamide | | 511 | 30 |

TABLE 1-continued

| Ex # | Structure | Name | Stereo-chemistry | [M + H]+ | General Procedures |
|---|---|---|---|---|---|
| 90 | 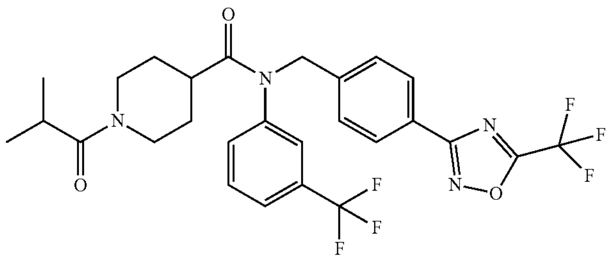 [SMILES: CC(C)C(=O)N1CCC(C(=O)N(Cc2ccc(-c3noc(C(F)(F)F)n3)cc2)c2cccc(C(F)(F)F)c2)CC1] | 1-isobutyryl-N-(4-(5-(trifluoromethyl)-1,2,4-oxadiazol-3-yl)benzyl)-N-(3-(trifluoromethyl)phenyl)piperidine-4-carboxamide | | 569 | 30 |
| 91 | 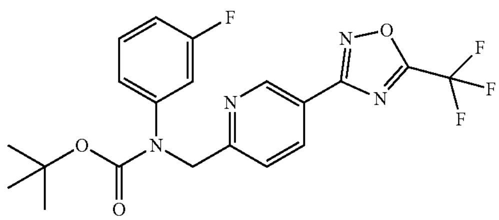 [SMILES: CC(C)(C)OC(=O)N(Cc1ccc(-c2noc(C(F)(F)F)n2)cn1)c1cccc(F)c1] | tert-butyl (3-fluorophenyl)((5-(5-(trifluoromethyl)-1,2,4-oxadiazol-3-yl)pyridin-2-yl)methyl)carbamate | | 439 | 30 |
| 92 | 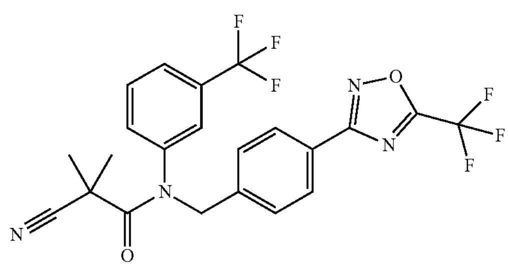 [SMILES: CC(C)(C#N)C(=O)N(Cc1ccc(-c2noc(C(F)(F)F)n2)cc1)c1cccc(C(F)(F)F)c1] | 2-cyano-2-methyl-N-(4-(5-(trifluoromethyl)-1,2,4-oxadiazol-3-yl)benzyl)-N-(3-(trifluoromethyl)phenyl)propanamide | | 483 | 30 |
| 93 | 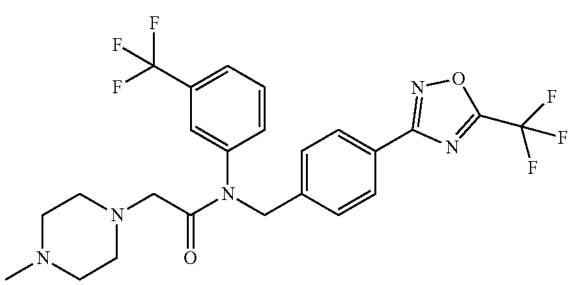 [SMILES: CN1CCN(CC(=O)N(Cc2ccc(-c3noc(C(F)(F)F)n3)cc2)c2cccc(C(F)(F)F)c2)CC1] | 2-(4-methylpiperazin-1-yl)-N-(4-(5-(trifluoromethyl)-1,2,4-oxadiazol-3-yl)benzyl)-N-(3-(trifluoromethyl)phenyl)acetamide | | 528 | 30 |
| 94 | 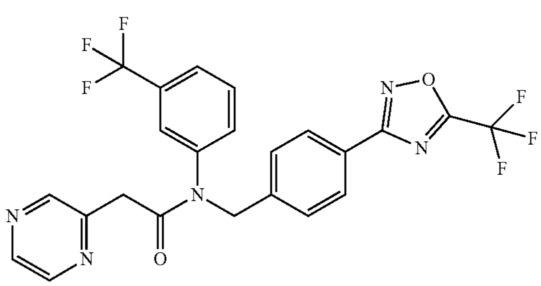 [SMILES: O=C(Cc1cnccn1)N(Cc1ccc(-c2noc(C(F)(F)F)n2)cc1)c1cccc(C(F)(F)F)c1] | 2-(pyrazin-2-yl)-N-(4-(5-(trifluoromethyl)-1,2,4-oxadiazol-3-yl)benzyl)-N-(3-(trifluoromethyl)phenyl)acetamide | | 508 | 30 |

TABLE 1-continued

| Ex # | Structure | Name | Stereo-chemistry | [M + H]+ | General Procedures |
|---|---|---|---|---|---|
| 95 | 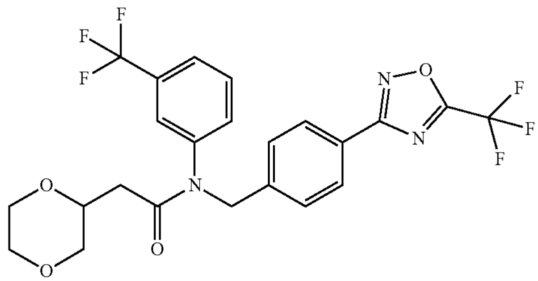 [SMILES: O=C(CC1COCCO1)N(Cc1ccc(-c2noc(C(F)(F)F)n2)cc1)c1cccc(C(F)(F)F)c1] | 2-(1,4-dioxan-2-yl)-N-(4-(5-(trifluoromethyl)-1,2,4-oxadiazol-3-yl)benzyl)-N-(3-(trifluoromethyl)phenyl)acetamide | RACEMIC | 516 | 30 |
| 96 | 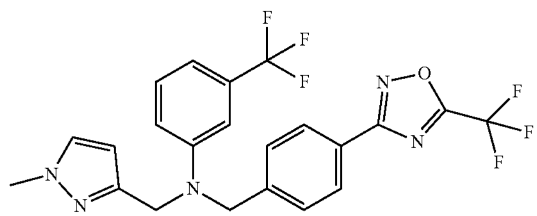 [SMILES: Cn1ccc(CN(Cc2ccc(-c3noc(C(F)(F)F)n3)cc2)c2cccc(C(F)(F)F)c2)n1] | N-((1-methyl-1H-pyrazol-3-yl)methyl)-3-(trifluoromethyl)-N-(4-(5-(trifluoromethyl)-1,2,4-oxadiazol-3-yl)benzyl)aniline | | 482 | 30 |
| 97 | 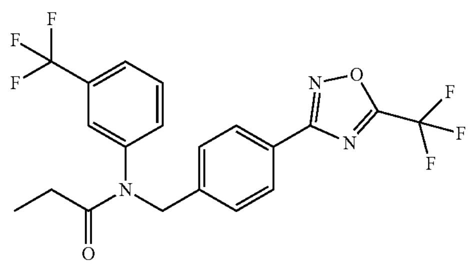 [SMILES: CCC(=O)N(Cc1ccc(-c2noc(C(F)(F)F)n2)cc1)c1cccc(C(F)(F)F)c1] | N-(4-(5-(trifluoromethyl)-1,2,4-oxadiazol-3-yl)benzyl)-N-(3-(trifluoromethyl)phenyl)propionamide | | 444 | 30 |
| 98 | 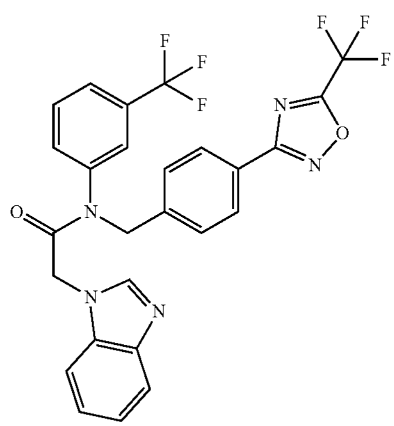 [SMILES: O=C(Cn1cnc2ccccc21)N(Cc1ccc(-c2noc(C(F)(F)F)n2)cc1)c1cccc(C(F)(F)F)c1] | 2-(1H-benzo[d]imidazol-1-yl)-N-(4-(5-(trifluoromethyl)-1,2,4-oxadiazol-3-yl)benzyl)-N-(3-(trifluoromethyl)phenyl)acetamide | | 546 | 30 |
| 99 | 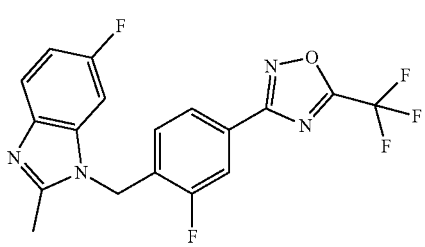 [SMILES: Cc1nc2ccc(F)cc2n1Cc1ccc(-c2noc(C(F)(F)F)n2)cc1F] | 3-(3-fluoro-4-((6-fluoro-2-methyl-1H-benzo[d]imidazol-1-yl)methyl)phenyl)-5-(trifluoromethyl)-1,2,4-oxadiazole | | 395 | 29 |

121                                                                                                                122

TABLE 1-continued

| Ex # | Structure | Name | Stereo-chemistry | [M + H]+ | General Procedures |
|---|---|---|---|---|---|
| 100 | 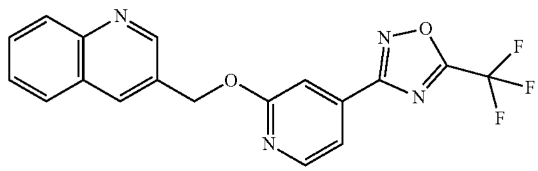 [SMILES: FC(F)(F)c1nc(-c2ccnc(OCc3cnc4ccccc4c3)c2)no1] | 3-(2-(quinolin-3-ylmethoxy)pyridin-4-yl)-5-(trifluoromethyl)-1,2,4-oxadiazole | | 373 | 24 |
| 101 | 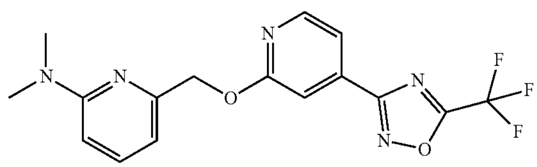 [SMILES: CN(C)c1cccc(COc2cc(-c3noc(C(F)(F)F)n3)ccn2)n1] | N,N-dimethyl-6-(((4-(5-(trifluoromethyl)-1,2,4-oxadiazol-3-yl)pyridin-2-yl)oxy)methyl)pyridin-2-amine | | 366 | 24 |
| 102 | 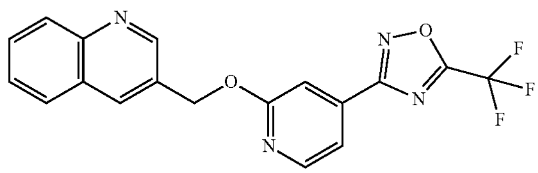 [SMILES: FC(F)(F)c1nc(-c2ccnc(OCc3cnc4ccccc4c3)c2)no1] | 3-(2-(quinolin-3-ylmethoxy)pyridin-4-yl)-5-(trifluoromethyl)-1,2,4-oxadiazole | | 373 | 24 |
| 103 | 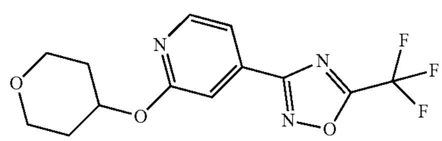 [SMILES: FC(F)(F)c1nc(-c2ccnc(OC3CCOCC3)c2)no1] | 3-(2-((tetrahydro-2H-pyran-4-yl)oxy)pyridin-4-yl)-5-(trifluoromethyl)-1,2,4-oxadiazole | | 316 | 22 |
| 104 | 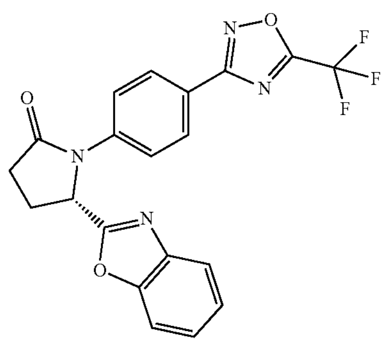 [SMILES: O=C1CC[C@@H](c2nc3ccccc3o2)N1c1ccc(-c2noc(C(F)(F)F)n2)cc1] | (S)-5-(benzo[d]oxazol-2-yl)-1-(4-(5-(trifluoromethyl)-1,2,4-oxadiazol-3-yl)phenyl)pyrrolidin-2-one | S | 415 | 22 |
| 105 | 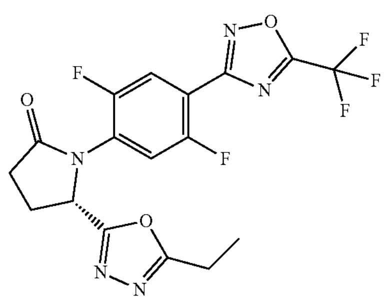 [SMILES: CCc1nnc([C@@H]2CCC(=O)N2c2cc(F)c(-c3noc(C(F)(F)F)n3)cc2F)o1] | (S)-1-(2,5-difluoro-4-(5-(trifluoromethyl)-1,2,4-oxadiazol-3-yl)phenyl)-5-(5-ethyl-1,3,4-oxadiazol-2-yl)pyrrolidin-2-one | S | 430 | 17 |

TABLE 1-continued

| Ex # | Structure | Name | Stereo-chemistry | [M + H]+ | General Procedures |
|---|---|---|---|---|---|
| 106 | 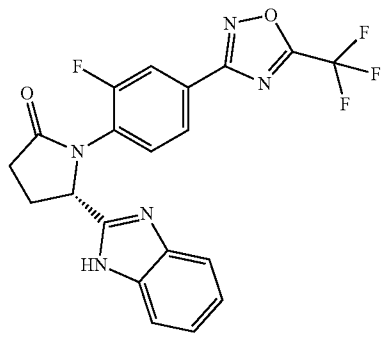 [SMILES: O=C1CC[C@@H](c2nc3ccccc3[nH]2)N1c1ccc(-c2noc(C(F)(F)F)n2)cc1F] | (S)-5-(1H-benzo[d]imidazol-2-yl)-1-(2-fluoro-4-(5-(trifluoromethyl)-1,2,4-oxadiazol-3-yl)phenyl)pyrrolidin-2-one | S | 432 | 21 |
| 107 | 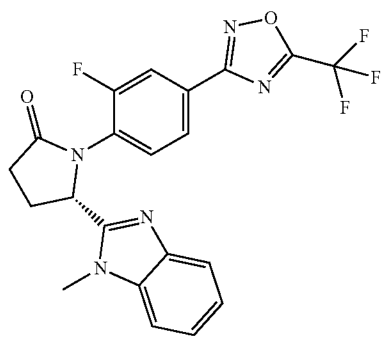 [SMILES: Cn1c([C@@H]2CCC(=O)N2c2ccc(-c3noc(C(F)(F)F)n3)cc2F)nc2ccccc21] | (S)-1-(2-fluoro-4-(5-(trifluoromethyl)-1,2,4-oxadiazol-3-yl)phenyl)-5-(1-methyl-1H-benzo[d]imidazol-2-yl)pyrrolidin-2-one | S | 446 | 21 |
| 108 | 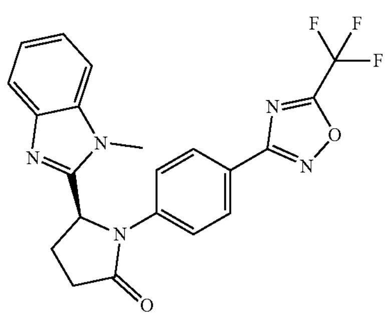 [SMILES: Cn1c([C@@H]2CCC(=O)N2c2ccc(-c3noc(C(F)(F)F)n3)cc2)nc2ccccc21] | (S)-5-(1-methyl-1H-benzo[d]imidazol-2-yl)-1-(4-(5-(trifluoromethyl)-1,2,4-oxadiazol-3-yl)phenyl)pyrrolidin-2-one | S | 428 | 21 |
| 109 | 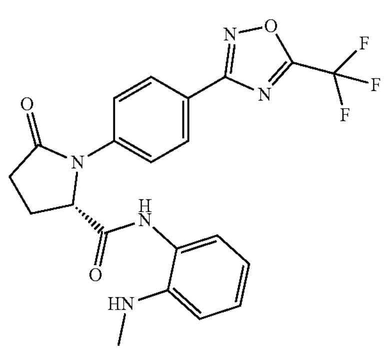 [SMILES: CNc1ccccc1NC(=O)[C@@H]1CCC(=O)N1c1ccc(-c2noc(C(F)(F)F)n2)cc1] | (S)-N-(2-(methylamino)phenyl)-5-oxo-1-(4-(5-(trifluoromethyl)-1,2,4-oxadiazol-3-yl)phenyl)pyrrolidine-2-carboxamide | S | 446 | 20 |

TABLE 1-continued

| Ex # | Structure | Name | Stereo-chemistry | [M + H]+ | General Procedures |
|---|---|---|---|---|---|
| 110 | 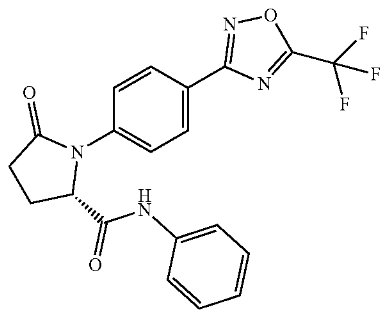 [SMILES: O=C(Nc1ccccc1)[C@@H]1CCC(=O)N1c1ccc(-c2noc(C(F)(F)F)n2)cc1] | (S)-5-oxo-N-phenyl-1-(4-(5-(trifluoromethyl)-1,2,4-oxadiazol-3-yl)phenyl) pyrrolidine-2-carboxamide | S | 417 | 19 |
| 111 | 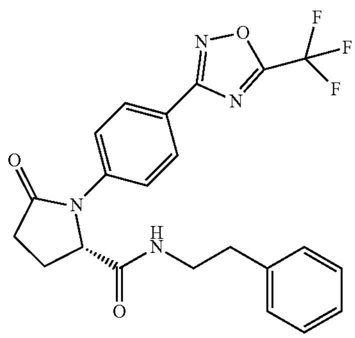 [SMILES: O=C(NCCc1ccccc1)[C@@H]1CCC(=O)N1c1ccc(-c2noc(C(F)(F)F)n2)cc1] | (S)-5-oxo-N-phenethyl-1-(4-(5-(trifluoromethyl)-1,2,4-oxadiazol-3-yl)phenyl) pyrrolidine-2-carboxamide | S | 445 | 19 |
| 112 | 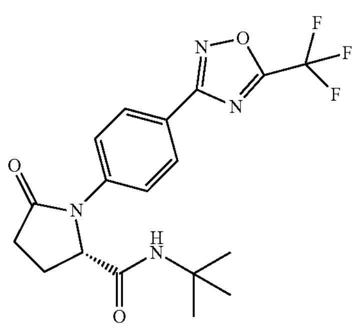 [SMILES: CC(C)(C)NC(=O)[C@@H]1CCC(=O)N1c1ccc(-c2noc(C(F)(F)F)n2)cc1] | (S)-N-(tert-butyl)-5-oxo-1-(4-(5-(trifluoromethyl)-1,2,4-oxadiazol-3-yl)phenyl) pyrrolidine-2-carboxamide | S | 397 | 19 |
| 113 | 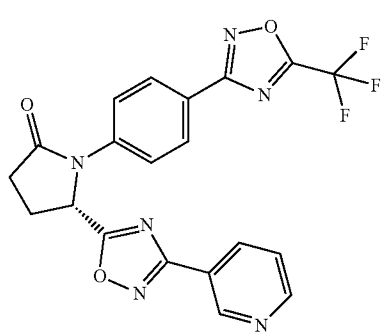 [SMILES: O=C1CC[C@@H](c2nc(-c3cccnc3)no2)N1c1ccc(-c2noc(C(F)(F)F)n2)cc1] | (S)-5-(3-(pyridin-3-yl)-1,2,4-oxadiazol-5-yl)-1-(4-(5-(trifluoromethyl)-1,2,4-oxadiazol-3-yl)phenyl) pyrrolidin-2-one | S | 443 | 17 |

TABLE 1-continued

| Ex # | Structure | Name | Stereo-chemistry | [M + H]+ | General Procedures |
|---|---|---|---|---|---|
| 114 | 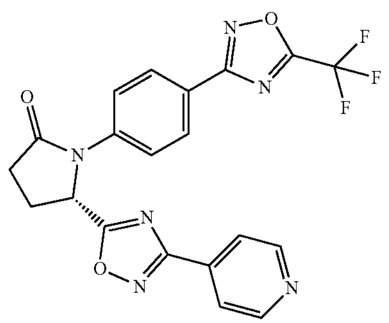 [SMILES: O=C1CC[C@@H](c2nc(-c3ccncc3)no2)N1c1ccc(-c2noc(C(F)(F)F)n2)cc1] | (S)-5-(3-(pyridin-4-yl)-1,2,4-oxadiazol-5-yl)-1-(4-(5-(trifluoromethyl)-1,2,4-oxadiazol-3-yl)phenyl)pyrrolidin-2-one | S | 443 | 17 |
| 115 | 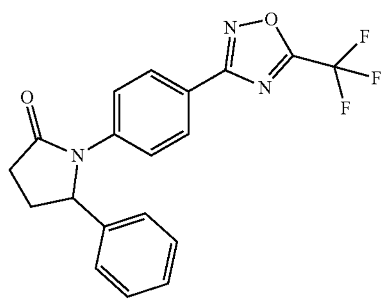 [SMILES: O=C1CCC(c2ccccc2)N1c1ccc(-c2noc(C(F)(F)F)n2)cc1] | 5-phenyl-1-(4-(5-(trifluoromethyl)-1,2,4-oxadiazol-3-yl)phenyl)pyrrolidin-2-one | R OR S | 374 | 14 |
| 116 | 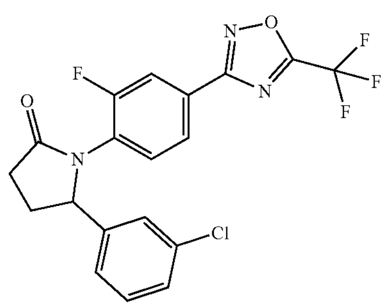 [SMILES: O=C1CCC(c2cccc(Cl)c2)N1c1ccc(-c2noc(C(F)(F)F)n2)cc1F] | 5-(3-chlorophenyl)-1-(2-fluoro-4-(5-(trifluoromethyl)-1,2,4-oxadiazol-3-yl)phenyl)pyrrolidin-2-one | RACEMIC | 426 | 14 |
| 117 | 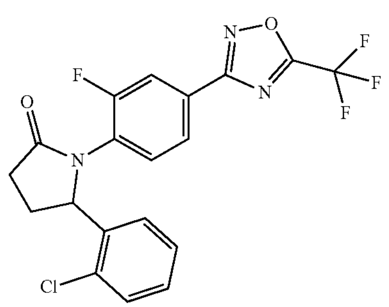 [SMILES: O=C1CCC(c2ccccc2Cl)N1c1ccc(-c2noc(C(F)(F)F)n2)cc1F] | 5-(2-chlorophenyl)-1-(2-fluoro-4-(5-(trifluoromethyl)-1,2,4-oxadiazol-3-yl)phenyl)pyrrolidin-2-one | R OR S | 426 | 14 |
| 118 | 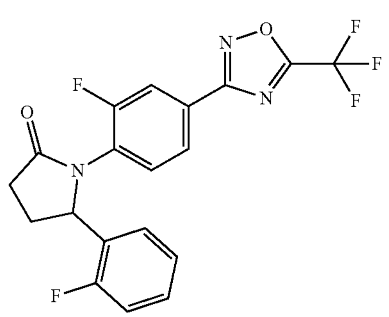 [SMILES: O=C1CCC(c2ccccc2F)N1c1ccc(-c2noc(C(F)(F)F)n2)cc1F] | 1-(2-fluoro-4-(5-(trifluoromethyl)-1,2,4-oxadiazol-3-yl)phenyl)-5-(2-fluorophenyl)pyrrolidin-2-one | RACEMIC | 410 | 14 |

TABLE 1-continued

| Ex # | Structure | Name | Stereo-chemistry | [M + H]+ | General Procedures |
|---|---|---|---|---|---|
| 119 | 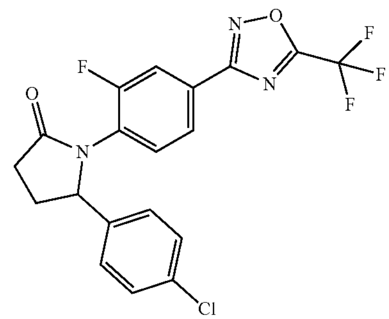 [SMILES: O=C1CCC(c2ccc(Cl)cc2)N1c1ccc(-c2noc(C(F)(F)F)n2)cc1F] | 5-(4-chlorophenyl)-1-(2-fluoro-4-(5-(trifluoromethyl)-1,2,4-oxadiazol-3-yl)phenyl)pyrrolidin-2-one | R OR S | 426 | 14 |
| 120 | 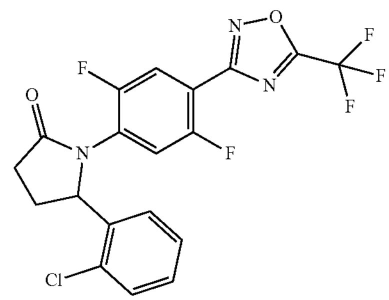 [SMILES: O=C1CCC(c2ccccc2Cl)N1c1cc(F)c(-c2noc(C(F)(F)F)n2)cc1F] | 5-(2-chlorophenyl)-1-(2,5-difluoro-4-(5-(trifluoromethyl)-1,2,4-oxadiazol-3-yl)phenyl)pyrrolidin-2-one | RACEMIC | 444 | 14 |
| 121 | 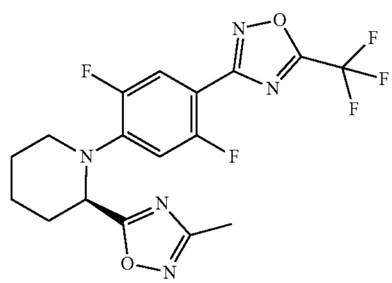 [SMILES: Cc1noc([C@H]2CCCCN2c2cc(F)c(-c3noc(C(F)(F)F)n3)cc2F)n1] | (R)-3-(2,5-difluoro-4-(2-(3-methyl-1,2,4-oxadiazol-5-yl)piperidin-1-yl)phenyl)-5-(trifluoromethyl)-1,2,4-oxadiazole | R | 416 | 10 |
| 122 | 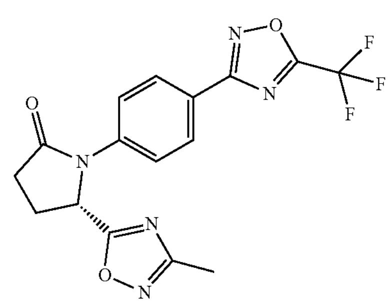 [SMILES: Cc1noc([C@@H]2CCC(=O)N2c2ccc(-c3noc(C(F)(F)F)n3)cc2)n1] | (S)-5-(3-methyl-1,2,4-oxadiazol-5-yl)-1-(4-(5-(trifluoromethyl)-1,2,4-oxadiazol-3-yl)phenyl)pyrrolidin-2-one | S | 380 | 9 |
| 123 | 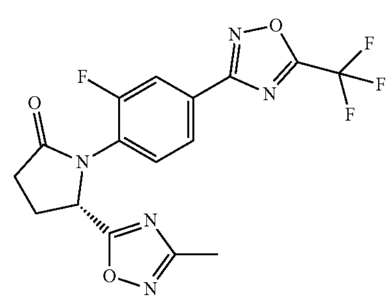 [SMILES: Cc1noc([C@@H]2CCC(=O)N2c2ccc(-c3noc(C(F)(F)F)n3)cc2F)n1] | (S)-1-(2-fluoro-4-(5-(trifluoromethyl)-1,2,4-oxadiazol-3-yl)phenyl)-5-(3-methyl-1,2,4-oxadiazol-5-yl)pyrrolidin-2-one | S | 398 | 9 |

TABLE 1-continued

| Ex # | Structure | Name | Stereo-chemistry | [M + H]+ | General Procedures |
|---|---|---|---|---|---|
| 124 | 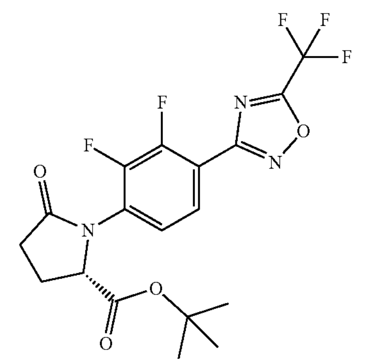 [SMILES: CC(C)(C)OC(=O)[C@@H]1CCC(=O)N1c1ccc(-c2noc(C(F)(F)F)n2)c(F)c1F] | tert-butyl (S)-1-(2,3-difluoro-4-(5-(trifluoromethyl)-1,2,4-oxadiazol-3-yl)phenyl)-5-oxopyrrolidine-2-carboxylate | S | 434 | 8 |
| 125 | 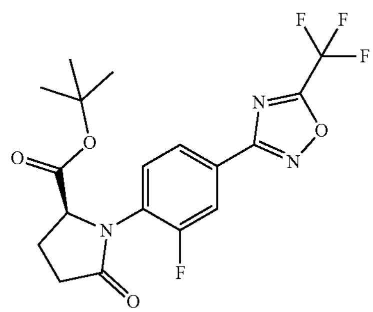 [SMILES: CC(C)(C)OC(=O)[C@@H]1CCC(=O)N1c1ccc(-c2noc(C(F)(F)F)n2)cc1F] | tert-butyl (S)-1-(2-fluoro-4-(5-(trifluoromethyl)-1,2,4-oxadiazol-3-yl)phenyl)-5-oxopyrrolidine-2-carboxylate | S | 416 | 8 |
| 126 | 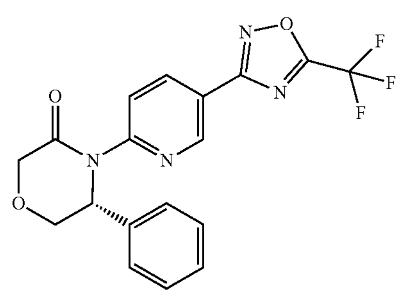 [SMILES: O=C1COC[C@@H](c2ccccc2)N1c1ccc(-c2noc(C(F)(F)F)n2)cn1] | (R)-5-phenyl-4-(5-(5-(trifluoromethyl)-1,2,4-oxadiazol-3-yl)pyridin-2-yl)morpholin-3-one | R | 391 | 5 |
| 127 | 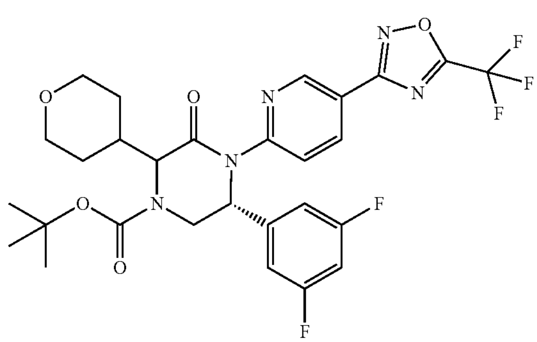 [SMILES: CC(C)(C)OC(=O)N1C[C@@H](c2cc(F)cc(F)c2)N(c2ccc(-c3noc(C(F)(F)F)n3)cn2)C(=O)C1C1CCOCC1] | tert-butyl (5R)-5-(3,5-difluorophenyl)-3-oxo-2-(tetrahydro-2H-pyran-4-yl)-4-(5-(5-(trifluoromethyl)-1,2,4-oxadiazol-3-yl)pyridin-2-yl)piperazine-1-carboxylate | R, R OR S | 610 | 5 |
| 128 | 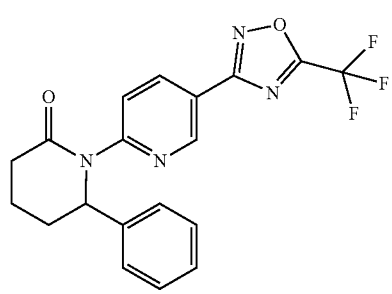 [SMILES: O=C1CCCC(c2ccccc2)N1c1ccc(-c2noc(C(F)(F)F)n2)cn1] | 6-phenyl-1-(5-(5-(trifluoromethyl)-1,2,4-oxadiazol-3-yl)pyridin-2-yl)piperidin-2-one | R OR S | 389 | 5 |

TABLE 1-continued

| Ex # | Structure | Name | Stereo-chemistry | [M + H]+ | General Procedures |
|---|---|---|---|---|---|
| 129 | 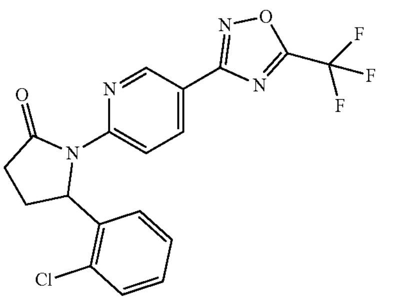 [SMILES: O=C1CCC(c2ccccc2Cl)N1c1ccc(-c2noc(C(F)(F)F)n2)cn1] | 5-(2-chlorophenyl)-1-(5-(5-(trifluoromethyl)-1,2,4-oxadiazol-3-yl)pyridin-2-yl)pyrrolidin-2-one | RACEMIC | 409 | 5 |
| 130 | 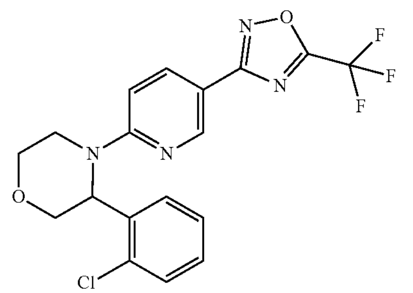 [SMILES: FC(F)(F)c1nc(-c2ccc(N3CCOCC3c3ccccc3Cl)nc2)no1] | 3-(2-chlorophenyl)-4-(5-(5-(trifluoromethyl)-1,2,4-oxadiazol-3-yl)pyridin-2-yl)morpholine | R OR S | 411 | 3 |
| 131 | 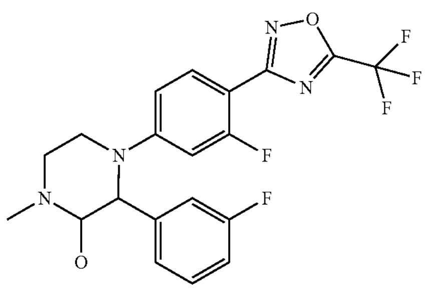 [SMILES: CN1CCN(c2ccc(-c3noc(C(F)(F)F)n3)c(F)c2)C(c2cccc(F)c2)C1O] | 4-(3-fluoro-4-(5-(trifluoromethyl)-1,2,4-oxadiazol-3-yl)phenyl)-3-(3-fluorophenyl)-1-methylpiperazin-2-one | RACEMIC | 439 | 3 |
| 132 | 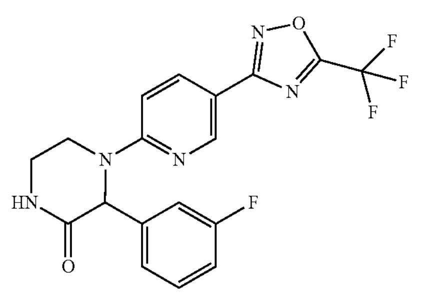 [SMILES: O=C1NCCN(c2ccc(-c3noc(C(F)(F)F)n3)cn2)C1c1cccc(F)c1] | 3-(3-fluorophenyl)-4-(5-(5-(trifluoromethyl)-1,2,4-oxadiazol-3-yl)pyridin-2-yl)piperazin-2-one | RACEMIC | 408 | 3 |
| 133 | 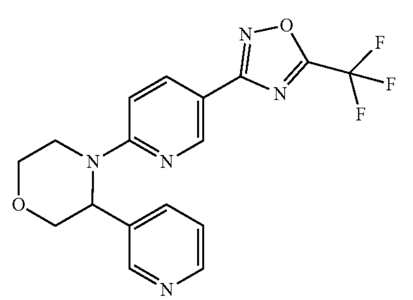 [SMILES: FC(F)(F)c1nc(-c2ccc(N3CCOCC3c3cccnc3)nc2)no1] | 3-(pyridin-3-yl)-4-(5-(5-(trifluoromethyl)-1,2,4-oxadiazol-3-yl)pyridin-2-yl)morpholine | R OR S | 378 | 3 |

TABLE 1-continued

| Ex # | Structure | Name | Stereo-chemistry | [M + H]+ | General Procedures |
|---|---|---|---|---|---|
| 134 | 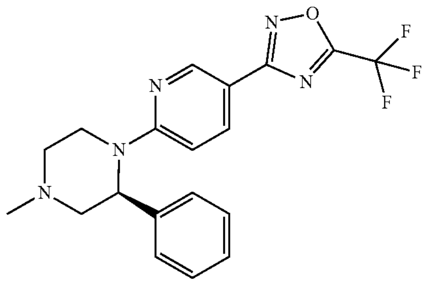 [SMILES: CN1CCN(c2ccc(-c3noc(C(F)(F)F)n3)cn2)[C@@H](c2ccccc2)C1] | (S)-3-(6-(4-methyl-2-phenylpiperazin-1-yl)pyridin-3-yl)-5-(trifluoromethyl)-1,2,4-oxadiazole | S | 390 | 3 |
| 135 | 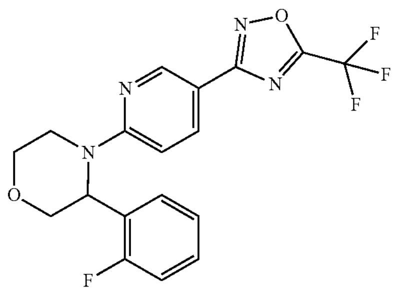 [SMILES: Fc1ccccc1C1COCCN1c1ccc(-c2noc(C(F)(F)F)n2)cn1] | 3-(2-fluorophenyl)-4-(5-(5-(trifluoromethyl)-1,2,4-oxadiazol-3-yl)pyridin-2-yl)morpholine | RACEMIC | 395 | 3 |
| 136 | 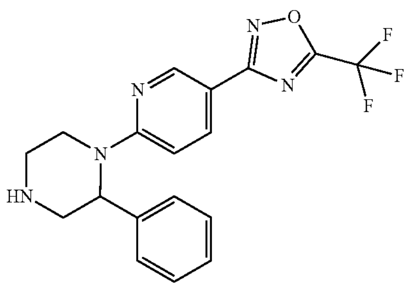 [SMILES: FC(F)(F)c1nc(-c2ccc(N3CCNCC3c3ccccc3)nc2)no1] | 3-(6-(2-phenylpiperazin-1-yl)pyridin-3-yl)-5-(trifluoromethyl)-1,2,4-oxadiazole | RACEMIC | 376 | 3 |
| 137 | 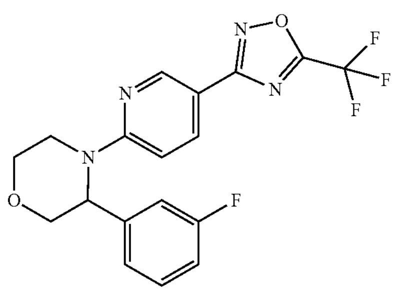 [SMILES: Fc1cccc(C2COCCN2c2ccc(-c3noc(C(F)(F)F)n3)cn2)c1] | 3-(3-fluorophenyl)-4-(5-(5-(trifluoromethyl)-1,2,4-oxadiazol-3-yl)pyridin-2-yl)morpholine | RACEMIC | 395 | 3 |
| 138 | 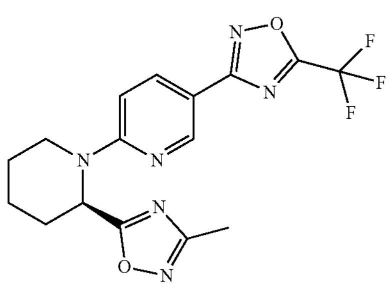 [SMILES: Cc1noc([C@H]2CCCCN2c2ccc(-c3noc(C(F)(F)F)n3)cn2)n1] | (R)-3-methyl-5-(1-(5-(5-(trifluoromethyl)-1,2,4-oxadiazol-3-yl)pyridin-2-yl)piperidin-2-yl)-1,2,4-oxadiazole | R | 381 | 3 |

TABLE 1-continued

| Ex # | Structure | Name | Stereo-chemistry | [M + H]+ | General Procedures |
|---|---|---|---|---|---|
| 139 | 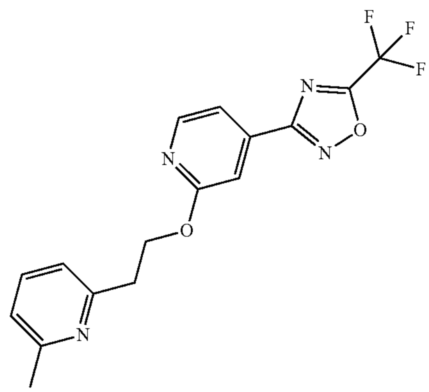 [SMILES: Cc1cccc(CCOc2cc(-c3noc(C(F)(F)F)n3)ccn2)n1] | 3-(2-(2-(6-methylpyridin-2-yl)ethoxy)pyridin-4-yl)-5-(trifluoromethyl)-1,2,4-oxadiazole | | 351 | 3 |
| 140 | 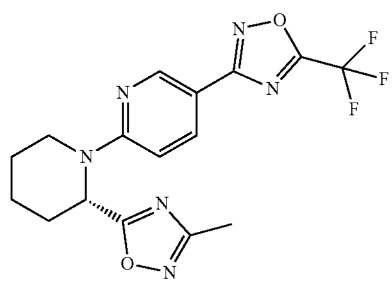 [SMILES: Cc1noc([C@@H]2CCCCN2c2ccc(-c3noc(C(F)(F)F)n3)cn2)n1] | (S)-3-methyl-5-(1-(5-(5-(trifluoromethyl)-1,2,4-oxadiazol-3-yl)pyridin-2-yl)piperidin-2-yl)-1,2,4-oxadiazole | S | 381 | 3 |
| 141 | 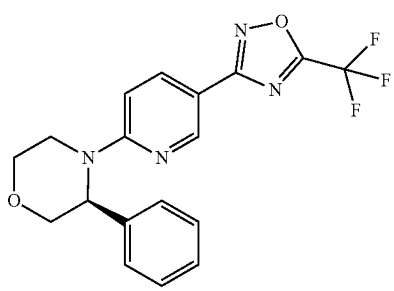 [SMILES: FC(F)(F)c1nc(-c2ccc(N3CCOC[C@@H]3c3ccccc3)nc2)no1] | (S)-3-phenyl-4-(5-(5-(trifluoromethyl)-1,2,4-oxadiazol-3-yl)pyridin-2-yl)morpholine | S | 377 | 3 |
| 142 | 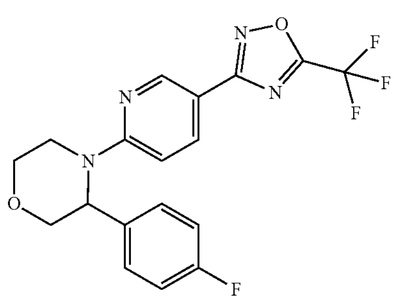 [SMILES: Fc1ccc(C2COCCN2c2ccc(-c3noc(C(F)(F)F)n3)cn2)cc1] | 3-(4-fluorophenyl)-4-(5-(5-(trifluoromethyl)-1,2,4-oxadiazol-3-yl)pyridin-2-yl)morpholine | RACEMIC | 395 | 3 |
| 143 | 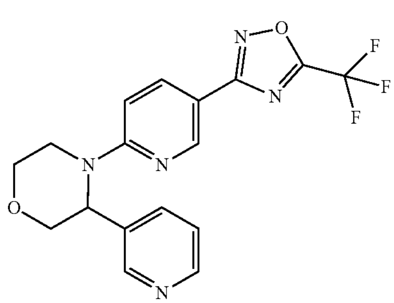 [SMILES: FC(F)(F)c1nc(-c2ccc(N3CCOCC3c3cccnc3)nc2)no1] | 3-(pyridin-3-yl)-4-(5-(5-(trifluoromethyl)-1,2,4-oxadiazol-3-yl)pyridin-2-yl)morpholine | R OR S | 378 | 3 |

TABLE 1-continued

| Ex # | Structure | Name | Stereo-chemistry | [M + H]+ | General Procedures |
|---|---|---|---|---|---|
| 144 | 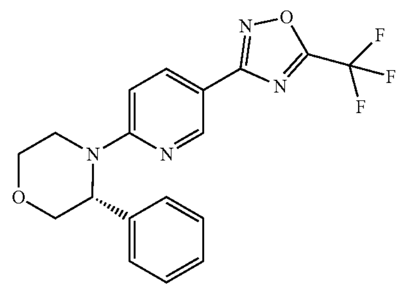 [SMILES: FC(F)(F)c1nc(-c2ccc(N3CCOC[C@H]3c3ccccc3)nc2)no1] | (R)-3-phenyl-4-(5-(5-(trifluoromethyl)-1,2,4-oxadiazol-3-yl)pyridin-2-yl)morpholine | R | 377 | 3 |
| 145 | 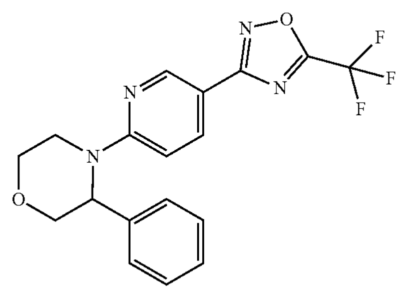 [SMILES: FC(F)(F)c1nc(-c2ccc(N3CCOCC3c3ccccc3)nc2)no1] | 3-phenyl-4-(5-(5-(trifluoromethyl)-1,2,4-oxadiazol-3-yl)pyridin-2-yl)morpholine | RACEMIC | 377 | 3 |
| 146 | 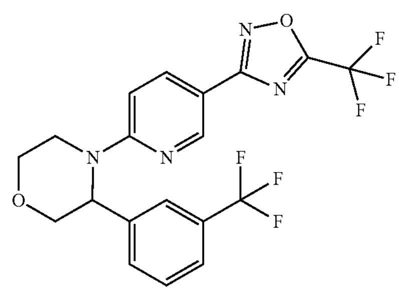 [SMILES: FC(F)(F)c1cccc(C2COCCN2c2ccc(-c3noc(C(F)(F)F)n3)cn2)c1] | 4-(5-(5-(trifluoromethyl)-1,2,4-oxadiazol-3-yl)pyridin-2-yl)-3-(3-(trifluoromethyl)phenyl)morpholine | RACEMIC | 445 | 3 |
| 147 | 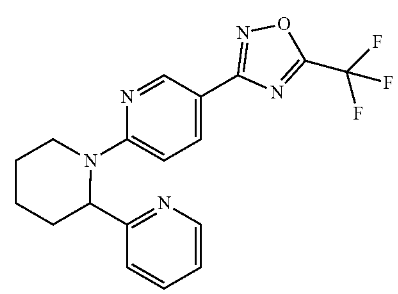 [SMILES: FC(F)(F)c1nc(-c2ccc(N3CCCCC3c3ccccn3)nc2)no1] | 3-(6-(2-(pyridin-2-yl)piperidin-1-yl)pyridin-3-yl)-5-(trifluoromethyl)-1,2,4-oxadiazole | RACEMIC | 376 | 3 |
| 148 | 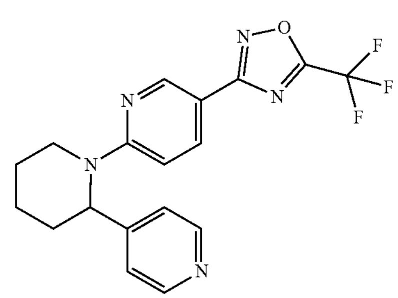 [SMILES: FC(F)(F)c1nc(-c2ccc(N3CCCCC3c3ccncc3)nc2)no1] | 3-(6-(2-(pyridin-4-yl)piperidin-1-yl)pyridin-3-yl)-5-(trifluoromethyl)-1,2,4-oxadiazole | RACEMIC | 376 | 3 |

| Ex # | Structure | Name | Stereo-chemistry | [M + H]+ | General Procedures |
|---|---|---|---|---|---|
| 149 | 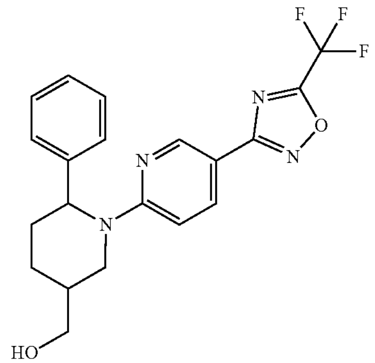 [SMILES: OCC1CCC(c2ccccc2)N(c2ccc(-c3noc(C(F)(F)F)n3)cn2)C1] | (6-phenyl-1-(5-(5-(trifluoromethyl)-1,2,4-oxadiazol-3-yl)pyridin-2-yl)piperidin-3-yl)methanol | RACEMIC | 405 | 3 |
| 150 | 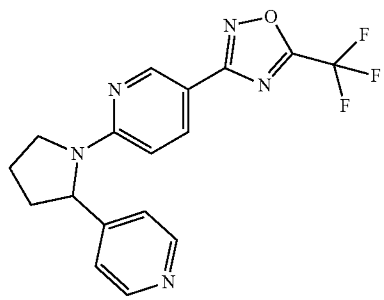 [SMILES: FC(F)(F)c1nc(-c2ccc(N3CCCC3c3ccncc3)nc2)no1] | 3-(6-(2-(pyridin-4-yl)pyrrolidin-1-yl)pyridin-3-yl)-5-(trifluoromethyl)-1,2,4-oxadiazole | RACEMIC | 362 | 3 |
| 151 | 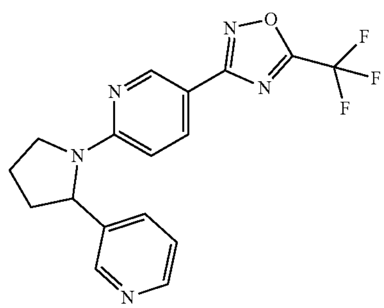 [SMILES: FC(F)(F)c1nc(-c2ccc(N3CCCC3c3cccnc3)nc2)no1] | 3-(6-(2-(pyridin-3-yl)pyrrolidin-1-yl)pyridin-3-yl)-5-(trifluoromethyl)-1,2,4-oxadiazole | RACEMIC | 362 | 3 |
| 152 | 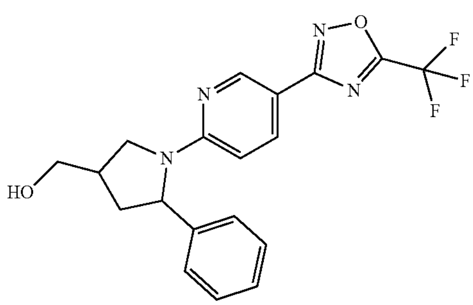 [SMILES: OCC1CC(c2ccccc2)N(c2ccc(-c3noc(C(F)(F)F)n3)cn2)C1] | (5-phenyl-1-(5-(5-(trifluoromethyl)-1,2,4-oxadiazol-3-yl)pyridin-2-yl)pyrrolidin-3-yl)methanol | RACEMIC | 391 | 3 |
| 153 | 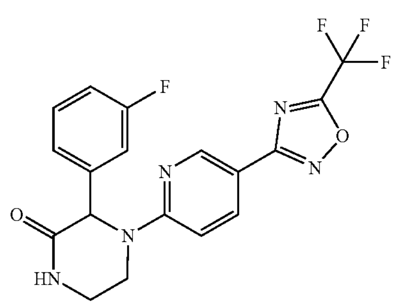 [SMILES: O=C1NCCN(c2ccc(-c3noc(C(F)(F)F)n3)cn2)C1c1cccc(F)c1] | 3-(3-fluorophenyl)-4-(5-(5-(trifluoromethyl)-1,2,4-oxadiazol-3-yl)pyridin-2-yl)piperazin-2-one | R OR S | 408 | 3 |

TABLE 1-continued

| Ex # | Structure | Name | Stereo-chemistry | [M + H]+ | General Procedures |
|---|---|---|---|---|---|
| 154 | 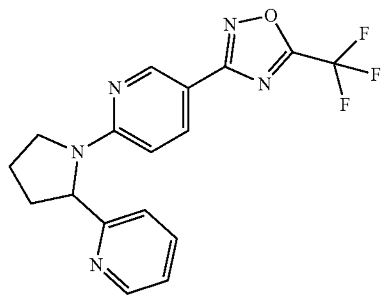 [SMILES: FC(F)(F)c1nc(-c2ccc(N3CCCC3c3ccccn3)nc2)no1] | 3-(6-(2-(pyridin-2-yl)pyrrolidin-1-yl)pyridin-3-yl)-5-(trifluoromethyl)-1,2,4-oxadiazole | RACEMIC | 362 | 3 |
| 155 | 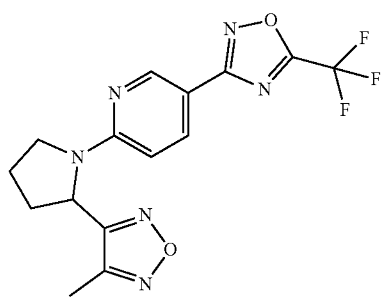 [SMILES: Cc1nonc1C1CCCN1c1ccc(-c2noc(C(F)(F)F)n2)cn1] | 3-(6-(2-(4-methyl-1,2,5-oxadiazol-3-yl)pyrrolidin-1-yl)pyridin-3-yl)-5-(trifluoromethyl)-1,2,4-oxadiazole | RACEMIC | 367 | 3 |
| 156 | 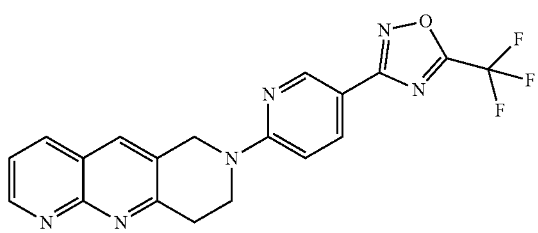 [SMILES: FC(F)(F)c1nc(-c2ccc(N3CCc4nc5ncccc5cc4C3)nc2)no1] | 3-(6-(8,9-dihydropyrido[2,3-b][1,6]naphthyridin-7(6H)-yl)pyridin-3-yl)-5-(trifluoromethyl)-1,2,4-oxadiazole | | 399 | 3 |
| 157 | 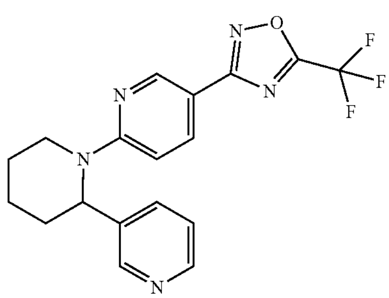 [SMILES: FC(F)(F)c1nc(-c2ccc(N3CCCCC3c3cccnc3)nc2)no1] | 3-(6-(2-(pyridin-3-yl)piperidin-1-yl)pyridin-3-yl)-5-(trifluoromethyl)-1,2,4-oxadiazole | RACEMIC | 376 | 3 |
| 158 | 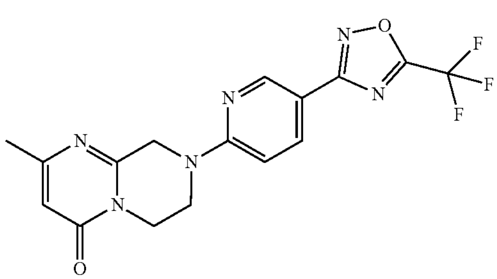 [SMILES: Cc1cc(=O)n2c(n1)CN(c1ccc(-c3noc(C(F)(F)F)n3)cn1)CC2] | 2-methyl-8-(5-(5-(trifluoromethyl)-1,2,4-oxadiazol-3-yl)pyridin-2-yl)-6,7,8,9-tetrahydro-4H-pyrazino[1,2-a]pyrimidin-4-one | | 379 | 3 |

TABLE 1-continued

| Ex # | Structure | Name | Stereo-chemistry | [M + H]+ | General Procedures |
|---|---|---|---|---|---|
| 159 | 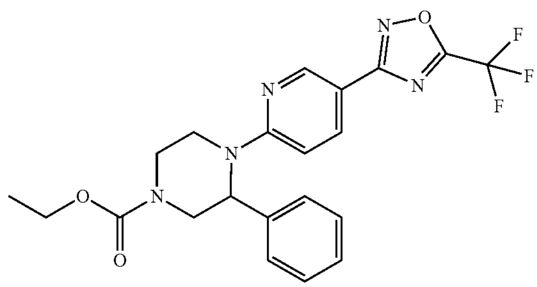 [SMILES: CCOC(=O)N1CCN(c2ccc(-c3noc(C(F)(F)F)n3)cn2)C(c2ccccc2)C1] | ethyl 3-phenyl-4-(5-(5-(trifluoromethyl)-1,2,4-oxadiazol-3-yl)pyridin-2-yl)piperazine-1-carboxylate | RACEMIC | 448 | 3 |
| 160 | 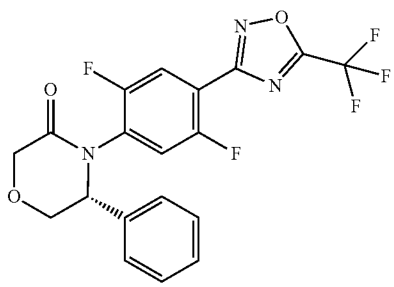 [SMILES: O=C1COC[C@@H](c2ccccc2)N1c1cc(F)c(-c2noc(C(F)(F)F)n2)cc1F] | (R)-4-(2,5-difluoro-4-(5-(trifluoromethyl)-1,2,4-oxadiazol-3-yl)phenyl)-5-phenylmorpholin-3-one | R | 426 | 2 |
| 161 | 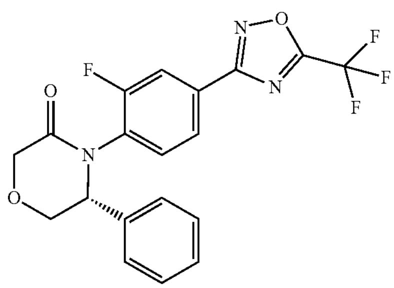 [SMILES: O=C1COC[C@@H](c2ccccc2)N1c1ccc(-c2noc(C(F)(F)F)n2)cc1F] | (R)-4-(2-fluoro-4-(5-(trifluoromethyl)-1,2,4-oxadiazol-3-yl)phenyl)-5-phenylmorpholin-3-one | R | 408 | 2 |
| 162 | 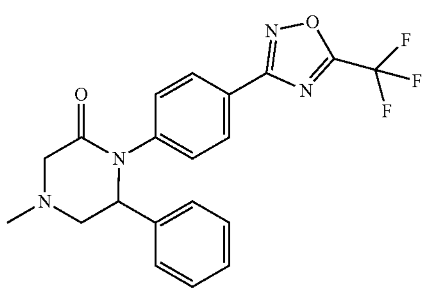 [SMILES: CN1CC(=O)N(c2ccc(-c3noc(C(F)(F)F)n3)cc2)C(c2ccccc2)C1] | 4-methyl-6-phenyl-1-(4-(5-(trifluoromethyl)-1,2,4-oxadiazol-3-yl)phenyl)piperazin-2-one | R OR S | 403 | 2 |
| 163 | 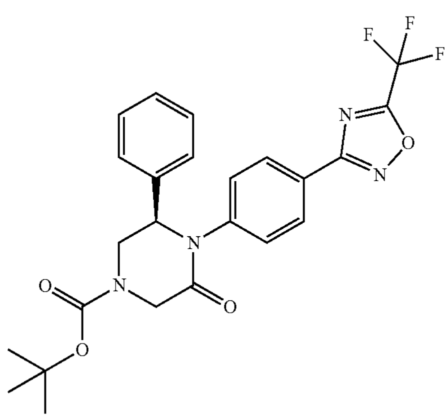 [SMILES: CC(C)(C)OC(=O)N1CC(=O)N(c2ccc(-c3noc(C(F)(F)F)n3)cc2)[C@H](c2ccccc2)C1] | tert-butyl 3-oxo-5-phenyl-4-(4-(5-(trifluoromethyl)-1,2,4-oxadiazol-3-yl)phenyl)piperazine-1-carboxylate | RACEMIC | 489 | 2 |

TABLE 1-continued

| Ex # | Structure | Name | Stereo-chemistry | [M + H]+ | General Procedures |
|---|---|---|---|---|---|
| 164 | 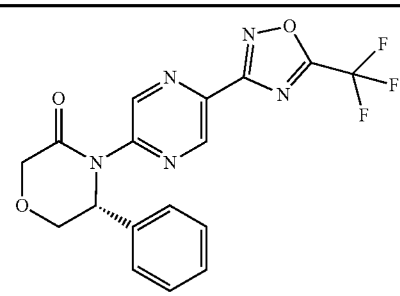 | (R)-5-phenyl-4-(5-(5-(trifluoromethyl)-1,2,4-oxadiazol-3-yl)pyrazin-2-yl)morpholin-3-one | R | 392 | 5 |
| 165 | 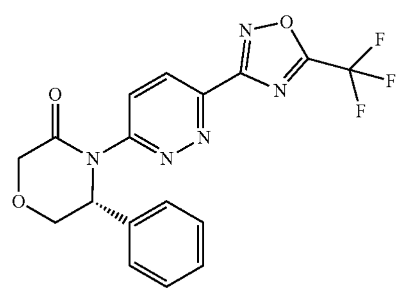 [SMILES: O=C1COC[C@@H](c2ccccc2)N1c1ccc(-c2noc(C(F)(F)F)n2)nn1] | (R)-5-phenyl-4-(6-(5-(trifluoromethyl)-1,2,4-oxadiazol-3-yl)pyridazin-3-yl)morpholin-3-one | R | 392 | 5 |
| 166 | 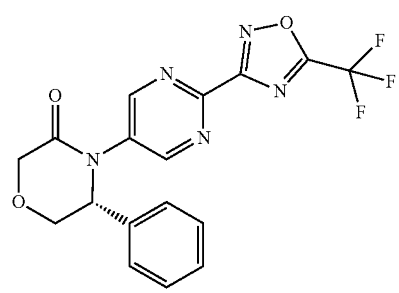 [SMILES: O=C1COC[C@@H](c2ccccc2)N1c1cnc(-c2noc(C(F)(F)F)n2)nc1] | (R)-5-phenyl-4-(2-(5-(trifluoromethyl)-1,2,4-oxadiazol-3-yl)pyrimidin-5-yl)morpholin-3-one | R | 392 | 5 |

Example 167

3-(2-(2-($^1$H-Indazol-7-yl))ethoxy)pyridin-4-yl)-5-(trifluoromethyl)-1,2,4-oxadiazole

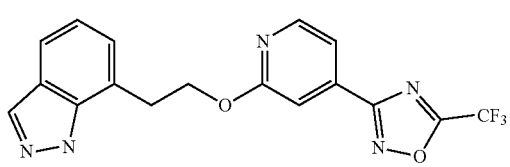 [SMILES: FC(F)(F)c1nc(-c2ccnc(OCCc3cccc4cn[nH]c34)c2)no1]

Step A: 7-Bromo-1-((2-(trimethylsilyl)ethoxy)methyl)-1H-indazole

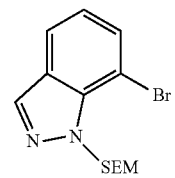 [SMILES: C[Si](C)(C)CCOCn1ncc2cccc(Br)c21]

Sodium hydride (0.568 g, 14.21 mmol) (60% in Mineral Oil) was added to a stirred mixture of 7-bromo-$^1$H-indazole (1.4 g, 7.11 mmol) in THF (30 mL) at 0° C. After 0.5 h, SEM-Cl (2.52 mL, 14.21 mmol) was added to the mixture at 0° C. and the mixture was stirred at 15° C. under N₂ for 16 h. The mixture was partitioned between ethyl acetate (50 mL), sat.NH₄Cl (50 mL) and H₂O (30 mL), and the aqueous layer was extracted with ethyl acetate (2×50 mL). The combined organic layers were washed with brine (50 mL), dried (MgSO₄), filtered and concentrated under reduced pressure to give 7-bromo-1-((2-(trimethylsilyl)ethoxy)methyl)-¹H-indazole as an oil. ESI-MS m/z [M+H]⁺: 327.0/329.0

Step B: 1-((2-(Trimethylsilyl)ethoxy)methyl)-7-vinyl-¹H-indazole

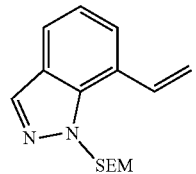

PdCl₂(PPh₃)₂(0.472 g, 0.672 mmol) was added to a stirred mixture of cesium carbonate (4.38 g, 13.4 mmol), potassium vinyltrifluoroborate (1.35 g, 10.1 mmol) and 7-bromo-1-((2-(trimethylsilyl)ethoxy)methyl)-¹H-indazole (2.20 g, 6.72 mmol) in THF (20 mL)/water (7.0 mL) and the mixture was heated at 90° C. under N₂ for 16 h. The mixture was partitioned between EtOAc (100 mL) and H₂O (100 mL), and the aqueous layer was extracted with EtOAc (2×50 mL). The combined organic layers were washed with brine (50 mL), dried (MgSO₄), filtered and concentrated under reduced pressure. The residue was purified by flash silica gel chromatography (ISCO®; 40 g SepaFlash® Silica Flash Column, Eluent of 0-20% EtOAc/PE gradient @ 40 mL/min) to give 1-((2-(trimethylsilyl)ethoxy)methyl)-7-vinyl-¹H-indazole as an oil. ESI-MS m/z [M+H]⁺: 275.1

Step C: 2-(1-((2-(Trimethylsilyl)ethoxy)methyl)-¹H-indazol-7-yl)ethan-1-ol

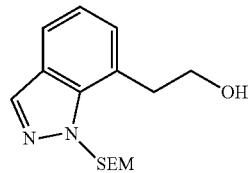 [SMILES: C[Si](C)(C)CCOCn1ncc2cccc(CCO)c21]

To a solution of 1-((2-(trimethylsilyl)ethoxy)methyl)-7-vinyl-¹H-indazole (800 mg, 2.92 mmol) in THF (20 mL) at 0° C. was added dropwise BH₃.THF (7.29 mL, 7.29 mmol) (1M in THF). The mixture was stirred for 16 h at 15° C. To this mixture was added NaOH (1750 mg, 4.37 mmol) (10% in H₂O) and H₂O₂(0.383 mL, 4.37 mmol) (35% in H₂O), and the mixture was stirred for another 6 h. The mixture was partitioned between ethyl acetate (100 mL) and H₂O (100 mL), and the aqueous layer was extracted with ethyl acetate (2×50 mL). The combined organic layers were washed with brine (50 mL), dried (MgSO4), filtered and concentrated under reduced pressure. The residue was purified by flash silica gel chromatography (ISCO®; 12 g SepaFlash® Silica Flash Column, Eluent of 0-20% EtOAc/PE gradient @ 20 mL/min) to give 2-(1-((2-(trimethylsilyl)ethoxy)methyl)-¹H-indazol-7-yl)ethanol as an oil. ESI-MS m/z [M+H]⁺: 293.1

Step D: 2-(1-((2-(Trimethylsilyl)ethoxy)methyl)-¹H-indazol-7-yl)ethyl methanesulfonate

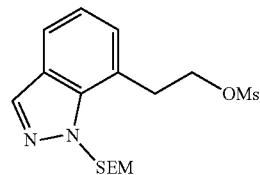 [SMILES: C[Si](C)(C)CCOCn1ncc2cccc(CCOS(C)(=O)=O)c21]

Methanesulfonyl chloride (0.052 mL, 0.667 mmol) was added to a mixture of triethylamine (0.124 mL, 0.889 mmol) and 2-(1-((2-(trimethylsilyl)ethoxy)methyl)-¹H-indazol-7-yl)ethanol (130 mg, 0.445 mmol) in DCM (5 mL) at 15° C. After the addition was complete, the mixture was stirred at 15° C. for 3 h. The mixture was partitioned between CH₂Cl₂ (20 mL) and H₂O (20 mL), and the aqueous layer was extracted with CH₂Cl₂ (2×10 mL). The combined organic layers were washed with brine (20 mL), dried (MgSO₄), filtered and concentrated under reduced pressure to give 2-(1-((2-(trimethylsilyl) ethoxy)methyl)-¹H-indazol-7-yl) ethyl methanesulfonate as an oil. ESI-MS m/z [M+H]⁺: 371.1

Step E: 5-(Trifluoromethyl)-3-(2-(2-(1-((2-(trimethylsilyl)ethoxy)methyl)-1H-indazol-7-yl)ethoxy)pyridin-4-yl)-1,2,4-oxadiazole

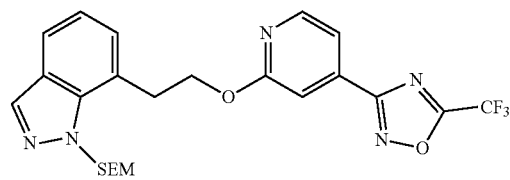 [SMILES: C[Si](C)(C)CCOCn1ncc2cccc(CCOc3cc(-c4noc(C(F)(F)F)n4)ccn3)c21]

A mixture of 4-(5-(trifluoromethyl)-1,2,4-oxadiazol-3-yl)pyridin-2(1H)-one (94 mg, 0.405 mmol) from Example 24, Step B, potassium carbonate (112 mg, 0.810 mmol) and 2-(1-((2-(trimethylsilyl)ethoxy)methyl)-¹H-indazol-7-yl) ethyl methanesulfonate (150 mg, 0.405 mmol) in CH₃CN (5 mL) was stirred at 90° C. for 16 h. After cooling to ambient temperature, the mixture was filtered, washed with EtOAc (50 mL) and concentrated under reduced pressure. The residue was purified by reverse-phase prep-HPLC (preparative HPLC on a GILSON 281 instrument fitted with Waters XSELECT C18 150*30 mm*5 um using water and acetonitrile as the eluents. Mobile phase A: water, mobile phase B: acetonitrile (containing: 0.1% TFA-ACN) Gradient: 28-68%, 0-10 min; 100% B, 10.5-12.5 min; 5% B, 13-15 min) to give 5-(trifluoromethyl)-3-(2-(2-(1-((2-(trimethylsilyl)ethoxy)methyl)-¹H-indazol-7-yl)ethoxy)pyridin-4-yl)-1,2,4-oxadiazole as an oil. ESI-MS m/z [M+H]⁺: 506.1.

Step F: 3-(2-(2-(¹H-Indazol-7-yl)ethoxy)pyridin-4-yl)-5-(trifluoromethyl)-1,2,4-oxadiazole

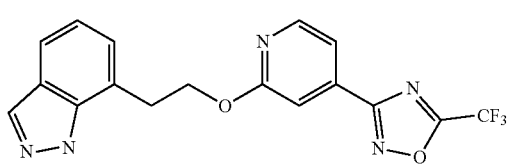 [SMILES: FC(F)(F)c1nc(-c2ccnc(OCCc3cccc4cn[nH]c34)c2)no1]

A mixture of 5-(trifluoromethyl)-3-(2-(2-(1-((2-(trimethylsilyl)ethoxy)methyl)-¹H-indazol-7-yl)ethoxy)pyridin-4-yl)-1,2,4-oxadiazole (65 mg, 0.129 mmol) in TFA:CH₂Cl₂=1:2 (2 mL) was stirred at 15° C. for 4 h. The mixture was concentrated under reduced pressure. The residue was purified by reverse-phase prep-HPLC (preparative HPLC on a GILSON 281 instrument fitted with Waters XSELECT C18 150*30 mm*5 um using water and acetonitrile as the eluents. Mobile phase A: water, mobile phase B: acetonitrile (containing: 0.1% TFA-ACN). Gradient: 38-68%, 0-10 min; 100% B, 10.5-12.5 min; 5% B, 13-15 min) to give 3-(2-(2-(¹H-indazol-7-yl)ethoxy)pyridin-4-yl)-5-(trifluoromethyl)-1,2,4-oxadiazole as an oil. ¹H NMR (400 MHz, CD₃OD): δ 8.32 (d, J=5.29 Hz, 1H), 8.07 (s, 1H), 7.65 (d, J=8.16 Hz, 1H), 7.56 (dd, J=5.29, 1.32 Hz, 1H), 7.38 (s, 1H), 7.30 (s, 1H), 7.06-7.14 (m, 1H), 4.70 (s, 2H), 3.43 (s, 2H); ESI-MS m/z [M+H]⁺: 376.0.

Example 168

3-(3-Fluoro-4-(phenoxymethyl)phenyl)-5-(trifluoromethyl)-1,2,4-oxadiazole

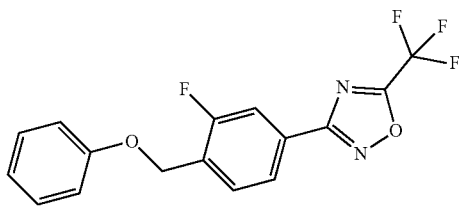 [SMILES: Fc1cc(-c2noc(C(F)(F)F)n2)ccc1COc1ccccc1]

Step A: 3-Fluoro-4-(hydroxymethyl)benzonitrile

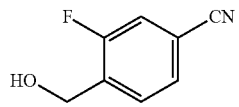 [SMILES: N#Cc1ccc(CO)c(F)c1]

To a solution of 4-cyano-2-fluorobenzoic acid (300 mg, 1.817 mmol) in THF (3 mL) was added BH₃.THF (3.63 mL, 3.63 mmol) at 0° C. The reaction mixture was warmed to 13° C. for 16 h. To the reaction mixture was added MeOH (30 mL), and the mixture was stirred for 1 h. The reaction mixture was evaporated under reduced pressure. The residue was purified by flash silica gel chromatography (ISCO®; 40 g SepaFlash® Silica Flash Column, Eluent of 0-50% EtOAc/PE gradient @ 30 mL/min) to give 3-fluoro-4-(hydroxymethyl)benzonitrile as a solid. ESI-MS m/z [M+H]⁺: low ionization.

Step B: 3-Fluoro-4-(phenoxymethyl)benzonitrile

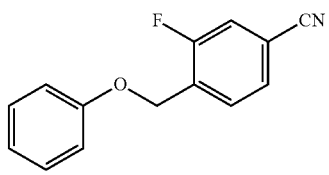 [SMILES: N#Cc1ccc(COc2ccccc2)c(F)c1]

(E)-di-tert-butyl diazene-1,2-dicarboxylate (134 mg, 0.582 mmol) was added to a mixture of 3-fluoro-4-(hydroxymethyl)benzonitrile (80 mg, 0.529 mmol), triphenylphosphine (167 mg, 0.635 mmol) and phenol (49.8 mg, 0.529 mmol) in THF (3 mL) at 15° C. After the addition was complete, the mixture was stirred at 15° C. for 16 h. The mixture was concentrated under reduced pressure and the residue was purified by flash silica gel chromatography (ISCO®; 12 g SepaFlash® Silica Flash Column, Eluent of 0-10% EA/PE gradient a 30 mL/min) to give 3-fluoro-4-(phenoxymethyl)benzonitrile as a solid. ESI-MS m/z [M+H]⁺: low ionization.

Step C: (Z)-3-Fluoro-N'-hydroxy-4-(phenoxymethyl)benzimidamide

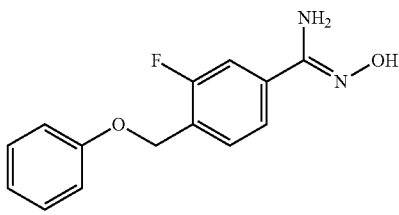 [SMILES: N/C(=N\O)c1ccc(COc2ccccc2)c(F)c1]

A mixture of 3-fluoro-4-(phenoxymethyl)benzonitrile (100 mg, 0.440 mmol), hydroxylamine hydrochloride (30.6 mg, 0.440 mmol) and triethylamine (44.5 mg, 0.440 mmol) in EtOH (5 mL) was heated at 80° C. for 2 h. The contents in the flask were concentrated in vacuo to give (Z)-3-fluoro-N'-hydroxy-4-(phenoxymethyl)benzimidamide as a solid. ESI-MS m/z [M+H]⁺: 261.0

Step D: 3-(3-Fluoro-4-(phenoxymethyl)phenyl)-5-(trifluoromethyl)-1,2,4-oxadiazole

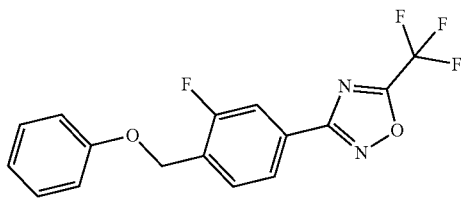 [SMILES: Fc1cc(-c2noc(C(F)(F)F)n2)ccc1COc1ccccc1]

To a solution of (Z)-3-fluoro-N'-hydroxy-4-(phenoxymethyl)benzimidamide (230 mg, 0.442 mmol) and potassium carbonate (92 mg, 0.663 mmol) in dioxane (10 mL) was added TFAA (0.250 mL, 1.767 mmol), and then the reaction mixture was stirred for 1.5 h. The contents in the flask were diluted with ethyl acetate (30 mL) and water (20 mL). The phases were separated, and washed with brine (30 mL×2), dried over Na₂SO₄, filtered and concentrated. The residue was purified by reverse-phase prep-HPLC (preparative HPLC on a GILSON 281 instrument fitted with Waters XSELECT C18 150*30 mm*5 um using water and acetonitrile as the eluents. Mobile phase A: water, mobile phase B: acetonitrile (containing: 0.1% TFA-ACN). Gradient: 60-90%, 0-10 min; 100% B, 10.5-12.5 min; 5% B, 13-15 min) to give 3-(3-fluoro-4-(phenoxymethyl)phenyl)-5-(trifluoromethyl)-1, 2,4-oxadiazole as a solid. ¹H NMR (400 MHz, CD₃OD): δ=7.97 (d, J=7.9 Hz, 1H), 7.87 (dd, J=1.1, 10.3 Hz, 1H), 7.76 (t, J=7.7 Hz, 1H), 7.33-7.25 (m, 1H), 7.33-7.25 (m, 2H), 7.06-6.92 (m, 3H), 5.23 (s, 2H). ESI-MS m/z [M+H]⁺: 339.0.

Example 169

1-(1,1-Dioxidothiomorpholino)-3-(5-(5-(trifluoromethyl)-1,2,4-oxadiazol-3-yl)pyridin-2-yl)-2-(3-(trifluoromethyl)phenyl)propan-1-one

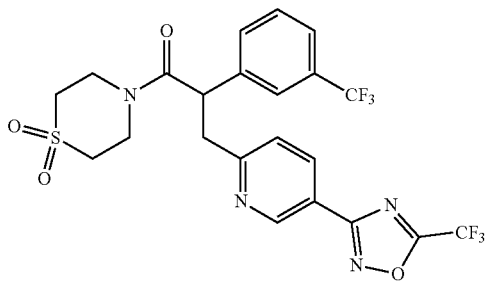 [SMILES: O=C(C(Cc1ccc(-c2noc(C(F)(F)F)n2)cn1)c1cccc(C(F)(F)F)c1)N1CCS(=O)(=O)CC1]

Step A: 1-(1,1-Dioxidothiomorpholino)-2-(3-(trifluoromethyl)phenyl)ethanone

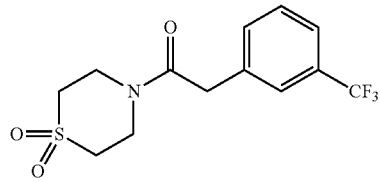 [SMILES: O=C(Cc1cccc(C(F)(F)F)c1)N1CCS(=O)(=O)CC1]

A mixture of 2-(3-(trifluoromethyl)phenyl)acetic acid (2.0 g, 9.8 mmol), thiomorpholine 1,1-dioxide (1.987 g, 14.70 mmol), DIPEA (2.053 mL, 11.76 mmol), and HATU (3.73 g, 9.80 mmol) in DCM (2 mL)/DMF (0.5 mL) was stirred at 25° C. for 10 h. The mixture was diluted with brine (15 mL) and extracted with DCM (3×20 mL). The combined organic layers were washed with brine (15 mL), dried (Na₂SO₄), filtered, and the solvent was evaporated under reduced pressure to give 1-(1,1-dioxidothiomorpholino)-2-(3-(trifluoromethyl)phenyl)ethanone as an oil. MS (ESI) m/z [M+H]⁺: 322.1.

Step B: Methyl 6-(3-(1,1-dioxidothiomorpholino)-3-oxo-2-(3-(trifluoromethyl)phenyl) propyl)-nicotinonitrile

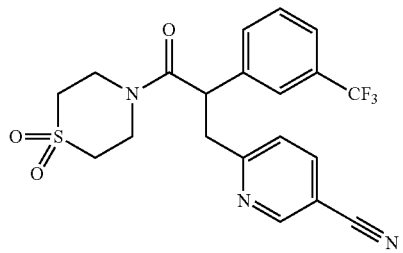 [SMILES: N#Cc1ccc(CC(C(=O)N2CCS(=O)(=O)CC2)c2cccc(C(F)(F)F)c2)nc1]

A mixture of methyl 1-(1,1-dioxidothiomorpholino)-2-(3-(trifluoromethyl)phenyl)ethanone (50 mg, 0.156 mmol) in THF (6 mL) was stirred at −78° C. for 1 h. Then potassium bis(trimethylsilyl)amide (0.187 mL, 0.187 mmol) was added at −78° C., and the mixture was stirred at −78° C. for 1 h. At last, 6-(bromomethyl)nicotinonitrile (39.9 mg, 0.202 mmol) was added into the reaction and the mixture was stirred at −78° C. for 1 h. The solution was quenched with 10 mL of saturated aqueous NH₄Cl solution and extracted with EtOAc (3×15 mL). The organic layer was dried over Na₂SO₄, filtered and concentrated in vacuo. The residue was purified by flash silica gel chromatography (ISCO®; 20 g SepaFlash® Silica Flash Column, Eluent of 0-20% EA/PE gradient @ 40 mL/min) to give methyl 6-(3-(1,1-dioxidothiomorpholino)-3-oxo-2-(3-(trifluoromethyl)phenyl) propyl)-nicotinonitrile as a solid. ESI-MS m/z [M+H]⁺: low ionization.

Step C: (Z)-6-(3-(1,1-Dioxidothiomorpholino)-3-oxo-2-(3-(trifluoromethyl)phenyl)propyl)-N'-hydroxynicotinimidamide

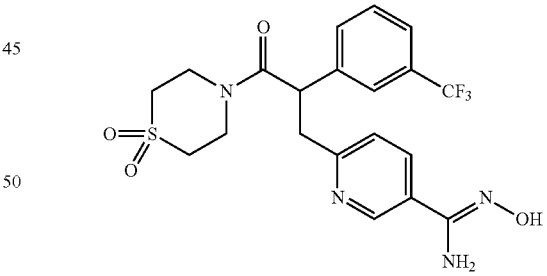

A mixture of TEA (0.127 mL, 0.914 mmol), hydroxylamine hydrochloride (63.5 mg, 0.914 mmol), and 6-(3-(1,1-dioxidothiomorpholino)-3-oxo-2-(3-(trifluoromethyl)phenyl)propyl)-nicotinonitrile (200 mg, 0.457 mmol) in ethanol (10 mL) was stirred at 30° C. for 14 h. After cooling to ambient temperature, the mixture was concentrated under reduced pressure to give a residue, which was diluted with H₂O (15 mL). The water layer was extracted with EtOAc (3×20 mL). The collected organic layers were washed with brine (10 mL) and dried over anhydrous Na₂SO₄. The mixture was filtered and the filtrate was concentrated under reduced pressure to give (Z)-6-(3-(1,1-dioxidothiomorpholino)-3-oxo-2-(3-(trifluoromethyl)-phenyl)propyl)-N'-hydroxynicotinimidamide as an oil. ESI-MS m/z [M+H]$^+$: 493.0.

Step D: 1-(1,1-Dioxidothiomorpholino)-3-(5-(5-(trifluoromethyl)-1,2,4-oxadiazol-3-yl)pyridin-2-yl)-2-(3-(trifluoromethyl)phenyl)propan-1-one

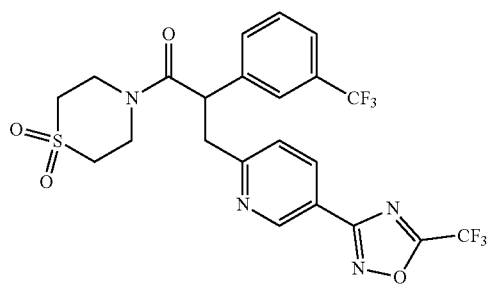 [SMILES: O=C(C(Cc1ccc(-c2noc(C(F)(F)F)n2)cn1)c1cccc(C(F)(F)F)c1)N1CCS(=O)(=O)CC1]

2,2,2-Trifluoroacetic anhydride (89 mg, 0.425 mmol) was added to a stirred mixture of (Z)-6-(3-(1,1-dioxidothiomorpholino)-3-oxo-2-(3-(trifluoromethyl)phenyl)propyl)-N'-hydroxynicotinimidamide (100 mg, 0.213 mmol) in pyridine (5 mL) at 25° C. and the mixture was stirred at 25° C. for 12 h. The mixture was evaporated under reduced pressure. The residue was purified by prep-HPLC (preparative HPLC on a GILSON 281 instrument fitted with a YMC-Actus Pro C18 150*30 5u using water and acetonitrile as the eluents. Mobile phase A: water (containing water (0.1% TFA)-ACN, v/v), mobile phase B: acetonitrile. Gradient: 46-76% B, 0-11 min; 100% B, 11-12.5 min) to give 1-(1,1-dioxidothiomorpholino)-3-(5-(5-(trifluoromethyl)-1,2,4-oxadiazol-3-yl)pyridin-2-yl)-2-(3-(trifluoromethyl)phenyl)propan-1-one as a solid. $^1$H NMR (400 MHz, CDCl$_3$): δ 2.33 (br s, 1H) 2.81-3.08 (m, 3H) 3.35 (dd, J=14.4, 5.4 Hz, 1H) 3.83 (br dd, J=14.3, 9.5 Hz, 2H) 3.88-3.96 (m, 1H) 4.05 (br s, 2H) 4.85 (br dd, J=9.4, 5.4 Hz, 1H) 7.48-7.67 (m, 5H) 8.54 (dd, J=8.2, 1.8 Hz, 1H) 9.33 (d, J=1.5 Hz, 1H); ESI-MS m/z [M+H]$^+$: 548.1.

Example 170 and 171

(R)-1-(1,1-Dioxidothiomorpholino)-3-(5-(5-(trifluoromethyl)-1,2,4-oxadiazol-3-yl)pyridin-2-yl)-2-(3-(trifluoromethyl)phenyl)propan-1-one and (S)-1-(1,1-Dioxidothiomorpholino)-3-(5-(5-(trifluoromethyl)-1,2,4-oxadiazol-3-yl)pyridin-2-yl)-2-(3-(trifluoromethyl)phenyl)propan-1-one

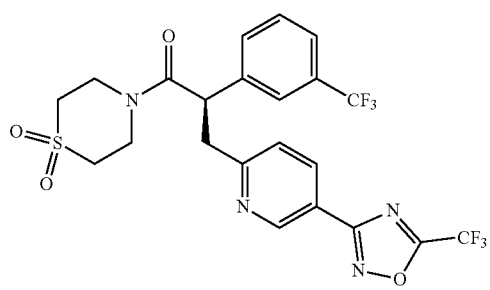

-continued

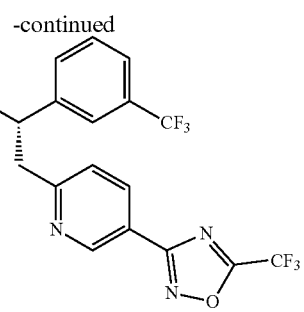

The enantiomers of 1-(1,1-dioxidothiomorpholino)-3-(5-(5-(trifluoromethyl)-1,2,4-oxadiazol-3-yl)pyridin-2-yl)-2-(3-(trifluoromethyl)phenyl)propan-1-one, obtained from Example 169, step D, were separated by supercritical fluid chromatography employing a Berger Multigram SFC equipped with a CHIRALPAK® CCJ column (3×25 cm) eluting with a 10% methanol in CO$_2$ mixture at 80 mL/min and 100 bar pressure. The first enantiomer to elute was assigned Example 170 and the second enantiomer to elute was assigned Example 171. The absolute stereochemistry was not determined for either Example 170 or Example 171.

Example 170: (R or S)-1-(1,1-Dioxidothiomorpholino)-3-(5-(5-(trifluoromethyl)-1,2,4-oxadiazol-3-yl)pyridin-2-yl)-2-(3-(trifluoromethyl)phenyl)propan-1-one Chiral analytical analysis was performed using a CHIRALPAK® CCJ column (25×0.46 cm) eluting with a 5 to 50% methanol gradient containing a diethylamine modifier in CO$_2$ mixture at 3 mL/min and 100 bar pressure. Elution time was 2.5 min. Enantiomeric excess determined to be >99%. $^1$H NMR (600 MHz, CDCl$_3$): δ 9.26 (s, 1H), 8.31 (dd, J=8.1, 2.2 Hz, 1H), 7.63-7.52 (m, 4H), 7.34 (dd, J=7.8 Hz, 1H), 4.85 (dd, J=10.0, 4.7 Hz, 1H), 4.61-4.26 (m, 1H), 4.19-4.10 (m, 1H), 3.92-3.81 (m, 2H), 3.89 (dd, J=15.8, 10.0 Hz, 1H), 3.42-3.34 (m, 1H), 3.23 (dd, J=16.1, 4.4 Hz, 1H), 3.25-2.90 (m, 2H), 2.94-2.60 (m, 1H); ESI-MS m/z [M+H]$^+$: 548.2.

Example 171: (R or S)-1-(1,1-Dioxidothiomorpholino)-3-(5-(5-(trifluoromethyl)-1,2,4-oxadiazol-3-yl)pyridin-2-yl)-2-(3-(trifluoromethyl)phenyl)propan-1-one Chiral analytical analysis was performed using a CHIRALPAK® CCJ column (25×0.46 cm) eluting with a 5 to 50% methanol gradient containing a diethylamine modifier in CO$_2$ mixture at 3 mL/min and 100 bar pressure. Elution time was 3.2 min. Enantiomeric excess determined to be >99%. $^1$H NMR (600 MHz, CDCl$_3$): δ 9.26 (s, 1H), 8.31 (dd, J=8.1, 2.2 Hz, 1H), 7.63-7.52 (m, 4H), 7.34 (dd, J=7.8 Hz, 1H), 4.85 (dd, J=10.0, 4.7 Hz, 1H), 4.61-4.26 (m, 1H), 4.19-4.10 (m, 1H), 3.92-3.81 (m, 2H), 3.89 (dd, J=15.8, 10.0 Hz, 1H), 3.42-3.34 (m, 1H), 3.23 (dd, J=16.1, 4.4 Hz, 1H), 3.25-2.90 (m, 2H), 2.94-2.60 (m, 1H); ESI-MS m/z [M+H]$^+$: 548.2.

Example 172

3-(2-Fluoro-4-(phenoxymethyl)phenyl)-5-(trifluoromethyl)-1,2,4-oxadiazole

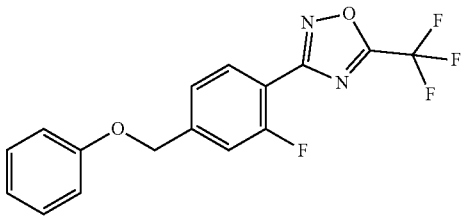 [SMILES: Fc1cc(COc2ccccc2)ccc1-c1noc(C(F)(F)F)n1]

Step A: 2-Fluoro-4-(hydroxymethyl)benzonitrile

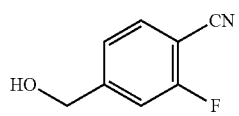 [SMILES: N#Cc1ccc(CO)cc1F]

To a solution of 4-cyano-3-fluorobenzoic acid (1.00 g, 6.06 mmol) in THF (15 mL) was added $BH_3$.THF (12.1 mL, 12.1 mmol)(1M) at 0° C. After addition, the reaction mixture was allowed to warm to 13° C. for 16 h. To the reaction mixture was added MeOH (15 mL), and the mixture was stirred for 1 h. The reaction mixture was evaporated under reduced pressure. The residue was purified by flash silica gel chromatography (ISCO®; 20 g SepaFlash® Silica Flash Column, Eluent of 0-30% EA/PE gradient @ 30 mL/min) to give 2-fluoro-4-(hydroxymethyl)benzonitrile as a solid. ESI-MS m/z [M+H]+: low ionization.

Step B: 4-Cyano-3-fluorobenzyl methanesulfonate

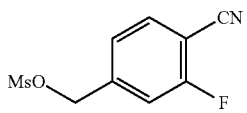 [SMILES: CS(=O)(=O)OCc1ccc(C#N)c(F)c1]

To a solution of 2-fluoro-4-(hydroxymethyl)benzonitrile (400 mg, 2.65 mmol) and TEA (0.738 mL, 5.29 mmol) in DCM (10 mL) was added methanesulfonyl chloride (1.27 g, 11.1 mmol) at 0° C., and the reaction mixture was stirred for 16 h at 16° C. The reaction mixture was concentrated in vacuo to give 4-cyano-3-fluorobenzyl methanesulfonate as an oil. ESI-MS m/z [M+H]+: low ionization.

Step C: 2-Fluoro-4-(phenoxymethyl)benzonitrile

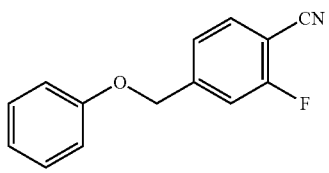 [SMILES: N#Cc1ccc(COc2ccccc2)cc1F]

A mixture of 4-cyano-3-fluorobenzyl methanesulfonate (607 mg, 2.65 mmol), phenol (748 mg, 7.94 mmol) and potassium carbonate (732 mg, 5.30 mmol) in DMF (20 mL) was heated at 100° C. for 16 h. The contents in the flask were diluted with ethyl acetate (30 mL) and water (60 mL). The phases were separated, and the organics washed with brine (30 mL), dried over $Na_2SO_4$, filtered and concentrated in vacuo. The residue was purified by flash silica gel chromatography (ISCO®; 12 g SepaFlash® Silica Flash Column, Eluent of 0-10% EtOAc/PE gradient @ 30 mL/min) to give 2-fluoro-4-(phenoxymethyl)benzonitrile as an oil. ESI-MS m/z [M+CN]+: 268.1.

Step D: (Z)-2-Fluoro-N'-hydroxy-4-(phenoxymethyl)benzimidamide

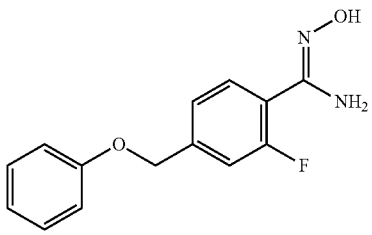 [SMILES: N/C(=N\O)c1ccc(COc2ccccc2)cc1F]

A mixture of 2-fluoro-4-(phenoxymethyl)benzonitrile (800 mg, 1.76 mmol), hydroxylamine hydrochloride (245 mg, 3.52 mmol) and triethylamine (356 mg, 3.52 mmol) in EtOH (15 mL) was heated at 80° C. for 2 h. The contents in the flask were concentrated in vacuo to give (Z)-2-fluoro-N'-hydroxy-4-(phenoxymethyl)benzimidamide as a solid. ESI-MS m/z [M+H]+: 261.0.

Step E: 3-(2-Fluoro-4-(phenoxymethyl)phenyl)-5-(trifluoromethyl)-1,2,4-oxadiazole

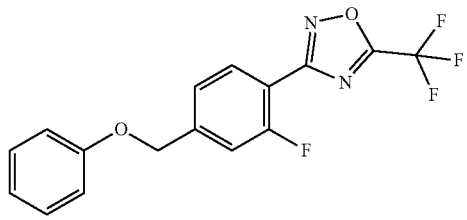 [SMILES: Fc1cc(COc2ccccc2)ccc1-c1noc(C(F)(F)F)n1]

To a solution of (Z)-2-fluoro-N'-hydroxy-4-(phenoxymethyl)benzimidamide (458 mg, 1.76 mmol) and potassium carbonate (486 mg, 3.52 mmol) in dioxane (10 mL) was added TFAA (1.24 mL, 8.80 mmol) and the reaction mixture was stirred for 2 h. The contents in the flask were diluted with ethyl acetate (30 mL) and water (20 mL). The phases were separated, and the organics washed with brine (2×30 mL), dried over $Na_2SO_4$, filtered and concentrated in vacuo. The residue was purified by flash silica gel chromatography (ISCO®; 12 g SepaFlash® Silica Flash Column, Eluent of 0-40% EtOAc/PE gradient @ 30 mL/min) to give 3-(2-fluoro-4-(phenoxymethyl)phenyl)-5-(trifluoromethyl)-1,2,4-oxadiazole as an oil. $^1$H NMR (400 MHz, $CD_3OD$): δ 8.10 (t, J=7.9 Hz, 1H), 7.50-7.40 (m, 2H), 7.32-7.24 (m, 2H), 7.04-6.90 (m, 3H), 5.19 (s, 2H). ESI-MS m/z [M+H]+: 338.8.

Example 173

N-((6-(5-(Trifluoromethyl)-1,2,4-oxadiazol-3-yl)pyridazin-3-yl)methyl)-N'-(3-(trifluoromethyl)phenyl)tetrahydro-2H-thiopyran-4-carboxamide 1,1-dioxide

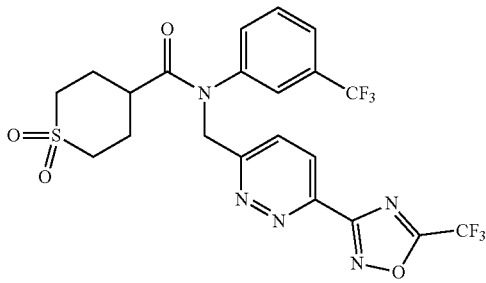 [SMILES: O=C(C1CCS(=O)(=O)CC1)N(Cc1ccc(-c2noc(C(F)(F)F)n2)nn1)c1cccc(C(F)(F)F)c1]

Step A: 3-Chloro-6-(chloromethyl)pyridazine

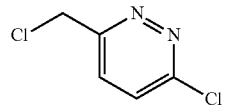

A mixture of 3-chloro-6-methylpyridazine (3.00 g, 23.3 mmol) and trichloroisocyanuric acid (2.17 g, 9.33 mmol) in DCE (150 mL) was stirred at 90° C. for 16 h. After cooling to ambient temperature, the mixture was filtered and washed with 1N NaHCO₃ (50 mL), brine (30 mL), and dried over anhydrous Na₂SO₄. The mixture was filtered and the filtrate was concentrated under reduced pressure. The residue was purified by flash silica gel chromatography (ISCO®; 40 g SepaFlash® Silica Flash Column, Eluent of 0-30% EA/PE gradient @ 40 mL/min) to give 3-chloro-6-(chloromethyl)pyridazine as a solid. ESI-MS m/z [M+H]⁺: 162.9/164.9.

Step B: N-((6-Chloropyridazin-3-yl)methyl)-N-(3-(trifluoromethyl)phenyl)tetrahydro-2H-thiopyran-4-carboxamide 1,1-dioxide

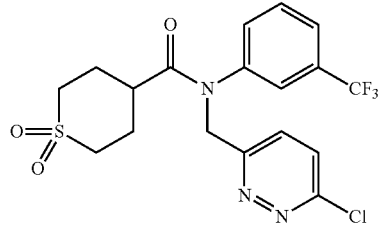 [SMILES: O=C(C1CCS(=O)(=O)CC1)N(Cc1ccc(Cl)nn1)c1cccc(C(F)(F)F)c1]

A mixture of N-(3-(trifluoromethyl)phenyl)tetrahydro-2H-thiopyran-4-carboxamide 1,1-dioxide (150 mg, 0.467 mmol), 3-chloro-6-(chloromethyl)pyridazine (152 mg, 0.934 mmol) and potassium carbonate (129 mg, 0.934 mmol) in DMF (3 mL) was placed in a microwave tube and heated at 80° C. for 0.5 h. The contents in the flask were diluted with ethyl acetate (30 mL) and water (20 mL). The phases were separated, and the organics washed with brine (2×30 mL), dried over Na₂SO₄, filtered and concentrated in vacuo. The residue was purified by flash silica gel chromatography (ISCO®; 4 g SepaFlash® Silica Flash Column, Eluent of 0-40% MeOH/DCM gradient @ 18 mL/min) followed by prep-TLC (SiO₂, DCM: MeOH=10:1) to give N-((6-chloropyridazin-3-yl)methyl)-N-(3-(trifluoromethyl)phenyl) tetrahydro-2H-thiopyran-4-carboxamide 1,1-dioxide as an oil. ESI-MS m/z [M+CN]⁺: 448.0.

Step C: N-((6-Cyanopyridazin-3-yl)methyl)-N-(3-(trifluoromethyl)phenyl)tetrahydro-2H-thiopyran-4-carboxamide 1,1-dioxide

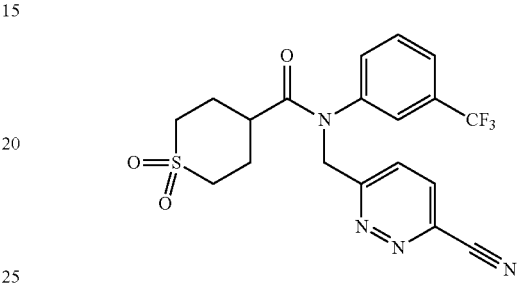

A mixture of N-((6-chloropyridazin-3-yl)methyl)-N-(3-(trifluoromethyl)phenyl)tetrahydro-2H-thiopyran-4-carboxamide 1,1-dioxide (60 mg, 0.134 mmol), 2-(dicyclohexylphosphino)-2'-methylbiphenyl (19.5 mg, 0.054 mmol), allylpalladium (II) chloride dimer (4.90 mg, 0.013 mmol) and zinc cyanide (56.6 mg, 0.134 mmol) in DMA (0.5 mL) and water (0.25 mL) was stirred at 100° C. for 16 h. After cooling to ambient temperature, water (15 mL) was added and the mixture was extracted with ethyl acetate (2×20 mL). The combined organic fractions were washed with brine (20 mL), dried (Na₂SO₄), filtered, and the solvent was evaporated under reduced pressure. The residue was purified by reverse-phase prep-HPLC (preparative HPLC on a GILSON 281 instrument fitted with Waters XSELECT C18 150*30 mm*5 um using water and acetonitrile as the eluents. Mobile phase A: water, mobile phase B: acetonitrile (containing: 0.1% TFA-ACN). Gradient: 25-55%, 0-10 min; 100% B, 10.5-12.5 min; 5% B, 13-15 min) to give N-((6-cyanopyridazin-3-yl)methyl)-N-(3-(trifluoromethyl)phenyl)tetrahydro-2H-thiopyran-4-carboxamide 1,1-dioxide as an oil. ESI-MS m/z [M+CN]⁺: 439.0.

Step D: (Z)—N-((6-(N'-Hydroxycarbamimidoyl)pyridazin-3-yl)methyl)-N-(3-(trifluoromethyl)phenyl)tetrahydro-2H-thiopyran-4-carboxamide 1,1-dioxide

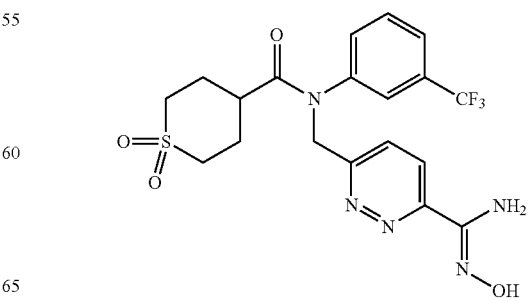

A mixture of N-((6-cyanopyridazin-3-yl)methyl)-N-(3-(trifluoromethyl)phenyl)tetrahydro-2H-thiopyran-4-carboxamide 1,1-dioxide (30 mg, 0.068 mmol), hydroxylamine hydrochloride (9.51 mg, 0.137 mmol) and triethylamine (13.8 mg, 0.137 mmol) in EtOH (5 mL) was heated at 80° C. for 30 min. The contents in the flask were concentrated in vacuo to give (Z)—N-((6-(N'-hydroxycarbamimidoyl)pyridazin-3-yl)methyl)-N-(3-(trifluoromethyl)phenyl)tetrahydro-2H-thiopyran-4-carboxamide 1,1-dioxide as a solid. ESI-MS m/z [M+H⁺]: 472.1.

Step E: N-((6-(5-(Trifluoromethyl)-1,2,4-oxadiazol-3-yl)pyridazin-3-yl)methyl)-N-(3-(trifluoromethyl)phenyl)tetrahydro-2H-thiopyran-4-carboxamide 1,1-dioxide

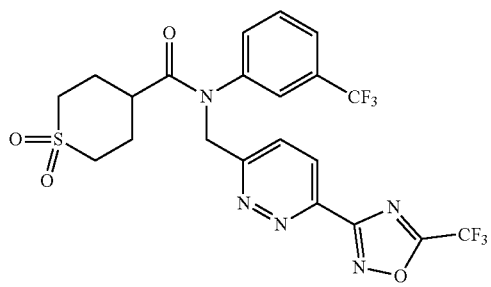 [SMILES: O=C(C1CCS(=O)(=O)CC1)N(Cc1ccc(-c2noc(C(F)(F)F)n2)nn1)c1cccc(C(F)(F)F)c1]

A mixture of (Z)—N-((6-(N'-hydroxycarbamimidoyl)pyridazin-3-yl)methyl)-N-(3-(trifluoromethyl)phenyl)tetrahydro-2H-thiopyran-4-carboxamide 1, 1-dioxide (32.3 mg, 0.069 mmol), potassium carbonate (9.47 mg, 0.069 mmol) and TFAA (9.68 μL, 0.069 mmol) in dioxane (20 mL) was stirred for 2 h. The contents in the flask were diluted with ethyl acetate (30 mL) and water (20 mL). The phases were separated, and the organics washed with brine (2×30 mL), dried over Na₂SO₄, filtered and concentrated in vacuo. The residue was purified by reverse-phase prep-HPLC (preparative HPLC on a GILSON 281 instrument fitted with Waters XSELECT C18 150*30 mm*5 um using water and acetonitrile as the eluents. Mobile phase A: water, mobile phase B: acetonitrile (containing: 0.1% TFA-ACN). Gradient: 36-66%, 0-10 min; 100% B, 10.5-12.5 min; 5% B, 13-15 min) to give N-((6-(5-(trifluoromethyl)-1,2,4-oxadiazol-3-yl)pyridazin-3-yl)methyl)-N-(3-(trifluoromethyl)phenyl)tetrahydro-2H-thiopyran-4-carboxamide 1,1-dioxide as a solid. ¹H NMR (400 MHz, CD₃OD): δ 8.40 (d, J=8.8 Hz, 1H), 8.01-7.88 (m, 2H), 7.72-7.64 (m, 1H), 5.27 (s, 2H), 3.10 (br d, J=13.6 Hz, 2H), 3.03-3.03 (m, 1H), 3.00-2.89 (m, 2H), 2.75-2.64 (m, 1H), 2.65-2.63 (m, 1H); ESI-MS m/z [M+H+]: 550.0.

Example 174

2-(((5-(5-(Trifluoromethyl)-1,2,4-oxadiazol-3-yl)pyridin-2-yl)methyl)amino)benzamide

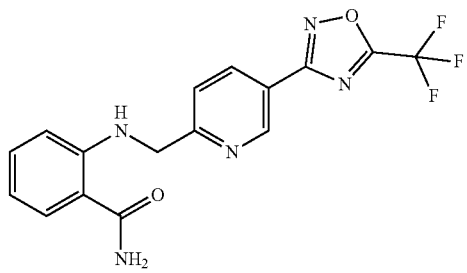

Step A: 5-(5-(Trifluoromethyl)-1,2,4-oxadiazol-3-yl)picolinaldehyde

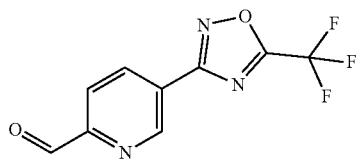 [SMILES: O=Cc1ccc(-c2noc(C(F)(F)F)n2)cn1]

To a solution of 3-(6-methylpyridin-3-yl)-5-(trifluoromethyl)-1,2,4-oxadiazole (7.00 g, 30.5 mmol) in dioxane (70 mL) was added selenium dioxide (6.78 g, 61.1 mmol), and the solution was stirred at 100° C. for 3 h. The mixture was filtered and the solvent was evaporated under reduced pressure. The residue was purified by flash silica gel chromatography (ISCO®; 12 g SepaFlash® Silica Flash Column, Eluent of 0-10% EtOAc/PE gradient @ 30 mL/min) to give 5-(5-(trifluoromethyl)-1,2,4-oxadiazol-3-yl)picolinaldehyde as a solid. ESI-MS m/z [M+H]⁺: low ionization.

Step B: 2-(((5-(5-(Trifluoromethyl)-1,2,4-oxadiazol-3-yl)pyridin-2-yl)methyl)amino)benzamide

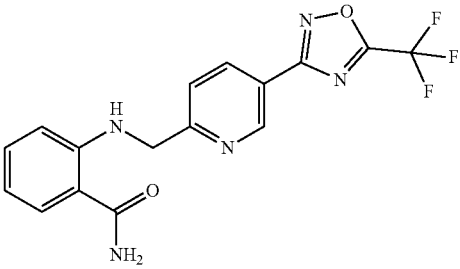

A solution of 5-(5-(trifluoromethyl)-1,2,4-oxadiazol-3-yl)picolinaldehyde (18.0 mg, 0.074 mmol) was dissolved in MeOH (1 mL) and AcOH (0.021 mL). 2-Aminobenzamide (22.0 mg, 0.16 mmol) was added and the solution was stirred for 0.5 h, then sodium cyanoborohydride (6.98 mg, 0.111 mmol) was added the solution was stirred for 18 h. The reaction mixture was diluted with DMF (1 mL) and purified on a Gilson HPLC (YMC Pro C18 column, eluting with a 10-95% acetonitrile in water gradient containing a 0.1% TFA modifier) to afford the title compound as a solid. $^1$H NMR (600 MHz, d$_6$-DMSO): δ 9.19 (s, 1H), 8.39 (d, 1H), 7.62-7.56 (m, 2H), 7.30-7.18 (m, 1H), 6.58-6.44 (m, 2H), 4.62 (s, 2H); MS (ESI) m/z [M+H]$^+$: 364.2.

Example 175

3-((4-(5-(Trifluoromethyl)-1,2,4-oxadiazol-3-yl)benzyl)amino)benzamide

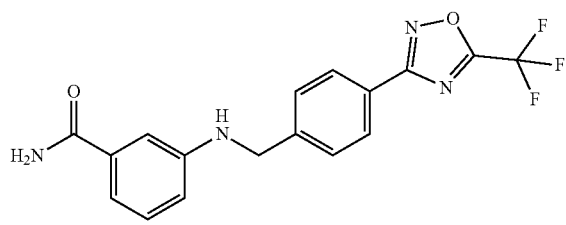

Step A: 4-(5-(Trifluoromethyl)-1,2,4-oxadiazol-3-yl)benzaldehyde

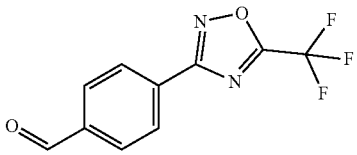 [SMILES: O=Cc1ccc(-c2noc(C(F)(F)F)n2)cc1]

Dess-Martin periodinane (2423 mg, 5.71 mmol) was added to a stirred mixture of (4-(5-(trifluoromethyl)-1,2,4-oxadiazol-3-yl)phenyl)methanol (930 mg, 3.81 mmol) in CH$_2$Cl$_2$ (15 mL) at 0° C. and the mixture was stirred for 2 h. To the reaction mixture was added aq Na$_2$SO$_3$ (20 mL) and it was extracted with EtOAc (3×30 mL). The combined organic fractions were washed with brine (50 mL), dried (Na$_2$SO$_4$), filtered, and the solvent was evaporated under reduced pressure. The residue was purified by flash silica gel chromatography (ISCO®; 12 g SepaFlash® Silica Flash Column, Eluent of 0-10% EA/PE gradient @ 30 mL/min) to give 4-(5-(trifluoromethyl)-1,2,4-oxadiazol-3-yl)benzaldehyde as a solid. ESI-MS m/z [M+H]$^+$: low ionization.

Step B: 3-((4-(5-(Trifluoromethyl)-1,2,4-oxadiazol-3-yl)benzyl)amino)benzamide

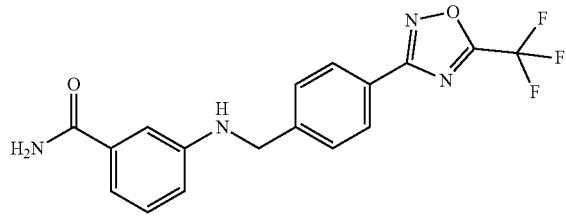

A solution of 4-(5-(trifluoromethyl)-1,2,4-oxadiazol-3-yl)benzaldehyde (10.0 mg, 0.041 mmol) was dissolved in MeOH (1 mL) and AcOH (0.012 mL). 3-Aminobenzamide (11.0 mg, 0.083 mmol) was added and the solution was stirred for 0.5 h, then sodium cyanoborohydride (3.89 mg, 0.062 mmol) was added the solution stirred for 18 h. The reaction mixture was diluted with DMF (1 mL) and purified on a Gilson HPLC (YMC Pro C18 column, eluting with a 10-95% acetonitrile in water gradient containing a 0.1% TFA modifier) to afford the title compound as a solid. $^1$H NMR (600 MHz, d$_6$-DMSO): δ8.05 (d, 2H), 7.68 (s, 1H), 7.59 (d, 2H), 7.18 (s, 1H), 7.16-7.00 (m, 2H), 6.65 (d, 1H), 4.41 (s, 2H); MS (ESI) m/z [M+H]$^+$: 363.0.

Example 176

2,2,2-Trifluoro-N-(2-(5-(5-(trifluoromethyl)-1,2,4-oxadiazol-3-yl)pyridin-2-yl)-1-(3-(trifluoromethyl)phenyl)ethyl)acetamide

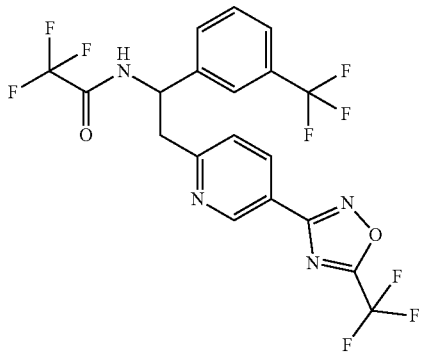

Step A: 1,1-Diphenyl-N-(3-(trifluoromethyl)benzyl)methanimine

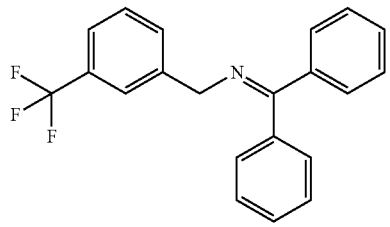 [SMILES: FC(F)(F)c1cccc(CN=C(c2ccccc2)c2ccccc2)c1]

A neat solution of (3-(trifluoromethyl)phenyl)methanamine (2.33 g, 13.3 mmol) and diphenylmethanimine (2.41 g, 13.3 mmol) was stirred at 50° C. for 20 h. The reaction mixture was cooled to ambient temperature to provide the title compound as an oil. MS (ESI) m/z [M+H]$^+$: 340.2.

Step B: 6-(2-((Diphenylmethylene)amino)-2-(3-(trifluoromethyl)phenyl)ethyl)nicotinonitrile

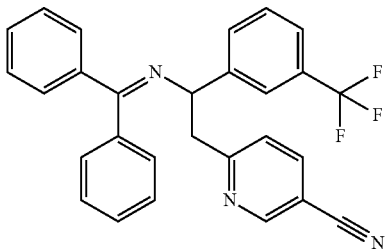 [SMILES: N#Cc1ccc(CC(N=C(c2ccccc2)c2ccccc2)c2cccc(C(F)(F)F)c2)nc1]

Sodium bis(trimethylsilyl)amide (1M in THF, 4.07 mL, 4.07 mmol) was added to a solution of 1,1-diphenyl-N-(3-(trifluoromethyl)benzyl)methanimine (1.15 g, 3.39 mmol) in THF (10 mL) at −78° C. and was stirred for 1 h. A solution of 6-(bromomethyl)nicotinonitrile (0.801 g, 4.07 mmol) in THF (3 mL) was then added and stirring continued at −78° C. for 1.5 h. The reaction mixture was quenched at −78° C. with ~10 drops of water. The mixture was concentrated to ~¼ volume and purified by flash silica gel chromatography (ISCO CombiFlash Rf Purification System®; 120 g SepaFlash® Silica Flash Column, eluting with a 0-30% ethyl acetate in hexanes gradient) to afford the title compound as a solid. MS (ESI) m/z [M+H]⁺: 456.2.

Step C: (Z)-6-(2-Amino-2-(3-(trifluoromethyl)phenyl)ethyl)-N'-hydroxynicotinimidamide

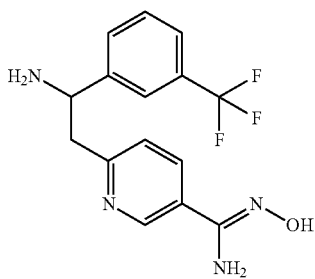

Hydroxylamine hydrate (50 wt % in water, 0.758 mL, 12.85 mmol) was added to a solution of 6-(2-((diphenylmethylene)amino)-2-(3-(trifluoromethyl)phenyl)ethyl)nicotinonitrile (836 mg, 1.835 mmol) in ethanol (4 mL) and the solution was heated at 40° C. for 2 h. The mixture was concentrated to ~½ volume and purified by flash silica gel chromatography [ISCO CombiFlash Rf Purification System®; 120 g SepaFlash® Silica Flash Column, eluting with a 0-100% ethyl acetate: ethanol (3:1) in hexanes gradient] to afford the title compound as a white solid. MS (ESI) m/z [M+H]⁺: 325.1.

Step D: 2,2,2-Trifluoro-N-(2-(5-(5-(trifluoromethyl)-1,2,4-oxadiazol-3-yl)pyridin-2-yl)-1-(3-(trifluoromethyl)phenyl)ethyl)acetamide

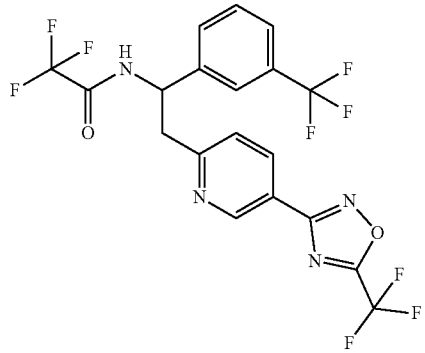

TFAA (0.703 mL, 4.98 mmol) was added to a solution of (Z)-6-(2-amino-2-(3-(trifluoromethyl)phenyl)ethyl)-N'-hydroxynicotinimidamide (538 mg, 1.659 mmol) in DCM (5 mL) at 0° C. and was stirred for 0.5 h. Triethylamine (0.694 mL, 4.98 mmol) was added and the solution was stirred for 2 h. Additional TFAA (0.703 mL, 4.98 mmol) was added and the solution was stirred for 6 h. The mixture was concentrated to ~½ volume and purified by flash silica gel chromatography (ISCO CombiFlash Rf Purification System®; 80 g SepaFlash® Silica Flash Column, eluting with a 0-50% ethyl acetate in hexanes gradient) to afford the title compound as a solid. ¹H NMR (600 MHz, CDCl₃): δ9.40-9.30 (m, 2H), 8.32 (dd, J=7.8, 2.0 Hz, 1H), 7.52 (d, J=7.3 Hz, 1H), 7.43-7.40 (m, 2H), 7.34 (d, J=7.3 Hz, 1H), 7.18 (d, J=8.3 Hz, 1H), 5.56-5.49 (m, 1H), 3.57 (dd, J=14.6, 4.4 Hz, 1H), 3.37 (dd, J=14.8, 6.5 Hz, 1H); MS (ESI) m/z [M+H]⁺: 499.2.

Example 177

2,2,2-Trifluoro-N-(2-(5-(5-(trifluoromethyl)-1,2,4-oxadiazol-3-yl)pyridin-2-yl)-1-(3-trifluoromethyl)phenyl)ethyl)acetamide

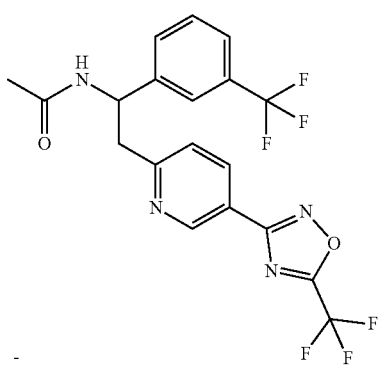

Step A: 2-(5-(5-(Trifluoromethyl)-1,2,4-oxadiazol-3-yl)pyridin-2-yl)-1-(3-(trifluoromethyl)phenyl)ethanamine

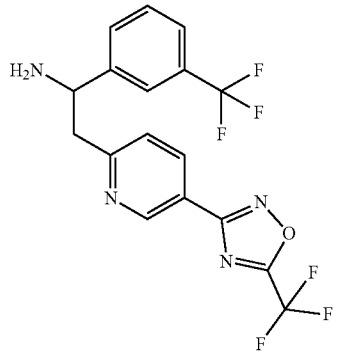 [SMILES: NC(Cc1ccc(-c2noc(C(F)(F)F)n2)cn1)c1cccc(C(F)(F)F)c1]

A solution of 2,2,2-trifluoro-N-(2-(5-(5-(trifluoromethyl)-1,2,4-oxadiazol-3-yl)pyridin-2-yl)-1-(3-(trifluoromethyl)phenyl)ethyl)acetamide from Example 176, Step D (827 mg, 1.66 mmol) and 7N ammonia in methanol (12 mL, 83 mmol) was stirred at 50° C. for 42 h. The solution was concentrated and dried to afford the title compound as a solid. MS (ESI) m/z [M+H]+: 403.2.

Step B: N-(2-(5-(5-(Trifluoromethyl)-1,2,4-oxadiazol-3-yl)pyridin-2-yl)-1-(3-(trifluoromethyl)phenyl)ethyl)acetamide

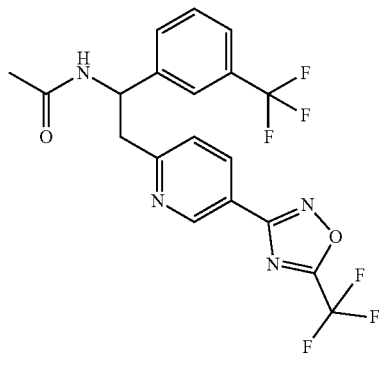 [SMILES: CC(=O)NC(Cc1ccc(-c2noc(C(F)(F)F)n2)cn1)c1cccc(C(F)(F)F)c1]

A solution of acetic acid (3.0 mg, 0.050 mmol), HATU (14.2 mg, 0.037 mmol)) and DIEA (0.013 mL, 0.075 mmol) was stirred in DMF (0.5 mL) for 0.5 h. A solution of 2-(5-(5-(trifluoromethyl)-1,2,4-oxadiazol-3-yl)pyridin-2-yl)-1-(3-(trifluoromethyl)phenyl)ethanamine (10 mg, 0.025 mmol) in DMF (0.5 mL) was then added and stirring continued for 3 d. The reaction mixture was purified directly on a Gilson HPLC (YMC Pro C18 column, eluting with a 10-95% acetonitrile in water gradient containing a 0.1% TFA modifier) to afford the title compound as a solid. $^1$H NMR (600 MHz, CDCl$_3$): δ9.13 (s, 1H), 8.62 (d, 1H), 8.33 (d, 1H), 7.68 (s, 1H), 7.63-7.51 (m, 4H), 5.45-5.38 (m, 1H), 3.42 (d, 1H), 3.26 (d, 1H), 1.76 (s, 3H); MS (ESI) m/z [M+H]+: 445.1.

Example 178

N-(2-(5-(5-(Trifluoromethyl)-1,2,4-oxadiazol-3-yl)pyridin-2-yl)-1-(3-(trifluoromethyl)phenyl)ethyl)methanesulfonamide

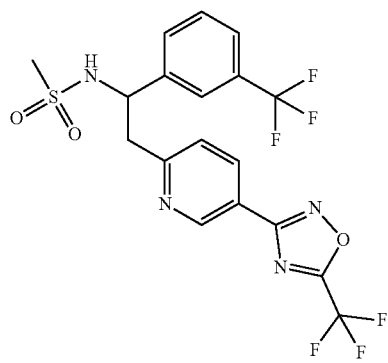 [SMILES: CS(=O)(=O)NC(Cc1ccc(-c2noc(C(F)(F)F)n2)cn1)c1cccc(C(F)(F)F)c1]

To a solution of 2-(5-(5-(trifluoromethyl)-1,2,4-oxadiazol-3-yl)pyridin-2-yl)-1-(3-(trifluoromethyl)phenyl)ethanamine from Example 176, Step D (10 mg, 0.025 mmol) and triethylamine (0.017 mL, 0.124 mmol) in DCM (0.3 mL) was added methanesulfonyl chloride (5.81 µl, 0.075 mmol) and the mixture was stirred at RT for 1 h. The DCM was removed and the crude dissolved in DMF (1 mL) and purified on a Gilson HPLC (YMC Pro C18 column, eluting with a 5-95% acetonitrile in water gradient containing a 0.1% TFA modifier) to afford the title compound as a solid. $^1$H NMR (600 MHz, CDCl$_3$): δ9.34 (d, J=1.5 Hz, 1H), 8.45 (d, J=8.3 Hz, 1H), 7.63-7.56 (m, 3H), 7.52 (d, J=7.8 Hz, 1H), 7.37 (d, J=8.3 Hz, 1H), 7.14-6.94 (bs, 1H), 5.09 (dd, J=8.6, 4.7 Hz, 1H), 3.44 (dd, J=14.1, 4.4 Hz, 1H), 3.37 (dd, J=14.4, 9.1 Hz, 1H), 2.66 (s, 3H); MS (ESI) m/z [M+H]+: 481.2.

Example 179

1-Ethyl-3-(2-(5-(5-(trifluoromethyl)-1,2,4-oxadiazol-3-yl)pyridin-2-yl)-1-(3-(trifluoromethyl)phenyl)ethyl)urea

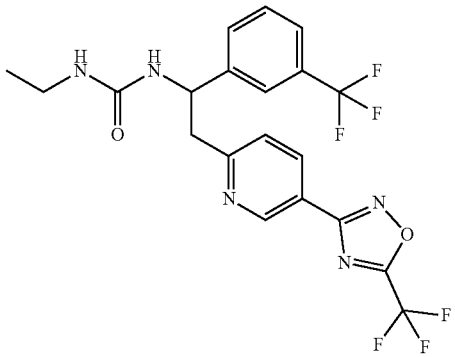 [SMILES: CCNC(=O)NC(Cc1ccc(-c2noc(C(F)(F)F)n2)cn1)c1cccc(C(F)(F)F)c1]

To a solution of 2-(5-(5-(trifluoromethyl)-1,2,4-oxadiazol-3-yl)pyridin-2-yl)-1-(3-(trifluoromethyl)phenyl)ethanamine from Example 176, Step D (20 mg, 0.050 mmol) and triethylamine (0.035 mL, 0.25 mmol) in DCM (0.5 mL) was added ethyl isocyanate (0.012 mL, 0.149 mmol) and the mixture was stirred at RT for 1.5 h. The DCM was removed and the crude dissolved in DMF (1 mL) and purified on a Gilson HPLC (YMC Pro C18 column, eluting with a 10-95% acetonitrile in water gradient containing a 0.1% TFA modifier) to afford the title compound as a solid. ¹H NMR (600 MHz, CDCl₃): δ9.30 (s, 1H), 8.66 (d, J=7.8 Hz, 1H), 7.68 (d, J=7.8 Hz, 1H), 7.58-7.28 (m, 4H), (dd, J=8.8, 5.4 Hz, 1H), 3.52-3.44 (m, 2H), 3.15 (q, J=7.1 Hz, 2H), 1.12 (t, J=14.4, 7.1 Hz, 2H); MS (ESI) m/z [M+H]⁺: 474.3.

Example 180

Methyl(2-(5-(5-(trifluoromethyl)-1,2,4-oxadiazol-3-l)pyridin-2-yl)-1-(3-(trifluoromethyl)phenyl)ethyl)carbamate

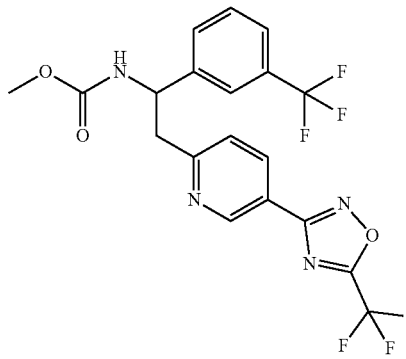

To a solution of 2-(5-(5-(trifluoromethyl)-1,2,4-oxadiazol-3-yl)pyridin-2-yl)-1-(3-(trifluoromethyl)phenyl)ethanamine from Example 176, Step D (18 mg, 0.045 mmol) and triethylamine (0.031 mL, 0.22 mmol) in DCM (0.5 mL) was added methyl chloroformate (10.4 µl, 0.13 mmol) and the mixture was stirred at RT for 1 h. The DCM was removed and the crude dissolved in DMF (1 mL) and purified on a Gilson HPLC (YMC Pro C18 column, eluting with a 20-95% acetonitrile in water gradient containing a 0.1% TFA modifier) to afford the title compound as a solid. ¹H NMR (600 MHz, CDCl₃): δ9.35 (s, 1H), 8.64-8.55 (m, 1H), 7.66-7.46 (m, 5H), 6.61 (d, J=8.3 Hz, 1H), 5.32-5.22 (m, 1H), 3.60 (s, 3H), 3.56-3.42 (m, 2H); MS (ESI) m/z [M+H]⁺: 461.2.

Example 181

Methyl(4-(5-(trifluoromethyl)-1,2,4-oxadiazol-3-yl)benzyl)(3-(trifluoromethyl)phenyl)carbamate

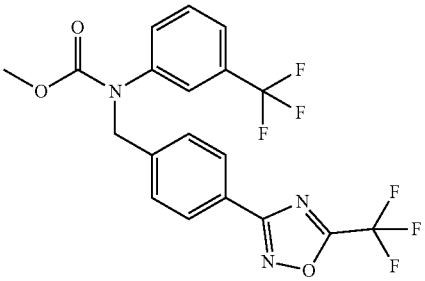 [SMILES: COC(=O)N(Cc1ccc(-c2noc(C(F)(F)F)n2)cc1)c1cccc(C(F)(F)F)c1]

To a suspension of 3-(trifluoromethyl)-N-(4-(5-(trifluoromethyl)-1,2,4-oxadiazol-3-yl)benzyl)aniline hydrochloride from Example 30, Step D (10 mg, 0.024 mmol) and triethylamine (0.016 mL, 0.12 mmol) in toluene (0.3 mL) was added methyl chloroformate (9.1 µl, 0.12 mmol) and the mixture was heated at 110° C. for 22 h. The toluene was removed and the crude dissolved in DMF (1 mL) and purified on a Gilson HPLC (YMC Pro C18 column, eluting with a 30-95% acetonitrile in water gradient containing a 0.1% TFA modifier) to afford the title compound as a solid. ¹H NMR (600 MHz, CDCl₃): δ8.08 (d, J=7.8 Hz, 2H), 7.50 (d, J=7.8 Hz, 1H), 7.46-7.41 (m, 2H), 7.39 (d, J=7.8 Hz, 2H), 7.32-7.27 (m, 1H), 4.97 (s, 2H), 3.77 (s, 3H); MS (ESI) m/z [M+H]⁺: 446.2.

Example 182

3-Ethyl-1-(4-(5-(trifluoromethyl)-1,2,4-oxadiazol-3-yl)benzyl)-1-(3-(trifluoromethyl)phenyl)urea

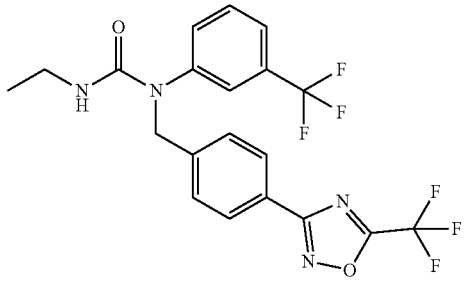 [SMILES: CCNC(=O)N(Cc1ccc(-c2noc(C(F)(F)F)n2)cc1)c1cccc(C(F)(F)F)c1]

To a suspension of 3-(trifluoromethyl)-N-(4-(5-(trifluoromethyl)-1,2,4-oxadiazol-3-yl)benzyl)aniline hydrochloride from Example 30, Step D (10 mg, 0.024 mmol) and triethylamine (0.016 mL, 0.12 mmol) in toluene (0.3 mL) was added ethyl isocyanate (5.60 µl, 0.071 mmol) and the mixture was heated at 110° C. for 20 h. The toluene was removed and the crude dissolved in DMF (1 mL) and purified on a Gilson HPLC (YMC Pro C18 column, eluting with a 30-95% acetonitrile in water gradient containing a 0.1% TFA modifier) to afford the title compound as a solid. ¹H NMR (600 MHz, CDCl₃): δ8.05 (d, J=7.8 Hz, 2H), 7.57 (d, J=7.8 Hz, 1H), 7.50 (t, J=7.8 Hz, 1H), 7.42 (s, 1H), 7.40 (d, J=7.8 Hz, 2H), 7.29 (d, J=7.8 Hz, 1H), 4.97 (s, 2H), 4.24 (bs, 1H), 3.31-3.26 (m, 2H), 1.09 (t, J=7.3 Hz, 3H); MS (ESI) m/z [M+H]⁺: 459.2.

Example 183

N-(4-(5-(Trifluoromethyl)-1,2,4-oxadiazol-3-yl)benzyl)-N-(3-(trifluoromethyl)phenyl)methanesulfonamide

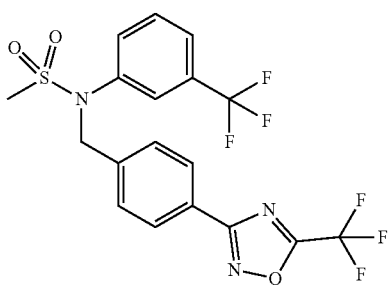 [SMILES: CS(=O)(=O)N(Cc1ccc(-c2noc(C(F)(F)F)n2)cc1)c1cccc(C(F)(F)F)c1]

To a suspension of 3-(trifluoromethyl)-N-(4-(5-(trifluoromethyl)-1,2,4-oxadiazol-3-yl)benzyl)aniline hydrochloride from Example 30, Step D (15 mg, 0.035 mmol) and DBU (0.016 mL, 0.11 mmol) in acetonitrile (0.5 mL) was added methanesulfonyl chloride (14.0 μl, 0.18 mmol) and the mixture was heated at 65° C. for 18 h. The acetonitrile was removed and the crude dissolved in DMF (1 mL) and purified on a Gilson HPLC (YMC Pro C18 column, eluting with a 30-95% acetonitrile in water gradient containing a 0.1% TFA modifier) to afford the title compound as a solid. $^1$H NMR (600 MHz, CDCl$_3$): δ8.05 (d, J=8.3 Hz, 2H), 7.57-753 (m, 2H), 7.49-7.46 (m, 2H), 7.44 (d, J=8.3 Hz, 2H), 4.97 (s, 2H), 3.02 (s, 3H); MS (ESI) m/z [M+H]$^+$: 465.9.

Example 184

3-(6-((5-Chloro-3-methylpyrazin-2-yl)methoxy)pyridin-3-yl)-5-(trifluoromethyl)-1,2,4-oxadiazole

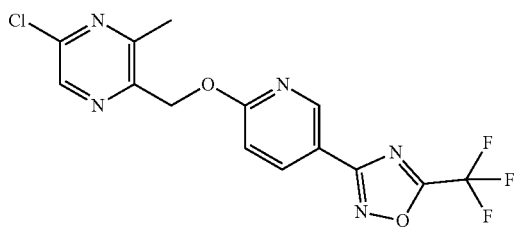 [SMILES: Cc1nc(Cl)cnc1COc1ccc(-c2noc(C(F)(F)F)n2)cn1]

Step A: 2-(Methoxycarbonyl)-3-methylpyrazine 1-oxide

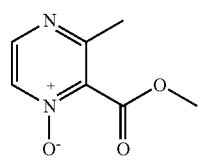

3-Chloroperoxybenzoic acid (2.94 g, 14.46 mmol) (85%) was added to methyl 3-methylpyrazine-2-carboxylate (2.0 g, 13.14 mmol) in CHCl$_3$ (30 mL) at 15° C. and the mixture was stirred at 70° C. for 16 h. After cooling to ambient temperature, the mixture was partitioned between CH$_2$Cl$_2$ (50 mL), sat.Na$_2$SO$_3$ (50 mL) and H$_2$O (50 mL), and the aqueous layer was further extracted with CH$_2$Cl$_2$ (3×50 mL). The combined organic layers were washed with brine (50 mL), dried (MgSO$_4$), filtered and concentrated under reduced pressure. The residue was purified by flash silica gel chromatography (ISCO®; 20 g SepaFlash® Silica Flash Column, Eluent of 0-100% EtOAc/PE gradient @ 20 mL/min) to give 2-(methoxycarbonyl)-3-methylpyrazine 1-oxide as a solid. ESI-MS m/z [M+H]$^+$: 169.0

Step B: Methyl 5-chloro-3-methylpyrazine-2-carboxylate

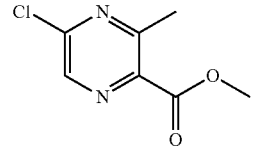

Phosphorus oxychloride (7.57 mL, 81.0 mmol) was added to 2-(methoxycarbonyl)-3-methylpyrazine-1-oxide (1.92 g, 11.4 mmol) in DMF (20 mL) at 15° C. and the mixture was stirred at 70° C. for 16 h. After cooling to ambient temperature, the mixture was partitioned between ethyl acetate (80 mL), sat.NaHCO$_3$ (50 mL) and H$_2$O (50 mL), and the aqueous layer was further extracted with ethyl acetate (2×50 mL). The combined organic layers were washed with brine (50 mL), dried (MgSO$_4$), filtered and concentrated under reduced pressure. The residue was purified by flash silica gel chromatography (ISCO®; 40 g SepaFlash® Silica Flash Column, Eluent of 0-20% EtOAc/PE gradient @40 mL/min) to give methyl 5-chloro-3-methylpyrazine-2-carboxylate as a solid. ESI-MS m/z [M+H]$^+$: 159.0.

Step C: (5-Chloro-3-methylpyrazin-2-yl)methanol

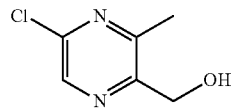

Sodium borohydride (235 mg, 6.22 mmol) was added to methyl 5-chloro-3-methylpyrazine-2-carboxylate (580 mg, 3.11 mmol) in MeOH (15 mL) at 15° C. and the mixture was stirred at 15° C. for 2 h. The mixture was partitioned between ethyl acetate (50 mL) and H$_2$O (50 mL), and the aqueous layer was further extracted with ethyl acetate (2×30 mL). The combined organic layers were washed with brine (50 mL), dried (MgSO$_4$), filtered and concentrated under reduced pressure. The residue was purified by prep-TLC (SiO$_2$, PE:EtOAc=1:1) to give (5-chloro-3-methylpyrazin-2-yl)methanol as an oil. ESI-MS m/z [M+H]$^+$: 159.0.

Step D: 3-(6-((5-Chloro-3-methylpyrazin-2-yl)methoxy)pyridin-3-yl)-5-(trifluoromethyl)-1,2,4-oxadiazole

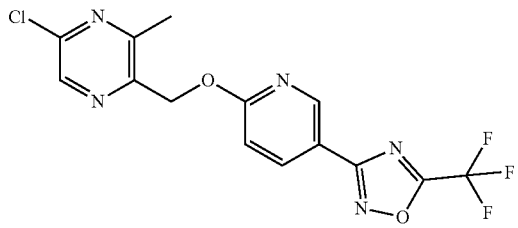 [SMILES: Cc1nc(Cl)cnc1COc1ccc(-c2noc(C(F)(F)F)n2)cn1]

(E)-di-tert-Butyl diazene-1,2-dicarboxylate (160 mg, 0.694 mmol) was added to a mixture of 5-(5-(trifluoromethyl)-1,2,4-oxadiazol-3-yl)pyridin-2-ol (146 mg, 0.631 mmol), triphenylphosphine (198 mg, 0.757 mmol) and (5-chloro-3-methylpyrazin-2-yl)methanol (100 mg, 0.631 mmol) in THF (3 mL) at 15° C. and the mixture was stirred at 15° C. for 16 h. The mixture was concentrated under reduced pressure. The residue was purified by reverse-phase prep-HPLC (preparative HPLC on a GILSON 281 instrument fitted with Waters XSELECT C18 150*30 mm*5 um using water and acetonitrile as the eluents. Mobile phase A: water, mobile phase B: acetonitrile (containing: 0.1% TFA-ACN). Gradient: 32-62%, 0-10 min; 100% B, 10.5-12.5 min; 5% B, 13-15 min) to give 3-(6-((5-chloro-3-methylpyrazin-2-yl)methoxy)pyridin-3-yl)-5-(trifluoromethyl)-1,2,4-oxadiazole as an oil. $^1$H NMR (400 MHz, CD$_3$OD): δ ppm 8.84-8.89 (m, 1H), 8.41-8.46 (m, 1H), 8.34-8.39 (m, 1H), 7.04-7.10 (m, 1H), 5.59-5.66 (m, 2H), 2.65 (s, 3H); ESI-MS m/z [M+H]$^+$: 371.9.

Example 185

3-(6-(((2-Methylpyrimidin-5-yl)methyl)pyridin-3-yl)-5-(trifluoromethyl)-1,2,4-oxadiazole

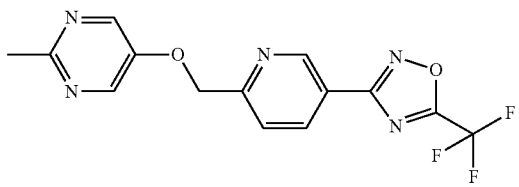 [SMILES: Cc1ncc(OCc2ccc(-c3noc(C(F)(F)F)n3)cn2)cn1]

A solution of (5-(5-(trifluoromethyl)-1,2,4-oxadiazol-3-yl)pyridin-2-yl)methanol (25.0 mg, 0.102 mmol) 2-methylpyrimidin-5-ol (11.2 mg, 0.102 mmol), PS-triphenylphosphine (80 mg, 0.306 mmol), and (E)-di-tert-butyl diazene-1,2-dicarboxylate (47.0 mg, 0.204 mmol) in THF (1.0 mL) was heated at 80° C. for 3 h, filtered, and concentrated. The residue was dissolved in DMF (1 mL) and purified on a Gilson HPLC (YMC Pro C18 column, eluting with a 5-95% acetonitrile in water gradient containing a 0.1% TFA modifier) to afford the title compound as a solid. $^1$H NMR (600 MHz, CDCl3): δ 9.23 (s, 1H)), 8.56 (s, 2H), 8.52 (d, 1H), 7.83 (d, 1H), 5.45 (s, 2H), 2.54 (s, 3H); MS (ESI) m/z [M+H]$^+$: 362.8.

Example 186

3-(3-Chloro-2-((4,6-dimethylpyrimidin-2-yl)methoxy)pyridin-4-yl)-5-(trifluoromethyl)-1,2,4-oxadiazole

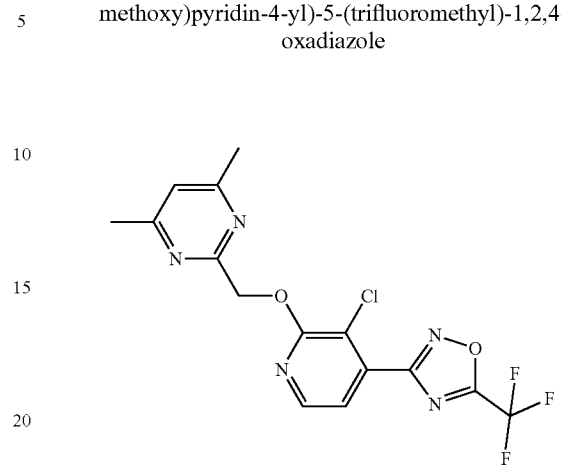

A solution of 3-chloro-2-fluoroisonicotinonitrile (50.0 mg, 0.319 mmol), (4,6-dimethylpyrimidin-2-yl)methanol (44.1 mg, 0.319 mmol), and cesium carbonate (312 mg, 0.958 mmol) in DMF (639 μl) was stirred at 80° C. for 1 h. The reaction mixture was concentrated, and the crude dissolved in EtOH (1.5 mL). Hydroxylamine (28.9 mg, 0.874 mmol) was added and the solution was heated at 60° C. for 2 h. The reaction mixture was concentrated, and the residue was dissolved in DCM (2.8 mL). TFAA (0.117 mL, 0.829 mmol) and Triethylamine were added and the solution was stirred for 0.5 h. The reaction mixture was concentrated and the residue was dissolved in DMF (1 mL) and purified on a Gilson HPLC (YMC Pro C18 column, eluting with a 0-95% acetonitrile in water gradient containing a 0.05% TFA modifier) to afford the title compound as an oil. $^1$H NMR (600 MHz, CDCl$_3$): δ8.10 (d, J=5.4 Hz, 1H), 7.45 (d, J=4.9 Hz, 1H), 7.00 (s, 1H), 5.66 (s, 2H), 2.49 (s, 6H); MS (ESI) m/z [M+H]$^+$: 386.2.

Example 187

3-Cyclopropyl-5-(((3-fluoro-4-(5-(trifluoromethyl)-1,2,4-oxadiazol-3-yl)pyridin-2-yl)oxy)methyl)-1,2,4-oxadiazole

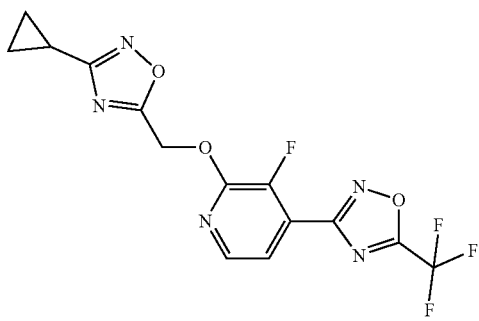 [SMILES: Fc1c(-c2noc(C(F)(F)F)n2)ccnc1OCc1nc(C2CC2)no1]

Step A: 2,3-Difluoroisonicotinamide

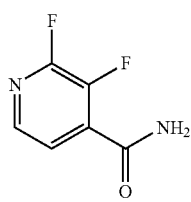 [SMILES: NC(=O)c1ccnc(F)c1F]

NH$_4$Cl (4.54 g, 85.0 mmol) was added to a stirred mixture of DIPEA (14.8 ml, 85.0 mmol), HATU (16.1 g, 42.4 mmol), and 2,3-difluoroisonicotinic acid (4.50 g, 28.3 mmol) in DMF (45 ml) and the mixture was stirred at 17° C. for 18 h. The reaction mixture was diluted with H$_2$O (40 mL), extracted with EtOAc (3×30 mL), and the extract was washed with brine (30 mL), dried over Na$_2$SO$_4$, filtered and concentrated in vacuo. The residue was purified by SiO$_2$ column chromatography (heptane: EtOAc=95:5 to 40:60) to give 2,3-difluoroisonicotinamide as a solid.

Step B: 2,3-Difluoroisonicotinonitrile

2,2,2-Trifluoroacetic anhydride (7.97 g, 37.9 mmol) was added to a stirred mixture of 2,3-difluoroisonicotinamide (3.00 g, 19.0 mmol), and triethylamine (5.76 g, 56.9 mmol) in DCM (30 ml) and the mixture was stirred at 15° C. for 17 h. The mixture was diluted with H$_2$O (50 mL) and extracted with DCM (3×40 mL). The combined organic layers were washed with brine (50 mL), dried over anhydrous Na$_2$SO$_4$, filtered and concentrated under reduced pressure. The residue was purified by SiO$_2$ column chromatography (heptane: EtOAc=95:5 to 40:60) to give 2,3-difluoroisonicotinonitrile as a solid.

Step C: 3-Fluoro-2-hydroxyisonicotinonitrile

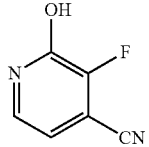

A mixture of 2,3-difluoroisonicotinonitrile (1.00 g, 7.14 mmol) and 2M hydrogen chloride (2.68 mL, 5.35 mmol) was placed in a microwave tube and heated at 150° C. for 10 min. The reaction mixture was concentrated under reduced pressure to give 3-fluoro-2-oxo-1, 2-dihydropyridine-4-carbonitrile as a solid.

Step D: (Z)-3-Fluoro-N',2-dihydroxyisonicotinimidamide

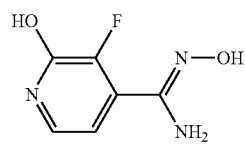 [SMILES: N/C(=N\O)c1ccnc(O)c1F]

A mixture of 3-fluoro-2-hydroxyisonicotinonitrile (900 mg, 6.52 mmol), hydroxylamine hydrochloride (906 mg, 13.0 mmol) and triethylamine (1.82 mL, 13.0 mmol) in EtOH (20 mL) was heated at 80° C. for 2 h. The contents in the flask were concentrated in vacuo to give (Z)-3-fluoro-N, 2-dihydroxyisonicotinimidamide as a solid.

Step E: 3-Fluoro-4-(5-(trifluoromethyl)-1,2,4-oxadiazol-3-yl)pyridin-2(1H)-one

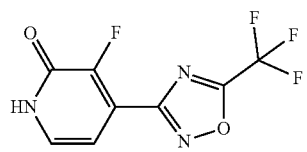 [SMILES: O=c1[nH]ccc(-c2noc(C(F)(F)F)n2)c1F]

A mixture of (Z)-3-fluoro-N',2-dihydroxyisonicotinimidamide (1.12 g, 6.52 mmol), potassium carbonate (1.08 g, 7.82 mmol) and TFAA (3.68 mL, 26.1 mmol) in dioxane (20 mL) was stirred for 4 h. The contents in the flask were diluted with ethyl acetate (30 mL) and water (20 mL). The phases were separated, washed with brine (2×30 mL), dried over Na$_2$SO$_4$, filtered and concentrated in vacuo. The residue was purified by column chromatography (ISCO®; 20 g SepaFlash® Silica Flash Column, Eluent of 0~10% MeOH/DCM gradient @ 30 mL/min) to give 3-fluoro-4-(5-(trifluoromethyl)-1,2,4-oxadiazol-3-yl)pyridin-2(1H)-one as a solid. ESI-MS m/z [M+H]$^+$: 250.0.

Step F: 3-Cyclopropyl-5-(((3-fluoro-4-(5-(trifluoromethyl)-1,2,4-oxadiazol-3-yl)pyridin-2-yl)oxy)methyl)-1,2,4-oxadiazole

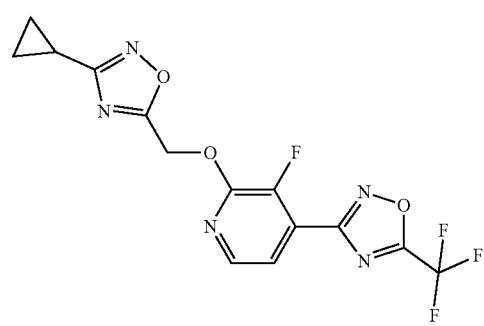 [SMILES: Fc1c(-c2noc(C(F)(F)F)n2)ccnc1OCc1nc(C2CC2)no1]

To a solution of 3-fluoro-4-(5-(trifluoromethyl)-1,2,4-oxadiazol-3-yl)pyridin-2(1H)-one (50 mg, 0.201 mmol) in CH$_2$Cl$_2$ (2007 µl) was added (3-cyclopropyl-1,2,4-oxadiazol-5-yl)methanol (42.2 mg, 0.301 mmol), polymer-supported triphenyl phosphine (~3 mmol/g, 158 mg, 0.600 mmol), and (E)-di-tert-butyl diazene-1,2-dicarboxylate (92 mg, 0.401 mmol) in CH$_2$Cl$_2$ (2.0 mL). The reaction was sealed and heated at 80° C. for 3 h, filtered, concentrated and chromatographed using HPLC purification (19 cm×150 cm C18, 30 min 0-95% acetonitrile-water gradient, 0.05% TFA added) to yield an oil. $^1$H NMR (CHCl$_3$-d, 600 MHz): δ 8.11 (s, 1H), 7.65 (s, 1H), 5.65 (s, 2H), 2.10-2.05 (m, 1H), 1.09-1.00 (m, 4H); ESI-MS m/z [M+H]$^+$: 372.2.

Example 188

(S)-1-(3-Fluoro-4-(5-(trifluoromethyl)-1,2,4-oxadiazol-3-yl)phenyl)-5-(hydroxymethyl)pyrrolidin-2-one

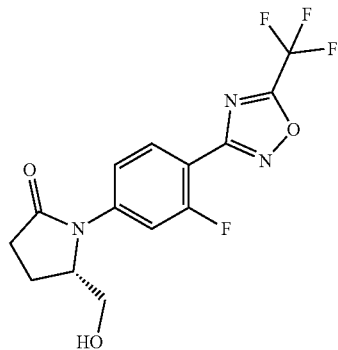 [SMILES: O=C1CC[C@@H](CO)N1c1ccc(-c2noc(C(F)(F)F)n2)c(F)c1]

Step A: (S)-5-(((tert-Butyldiphenylsilyl)oxy)methyl)pyrrolidin-2-one

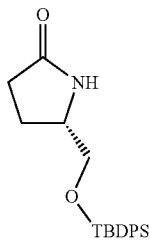

To a solution of 5S-(hydroxymethyl)pyrrolidin-2-one (1.00 g, 8.69 mmol) and imidazole (1.30 g, 19.1 mmol) in DMF (3 mL) was added tert-butylchlorodiphenylsilane (2.48 mL, 9.55 mmol). The mixture was stirred at ambient temperature for 16 h. The mixture was concentrated in vacuo, diluted with water, and extracted with EtOAc (3×60 mL). The combined organics were washed with brine (60 mL), dried over Na$_2$SO$_4$, filtered and concentrated in vacuo. The residue was dissolved in DCM (10 mL) and purified on an Isco Rf silica gel column (100 g prepacked, EtOAc/hexane, 0-50% over 45 min) to give the title compound. MS (ESI) m/z [M+H]$^+$: 354.3.

Step B: (S)-4-(2-(((tert-Butyldiphenylsilyl)oxy)methyl)-5-oxopyrrolidin-1-yl)-2-fluorobenzonitrile

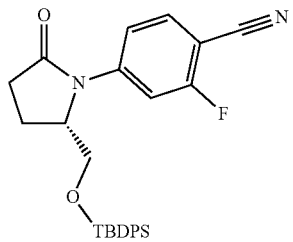

(S)-5-(((tert-Butyldiphenylsilyl)oxy)methyl)pyrrolidin-2-one (2.60 g, 7.35 mmol), 4-bromo-2-fluorobenzonitrile (1.47 g, 7.35 mmol), cesium carbonate (7.19 g, 22.1 mmol), Pd$_2$(dba)$_3$ (0.606 g, 0.662 mmol), and Xantphos (0.426 g, 0.735 mmol) were suspended in dioxane (8.0 mL) and heated at 90° C. for 16 h. The mixture was cooled, diluted with ethyl acetate (40 mL), washed with saturated aqueous sodium hydrogen carbonate (2×50 mL), water (25 mL), and brine (25 mL). The organic layer was dried (Na$_2$ SO$_4$) filtered, and the solvent was evaporated under reduced pressure. The residue was dissolved in DCM and purified via ISCO Rf (0-50% ethyl acetate/hexanes over 30 min, 80 g Isco Gold silica gel column) to give the title compound. MS (ESI) m/z [M+H]$^+$: 473.4.

Step C: (S,Z)-4-(2-(((tert-Butyldiphenylsilyl)oxy)methyl)-5-oxopyrrolidin-1-yl)-2-fluoro-N'-hydroxybenzimidamide

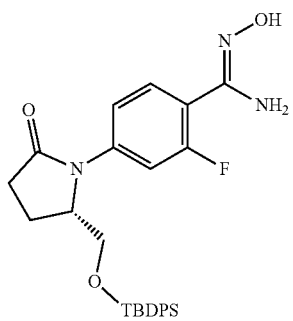

(S)-4-(2-(((tert-Butyldiphenylsilyl)oxy)methyl)-5-oxopyrrolidin-1-yl)-2-fluorobenzonitrile (1.60 g, 3.39 mmol) was suspended in water (2.5 mL) and ethanol (5 mL). To the suspension was added hydroxylamine (415 μL, 6.77 mmol) and heated at 50° C. for 6 h. The solution was cooled to ambient temperature and stirred for 16 h. The mixture was concentrated and diluted with water (60 mL), then extracted with ethyl acetate (3×60 mL). The combined organics were washed with brine (20 mL), dried over magnesium suflate, filtered, and concentrated to afford the title compound. MS (ESI) m/z [M+H]$^+$: 506.4.

Step D: (S)-5-(((tert-Butyldiphenylsilyl)oxy)methyl)-1-(3-fluoro-4-(5-(trifluoromethyl)-1,2,4-oxadiazol-3-yl)phenyl)pyrrolidin-2-one

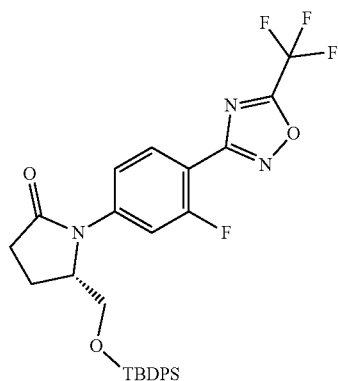

(S,Z)-4-(2-(((tert-Butyldiphenylsilyl)oxy)methyl)-5-oxopyrrolidin-1-yl)-2-fluoro-N'-hydroxybenzimidamide (1.71 g, 3.39 mmol) was dissolved in CH$_2$Cl$_2$ (10 mL) at 0° C. Trifluoroacetic anhydride (1.44 mL, 10.2 mmol) was added and the mixture was stirred at ambient temperature for 16 h. The mixture was then cooled to 0° C. and TEA (1.89 mL, 13.56 mmol) was added, and the resulting mixture was stirred at ambient temperature for 1 h. The mixture was concentrated in vacuo, and the residue was purified on an Isco Rf silica gel column (100 g prepacked, EtOAc/hexane 0-25% over 30 min) to afford the title compound. MS (ESI) m/z [M+H]$^+$: 584.4.

Step E: (S)-1-(3-Fluoro-4-(5-(trifluoromethyl)-1,2,4-oxadiazol-3-yl)phenyl)-5-(hydroxymethyl)pyrrolidin-2-one

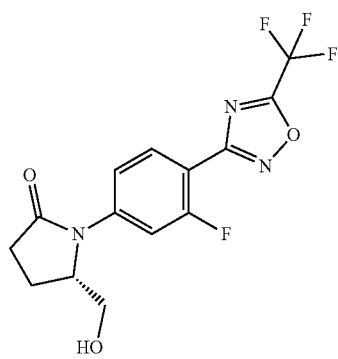 [SMILES: O=C1CC[C@@H](CO)N1c1ccc(-c2noc(C(F)(F)F)n2)c(F)c1]

To a solution of (S)-5-(((tert-butyldiphenylsilyl)oxy)methyl)-1-(3-fluoro-4-(5-(trifluoromethyl)-1,2,4-oxadiazol-3-yl)phenyl)pyrrolidin-2-one (800 mg, 1.37 mmol) in THF (6 mL) was added HF-TEA (in TEA) (1.60 mL, 3.47 mmol) at 0° C. The mixture was then warmed to ambient temperature and stirred for 16 h. The solvent was removed in vacuo and the residue was purified on silica gel (Isco Rf, 12 g, 0-40% EtOAc/hexanes) to yield the title compound. $^1$H NMR (600 MHz, Methanol-d$_4$) δ 8.10 (t, J=8.3 Hz, 1H), 7.81 (d, J=13.0 Hz, 1H), 7.55 (d, J=8.6 Hz, 1H), 4.53-4.49 (m, 1H), 3.72 (dd, J=11.9, 4.0 Hz, 1H), 3.60 (dd, J=12.0, 2.5 Hz, 1H), 2.82-2.72 (m, 1H), 2.50 (ddd, J=17.3, 10.3, 3.8 Hz, 1H), 2.38-2.28 (m, 1H), 2.19-2.12 (m, 1H); MS (ESI) m/z [M+H]$^+$: 346.2.

Example 189

(S)-1-(3-Fluoro-4-(5-(trifluoromethyl)-1,2,4-oxadiazol-3-yl)phenyl)-5-(morpholinomethyl)pyrrolidin-2-one

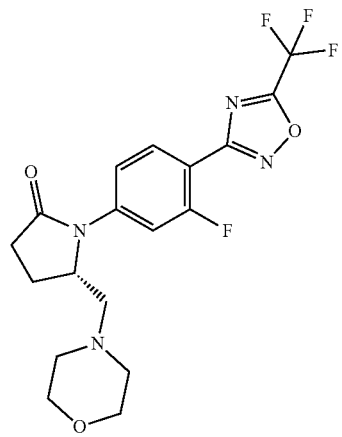 [SMILES: O=C1CC[C@@H](CN2CCOCC2)N1c1ccc(-c2noc(C(F)(F)F)n2)c(F)c1]

Step A: (S)-2-Fluoro-4-(2-(hydroxymethyl)-5-oxopyrrolidin-1-yl)benzonitrile

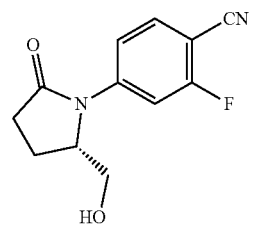 [SMILES: N#Cc1ccc(N2C(=O)CC[C@H]2CO)cc1F]

To a solution of (S)-4-(2-(((tert-butyldiphenylsilyl)oxy)methyl)-5-oxopyrrolidin-1-yl)-2-fluorobenzonitrile (1.60 g, 3.39 mmol) in THF (6 mL) was added HF-TEA (in TEA) (3.90 mL, 8.46 mmol) at 0° C. The mixture was warmed to ambient temperature and stirred for 16 h. The solvent was removed in vacuo, and the residue was purified on silica gel (Isco Rf, 80 g, 0-100% EtOAc/hexane) to yield the title compound. MS (ESI) m/z [M+H]$^+$: 235.2.

Step B: (S)-2-Fluoro-4-(2-formyl-5-oxopyrrolidin-1-yl)benzonitrile

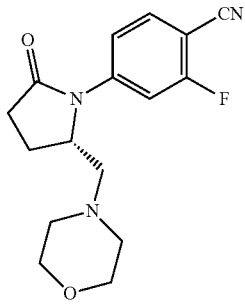 [SMILES: N#Cc1ccc(N2C(=O)CC[C@H]2CN2CCOCC2)cc1F]

To a solution of DMSO (0.111 mL, 1.56 mmol) in DCM (30 mL) at −78° C. was added oxalyl chloride (0.781 mL, 1.56 mmol) dropwise and the solution was stirred for 20 min. To this solution was added (S)-2-fluoro-4-(2-(hydroxymethyl)-5-oxopyrrolidin-1-yl)benzonitrile (183 mg, 0.781 mmol) in DCM (10 mL) and the solution was stirred for 20 min before triethylamine (0.436 mL, 3.13 mmol) was added. The mixture was warmed to ambient temperature, then diluted with water (30 mL) and extracted with DCM (3×30 mL). The combined organics were washed with water (20 mL), brine (20 mL), dried over magnesium sulfate, and concentrated in vacuo. The residue was dissolved in DCM (10 mL) and purified on Isco Rf silica gel column [40 g, EtOAc/isohexane 0-15%) to give (S)-2-fluoro-4-(2-formyl-5-oxopyrrolidin-1-yl)benzonitrile intermediate. To this intermediate was added MeOH (5 mL) and morpholine (0.098 mL, 1.12 mmol), followed by acetic acid (0.049 mL, 0.861 mmol) and sodium cyanoborohydride (70.4 mg, 1.120 mmol). The mixture was allowed to stir for 16 h at ambient temperature. The mixture was concentrated in vacuo, diluted with DMSO (1 mL) and purified via Gilson PLC2020 [SunFire Prep C18 OBD Column, 5 μm, 30×150 mm, 5_95 Water/ACN (+0.1% TFA) over 25 min] to afford the title compound. MS (ESI) m/z [M+H]$^+$: 304.2.

Step C: (S)-1-(3-Fluoro-4-(5-(trifluoromethyl)-1,2,4-oxadiazol-3-yl)phenyl)-5-(morpholinomethyl)pyrrolidin-2-one

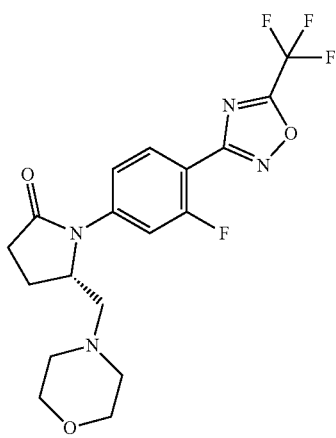 [SMILES: O=C1CC[C@@H](CN2CCOCC2)N1c1ccc(-c2noc(C(F)(F)F)n2)c(F)c1]

The title compound was prepared from the product of step B above according to the procedure outlined in Example 1, steps B and C. The crude material was purified via Gilson PLC2020 [SunFire Prep C18 OBD Column, 5 μm, 30×150 mm, 5_95 Water/ACN (+0.1% TFA) over 25 min] to afford the title compound. $^1$H NMR (600 MHz, Chloroform-d) δ 8.12 (t, J=8.2 Hz, 2H), 7.68 (dd, J=12.1, 1.9 Hz, 2H), 7.37 (dd, J=8.6, 2.0 Hz, 2H), 4.93 (t, J=7.8 Hz, 2H), 3.95 (t, J=4.7 Hz, 8H), 3.18 (s, 1H), 3.05 (d, J=8.5 Hz, 5H), 2.74 (dt, J=18.0, 9.1 Hz, 2H), 2.69-2.52 (m, 4H), 2.26-2.19 (m, 2H). MS (ESI) m/z [M+H]$^+$: 415.3.

Example 190

1-Morpholino-2-((4-(5-(trifluoromethyl)-1,2,4-oxadiazol-3-yl)pyridin-2-yl)oxy)ethan-1-one

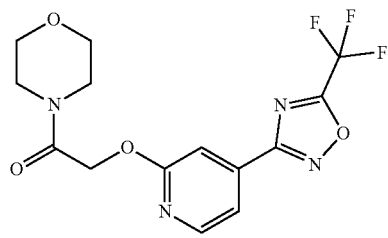 [SMILES: O=C(COc1cc(-c2noc(C(F)(F)F)n2)ccn1)N1CCOCC1]

Step A: tert-Butyl 2-((4-(5-(trifluoromethyl)-1,2,4-oxadiazol-3-yl)pyridin-2-yl)oxy)acetate

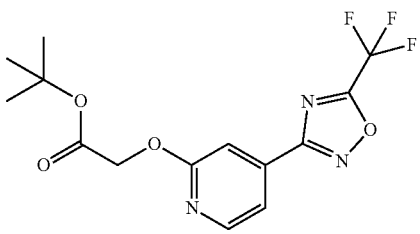 [SMILES: CC(C)(C)OC(=O)COc1cc(-c2noc(C(F)(F)F)n2)ccn1]

To a solution of 4-(5-(trifluoromethyl)-1,2,4-oxadiazol-3-yl)pyridin-2(1H)-one 4-(5-(trifluoromethyl)-1,2,4-oxadiazol-3-yl)pyridin-2-ol (157 mg, 0.681 mmol) and tert-butyl 2-hydroxyacetate (180 mg, 1.36 mmol) in THF (10 mL) was added PS—PPh$_3$ (triphenylphosphine resin) (657 mg, 1.50 mmol). The suspension was degassed, put under N$_2$ and di-tert-butyl azodicarboxylate (251 mg, 1.09 mmol) was added. The suspension was stirred at RT for 16 h, filtered, and concentrated. The residue was dissolved in DCM (10 mL) and purified on an Isco Rf silica gel column (40 g, EtOAc/hexanes 0-25%) to give the title compound. MS (ESI) m/z [M+H]$^+$: 346.1.

Step B: 2-((4-(5-(Trifluoromethyl)-1,2,4-oxadiazol-3-yl)pyridin-2-yl)oxy)acetic acid

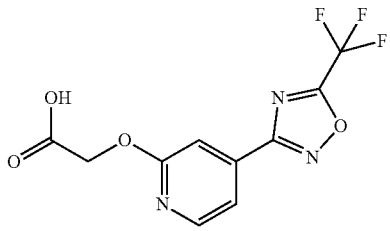 [SMILES: O=C(O)COc1cc(-c2noc(C(F)(F)F)n2)ccn1]

A solution of tert-butyl 2-((4-(5-(trifluoromethyl)-1,2,4-oxadiazol-3-yl)pyridin-2-yl)oxy)acetate] (40 mg, 0.116 mmol) in DCM (3 mL) and TFA (1.00 mL, 13.0 mmol) was stirred for 16 h at ambient temperature. The reaction mixture was concentrated to give the title compound. MS (ESI) m/z [M+H]$^+$: 290.1.

Step C: 1-Morpholino-2-((4-(5-(trifluoromethyl)-1,2,4-oxadiazol-3-yl)pyridin-2-yl)oxy)ethan-1-one

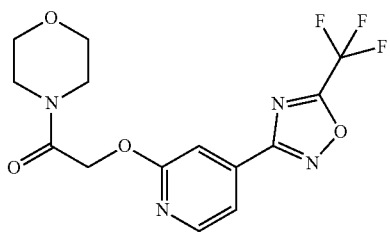 [SMILES: O=C(COc1cc(-c2noc(C(F)(F)F)n2)ccn1)N1CCOCC1]

To a solution of 2-((4-(5-(trifluoromethyl)-1,2,4-oxadiazol-3-yl)pyridin-2-yl)oxy)acetic acid (30 mg, 0.104 mmol) and HATU (79.0 mg, 0.207 mmol) in DMF (1.0 mL) was added DIEA (54.4 µL, 0.311 mmol) and morpholine (13.6 µL, 0.156 mmol). The reaction was stirred at ambient temperature for 16 h. Added DMSO (1 mL) and purified via Gilson PLC2020 [SunFire Prep C18 OBD Column, 5 µm, 30×150 mm, 5_95 Water/ACN (+0.1% TFA) over 25 min] to give desired product. $^1$H NMR (600 MHz, Chloroform-d) δ 8.28 (d, J=5.2 Hz, 1H), 7.66-7.48 (m, 1H), 5.07 (s, 1H), 3.71 (d, J=13.2 Hz, 3H), 3.63 (s, 2H), 3.53 (s, 1H), 3.47 (s, OH).

Example 191

N-(4-(5-(Trifluoromethyl)-1,2,4-oxadiazol-3-yl)benzyl)cyclopentanecarboxamide

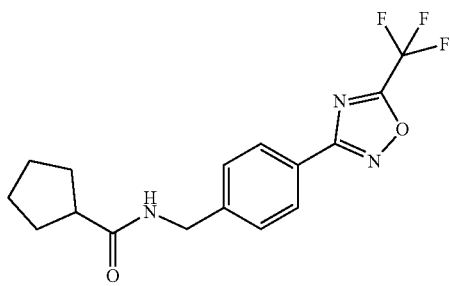 [SMILES: O=C(NCc1ccc(-c2noc(C(F)(F)F)n2)cc1)C1CCCC1]

Step A: (5-(5-(Trifluoromethyl)-1,2,4-oxadiazol-3-yl)pyridin-2-yl)methanol

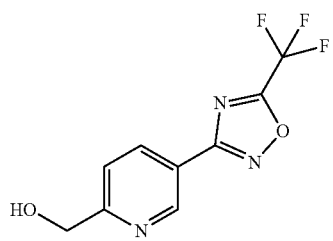 [SMILES: OCc1ccc(-c2noc(C(F)(F)F)n2)cn1]

To a solution of 5-(5-(trifluoromethyl)-1,2,4-oxadiazol-3-yl)picolinaldehyde (1.8 g, 7.40 mmol) and acetic acid (0.424 mL, 7.40 mmol) in MeOH (1 mL) and THF (1 mL) at 0° C. was added sodium cyanoborohydride (0.558 g, 8.88 mmol). The reaction was warmed to ambient temperature and stirred for 2 h. The reaction mixture was concentrated in vacuo, diluted with saturated aqueous sodium hydrogen carbonate (20 mL), and extracted with ethyl acetate (3×20 mL). The combined organic fractions were washed with water (20 mL), brine (20 mL), dried (Na$_2$SO$_4$), filtered and the solvent was evaporated under reduced pressure. The residue was dissolved in DCM (10 mL) and purified on an Isco Rf silica gel column (40 g, EtOAc/hexane 0-75%) to give the title compound. MS (ESI) m/z [M+H]$^+$: 246.1.

Step B: (5-(5-(Trifluoromethyl)-1,2,4-oxadiazol-3-yl)pyridin-2-yl)methanamine

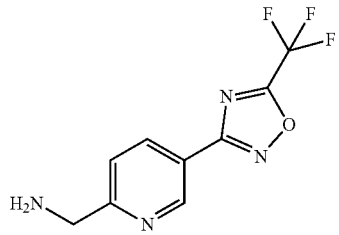 [SMILES: NCc1ccc(-c2noc(C(F)(F)F)n2)cn1]

To a solution of (5-(5-(trifluoromethyl)-1,2,4-oxadiazol-3-yl)pyridin-2-yl)methanol (500 mg, 2.04 mmol) in THF (2 mL) at 0° C. was added diphenyl phosphorazidate (0.483 mL, 2.24 mmol) and 2,3,4,6,7,8,9,10-octahydropyrimido[1,2-a]azepine (373 mg, 2.45 mmol) and the solution was stirred for 20 h. Added diphenylphosphorylazide (0.030 mL) and DBU (0.030 mL) and continued stirring for 20 h. An additional 0.5 equivalents of both diphenyl phosphorazide and DBU were added and the mixture was stirred an additional 72 h at ambient temperature. The reaction mixture was poured onto sat. NaHCO$_3$(10 mL) and extracted with EtOAc (3×10 mL). The combined organics were dried over Na$_2$SO$_4$, filtered and concentrated. The residue was dissolved in DCM (10 mL) and purifieded on an Isco Rf silica gel column (12 g, EtOAc/hexane 15% isocratic) to give 3-(6-(azidomethyl)pyridin-3-yl)-5-(trifluoromethyl)-1,2,4-oxadiazole. To a solution of 3-(6-(azidomethyl)pyridin-3-yl)-5-(trifluoromethyl)-1,2,4-oxadiazole in THF (6 mL) was added triphenylphosphine polymer-bound (1090 mg, 3.26 mmol). The suspension bubbled with gas evolution and was allowed to stir for 1 h. Water (9.80 µL, 0.544 mmol) was added and the suspension was heated at 50° C. for 16 h. The mixture was filtered, washed with EtOAc, and concentrated. The residue was purified on an Isco Rf silica gel column (25 g, 0-10% MeOH (DCM) over 15 min) to give the title compound. MS (ESI) m/z [M+H]⁺: 245.1.

Step C: N-(4-(5-(Trifluoromethyl)-1,2,4-oxadiazol-3-yl)benzyl)cyclopentanecarboxamide

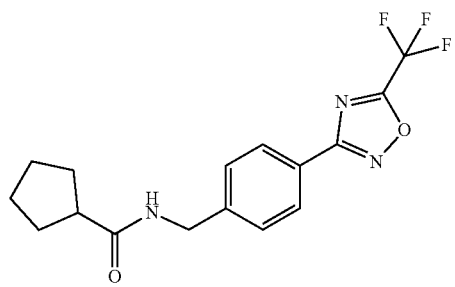 [SMILES: O=C(NCc1ccc(-c2noc(C(F)(F)F)n2)cc1)C1CCCC1]

To a solution of (5-(5-(trifluoromethyl)-1,2,4-oxadiazol-3-yl)pyridin-2-yl)methanamine (19 mg, 0.078 mmol) in DCM (2 mL) was added N-ethyl-N,N-diisopropylpropan-2-amine (13.1 mg, 0.101 mmol), followed by cyclopentane carboxylic acid (8.88 mg, 0.078 mmol) and HATU (29.6 mg, 0.078 mmol). The solution was allowed to stir at ambient temperature for 16 h and then concentrated. The residue was dissolved in DMSO (1 mL) and purified via Gilson PLC2020 [SunFire Prep C18 OBD Column, 5 μm, 30×150 mm, 5_95 Water/ACN (+0.1% TFA) over 25 min] to give the title compound. ¹H NMR (600 MHz, Methanol-d₄) δ 9.19 (s, 6H), 8.47 (dd, J=8.3, 2.1 Hz, 6H), 7.54 (d, J=8.3 Hz, 6H), 4.57 (s, 13H), 2.79-2.73 (m, 6H), 1.92 (d, J=8.4 Hz, 11H), 1.77 (d, J=19.5 Hz, 22H), 1.62 (s, 9H), 1.22 (d, J=6.5 Hz, 1H). [M+H]⁺: 341.2.

Example 192

(5-(5-(Trifluoromethyl)-1,2,4-oxadiazol-3-yl)pyridin-2-yl)methyl isopropylcarbamate

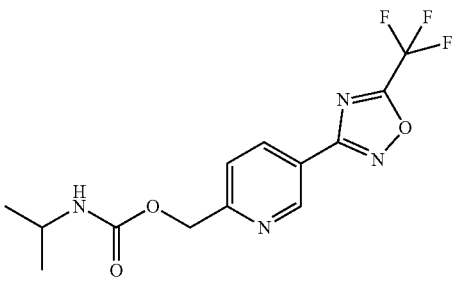 [SMILES: CC(C)NC(=O)OCc1ccc(-c2noc(C(F)(F)F)n2)cn1]

To a solution of (5-(5-(trifluoromethyl)-1,2,4-oxadiazol-3-yl)pyridin-2-yl)methanol (50 mg, 0.204 mmol) in dichloromethane (1 mL) was added 2-isocyanatopropane (20.8 mg, 0.245 mmol). The solution was degassed, then copper(I) trifluoromethaneulfonate toluene complex [2 to 1] (21.1 mg, 0.041 mmol) was added and the solution stirred for 16 h at ambient temperature. The solution was concentrated and the residue was dissolved in DMSO (1 mL) and purified via Gilson PLC2020 [SunFire Prep C18 OBD Column, 5 μm, 30×150 mm, 5_95 Water/ACN (+0.1% TFA) over 25 min] to give the title compound. ¹H NMR (600 MHz, Methanol-d₄) δ 9.19 (s, 1H), 8.50 (d, J=8.0 Hz, 1H), 7.64 (d, J=7.9 Hz, 1H), 5.22 (s, 2H), 3.72 (s, 1H), 1.15 (d, J=6.6 Hz, 6H). [M+H]⁺: 331.3.

The following examples displayed in TABLE 2 were prepared according to the identified procedures using the appropriate commercially available starting materials.

TABLE 2

| Ex # | Structure | Name | Stereochemistry | [M + H]⁺ | General Procedures |
|---|---|---|---|---|---|
| 193 | 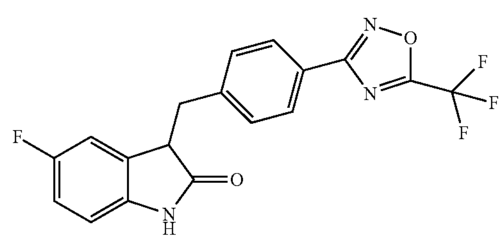 [SMILES: O=C1Nc2ccc(F)cc2C1Cc1ccc(-c2noc(C(F)(F)F)n2)cc1] | 5-fluoro-3-{4-[5-(trifluoromethyl)-1,2,4-oxadiazol-3-yl]benzyl}-1,3-dihydro-2H-indol-2-one | RACEMIC | 378.2 | 29 |
| 194 | 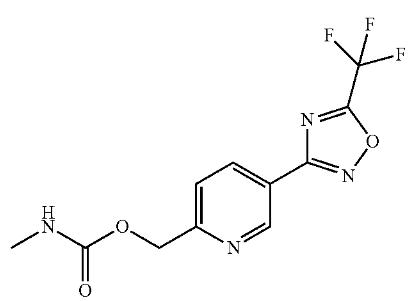 [SMILES: CNC(=O)OCc1ccc(-c2noc(C(F)(F)F)n2)cn1] | {5-[5-(trifluoromethyl)-1,2,4-oxadiazol-3-yl]pyridin-2-yl}methyl methylcarbamate | | 303.0 | 192 |

TABLE 2-continued

| Ex # | Structure | Name | Stereo-chemistry | [M + H]+ | General Procedures |
|---|---|---|---|---|---|
| 195 | 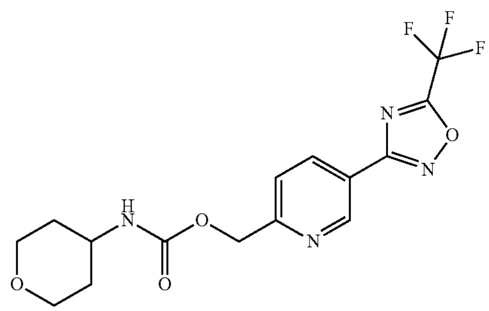 [SMILES: O=C(NC1CCOCC1)OCc1ccc(-c2noc(C(F)(F)F)n2)cn1] | {5-[5-(trifluoro-methyl)-1,2,4-oxa-diazol-3-yl]pyridin-2-yl}methyl oxan-4-yl-carbamate | | 373.2 | 192 |
| 196 | 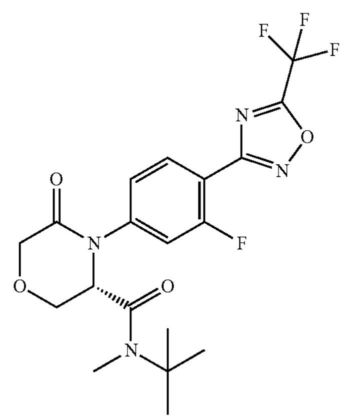 [SMILES: CN(C(=O)[C@@H]1COCC(=O)N1c1ccc(-c2noc(C(F)(F)F)n2)c(F)c1)C(C)(C)C] | (3S)-N-tert-butyl-4-{3-fluoro-4-[5-(trifluoro-methyl)-1,2,4-oxa-diazol-3-yl]phenyl}-N-methyl-5-oxo-morpholine-3-carboxamide | S | 445.3 | 19 |
| 197 | 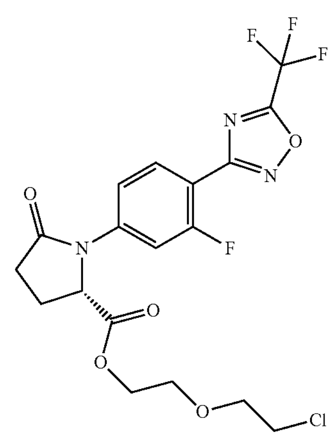 [SMILES: O=C(OCCOCCCl)[C@@H]1CCC(=O)N1c1ccc(-c2noc(C(F)(F)F)n2)c(F)c1] | 2-(2-chloro-ethoxy)ethyl 1-{3-fluoro-4-[5-(trifluoro-methyl)-1,2,4-oxa-diazol-3-yl]phenyl}-5-oxo-L-prolinate | S | 466.2 | 8 |
| 198 | 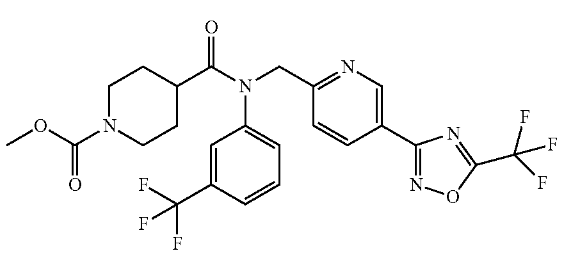 [SMILES: COC(=O)N1CCC(C(=O)N(Cc2ccc(-c3noc(C(F)(F)F)n3)cn2)c2cccc(C(F)(F)F)c2)CC1] | methyl 4-{({5-[5-(trifluoro-methyl)-1,2,4-oxa-diazol-3-yl]pyridin-2-yl}methyl)[3-(trifluoro-methyl)phenyl]carbamoyl}piperidine-1-carboxylate | | 557.9 | 30 |

TABLE 2-continued

| Ex # | Structure | Name | Stereo-chemistry | [M + H]+ | General Procedures |
|---|---|---|---|---|---|
| 199 | 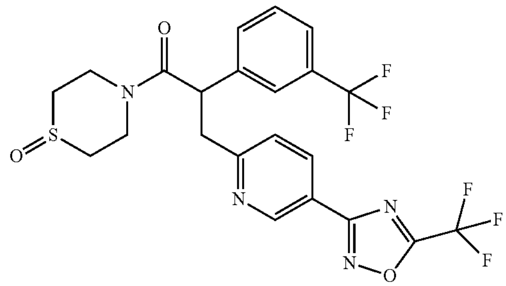 [SMILES: O=C(C(Cc1ccc(-c2noc(C(F)(F)F)n2)cn1)c1cccc(C(F)(F)F)c1)N1CCS(=O)CC1] | 4-(3-{5-[5-(trifluoro-methyl)-1,2,4-oxa-diazol-3-yl]pyridin-2-yl}-2-[3-(trifluoro-methyl)phenyl]propanoyl)-1lambda~4~,4-thiazinan-1-one | RACEMIC | 532.9 | 30 |
| 200 | 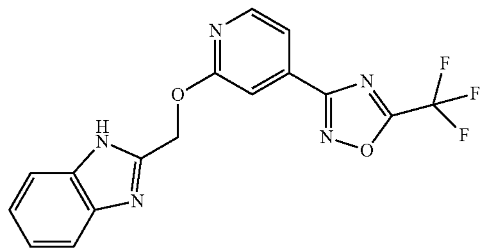 [SMILES: FC(F)(F)c1nc(-c2ccnc(OCc3nc4ccccc4[nH]3)c2)no1] | 2-[({4-[5-(trifluoro-methyl)-1,2,4-oxa-diazol-3-yl]pyridin-2-yl}oxy)methyl]-1H-benzimi-dazole | | 362.0 | 24 |
| 201 | 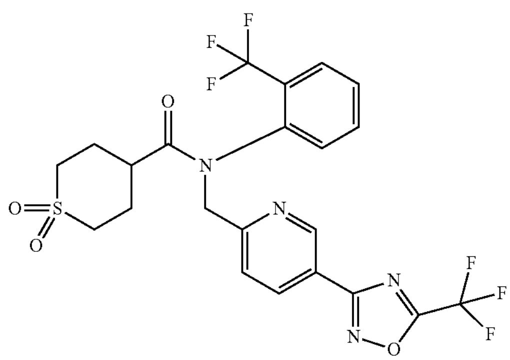 [SMILES: O=C(C1CCS(=O)(=O)CC1)N(Cc1ccc(-c2noc(C(F)(F)F)n2)cn1)c1ccccc1C(F)(F)F] | 1,1-dioxo-N-({5-[5-(trifluoro-methyl)-1,2,4-oxa-diazol-3-yl]pyridin-2-yl}methyl)-N-[2-(trifluoro-methyl)phenyl]-1lambda~6~-thiane-4-carboxamide | | 548.9 | 30 |
| 202 | 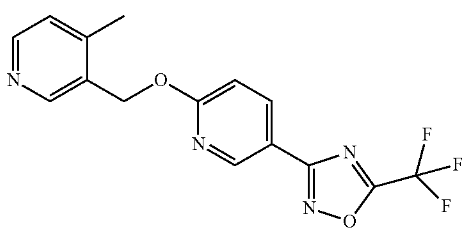 [SMILES: Cc1ccncc1COc1ccc(-c2noc(C(F)(F)F)n2)cn1] | 2-[(4-methyl-pyridin-3-yl)methoxy]-5-[5-(trifluoro-methyl)-1,2,4-oxa-diazol-3-yl]pyridine | | 337.0 | 184 |
| 203 | 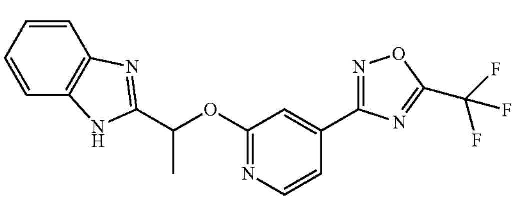 [SMILES: CC(Oc1cc(-c2noc(C(F)(F)F)n2)ccn1)c1nc2ccccc2[nH]1] | 2-[1-({4-[5-(trifluoro-methyl)-1,2,4-oxa-diazol-3-yl]pyridin-2-yl}oxy)ethyl]-1H-benzimi-dazole | RACEMIC | 376.0 | 184 |

TABLE 2-continued

| Ex # | Structure | Name | Stereo-chemistry | [M + H]+ | General Procedures |
|---|---|---|---|---|---|
| 204 | 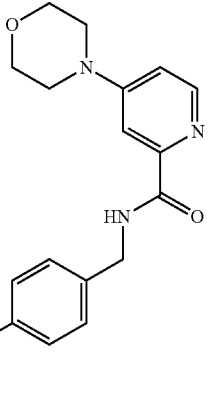 | 4-morpholin-4-yl-N-{4-[5-(trifluoro-methyl)-1,2,4-oxa-diazol-3-yl]benzyl}pyridine-2-carboxamide | | 434.3 | 191 |
| 205 | 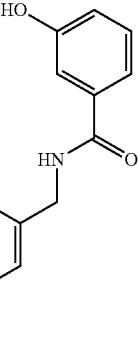 | 3-hydroxy-N-{4-[5-(trifluoro-methyl)-1,2,4-oxa-diazol-3-yl]benzyl}benzamide | | 364.1 | 191 |
| 206 | 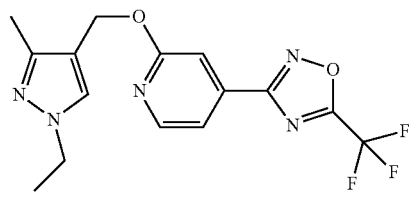 [SMILES: CCn1cc(COc2cc(-c3noc(C(F)(F)F)n3)ccn2)c(C)n1] | 2-[(1-ethyl-3-methyl-1H-pyrazol-4-yl)methoxy]-4-[5-(trifluoro-methyl)-1,2,4-oxa-diazol-3-yl]pyridine | | 354.1 | 24 |
| 207 | 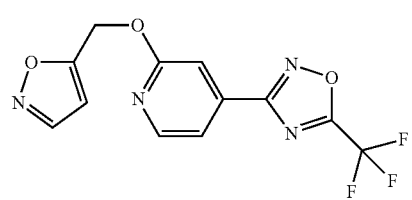 [SMILES: FC(F)(F)c1nc(-c2ccnc(OCc3ccno3)c2)no1] | 2-(isoxazol-5-ylmethoxy)-4-[5-(trifluoro-methyl)-1,2,4-oxa-diazol-3-yl]pyridine | | 313.1 | 24 |
| 208 | 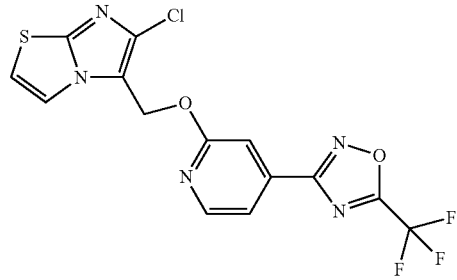 [SMILES: FC(F)(F)c1nc(-c2ccnc(OCc3c(Cl)nc4sccn34)c2)no1] | 6-chloro-5-[({4-[5-(trifluoro-methyl)-1,2,4-oxa-diazol-3-yl]pyridin-2-yl}oxy)methyl]imidazo[2,1-b][1,3]thiazole | | 402.1 | 24 |

TABLE 2-continued

| Ex # | Structure | Name | Stereo-chemistry | [M + H]+ | General Procedures |
|---|---|---|---|---|---|
| 209 | 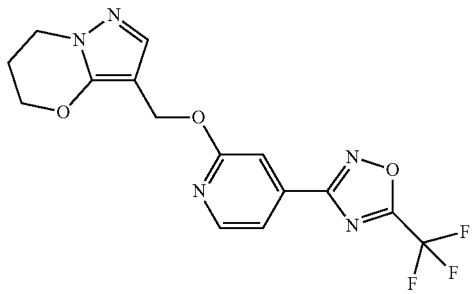 [SMILES: FC(F)(F)c1nc(-c2ccnc(OCc3cnn4c3OCCC4)c2)no1] | 3-[({4-[5-(trifluoro-methyl)-1,2,4-oxa-diazol-3-yl]pyridin-2-yl}oxy)methyl]-6,7-dihydro-5H-pyrazolo[5,1-b][1,3]oxazine | | 368.2 | 24 |
| 210 | 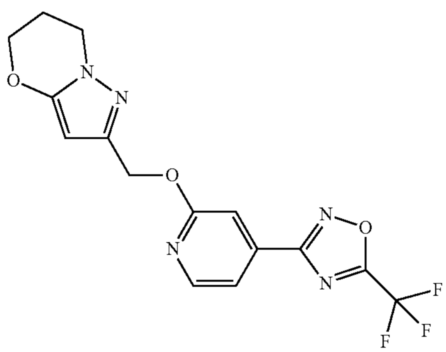 [SMILES: FC(F)(F)c1nc(-c2ccnc(OCc3cc4n(n3)CCCO4)c2)no1] | 2-[({4-[5-(trifluoro-methyl)-1,2,4-oxa-diazol-3-yl]pyridin-2-yl}oxy)methyl]-6,7-dihydro-5H-pyrazolo[5,1-b][1,3]oxazine | | 368.2 | 24 |
| 211 | 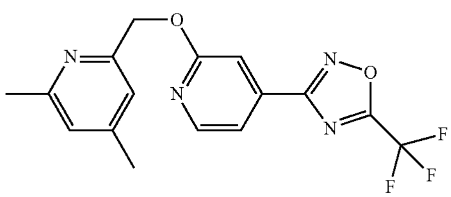 [SMILES: Cc1cc(C)nc(COc2cc(-c3noc(C(F)(F)F)n3)ccn2)c1] | 2,4-dimethyl-6-[({4-[5-(trifluoro-methyl)-1,2,4-oxa-diazol-3-yl]pyridin-2-yl}oxy)methyl]pyridine | | 351.2 | 24 |
| 212 | 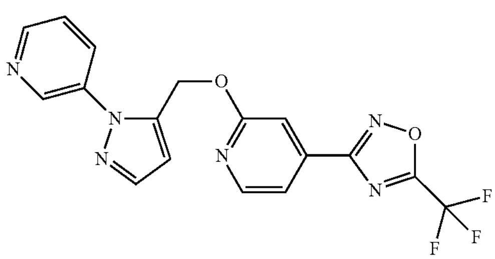 [SMILES: FC(F)(F)c1nc(-c2ccnc(OCc3ccnn3-c3cccnc3)c2)no1] | 2-[(1-pyridin-3-yl-1H-pyrazol-5-yl)methoxy]-4-[5-(trifluoro-methyl)-1,2,4-oxa-diazol-3-yl]pyridine | | 389.3 | 24 |
| 213 | 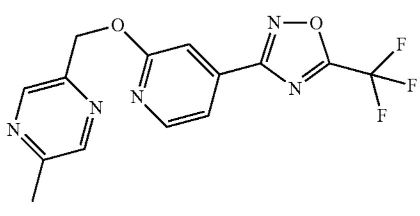 [SMILES: Cc1cnc(COc2cc(-c3noc(C(F)(F)F)n3)ccn2)cn1] | 2-methyl-5-[({4-[5-(trifluoro-methyl)-1,2,4-oxa-diazol-3-yl]pyridin-2-yl}oxy)methyl]pyrazine | | 338.0 | 24 |
| 214 | 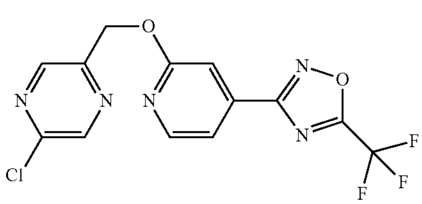 [SMILES: FC(F)(F)c1nc(-c2ccnc(OCc3cnc(Cl)cn3)c2)no1] | 2-chloro-5-[({4-[5-(trifluoro-methyl)-1,2,4-oxa-diazol-3-yl]pyridin-2-yl}oxy)methyl]pyrazine | | 357.9 | 24 |

TABLE 2-continued

| Ex # | Structure | Name | Stereo-chemistry | [M + H]+ | General Procedures |
|---|---|---|---|---|---|
| 215 | 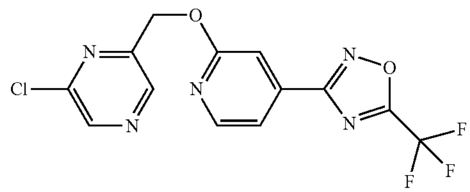 [SMILES: FC(F)(F)c1nc(-c2ccnc(OCc3cncc(Cl)n3)c2)no1] | 2-chloro-6-[({4-[5-(trifluoro-methyl)-1,2,4-oxa-diazol-3-yl]pyridin-2-yl}oxy)methyl]pyrazine | | 357.9 | 24 |
| 216 | 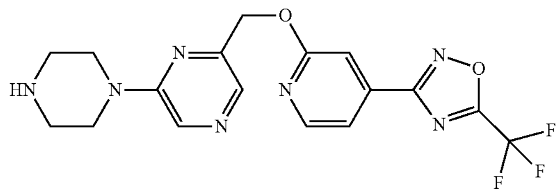 [SMILES: FC(F)(F)c1nc(-c2ccnc(OCc3cncc(N4CCNCC4)n3)c2)no1] | 2-piperazin-1-yl-6-[({4-[5-(trifluoro-methyl)-1,2,4-oxa-diazol-3-yl]pyridin-2-yl}oxy)methyl]pyrazine | | 408.0 | 24 |
| 217 | 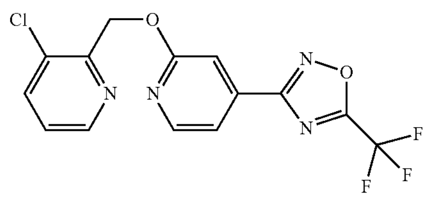 [SMILES: FC(F)(F)c1nc(-c2ccnc(OCc3ncccc3Cl)c2)no1] | 3-chloro-2-[({4-[5-(trifluoro-methyl)-1,2,4-oxa-diazol-3-yl]pyridin-2-yl}oxy)methyl]pyridine | | 356.9 | 24 |
| 218 | 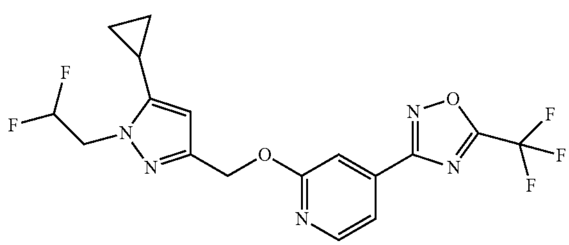 [SMILES: FC(F)Cn1nc(COc2cc(-c3noc(C(F)(F)F)n3)ccn2)cc1C1CC1] | 2-{[5-cyclopropyl-1-(2,2-difluoro-ethyl)-1H-pyrazol-3-yl]methoxy}-4-[5-(trifluoro-methyl)-1,2,4-oxa-diazol-3-yl]pyridine | | 416.3 | 24 |
| 219 | 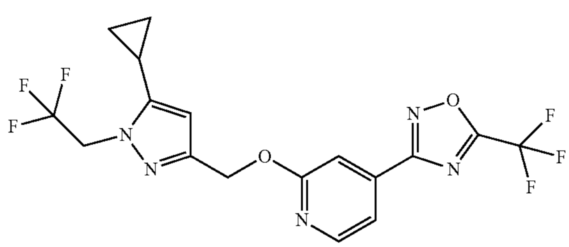 [SMILES: FC(F)(F)Cn1nc(COc2cc(-c3noc(C(F)(F)F)n3)ccn2)cc1C1CC1] | 2-{[5-cyclopropyl-1-(2,2,2-trifluoro-ethyl)-1H-pyrazol-3-yl]methoxy}-4-[5-(trifluoro-methyl)-1,2,4-oxa-diazol-3-yl]pyridine | | 434.3 | 24 |
| 220 | 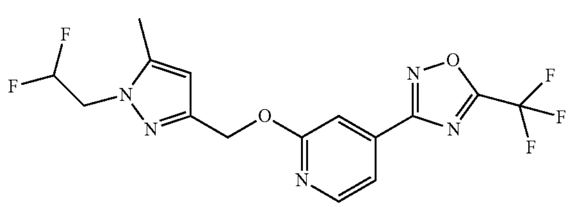 [SMILES: Cc1cc(COc2cc(-c3noc(C(F)(F)F)n3)ccn2)nn1CC(F)F] | 2-{[1-(2,2-difluoro-ethyl)-5-methyl-1H-pyrazol-3-yl]methoxy}-4-[5-(trifluoro-methyl)-1,2,4-oxa-diazol-3-yl]pyridine | | 390.3 | 24 |

TABLE 2-continued

| Ex # | Name | Stereo-chemistry | [M + H]+ | General Procedures |
|---|---|---|---|---|
| 221 | 2-[(1-methyl-1H-pyrazol-5-yl)methoxy]-4-[5-(trifluoromethyl)-1,2,4-oxadiazol-3-yl]pyridine | | 326.2 | 24 |
| 222 | 2-[(1-cyclopropyl-1H-pyrazol-3-yl)methoxy]-4-[5-(trifluoromethyl)-1,2,4-oxadiazol-3-yl]pyridine | | 352.2 | 24 |
| 223 | 2-{[1-(1-methylethyl)-1H-pyrazol-3-yl]methoxy}-4-[5-(trifluoromethyl)-1,2,4-oxadiazol-3-yl]pyridine | | 354.3 | 24 |
| 224 | 2-[(5-tert-butyl-1-methyl-1H-pyrazol-3-yl)methoxy]-4-[5-(trifluoromethyl)-1,2,4-oxadiazol-3-yl]pyridine | | 382.3 | 24 |
| 225 | 2-[(5-methyl-1,2,4-oxadiazol-3-yl)methoxy]-4-[5-(trifluoromethyl)-1,2,4-oxadiazol-3-yl]pyridine | | 328.2 | 24 |
| 226 | 2-chloro-8-({4-[5-(trifluoromethyl)-1,2,4-oxadiazol-3-yl]pyridin-2-yl}oxy)-5,6,7,8-tetrahydroquinoline | RACEMIC | 397.2 | 24 |

TABLE 2-continued

| Ex # | Structure | Name | Stereo-chemistry | [M + H]+ | General Procedures |
|---|---|---|---|---|---|
| 227 | 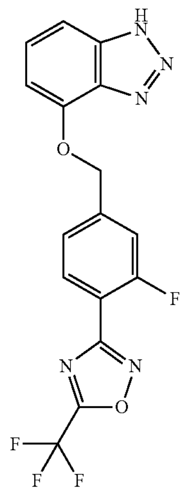 [SMILES: Fc1cc(COc2cccc3[nH]nnc23)ccc1-c1noc(C(F)(F)F)n1] | 4-({3-fluoro-4-[5-(trifluoro-methyl)-1,2,4-oxa-diazol-3-yl]phenyl}methoxy)-1H-benzo-triazole | | 379.8 | 168 |
| 228 | 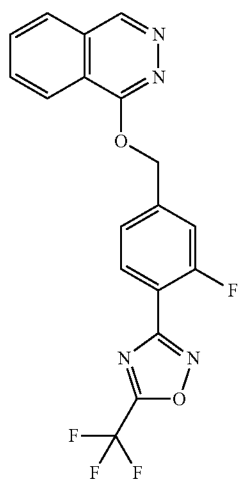 [SMILES: Fc1cc(COc2nncc3ccccc23)ccc1-c1noc(C(F)(F)F)n1] | 1-({3-fluoro-4-[5-(trifluoro-methyl)-1,2,4-oxa-diazol-3-yl]phenyl}methoxy)phthalazine | | 390.8 | 168 |
| 229 | 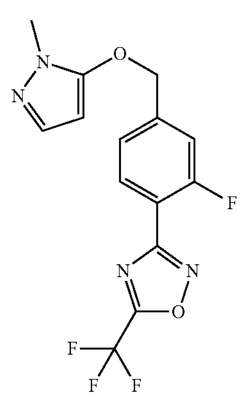 [SMILES: Cn1nccc1OCc1ccc(-c2noc(C(F)(F)F)n2)c(F)c1] | 3-(2-fluoro-4-{[(1-methyl-1H-pyrazol-5-yl)oxy]methyl}phenyl)-5-(trifluoro-methyl)-1,2,4-oxa-diazole | | 342.9 | 168 |

TABLE 2-continued

| Ex # | Structure | Name | Stereo-chemistry | [M + H]+ | General Procedures |
|------|-----------|------|------------------|----------|--------------------|
| 230 | 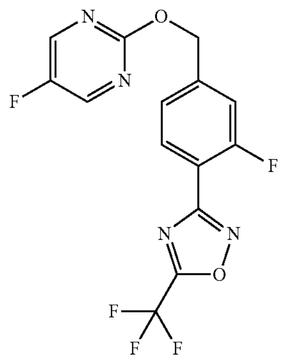 [SMILES: Fc1cnc(OCc2ccc(-c3noc(C(F)(F)F)n3)c(F)c2)nc1] | 5-fluoro-2-({3-fluoro-4-[5-(trifluoro-methyl)-1,2,4-oxa-diazol-3-yl]phenyl}methoxy)pyrimidine | | 358.8 | 168 |
| 231 | 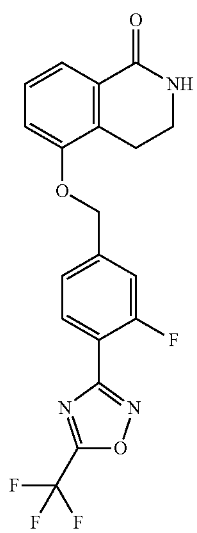 [SMILES: O=C1NCCc2c(OCc3ccc(-c4noc(C(F)(F)F)n4)c(F)c3)cccc21] | 5-({3-fluoro-4-[5-(trifluoro-methyl)-1,2,4-oxa-diazol-3-yl]phenyl}methoxy)-3,4-dihydro-isoquinolin-1(2H)-one | | 407.9 | 168 |
| 232 | 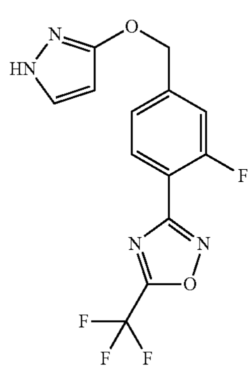 [SMILES: Fc1cc(COc2cc[nH]n2)ccc1-c1noc(C(F)(F)F)n1] | 3-(2-fluoro-4-{[(1H-pyrazol-3-yl)oxy]methyl}phenyl)-5-(trifluoro-methyl)-1,2,4-oxa-diazole | | 328.9 | 168 |

TABLE 2-continued

| Ex # | Structure | Name | Stereo-chemistry | [M + H]+ | General Procedures |
|---|---|---|---|---|---|
| 233 | 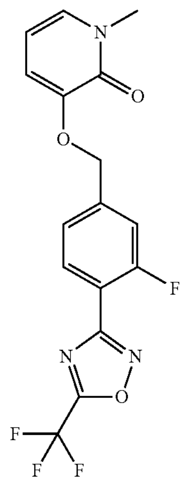 [SMILES: Cn1cccc(OCc2ccc(-c3noc(C(F)(F)F)n3)c(F)c2)c1=O] | 3-({3-fluoro-4-[5-(trifluoro-methyl)-1,2,4-oxa-diazol-3-yl]phenyl}methoxy)-1-methyl-pyridin-2(1H)-one | | 369.8 | 168 |
| 234 | 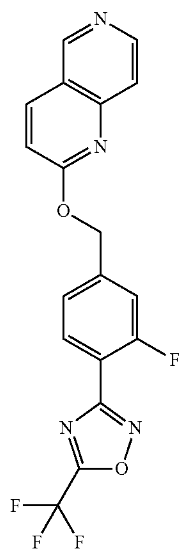 [SMILES: Fc1cc(COc2ccc3cnccc3n2)ccc1-c1noc(C(F)(F)F)n1] | 2-({3-fluoro-4-[5-(trifluoro-methyl)-1,2,4-oxa-diazol-3-yl]phenyl}methoxy)-1,6-naph-thyridine | | 390.9 | 168 |
| 235 | 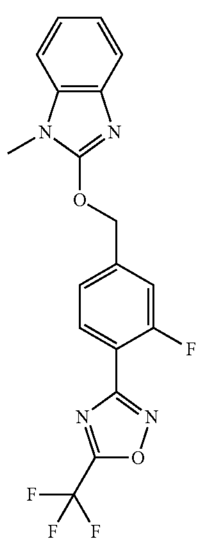 [SMILES: Cn1c(OCc2ccc(-c3noc(C(F)(F)F)n3)c(F)c2)nc2ccccc21] | 2-({3-fluoro-4-[5-(trifluoro-methyl)-1,2,4-oxa-diazol-3-yl]phenyl}methoxy)-1-methyl-1H-benz-imidazole | | 392.9 | 168 |

TABLE 2-continued

| Ex # | Structure | Name | Stereo-chemistry | [M + H]+ | General Procedures |
|---|---|---|---|---|---|
| 236 | 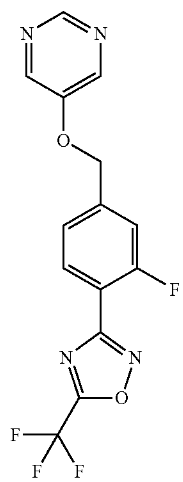 [SMILES: Fc1cc(COc2cncnc2)ccc1-c1noc(C(F)(F)F)n1] | 5-({3-fluoro-4-[5-(trifluoro-methyl)-1,2,4-oxa-diazol-3-yl]phenyl}methoxy)pyrimidine | | 340.8 | 168 |
| 237 | 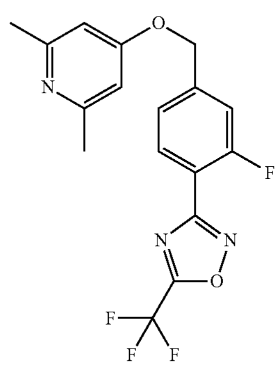 [SMILES: Cc1cc(OCc2ccc(-c3noc(C(F)(F)F)n3)c(F)c2)cc(C)n1] | 4-({3-fluoro-4-[5-(trifluoro-methyl)-1,2,4-oxa-diazol-3-yl]phenyl}methoxy)-2,6-dimethyl-pyridine | | 367.8 | 168 |
| 238 | 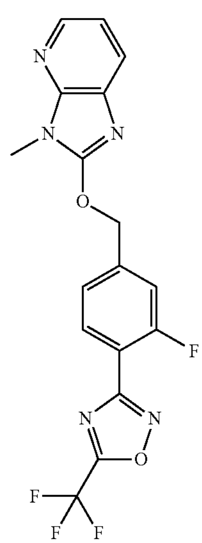 [SMILES: Cn1c(OCc2ccc(-c3noc(C(F)(F)F)n3)c(F)c2)nc2cccnc21] | 2-({3-fluoro-4-[5-(trifluoro-methyl)-1,2,4-oxa-diazol-3-yl]phenyl}methoxy)-3-methyl-3H-imidazo[4,5-b]pyridine | | 393.9 | 168 |

TABLE 2-continued

| Ex # | Structure | Name | Stereo-chemistry | [M + H]+ | General Procedures |
|---|---|---|---|---|---|
| 239 | 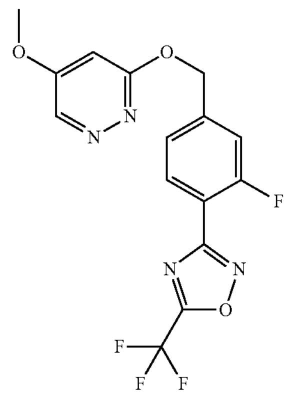 [SMILES: COc1cnnc(OCc2ccc(-c3noc(C(F)(F)F)n3)c(F)c2)c1] | 3-({3-fluoro-4-[5-(trifluoro-methyl)-1,2,4-oxa-diazol-3-yl]phenyl}methoxy)-5-methoxy-pyridazine | | 370.8 | 168 |
| 240 | 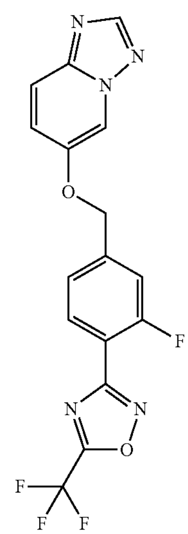 [SMILES: Fc1cc(COc2ccc3ncnn3c2)ccc1-c1noc(C(F)(F)F)n1] | 6-({3-fluoro-4-[5-(trifluoro-methyl)-1,2,4-oxa-diazol-3-yl]phenyl}methoxy)[1,2,4]triazolo[1,5-a]pyridine | | 379.8 | 168 |
| 241 | 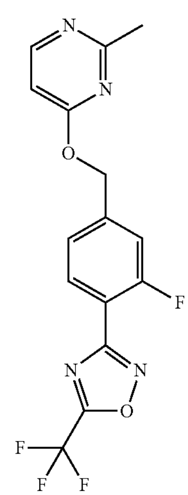 [SMILES: Cc1nccc(OCc2ccc(-c3noc(C(F)(F)F)n3)c(F)c2)n1] | 4-({3-fluoro-4-[5-(trifluoro-methyl)-1,2,4-oxa-diazol-3-yl]phenyl}methoxy)-2-methyl-pyrimidine | | 354.8 | 168 |

TABLE 2-continued
| Ex # | Structure | Name | Stereo-chemistry | [M + H]+ | General Procedures |
|---|---|---|---|---|---|
| 242 | 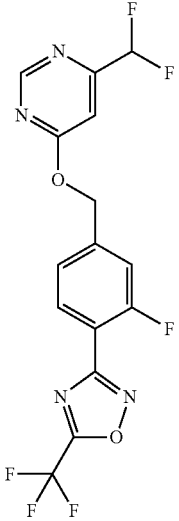 | 4-(difluoro-methyl)-6-({3-fluoro-4-[5-(trifluoro-methyl)-1,2,4-oxa-diazol-3-yl]phenyl}methoxy)pyrimidine | | 390.8 | 168 |
| 243 | 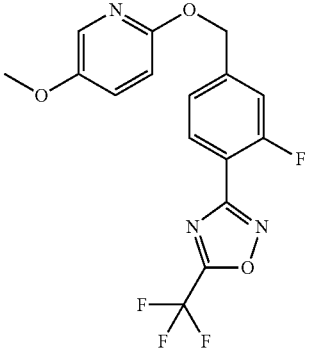 [SMILES: COc1ccc(OCc2ccc(-c3noc(C(F)(F)F)n3)c(F)c2)nc1] | 2-({3-fluoro-4-[5-(trifluoro-methyl)-1,2,4-oxa-diazol-3-yl]phenyl}methoxy)-5-methoxy-pyridine | | 369.8 | 168 |
| 244 | 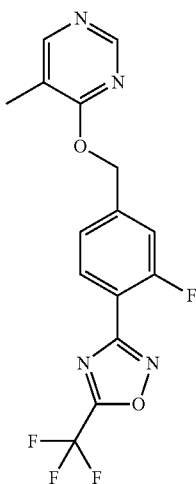 [SMILES: Cc1cncnc1OCc1ccc(-c2noc(C(F)(F)F)n2)c(F)c1] | 4-({3-fluoro-4-[5-(trifluoro-methyl)-1,2,4-oxa-diazol-3-yl]phenyl}methoxy)-5-methyl-pyrimidine | | 354.8 | 168 |

TABLE 2-continued

| Ex # | Structure | Name | Stereo-chemistry | [M + H]+ | General Procedures |
|---|---|---|---|---|---|
| 245 | 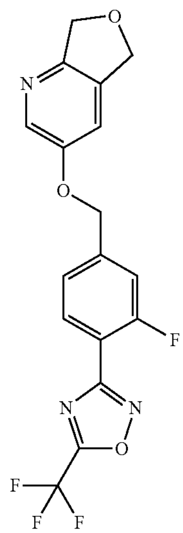 [SMILES: Fc1cc(COc2cnc3c(c2)COC3)ccc1-c1noc(C(F)(F)F)n1] | 3-({3-fluoro-4-[5-(trifluoromethyl)-1,2,4-oxadiazol-3-yl]phenyl}methoxy)-5,7-dihydrofuro[3,4-b]pyridine | | 381.8 | 168 |
| 246 | 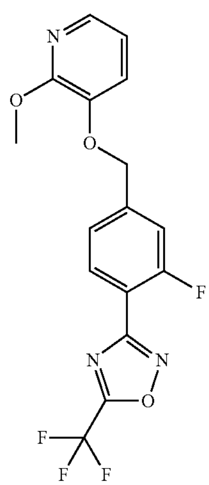 [SMILES: COc1ncccc1OCc1ccc(-c2noc(C(F)(F)F)n2)c(F)c1] | 3-({3-fluoro-4-[5-(trifluoromethyl)-1,2,4-oxadiazol-3-yl]phenyl}methoxy)-2-methoxypyridine | | 369.8 | 168 |
| 247 | 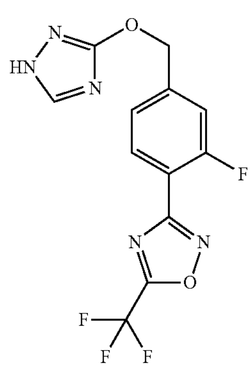 [SMILES: Fc1cc(COc2nc[nH]n2)ccc1-c1noc(C(F)(F)F)n1] | 3-(2-fluoro-4-{[(1H-1,2,4-triazol-3-yl)oxy]methyl}phenyl)-5-(trifluoromethyl)-1,2,4-oxadiazole | | 329.9 | 168 |

TABLE 2-continued

| Ex # | Structure | Name | Stereo-chemistry | [M + H]+ | General Procedures |
|---|---|---|---|---|---|
| 248 | 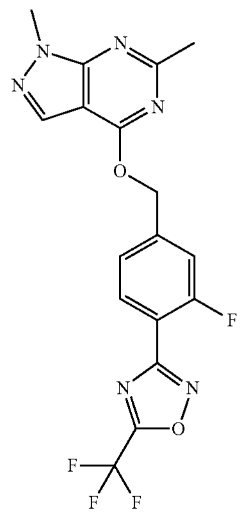 [SMILES: Cc1nc(OCc2ccc(-c3noc(C(F)(F)F)n3)c(F)c2)c2cnn(C)c2n1] | 4-({3-fluoro-4-[5-(trifluoro-methyl)-1,2,4-oxa-diazol-3-yl]phenyl}methoxy)-1,6-dimethyl-1H-pyrazolo[3,4-d]pyrimidine | | 408.9 | 168 |
| 249 | 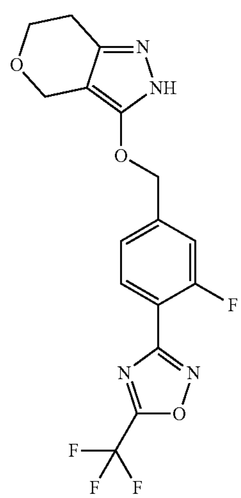 [SMILES: Fc1cc(COc2[nH]nc3c2COCC3)ccc1-c1noc(C(F)(F)F)n1] | 3-({3-fluoro-4-[5-(trifluoro-methyl)-1,2,4-oxa-diazol-3-yl]phenyl}methoxy)-2,4,6,7-tetrahydro-pyrano[4,3-c]pyrazole | | 384.8 | 168 |
| 250 | 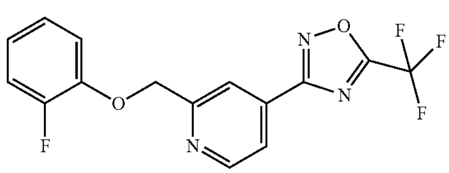 [SMILES: Fc1ccccc1OCc1cc(-c2noc(C(F)(F)F)n2)ccn1] | 2-[(2-fluoro-phenoxy)methyl]-4-[5-(trifluoro-methyl)-1,2,4-oxa-diazol-3-yl]pyridine | | 340.1 | 24 |
| 251 | 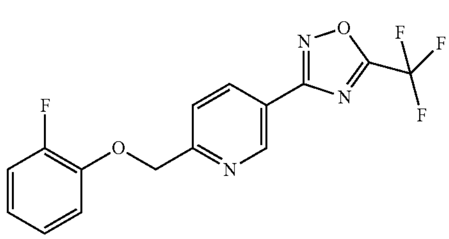 [SMILES: Fc1ccccc1OCc1ccc(-c2noc(C(F)(F)F)n2)cn1] | 2-[(2-fluoro-phenoxy)methyl]-5-[5-(trifluoro-methyl)-1,2,4-oxa-diazol-3-yl]pyridine | | 340.1 | 185 |

TABLE 2-continued

| Ex # | Name | Stereo-chemistry | [M + H]+ | General Procedures |
|---|---|---|---|---|
| 252 | 2-[({3-fluoro-4-[5-(trifluoro-methyl)-1,2,4-oxa-diazol-3-yl]phenyl}methoxy)methyl]pyridin-3-amine | | 368.8 | 185 |
| 253 | N-({3-fluoro-4-[5-(trifluoro-methyl)-1,2,4-oxa-diazol-3-yl]phenyl}methyl)-6-methyl-pyridin-3-amine | | 353.1 | 175 |
| 254 | N-({3-fluoro-4-[5-(trifluoro-methyl)-1,2,4-oxa-diazol-3-yl]phenyl}methyl)isoquinolin-7-amine | | 389.1 | 175 |
| 255 | 5-[({3-chloro-4-[5-(trifluoro-methyl)-1,2,4-oxa-diazol-3-yl]pyridin-2-yl}oxy)methyl]-1-methyl-1H-benz-imidazole | | 409.8 | 186 |
| 256 | 3-chloro-2-[1-(pyridin-3-yl)ethoxy]-4-[5-(trifluoro-methyl)-1,2,4-oxa-diazol-3-yl]pyridine | RACEMIC | 370.8 | 186 |
| 257 | 3-({3-fluoro-4-[5-(trifluoro-methyl)-1,2,4-oxa-diazol-3-yl]phenyl}methoxy)pyridazine | | 340.8 | 168 |

TABLE 2-continued

| Ex # | Structure | Name | Stereo-chemistry | [M + H]+ | General Procedures |
|---|---|---|---|---|---|
| 258 | 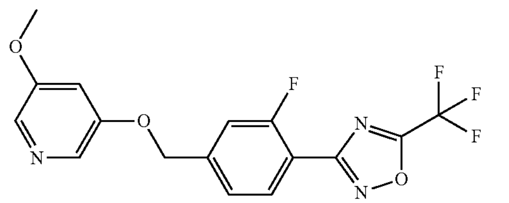 [SMILES: COc1cncc(OCc2ccc(-c3noc(C(F)(F)F)n3)c(F)c2)c1] | 3-({3-fluoro-4-[5-(trifluoromethyl)-1,2,4-oxadiazol-3-yl]phenyl}methoxy)-5-methoxypyridine | | 369.8 | 168 |
| 259 | 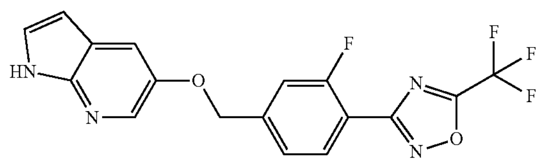 [SMILES: Fc1cc(COc2cnc3[nH]ccc3c2)ccc1-c1noc(C(F)(F)F)n1] | 5-({3-fluoro-4-[5-(trifluoromethyl)-1,2,4-oxadiazol-3-yl]phenyl}methoxy)-1H-pyrrolo[2,3-b]pyridine | | 378.8 | 168 |
| 260 | 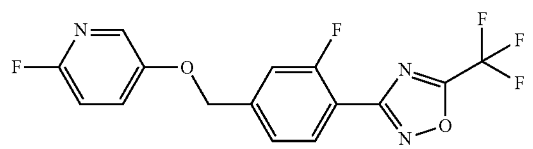 [SMILES: Fc1ccc(OCc2ccc(-c3noc(C(F)(F)F)n3)c(F)c2)cn1] | 2-fluoro-5-({3-fluoro-4-[5-(trifluoromethyl)-1,2,4-oxadiazol-3-yl]phenyl}methoxy)pyridine | | 357.8 | 168 |
| 261 | 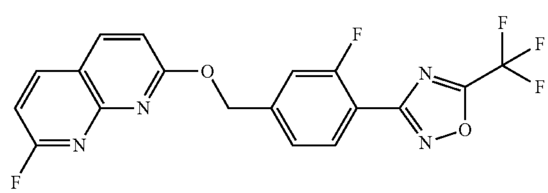 [SMILES: Fc1ccc2ccc(OCc3ccc(-c4noc(C(F)(F)F)n4)c(F)c3)nc2n1] | 2-fluoro-7-({3-fluoro-4-[5-(trifluoromethyl)-1,2,4-oxadiazol-3-yl]phenyl}methoxy)-1,8-naphthyridine | | 408.8 | 168 |
| 262 | 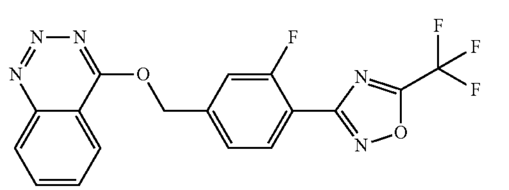 [SMILES: Fc1cc(COc2nnnc3ccccc23)ccc1-c1noc(C(F)(F)F)n1] | 4-({3-fluoro-4-[5-(trifluoromethyl)-1,2,4-oxadiazol-3-yl]phenyl}methoxy)-1,2,3-benzotriazine | | 391.8 | 168 |
| 263 | 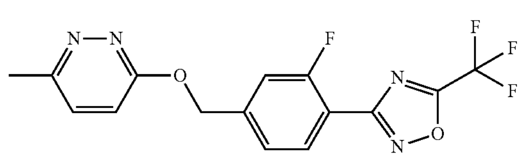 [SMILES: Cc1ccc(OCc2ccc(-c3noc(C(F)(F)F)n3)c(F)c2)nn1] | 3-({3-fluoro-4-[5-(trifluoromethyl)-1,2,4-oxadiazol-3-yl]phenyl}methoxy)-6-methylpyridazine | | 354.8 | 168 |

TABLE 2-continued

| Ex # | Structure | Name | Stereo-chemistry | [M + H]+ | General Procedures |
|---|---|---|---|---|---|
| 264 | 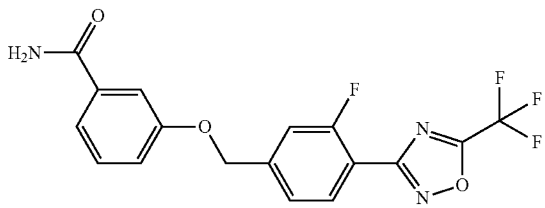 [SMILES: NC(=O)c1cccc(OCc2ccc(-c3noc(C(F)(F)F)n3)c(F)c2)c1] | 3-({3-fluoro-4-[5-(trifluoro-methyl)-1,2,4-oxa-diazol-3-yl]phenyl}methoxy)benzamide | | 381.8 | 168 |
| 265 | 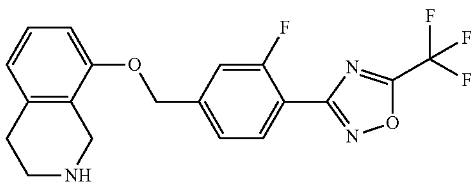 [SMILES: Fc1cc(COc2cccc3c2CNCC3)ccc1-c1noc(C(F)(F)F)n1] | 8-({3-fluoro-4-[5-(trifluoro-methyl)-1,2,4-oxa-diazol-3-yl]phenyl}methoxy)-1,2,3,4-tetrahydro-isoquinoline | | 393.8 | 168 |
| 266 | 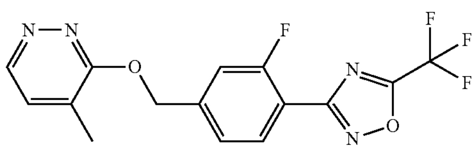 [SMILES: Cc1ccnnc1OCc1ccc(-c2noc(C(F)(F)F)n2)c(F)c1] | 3-({3-fluoro-4-[5-(trifluoro-methyl)-1,2,4-oxa-diazol-3-yl]phenyl}methoxy)-4-methyl-pyridazine | | 354.8 | 168 |
| 267 | 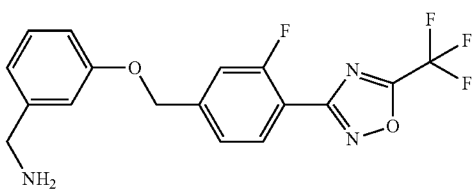 [SMILES: NCc1cccc(OCc2ccc(-c3noc(C(F)(F)F)n3)c(F)c2)c1] | 1-[3-({3-fluoro-4-[5-(trifluoro-methyl)-1,2,4-oxa-diazol-3-yl]phenyl}methoxy)phenyl]methana-mine | | 367.8 | 168 |
| 268 | 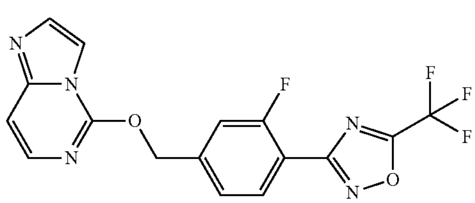 [SMILES: Fc1cc(COc2nccc3nccn23)ccc1-c1noc(C(F)(F)F)n1] | 5-({3-fluoro-4-[5-(trifluoro-methyl)-1,2,4-oxa-diazol-3-yl]phenyl}methoxy)imidazo[1,2-c]pyrimidine | | 379.8 | 168 |
| 269 | 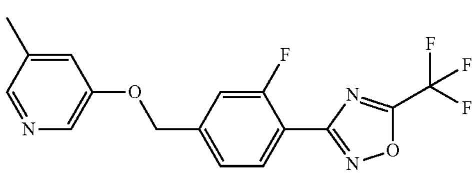 [SMILES: Cc1cncc(OCc2ccc(-c3noc(C(F)(F)F)n3)c(F)c2)c1] | 3-({3-fluoro-4-[5-(trifluoro-methyl)-1,2,4-oxa-diazol-3-yl]phenyl}methoxy)-5-methyl-pyridine | | 353.8 | 168 |

TABLE 2-continued

| Ex # | Structure | Name | Stereo-chemistry | [M + H]+ | General Procedures |
|---|---|---|---|---|---|
| 270 | 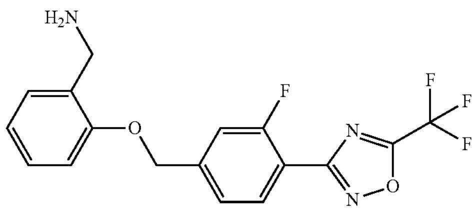 [SMILES: NCc1ccccc1OCc1ccc(-c2noc(C(F)(F)F)n2)c(F)c1] | 1-[2-({3-fluoro-4-[5-(trifluoro-methyl)-1,2,4-oxa-diazol-3-yl]phenyl} methoxy) phenyl] methanamine | | 367.8 | 168 |
| 271 | 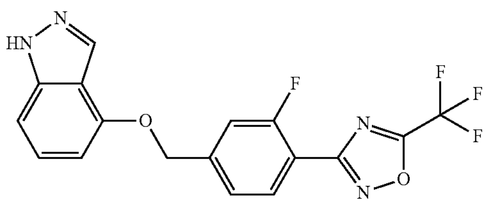 [SMILES: Fc1cc(COc2cccc3[nH]ncc23)ccc1-c1noc(C(F)(F)F)n1] | 4-({3-fluoro-4-[5-(trifluoro-methyl)-1,2,4-oxa-diazol-3-yl]phenyl} methoxy)-1H-indazole | | 378.8 | 168 |
| 272 | 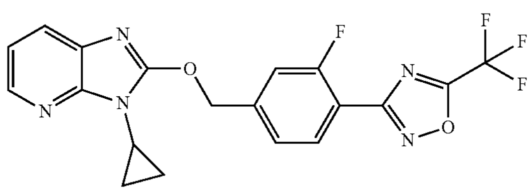 [SMILES: Fc1cc(COc2nc3cccnc3n2C2CC2)ccc1-c1noc(C(F)(F)F)n1] | 3-cyclo-propyl-2-({3-fluoro-4-[5-(trifluoro-methyl)-1,2,4-oxa-diazol-3-yl]phenyl} methoxy)-3H-imidazo[4,5-b]pyridine | | 419.9 | 168 |
| 273 | 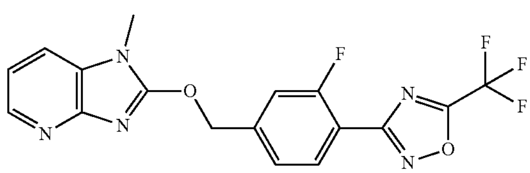 [SMILES: Cn1c(OCc2ccc(-c3noc(C(F)(F)F)n3)c(F)c2)nc2ncccc21] | 2-({3-fluoro-4-[5-(trifluoro-methyl)-1,2,4-oxa-diazol-3-yl]phenyl} methoxy)-1-methyl-1H-imidazo[4,5-b]pyridine | | 393.8 | 168 |
| 274 | 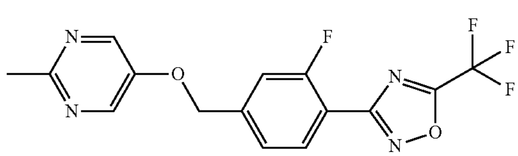 [SMILES: Cc1ncc(OCc2ccc(-c3noc(C(F)(F)F)n3)c(F)c2)cn1] | 5-({3-fluoro-4-[5-(trifluoro-methyl)-1,2,4-oxa-diazol-3-yl]phenyl} methoxy)-2-methyl-pyrimidine | | 354.8 | 168 |
| 275 | 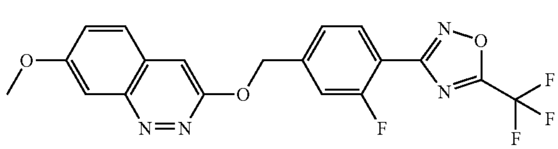 [SMILES: COc1ccc2cc(OCc3ccc(-c4noc(C(F)(F)F)n4)c(F)c3)nnc2c1] | 3-({3-fluoro-4-[5-(trifluoro-methyl)-1,2,4-oxa-diazol-3-yl]phenyl} methoxy)-7-methoxy-cinnoline | | 420.8 | 168 |

TABLE 2-continued

| Ex # | Structure | Name | Stereo-chemistry | [M + H]+ | General Procedures |
|---|---|---|---|---|---|
| 276 | 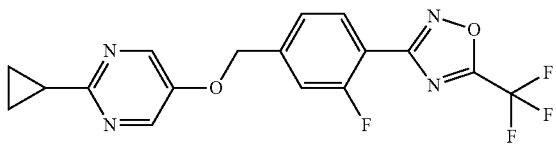 [SMILES: Fc1cc(COc2cnc(C3CC3)nc2)ccc1-c1noc(C(F)(F)F)n1] | 2-cyclopropyl-5-({3-fluoro-4-[5-(trifluoromethyl)-1,2,4-oxadiazol-3-yl]phenyl}methoxy)pyrimidine | | 380.8 | 168 |
| 277 | 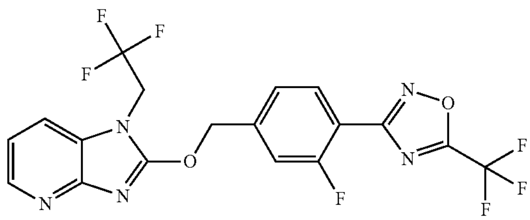 [SMILES: Fc1cc(COc2nc3ncccc3n2CC(F)(F)F)ccc1-c1noc(C(F)(F)F)n1] | 2-({3-fluoro-4-[5-(trifluoromethyl)-1,2,4-oxadiazol-3-yl]phenyl}methoxy)-1-(2,2,2-trifluoroethyl)-1H-imidazo[4,5-b]pyridine | | 461.8 | 168 |
| 278 | 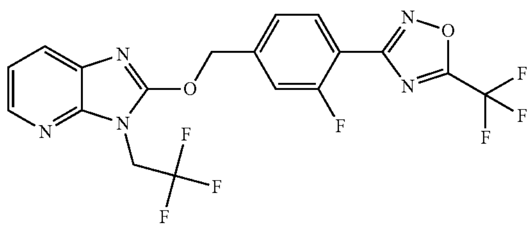 [SMILES: Fc1cc(COc2nc3cccnc3n2CC(F)(F)F)ccc1-c1noc(C(F)(F)F)n1] | 2-({3-fluoro-4-[5-(trifluoromethyl)-1,2,4-oxadiazol-3-yl]phenyl}methoxy)-3-(2,2,2-trifluoroethyl)-3H-imidazo[4,5-b]pyridine | | 461.8 | 168 |
| 279 | 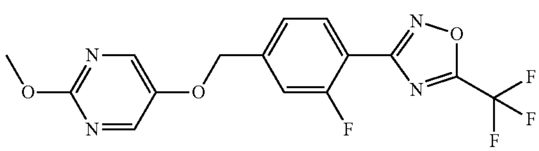 [SMILES: COc1ncc(OCc2ccc(-c3noc(C(F)(F)F)n3)c(F)c2)cn1] | 5-({3-fluoro-4-[5-(trifluoromethyl)-1,2,4-oxadiazol-3-yl]phenyl}methoxy)-2-methoxypyrimidine | | 370.8 | 168 |
| 280 | 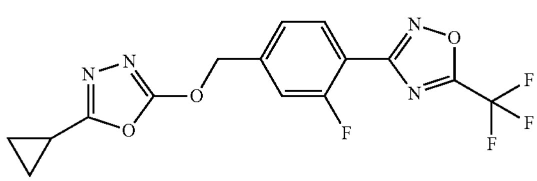 [SMILES: Fc1cc(COc2nnc(C3CC3)o2)ccc1-c1noc(C(F)(F)F)n1] | 3-(4-{[(5-cyclopropyl-1,3,4-oxadiazol-2-yl)oxy]methyl}-2-fluorophenyl)-5-(trifluoromethyl)-1,2,4-oxadiazole | | 370.8 | 168 |
| 281 | 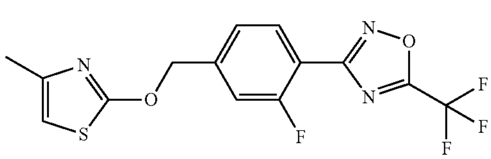 [SMILES: Cc1csc(OCc2ccc(-c3noc(C(F)(F)F)n3)c(F)c2)n1] | 3-(2-fluoro-4-{[(4-methyl-1,3-thiazol-2-yl)oxy]methyl}phenyl)-5-(trifluoromethyl)-1,2,4-oxadiazole | | 359.7 | 168 |

TABLE 2-continued

| Ex # | Structure | Name | Stereo-chemistry | [M + H]+ | General Procedures |
|---|---|---|---|---|---|
| 282 | 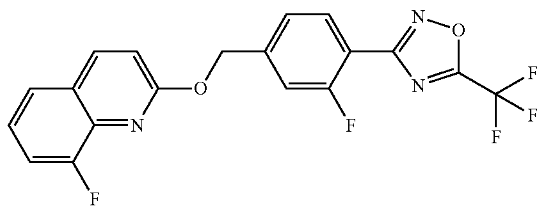 [SMILES: Fc1cc(COc2ccc3cccc(F)c3n2)ccc1-c1noc(C(F)(F)F)n1] | 8-fluoro-2-({3-fluoro-4-[5-(trifluoro-methyl)-1,2,4-oxa-diazol-3-yl]phenyl}methoxy)quinoline | | 407.8 | 168 |
| 283 | 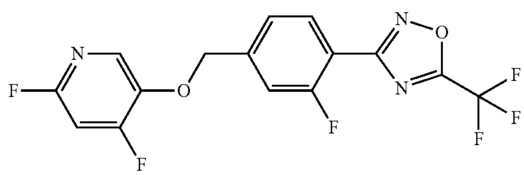 [SMILES: Fc1cc(F)c(OCc2ccc(-c3noc(C(F)(F)F)n3)c(F)c2)cn1] | 2,4-difluoro-5-({3-fluoro-4-[5-(trifluoro-methyl)-1,2,4-oxa-diazol-3-yl]phenyl}methoxy)pyridine | | 375.8 | 168 |
| 284 | 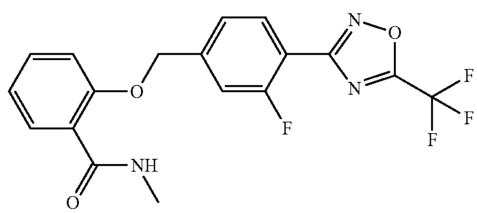 [SMILES: CNC(=O)c1ccccc1OCc1ccc(-c2noc(C(F)(F)F)n2)c(F)c1] | 2-({3-fluoro-4-[5-(trifluoro-methyl)-1,2,4-oxa-diazol-3-yl]phenyl}methoxy)-N-methyl-benzamide | | 395.8 | 168 |
| 285 | 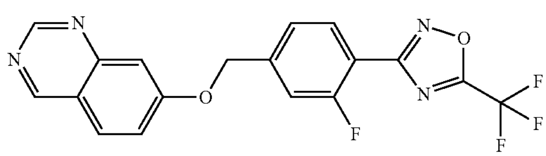 [SMILES: Fc1cc(COc2ccc3cncnc3c2)ccc1-c1noc(C(F)(F)F)n1] | 7-({3-fluoro-4-[5-(trifluoro-methyl)-1,2,4-oxa-diazol-3-yl]phenyl}methoxy)quinazoline | | 390.8 | 168 |
| 286 | 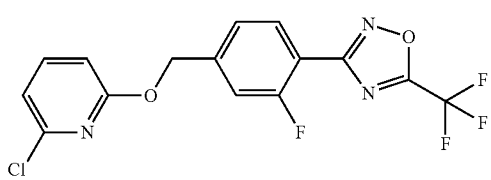 [SMILES: Fc1cc(COc2cccc(Cl)n2)ccc1-c1noc(C(F)(F)F)n1] | 2-chloro-6-({3-fluoro-4-[5-(trifluoro-methyl)-1,2,4-oxa-diazol-3-yl]phenyl}methoxy)pyridine | | 373.7 | 168 |
| 287 | 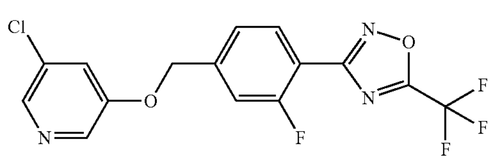 [SMILES: Fc1cc(COc2cncc(Cl)c2)ccc1-c1noc(C(F)(F)F)n1] | 3-chloro-5-({3-fluoro-4-[5-(trifluoro-methyl)-1,2,4-oxa-diazol-3-yl]phenyl}methoxy)pyridine | | 373.7 | 168 |
| 288 | 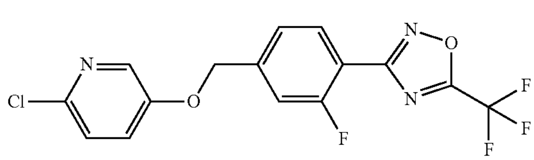 [SMILES: Fc1cc(COc2ccc(Cl)nc2)ccc1-c1noc(C(F)(F)F)n1] | 2-chloro-5-({3-fluoro-4-[5-(trifluoro-methyl)-1,2,4-oxa-diazol-3-yl]phenyl}methoxy)pyridine | | 373.7 | 168 |

TABLE 2-continued

| Ex # | Structure | Name | Stereo-chemistry | [M + H]+ | General Procedures |
|---|---|---|---|---|---|
| 289 | 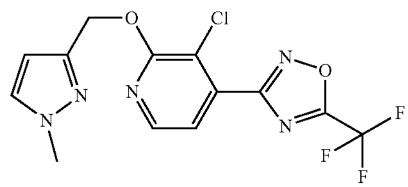 [SMILES: Cn1ccc(COc2nccc(-c3noc(C(F)(F)F)n3)c2Cl)n1] | 3-chloro-2-[(1-methyl-1H-pyrazol-3-yl)methoxy]-4-[5-(trifluoromethyl)-1,2,4-oxadiazol-3-yl]pyridine | | 359.8 | 186 |
| 290 | 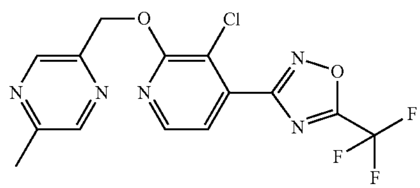 [SMILES: Cc1cnc(COc2nccc(-c3noc(C(F)(F)F)n3)c2Cl)cn1] | 2-[({3-chloro-4-[5-(trifluoromethyl)-1,2,4-oxadiazol-3-yl]pyridin-2-yl}oxy)methyl]-5-methyl-pyrazine | | 371.8 | 186 |
| 291 | 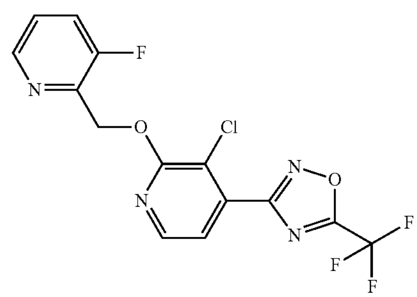 [SMILES: Fc1cccnc1COc1nccc(-c2noc(C(F)(F)F)n2)c1Cl] | 3-chloro-2-[(3-fluoro-pyridin-2-yl)methoxy]-4-[5-(trifluoromethyl)-1,2,4-oxadiazol-3-yl]pyridine | | 374.7 | 186 |
| 292 | 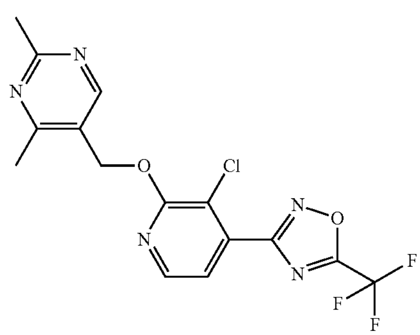 [SMILES: Cc1ncc(COc2nccc(-c3noc(C(F)(F)F)n3)c2Cl)c(C)n1] | 5-[({3-chloro-4-[5-(trifluoromethyl)-1,2,4-oxadiazol-3-yl]pyridin-2-yl}oxy)methyl]-2,4-dimethyl-pyrimidine | | 385.8 | 186 |
| 293 | 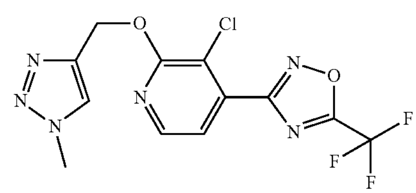 [SMILES: Cn1cc(COc2nccc(-c3noc(C(F)(F)F)n3)c2Cl)nn1] | 3-chloro-2-[(1-methyl-1H-1,2,3-triazol-4-yl)methoxy]-4-[5-(trifluoromethyl)-1,2,4-oxadiazol-3-yl]pyridine | | 360.8 | 186 |

TABLE 2-continued

| Ex # | Structure | Name | Stereo-chemistry | [M + H]+ | General Procedures |
|---|---|---|---|---|---|
| 294 | 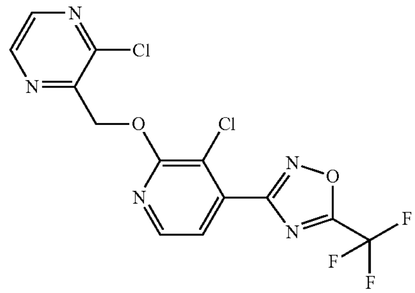 [SMILES: FC(F)(F)c1nc(-c2ccnc(OCc3nccnc3Cl)c2Cl)no1] | 2-chloro-3-[({3-chloro-4-[5-(trifluoro-methyl)-1,2,4-oxa-diazol-3-yl]pyridin-2-yl}oxy)methyl]pyrazine | | 391.8 | 186 |
| 295 | 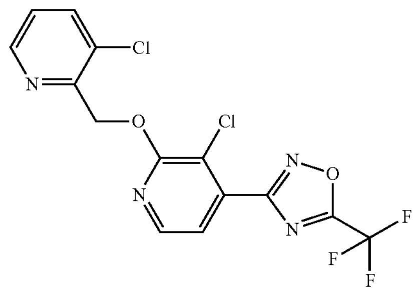 [SMILES: FC(F)(F)c1nc(-c2ccnc(OCc3ncccc3Cl)c2Cl)no1] | 3-chloro-2-[(3-chloro-pyridin-2-yl)methoxy]-4-[5-(trifluoro-methyl)-1,2,4-oxa-diazol-3-yl]pyridine | | 390.8 | 186 |
| 296 | 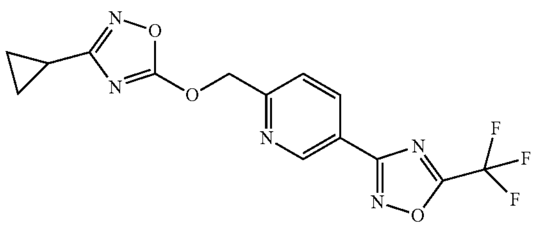 [SMILES: FC(F)(F)c1nc(-c2ccc(COc3nc(C4CC4)no3)nc2)no1] | 2-{[(3-cyclopropyl-1,2,4-oxa-diazol-5-yl)oxy]methyl}-5-[5-(trifluoro-methyl)-1,2,4-oxa-diazol-3-yl]pyridine | | 354.1 | 185 |
| 297 | 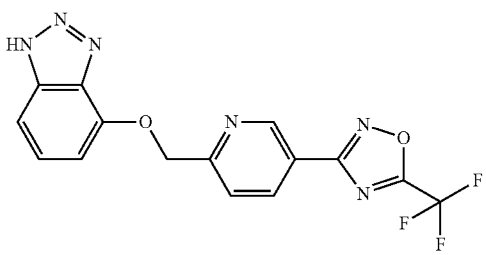 [SMILES: FC(F)(F)c1nc(-c2ccc(COc3cccc4[nH]nnc34)nc2)no1] | 4-({5-[5-(trifluoro-methyl)-1,2,4-oxa-diazol-3-yl]pyridin-2-yl}methoxy)-1H-benzo-triazole | | 362.8 | 185 |
| 298 | 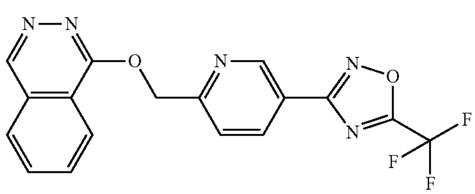 [SMILES: FC(F)(F)c1nc(-c2ccc(COc3nncc4ccccc34)nc2)no1] | 1-({5-[5-(trifluoro-methyl)-1,2,4-oxa-diazol-3-yl]pyridin-2-yl}methoxy)phthalazine | | 373.8 | 185 |
| 299 | 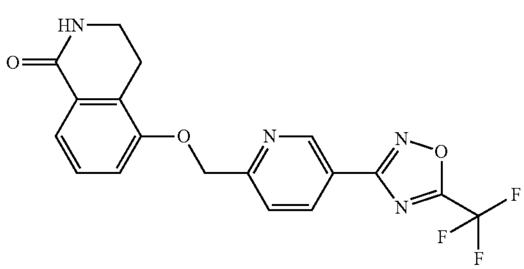 [SMILES: O=C1NCCc2c(OCc3ccc(-c4noc(C(F)(F)F)n4)cn3)cccc21] | 5-({5-[5-(trifluoro-methyl)-1,2,4-oxa-diazol-3-yl]pyridin-2-yl}methoxy)-3,4-dihydro-isoquinolin-1(2H)-one | | 390.8 | 185 |

| Ex # | Structure | Name | Stereo-chemistry | [M + H]+ | General Procedures |
|---|---|---|---|---|---|
| 300 | 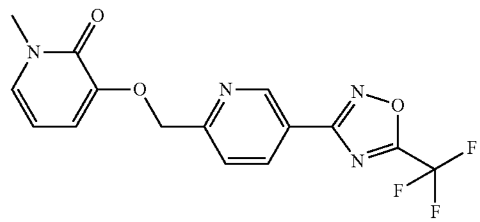 [SMILES: Cn1cccc(OCc2ccc(-c3noc(C(F)(F)F)n3)cn2)c1=O] | 1-methyl-3-({5-[5-(trifluoromethyl)-1,2,4-oxadiazol-3-yl]pyridin-2-yl}methoxy)pyridin-2(1H)-one | | 374.8 | 185 |
| 301 | 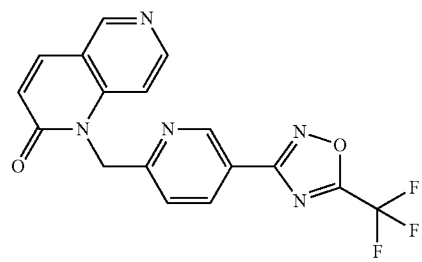 [SMILES: O=c1ccc2cnccc2n1Cc1ccc(-c2noc(C(F)(F)F)n2)cn1] | 1-({5-[5-(trifluoromethyl)-1,2,4-oxadiazol-3-yl]pyridin-2-yl}methyl)-1,6-naphthyridin-2(1H)-one | | 373.8 | 185 |
| 302 | 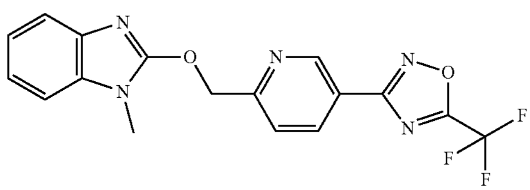 [SMILES: Cn1c(OCc2ccc(-c3noc(C(F)(F)F)n3)cn2)nc2ccccc21] | 1-methyl-2-({5-[5-(trifluoromethyl)-1,2,4-oxadiazol-3-yl]pyridin-2-yl}methoxy)-1H-benzimidazole | | 397.8 | 185 |
| 303 | 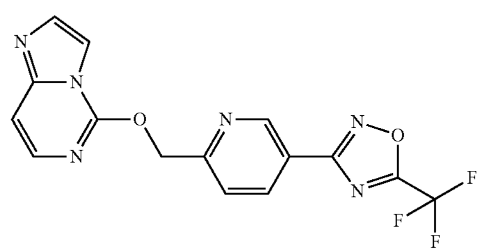 [SMILES: FC(F)(F)c1nc(-c2ccc(COc3nccc4nccn34)nc2)no1] | 5-({5-[5-(trifluoromethyl)-1,2,4-oxadiazol-3-yl]pyridin-2-yl}methoxy)imidazo[1,2-c]pyrimidine | | 362.8 | 185 |
| 304 | 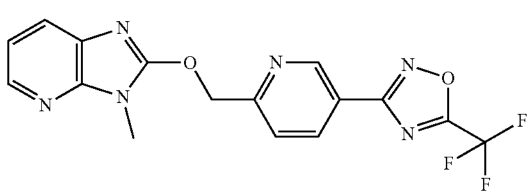 [SMILES: Cn1c(OCc2ccc(-c3noc(C(F)(F)F)n3)cn2)nc2cccnc21] | 3-methyl-2-({5-[5-(trifluoromethyl)-1,2,4-oxadiazol-3-yl]pyridin-2-yl}methoxy)-3H-imidazo[4,5-b]pyridine | | 376.8 | 185 |
| 305 | 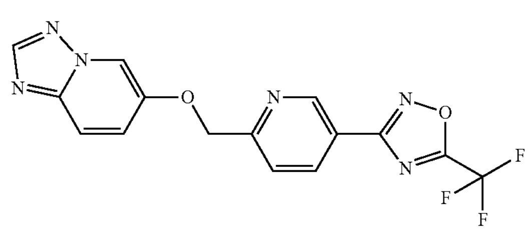 [SMILES: FC(F)(F)c1nc(-c2ccc(COc3ccc4ncnn4c3)nc2)no1] | 6-({5-[5-(trifluoromethyl)-1,2,4-oxadiazol-3-yl]pyridin-2-yl}methoxy)[1,2,4]triazolo[1,5-a]pyridine | | 362.8 | 185 |

TABLE 2-continued

| Ex # | Structure | Name | Stereo-chemistry | [M + H]+ | General Procedures |
|---|---|---|---|---|---|
| 306 | 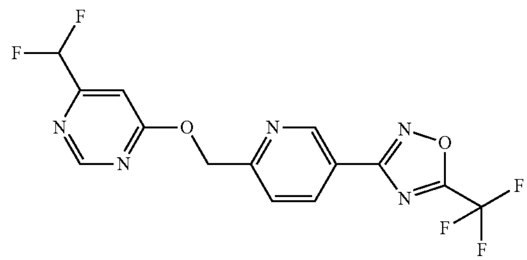 [SMILES: FC(F)c1cc(OCc2ccc(-c3noc(C(F)(F)F)n3)cn2)ncn1] | 4-(difluoro-methyl)-6-({5-[5-(trifluoro-methyl)-1,2,4-oxa-diazol-3-yl]pyridin-2-yl}methoxy)pyrimidine | | 373.8 | 185 |
| 307 | 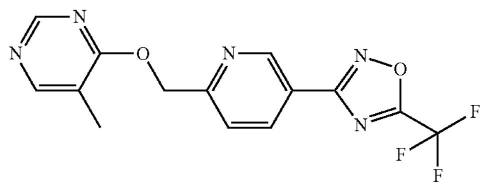 [SMILES: Cc1cncnc1OCc1ccc(-c2noc(C(F)(F)F)n2)cn1] | 5-methyl-4-({5-[5-(trifluoro-methyl)-1,2,4-oxa-diazol-3-yl]pyridin-2-yl}methoxy)pyrimidine | | 337.8 | 185 |
| 308 | 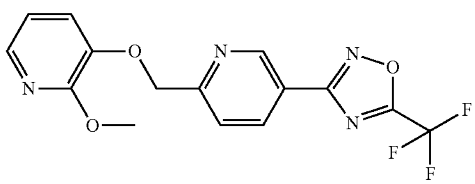 [SMILES: COc1ncccc1OCc1ccc(-c2noc(C(F)(F)F)n2)cn1] | 2-methoxy-3-({5-[5-(trifluoro-methyl)-1,2,4-oxa-diazol-3-yl]pyridin-2-yl}methoxy)pyridine | | 352.8 | 185 |
| 309 | 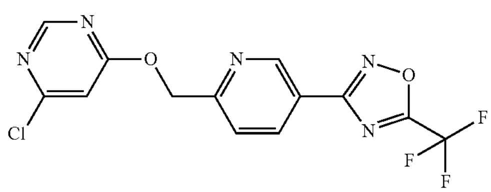 [SMILES: FC(F)(F)c1nc(-c2ccc(COc3cc(Cl)ncn3)nc2)no1] | 4-chloro-6-({5-[5-(trifluoro-methyl)-1,2,4-oxa-diazol-3-yl]pyridin-2-yl}methoxy)pyrimidine | | 357.7 | 185 |
| 310 | 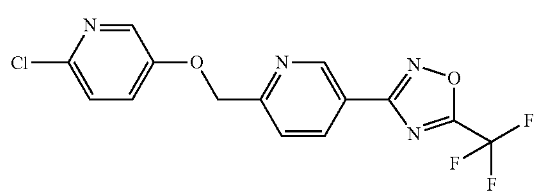 [SMILES: FC(F)(F)c1nc(-c2ccc(COc3ccc(Cl)nc3)nc2)no1] | 2-chloro-5-({5-[5-(trifluoro-methyl)-1,2,4-oxa-diazol-3-yl]pyridin-2-yl}methoxy)pyridine | | 356.7 | 185 |
| 311 | 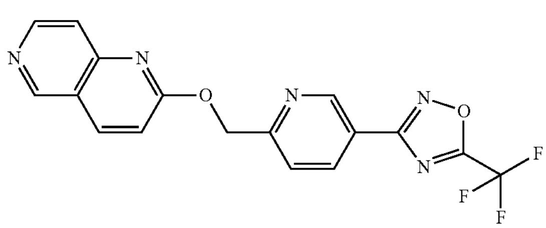 [SMILES: FC(F)(F)c1nc(-c2ccc(COc3ccc4cnccc4n3)nc2)no1] | 2-({5-[5-(trifluoro-methyl)-1,2,4-oxa-diazol-3-yl]pyridin-2-yl}methoxy)-1,6-naph-thyridine | | 373.8 | 185 |

TABLE 2-continued

| Ex # | Structure | Name | Stereo-chemistry | [M + H]+ | General Procedures |
|---|---|---|---|---|---|
| 312 | 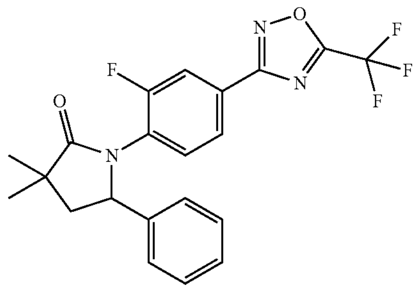 [SMILES: CC1(C)CC(c2ccccc2)N(c2ccc(-c3noc(C(F)(F)F)n3)cc2F)C1=O] | 1-{2-fluoro-4-[5-(trifluoro-methyl)-1,2,4-oxa-diazol-3-yl]phenyl}-3,3-dimethyl-5-phenyl-pyrrolidin-2-one | RACEMIC | 420.1 | 2 |
| 313 | 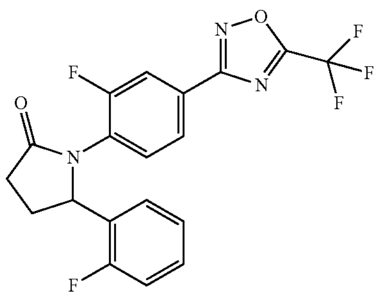 [SMILES: O=C1CCC(c2ccccc2F)N1c1ccc(-c2noc(C(F)(F)F)n2)cc1F] | 5-(2-fluoro-phenyl)-1-{2-fluoro-4-[5-(trifluoro-methyl)-1,2,4-oxa-diazol-3-yl]phenyl}pyrrolidin-2-one | R or S | 410.1 | 2 |
| 314 | 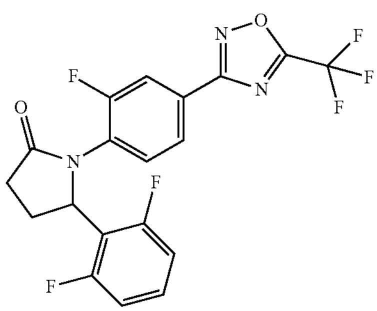 [SMILES: O=C1CCC(c2c(F)cccc2F)N1c1ccc(-c2noc(C(F)(F)F)n2)cc1F] | 5-(2,6-difluoro-phenyl)-1-{2-fluoro-4-[5-(trifluoro-methyl)-1,2,4-oxa-diazol-3-yl]phenyl}pyrrolidin-2-one | RACEMIC | 428.1 | 2 |
| 315 | 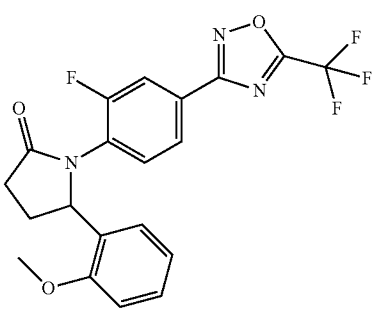 [SMILES: COc1ccccc1C1CCC(=O)N1c1ccc(-c2noc(C(F)(F)F)n2)cc1F] | 1-{2-fluoro-4-[5-(trifluoro-methyl)-1,2,4-oxa-diazol-3-yl]phenyl}-5-(2-methoxy-phenyl)pyrrolidin-2-one | RACEMIC | 422.2 | 2 |
| 316 | 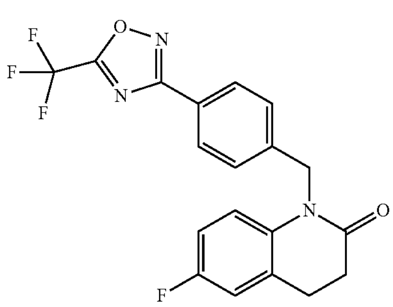 [SMILES: O=C1CCc2cc(F)ccc2N1Cc1ccc(-c2noc(C(F)(F)F)n2)cc1] | 6-fluoro-1-{4-[5-(trifluoro-methyl)-1,2,4-oxa-diazol-3-yl]benzyl}-3,4-dihydro-quinolin-2(1H)-one | | 392.0 | 28 |

TABLE 2-continued

| Ex # | Structure | Name | Stereo-chemistry | [M + H]+ | General Procedures |
|---|---|---|---|---|---|
| 317 | 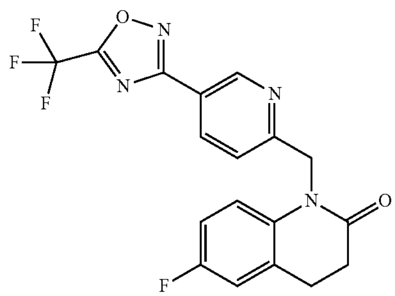 [SMILES: O=C1CCc2cc(F)ccc2N1Cc1ccc(-c2noc(C(F)(F)F)n2)cn1] | 6-fluoro-1-({5-[5-(trifluoro-methyl)-1,2,4-oxa-diazol-3-yl]pyridin-2-yl}methyl)-3,4-dihydro-quinolin-2(1H)-one | | 393.1 | 28 |
| 318 | 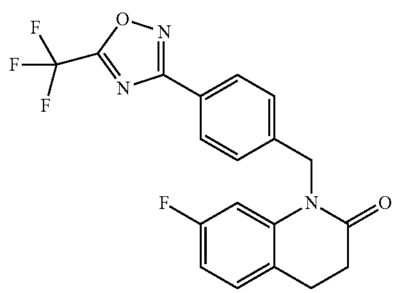 [SMILES: O=C1CCc2ccc(F)cc2N1Cc1ccc(-c2noc(C(F)(F)F)n2)cc1] | 7-fluoro-1-{4-[5-(trifluoro-methyl)-1,2,4-oxa-diazol-3-yl]benzyl}-3,4-dihydro-quinolin-2(1H)-one | | 392.1 | 28 |
| 319 | 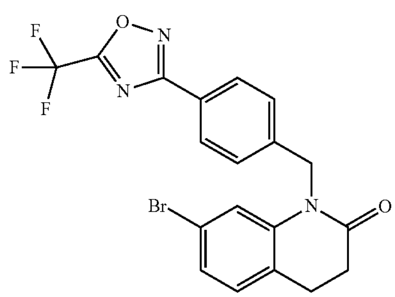 [SMILES: O=C1CCc2ccc(Br)cc2N1Cc1ccc(-c2noc(C(F)(F)F)n2)cc1] | 7-bromo-1-{4-[5-(trifluoro-methyl)-1,2,4-oxa-diazol-3-yl]benzyl}-3,4-dihydro-quinolin-2(1H)-one | | 452.1 | 28 |
| 320 | 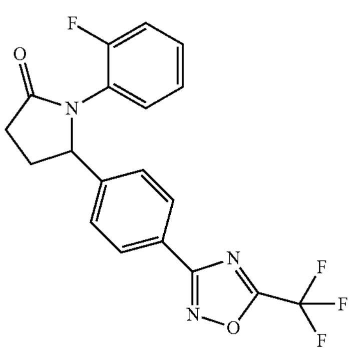 [SMILES: O=C1CCC(c2ccc(-c3noc(C(F)(F)F)n3)cc2)N1c1ccccc1F] | 1-(2-fluoro-phenyl)-5-{4-[5-(trifluoro-methyl)-1,2,4-oxa-diazol-3-yl]phenyl}pyrrolidin-2-one | RACEMIC | 392.2 | 23 |
| 321 | 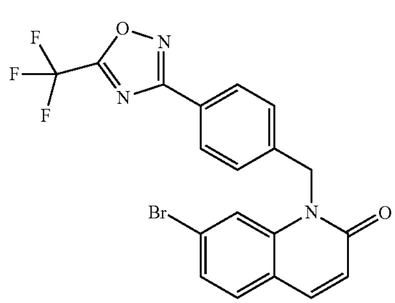 [SMILES: O=c1ccc2ccc(Br)cc2n1Cc1ccc(-c2noc(C(F)(F)F)n2)cc1] | 7-bromo-1-{4-[5-(trifluoro-methyl)-1,2,4-oxa-diazol-3-yl]benzyl}quinolin-2(1H)-one | | 452.1 | 28 |

TABLE 2-continued

| Ex # | Structure | Name | Stereo-chemistry | [M + H]+ | General Procedures |
|---|---|---|---|---|---|
| 322 | 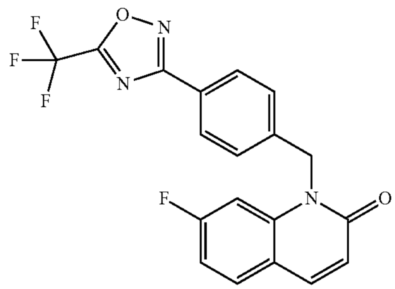 [SMILES: O=c1ccc2ccc(F)cc2n1Cc1ccc(-c2noc(C(F)(F)F)n2)cc1] | 7-fluoro-1-{4-[5-(trifluoro-methyl)-1,2,4-oxa-diazol-3-yl]benzyl}quinolin-2(1H)-one | | 390.2 | 28 |
| 323 | 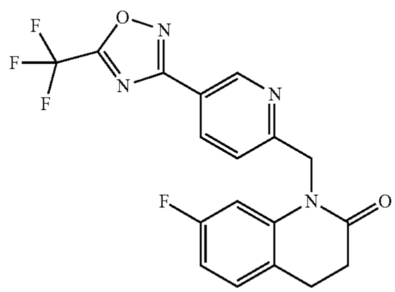 [SMILES: O=C1CCc2ccc(F)cc2N1Cc1ccc(-c2noc(C(F)(F)F)n2)cn1] | 7-fluoro-1-({5-[5-(trifluoro-methyl)-1,2,4-oxa-diazol-3-yl]pyridin-2-yl}methyl)-3,4-dihydro-quinolin-2(1H)-one | | 393.2 | 28 |
| 324 | 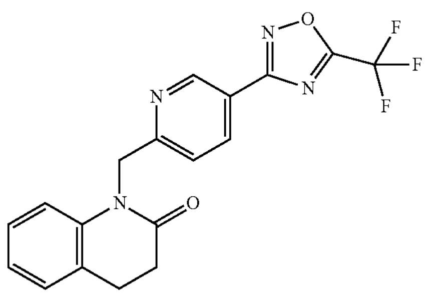 [SMILES: O=C1CCc2ccccc2N1Cc1ccc(-c2noc(C(F)(F)F)n2)cn1] | 1-({5-[5-(trifluoro-methyl)-1,2,4-oxa-diazol-3-yl]pyridin-2-yl}methyl)-3,4-dihydro-quinolin-2(1H)-one | | 375.2 | 28 |
| 325 | 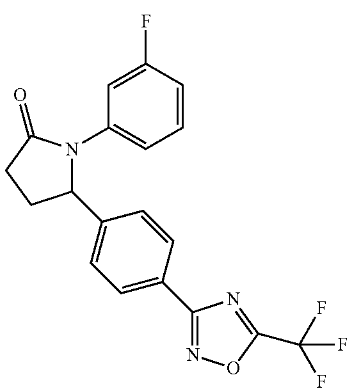 [SMILES: O=C1CCC(c2ccc(-c3noc(C(F)(F)F)n3)cc2)N1c1cccc(F)c1] | 1-(3-fluoro-phenyl)-5-{4-[5-(trifluoro-methyl)-1,2,4-oxa-diazol-3-yl]phenyl}pyrrolidin-2-one | RACEMIC | 392.2 | 23 |
| 326 | 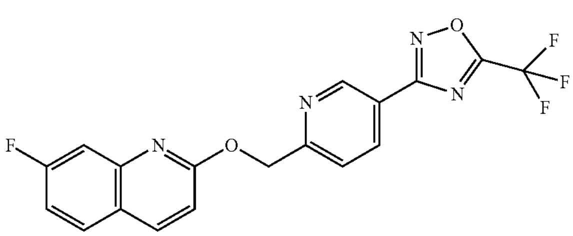 [SMILES: Fc1ccc2ccc(OCc3ccc(-c4noc(C(F)(F)F)n4)cn3)nc2c1] | 7-fluoro-2-({5-[5-(trifluoro-methyl)-1,2,4-oxa-diazol-3-yl]pyridin-2-yl}methoxy)quinoline | | 391.2 | 185 |

TABLE 2-continued

| Ex # | Structure | Name | Stereo-chemistry | [M + H]+ | General Procedures |
|---|---|---|---|---|---|
| 327 | 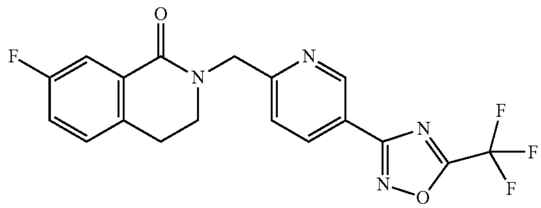 [SMILES: O=C1c2cc(F)ccc2CCN1Cc1ccc(-c2noc(C(F)(F)F)n2)cn1] | 7-fluoro-2-({5-[5-(trifluoro-methyl)-1,2,4-oxa-diazol-3-yl]pyridin-2-yl}methyl)-3,4-dihydro-isoquinolin-1(2H)-one | | 393.2 | 28 |
| 328 | 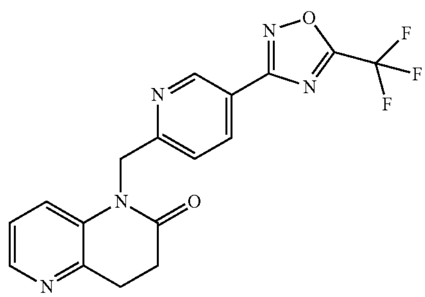 [SMILES: O=C1CCc2ncccc2N1Cc1ccc(-c2noc(C(F)(F)F)n2)cn1] | 1-({5-[5-(trifluoro-methyl)-1,2,4-oxa-diazol-3-yl]pyridin-2-yl}methyl)-3,4-dihydro-1,5-naph-thyridin-2(1H)-one | | 376.2 | 28 |
| 329 | 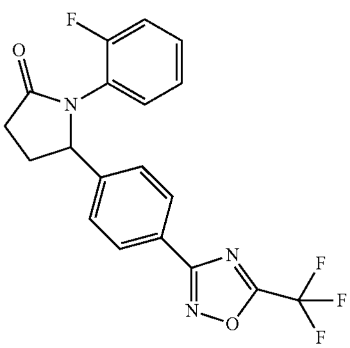 [SMILES: O=C1CCC(c2ccc(-c3noc(C(F)(F)F)n3)cc2)N1c1ccccc1F] | | R or S | 392.2 | 23 |
| 330 | 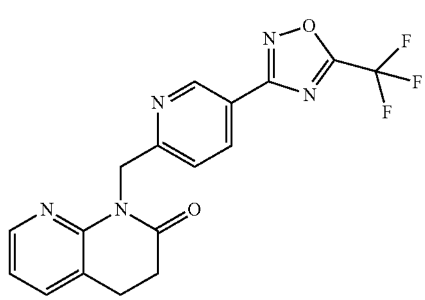 [SMILES: O=C1CCc2cccnc2N1Cc1ccc(-c2noc(C(F)(F)F)n2)cn1] | 1-({5-[5-(trifluoro-methyl)-1,2,4-oxa-diazol-3-yl]pyridin-2-yl}methyl)-3,4-dihydro-1,8-naph-thyridin-2(1H)-one | | 376.2 | 28 |

TABLE 2-continued

| Ex # | Structure | Name | Stereo-chemistry | [M + H]+ | General Procedures |
|---|---|---|---|---|---|
| 331 | 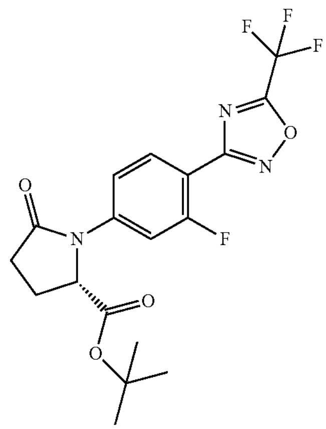 [SMILES: CC(C)(C)OC(=O)[C@@H]1CCC(=O)N1c1ccc(-c2noc(C(F)(F)F)n2)c(F)c1] | tert-butyl 1-{3-fluoro-4-[5-(trifluoro-methyl)-1,2,4-oxa-diazol-3-yl]phenyl}-5-oxo-L-prolinate | S | 416.3 | 8 |
| 332 | 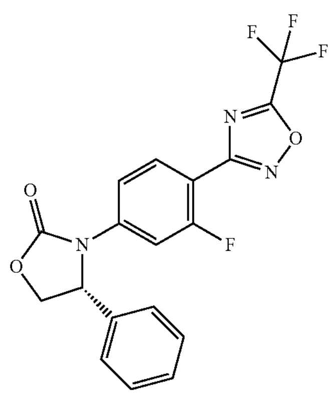 [SMILES: O=C1OC[C@@H](c2ccccc2)N1c1ccc(-c2noc(C(F)(F)F)n2)c(F)c1] | (4R)-3-{3-fluoro-4-[5-(trifluoro-methyl)-1,2,4-oxa-diazol-3-yl]phenyl}-4-phenyl-1,3-oxa-zolidin-2-one | R | 394.2 | 16 |
| 333 | 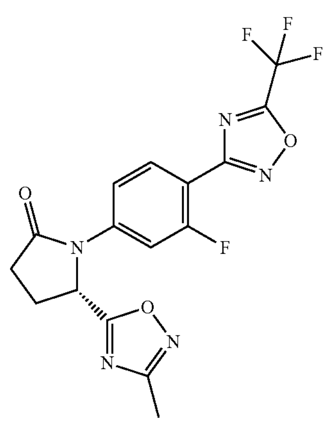 [SMILES: Cc1noc([C@@H]2CCC(=O)N2c2ccc(-c3noc(C(F)(F)F)n3)c(F)c2)n1] | (5S)-1-{3-fluoro-4-[5-(trifluoro-methyl)-1,2,4-oxa-diazol-3-yl]phenyl}-5-(3-methyl-1,2,4-oxadiazol-5-yl)pyrrolidin-2-one | S | 398.3 | 12 |

TABLE 2-continued

| Ex # | Structure | Name | Stereo-chemistry | [M + H]+ | General Procedures |
|---|---|---|---|---|---|
| 334 | 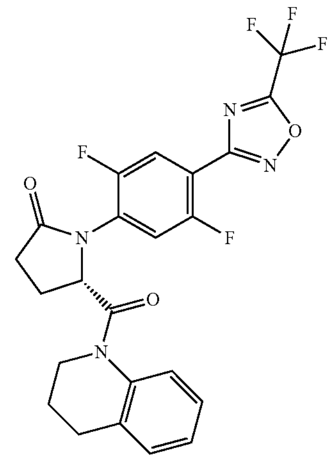 [SMILES: O=C([C@@H]1CCC(=O)N1c1cc(F)c(-c2noc(C(F)(F)F)n2)cc1F)N1CCCc2ccccc21] | (5S)-1-{2,5-difluoro-4-[5-(trifluoro-methyl)-1,2,4-oxa-diazol-3-yl]phenyl}-5-(3,4-dihydro-quinolin-1(2H)-ylcarbonyl)pyrrolidin-2-one | S | 493.3 | 19 |
| 335 | 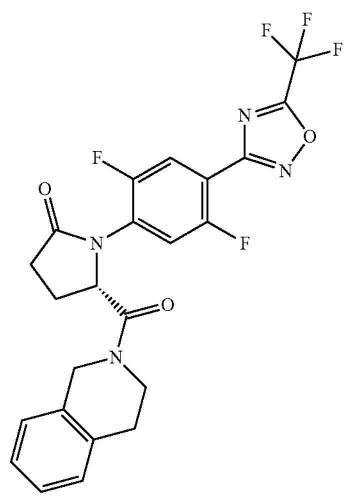 [SMILES: O=C([C@@H]1CCC(=O)N1c1cc(F)c(-c2noc(C(F)(F)F)n2)cc1F)N1CCc2ccccc2C1] | (5S)-1-{2,5-difluoro-4-[5-(trifluoro-methyl)-1,2,4-oxa-diazol-3-yl]phenyl}-5-(3,4-dihydro-isoquinolin-2(1H)-ylcarbonyl)pyrrolidin-2-one | S | 493.3 | 19 |
| 336 | 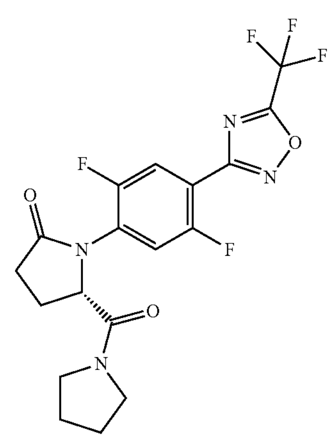 [SMILES: O=C([C@@H]1CCC(=O)N1c1cc(F)c(-c2noc(C(F)(F)F)n2)cc1F)N1CCCC1] | (5S)-1-{2,5-difluoro-4-[5-(trifluoro-methyl)-1,2,4-oxa-diazol-3-yl]phenyl}-5-(pyrrolidin-1-ylcarbonyl)pyrrolidin-2-one | S | 431.3 | 19 |

TABLE 2-continued

| Ex # | Structure | Name | Stereo-chemistry | [M + H]+ | General Procedures |
|---|---|---|---|---|---|
| 337 | 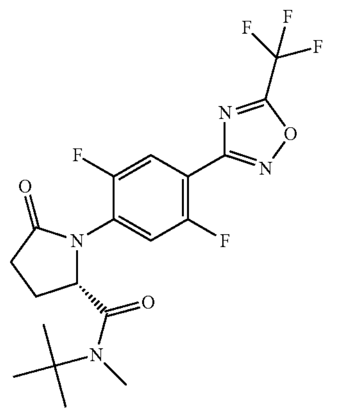 [SMILES: CN(C(=O)[C@@H]1CCC(=O)N1c1cc(F)c(-c2noc(C(F)(F)F)n2)cc1F)C(C)(C)C] | N-tert-butyl-1-{2,5-difluoro-4-[5-(trifluoro-methyl)-1,2,4-oxa-diazol-3-yl]phenyl}-N-methyl-5-oxo-L-prolinamide | S | 447.3 | 19 |
| 338 | 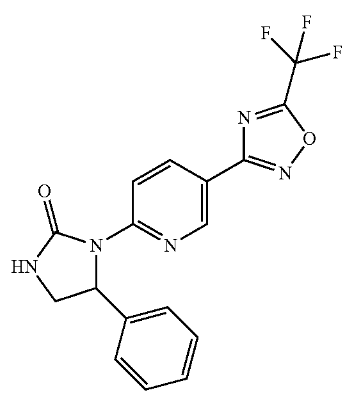 [SMILES: O=C1NCC(c2ccccc2)N1c1ccc(-c2noc(C(F)(F)F)n2)cn1] | 5-phenyl-1-{5-[5-(trifluoro-methyl)-1,2,4-oxa-diazol-3-yl]pyridin-2-yl}imidazo-lidin-2-one | RACEMIC | 376.3 | 5 |
| 339 | 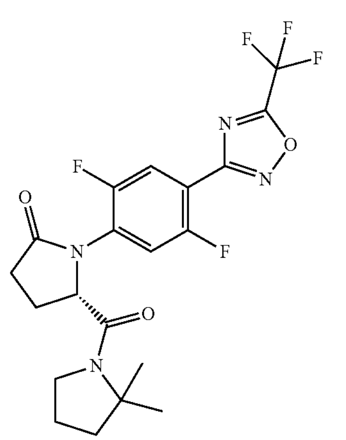 [SMILES: CC1(C)CCCN1C(=O)[C@@H]1CCC(=O)N1c1cc(F)c(-c2noc(C(F)(F)F)n2)cc1F] | (5S)-1-{2,5-difluoro-4-[5-(trifluoro-methyl)-1,2,4-oxa-diazol-3-yl]phenyl}-5-[(2,2-dimethyl-pyrrolidin-1-yl)carbonyl]pyrrolidin-2-one | S | 459.3 | 19 |

| Ex # | Structure | Name | Stereo-chemistry | [M + H]⁺ | General Procedures |
|---|---|---|---|---|---|
| 340 | 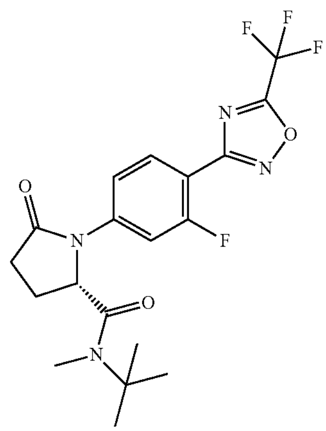 [SMILES: CN(C(=O)[C@@H]1CCC(=O)N1c1ccc(-c2noc(C(F)(F)F)n2)c(F)c1)C(C)(C)C] | N-tert-butyl-1-{3-fluoro-4-[5-(trifluoro-methyl)-1,2,4-oxa-diazol-3-yl]phenyl}-N-methyl-5-oxo-L-prolinamide | S | 429.3 | 19 |
| 341 | 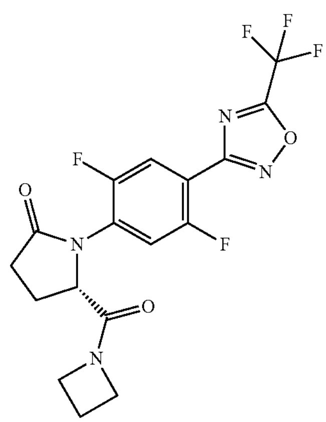 [SMILES: O=C([C@@H]1CCC(=O)N1c1cc(F)c(-c2noc(C(F)(F)F)n2)cc1F)N1CCC1] | (5S)-5-(azetidin-1-yl-carbonyl)-1-{2,5-difluoro-4-[5-(trifluoro-methyl)-1,2,4-oxa-diazol-3-yl]phenyl}pyrrolidin-2-one | S | 417.2 | 19 |
| 342 | 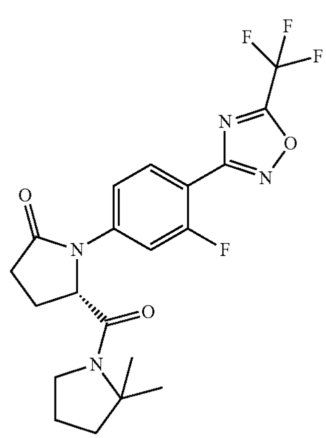 [SMILES: CC1(C)CCCN1C(=O)[C@@H]1CCC(=O)N1c1ccc(-c2noc(C(F)(F)F)n2)c(F)c1] | (5S)-5-[(2,2-dimethyl-pyrrolidin-1-yl)carbonyl]-1-{3-fluoro-4-[5-(trifluoro-methyl)-1,2,4-oxa-diazol-3-yl]phenyl}pyrrolidin-2-one | S | 441.3 | 19 |

TABLE 2-continued

| Ex # | Structure | Name | Stereo-chemistry | [M + H]+ | General Procedures |
|---|---|---|---|---|---|
| 343 | 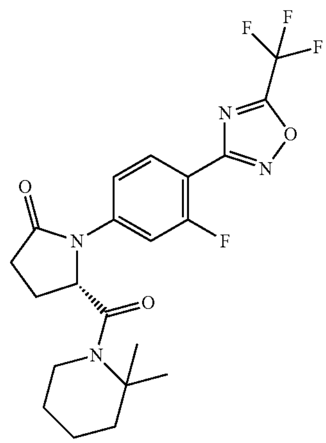 [SMILES: CC1(C)CCCCN1C(=O)[C@@H]1CCC(=O)N1c1ccc(-c2noc(C(F)(F)F)n2)c(F)c1] | (5S)-5-[(2,2-dimethyl-piperidin-1-yl)carbonyl]-1-{3-fluoro-4-[5-(trifluoro-methyl)-1,2,4-oxa-diazol-3-yl]phenyl}pyrrolidin-2-one | S | 455.3 | 19 |
| 344 | 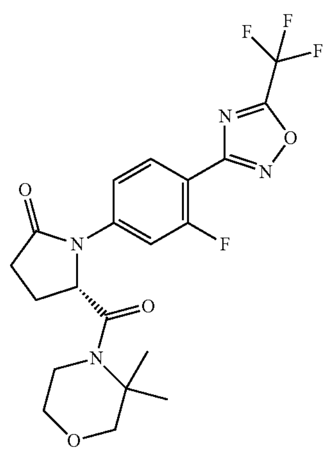 [SMILES: CC1(C)COCCN1C(=O)[C@@H]1CCC(=O)N1c1ccc(-c2noc(C(F)(F)F)n2)c(F)c1] | (5S)-5-[(3,3-dimethyl-morpholin-4-yl)carbonyl]-1-{3-fluoro-4-[5-(trifluoro-methyl)-1,2,4-oxa-diazol-3-yl]phenyl}pyrrolidin-2-one | S | 457.3 | 19 |
| 345 | 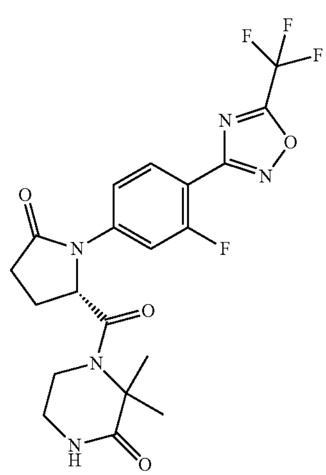 [SMILES: CC1(C)C(=O)NCCN1C(=O)[C@@H]1CCC(=O)N1c1ccc(-c2noc(C(F)(F)F)n2)c(F)c1] | 4-(1-{3-fluoro-4-[5-(trifluoro-methyl)-1,2,4-oxa-diazol-3-yl]phenyl}-5-oxo-L-prolyl)-3,3-dimethyl-piperazin-2-one | S | 470.3 | 19 |

TABLE 2-continued

| Ex # | Structure | Name | Stereo-chemistry | [M + H]+ | General Procedures |
|---|---|---|---|---|---|
| 346 | 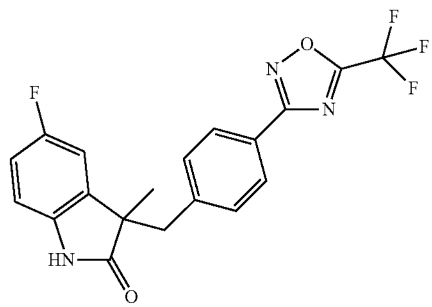 [SMILES: CC1(Cc2ccc(-c3noc(C(F)(F)F)n3)cc2)C(=O)Nc2ccc(F)cc21] | 5-fluoro-3-methyl-3-{4-[5-(trifluoro-methyl)-1,2,4-oxa-diazol-3-yl]benzyl}-1,3-dihydro-2H-indol-2-one | RACEMIC | 392.3 | 28 |
| 347 | 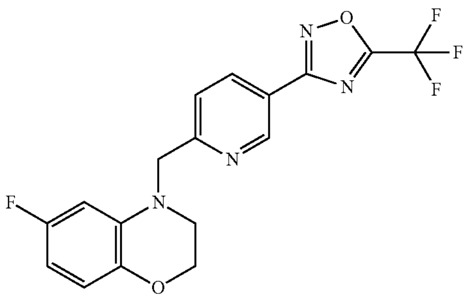 [SMILES: Fc1ccc2c(c1)N(Cc1ccc(-c3noc(C(F)(F)F)n3)cn1)CCO2] | 6-fluoro-4-({5-[5-(trifluoro-methyl)-1,2,4-oxa-diazol-3-yl]pyridin-2-yl}methyl)-3,4-dihydro-2H-1,4-benzoxazine | | 381.2 | 28 |
| 348 | 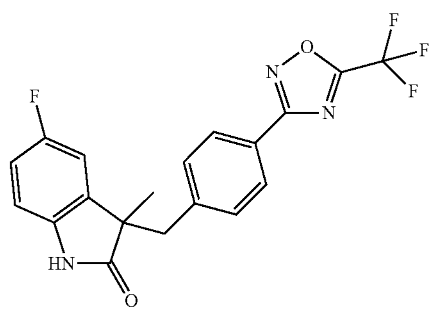 [SMILES: CC1(Cc2ccc(-c3noc(C(F)(F)F)n3)cc2)C(=O)Nc2ccc(F)cc21] | 5-fluoro-3-methyl-3-{4-[5-(trifluoro-methyl)-1,2,4-oxa-diazol-3-yl]benzyl}-1,3-dihydro-2H-indol-2-one | R OR S | 392.2 | 28 |
| 349 | 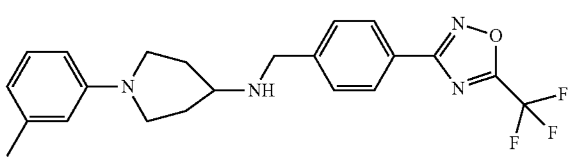 [SMILES: Cc1cccc(N2CCC(NCc3ccc(-c4noc(C(F)(F)F)n4)cc3)CC2)c1] | 1-(3-methyl-phenyl)-N-({4-[5-(trifluoro-methyl)-1,2,4-oxa-diazol-3-yl]phenyl}methyl) piperidin-4-amine | | 417.0 | 175 |
| 350 | 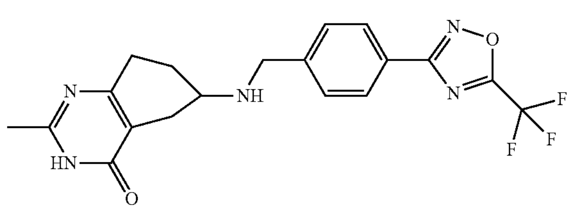 [SMILES: Cc1nc2c(c(=O)[nH]1)CC(NCc1ccc(-c3noc(C(F)(F)F)n3)cc1)CC2] | 2-methyl-6-[({4-[5-(trifluoro-methyl)-1,2,4-oxa-diazol-3-yl]phenyl}methyl) amino]-5,6,7,8-tetrahydro-quinazolin-4(3H)-one | RACEMIC | 406.0 | 175 |

TABLE 2-continued

| Ex # | Structure | Name | Stereo-chemistry | [M + H]+ | General Procedures |
|---|---|---|---|---|---|
| 351 | 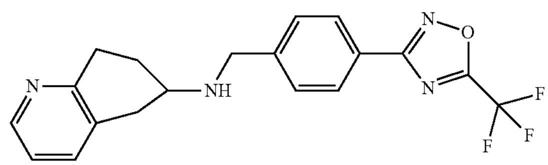 [SMILES: FC(F)(F)c1nc(-c2ccc(CNC3CCc4ncccc4C3)cc2)no1] | N-({4-[5-(trifluoro-methyl)-1,2,4-oxa-diazol-3-yl]phenyl}methyl)-5,6,7,8-tetrahydro-quinolin-6-amine | RACEMIC | 374.9 | 175 |
| 352 | 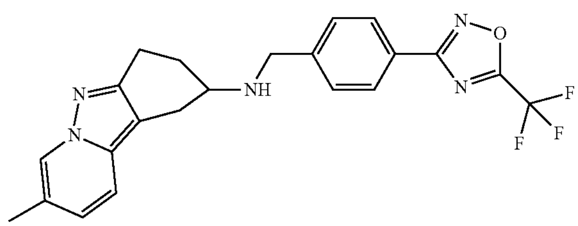 [SMILES: Cc1ccc2c3c(nn2c1)CCC(NCc1ccc(-c2noc(C(F)(F)F)n2)cc1)C3] | 8-methyl-N-({4-[5-(trifluoro-methyl)-1,2,4-oxa-diazol-3-yl]phenyl}methyl)-1,2,3,4-tetrahydro-pyrido[1,2-b]indazol-2-amine | RACEMIC | 428.0 | 175 |
| 353 | 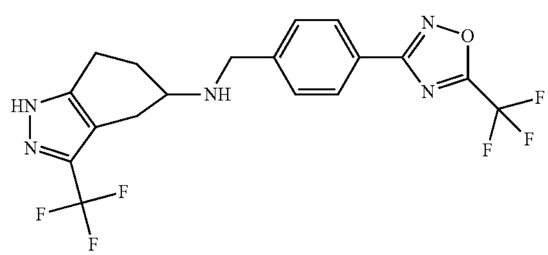 [SMILES: FC(F)(F)c1nc(-c2ccc(CNC3CCc4[nH]nc(C(F)(F)F)c4C3)cc2)no1] | 3-(trifluoro-methyl)-N-({4-[5-(trifluoro-methyl)-1,2,4-oxa-diazol-3-yl]phenyl}methyl)-4,5,6,7-tetrahydro-1H-indazol-5-amine | RACEMIC | 431.9 | 175 |
| 354 | 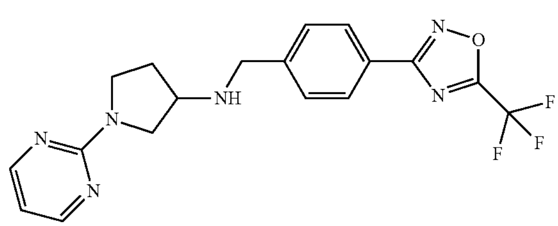 [SMILES: FC(F)(F)c1nc(-c2ccc(CNC3CCN(c4ncccn4)C3)cc2)no1] | 1-(pyrimidin-2-yl)-N-({4-[5-(trifluoro-methyl)-1,2,4-oxa-diazol-3-yl]phenyl}methyl)pyrrolidin-3-amine | RACEMIC | 390.9 | 175 |
| 355 | 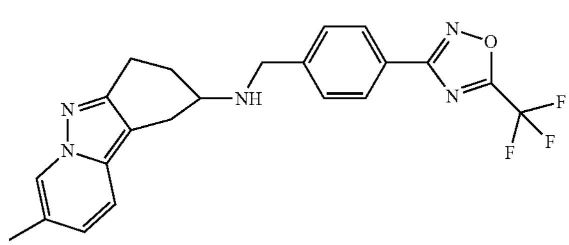 [SMILES: Cc1ccc2c3c(nn2c1)CCC(NCc1ccc(-c2noc(C(F)(F)F)n2)cc1)C3] | 8-methyl-N-({4-[5-(trifluoro-methyl)-1,2,4-oxa-diazol-3-yl]phenyl}methyl)-1,2,3,4-tetrahydro-pyrido[1,2-b]indazol-2-amine | RACEMIC | 428.0 | 175 |

TABLE 2-continued

| Ex # | Structure | Name | Stereo-chemistry | [M + H]+ | General Procedures |
|---|---|---|---|---|---|
| 356 | 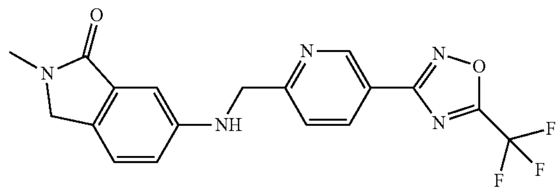 [SMILES: CN1Cc2ccc(NCc3ccc(-c4noc(C(F)(F)F)n4)cn3)cc2C1=O] | 2-methyl-6-[({5-[5-(trifluoromethyl)-1,2,4-oxadiazol-3-yl]pyridin-2-yl}methyl)amino]-2,3-dihydro-1H-isoindol-1-one | | 389.9 | 174 |
| 357 | 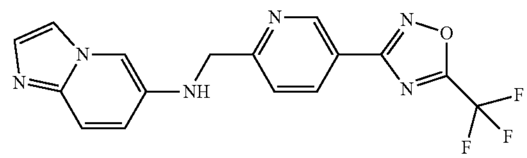 [SMILES: FC(F)(F)c1nc(-c2ccc(CNc3ccc4nccn4c3)nc2)no1] | N-({5-[5-(trifluoromethyl)-1,2,4-oxadiazol-3-yl]pyridin-2-yl}methyl)imidazo[1,2-a]pyridin-6-amine | | 360.9 | 174 |
| 358 | 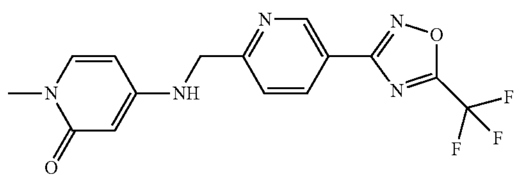 [SMILES: Cn1ccc(NCc2ccc(-c3noc(C(F)(F)F)n3)cn2)cc1=O] | 1-methyl-4-[({5-[5-(trifluoromethyl)-1,2,4-oxadiazol-3-yl]pyridin-2-yl}methyl)amino]pyridin-2(1H)-one | | 351.9 | 174 |
| 359 | 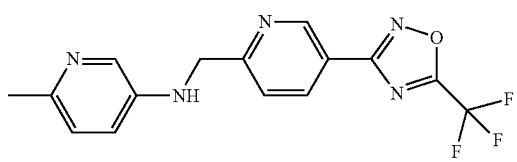 [SMILES: Cc1ccc(NCc2ccc(-c3noc(C(F)(F)F)n3)cn2)cn1] | 6-methyl-N-({5-[5-(trifluoromethyl)-1,2,4-oxadiazol-3-yl]pyridin-2-yl}methyl)pyridin-3-amine | | 335.9 | 174 |
| 360 | 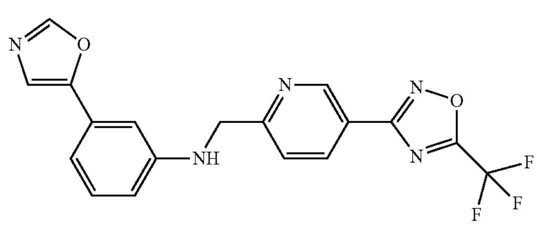 [SMILES: FC(F)(F)c1nc(-c2ccc(CNc3cccc(-c4cnco4)c3)nc2)no1] | 3-(1,3-oxazol-5-yl)-N-({5-[5-(trifluoromethyl)-1,2,4-oxadiazol-3-yl]pyridin-2-yl}methyl)aniline | | 387.9 | 174 |

TABLE 2-continued

| Ex # | Structure | Name | Stereo-chemistry | [M + H]+ | General Procedures |
|---|---|---|---|---|---|
| 361 | 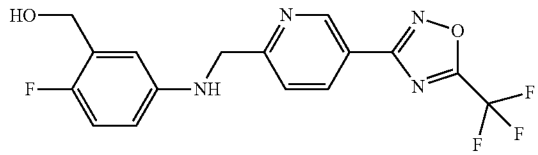 [SMILES: OCc1cc(NCc2ccc(-c3noc(C(F)(F)F)n3)cn2)ccc1F] | {2-fluoro-5-[({5-[5-(trifluoro-methyl)-1,2,4-oxa-diazol-3-yl]pyridin-2-yl}methyl)amino]phenyl}methanol | | 368.9 | 174 |
| 362 | 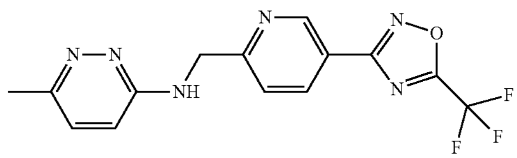 [SMILES: Cc1ccc(NCc2ccc(-c3noc(C(F)(F)F)n3)cn2)nn1] | 6-methyl-N-({5-[5-(trifluoro-methyl)-1,2,4-oxa-diazol-3-yl]pyridin-2-yl}methyl)pyridazin-3-amine | | 337.1 | 174 |
| 363 | 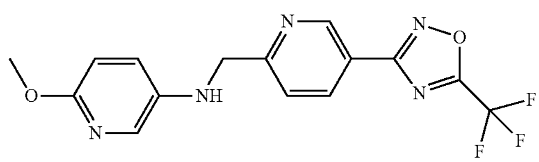 [SMILES: COc1ccc(NCc2ccc(-c3noc(C(F)(F)F)n3)cn2)cn1] | 6-methoxy-N-({5-[5-(trifluoro-methyl)-1,2,4-oxa-diazol-3-yl]pyridin-2-yl}methyl)pyridin-3-amine | | 351.9 | 174 |
| 364 | 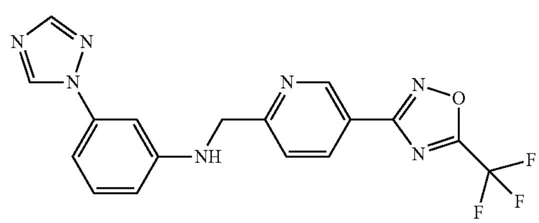 [SMILES: FC(F)(F)c1nc(-c2ccc(CNc3cccc(-n4cncn4)c3)nc2)no1] | 3-(1H-1,2,4-triazol-1-yl)-N-({5-[5-(trifluoro-methyl)-1,2,4-oxa-diazol-3-yl]pyridin-2-yl}methyl)aniline | | 387.9 | 174 |
| 365 | 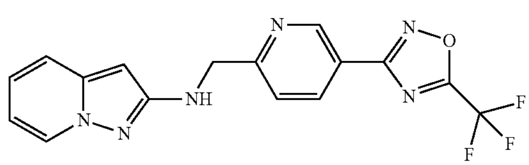 [SMILES: FC(F)(F)c1nc(-c2ccc(CNc3cc4ccccn4n3)nc2)no1] | N-({5-[5-(trifluoro-methyl)-1,2,4-oxa-diazol-3-yl]pyridin-2-yl}methyl)pyrazolo[1,5-a]pyridin-2-amine | | 360.9 | 174 |
| 366 | 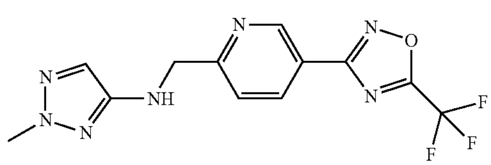 [SMILES: Cn1ncc(NCc2ccc(-c3noc(C(F)(F)F)n3)cn2)n1] | 2-methyl-N-({5-[5-(trifluoro-methyl)-1,2,4-oxa-diazol-3-yl]pyridin-2-yl}methyl)-2H-1,2,3-triazol-4-amine | | 326.0 | 174 |

TABLE 2-continued

| Ex # | Structure | Name | Stereo-chemistry | [M + H]+ | General Procedures |
|---|---|---|---|---|---|
| 367 | 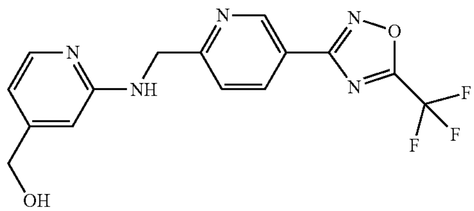 [SMILES: OCc1ccnc(NCc2ccc(-c3noc(C(F)(F)F)n3)cn2)c1] | {2-[({5-[5-(trifluoromethyl)-1,2,4-oxadiazol-3-yl]pyridin-2-yl}methyl)amino]pyridin-4-yl}methanol | | 351.9 | 174 |
| 368 | 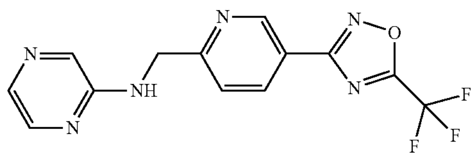 [SMILES: FC(F)(F)c1nc(-c2ccc(CNc3cnccn3)nc2)no1] | N-({5-[5-(trifluoromethyl)-1,2,4-oxadiazol-3-yl]pyridin-2-yl}methyl)pyrazin-2-amine | | 322.9 | 174 |
| 369 | 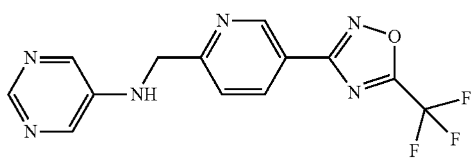 [SMILES: FC(F)(F)c1nc(-c2ccc(CNc3cncnc3)nc2)no1] | N-({5-[5-(trifluoromethyl)-1,2,4-oxadiazol-3-yl]pyridin-2-yl}methyl)pyrimidin-5-amine | | 323.0 | 174 |
| 370 | 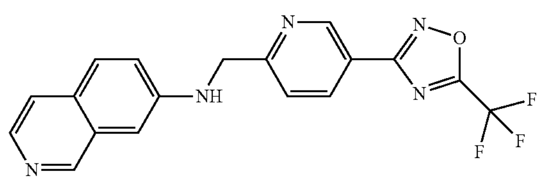 [SMILES: FC(F)(F)c1nc(-c2ccc(CNc3ccc4ccncc4c3)nc2)no1] | N-({5-[5-(trifluoromethyl)-1,2,4-oxadiazol-3-yl]pyridin-2-yl}methyl)isoquinolin-7-amine | | 371.9 | 174 |
| 371 | 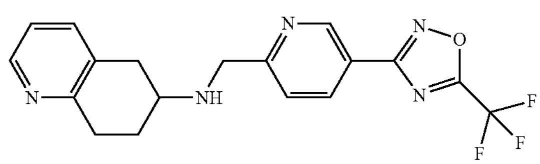 [SMILES: FC(F)(F)c1nc(-c2ccc(CNC3CCc4ncccc4C3)nc2)no1] | N-({5-[5-(trifluoromethyl)-1,2,4-oxadiazol-3-yl]pyridin-2-yl}methyl)-5,6,7,8-tetrahydroquinolin-6-amine | RACEMIC | 375.9 | 174 |
| 372 | 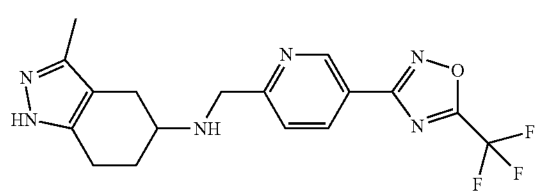 [SMILES: Cc1n[nH]c2c1CC(NCc1ccc(-c3noc(C(F)(F)F)n3)cn1)CC2] | 3-methyl-N-({5-[5-(trifluoromethyl)-1,2,4-oxadiazol-3-yl]pyridin-2-yl}methyl)-4,5,6,7-tetrahydro-1H-indazol-5-amine | RACEMIC | 379.0 | 174 |

TABLE 2-continued

| Ex # | Structure | Name | Stereo-chemistry | [M + H]+ | General Procedures |
|---|---|---|---|---|---|
| 373 | 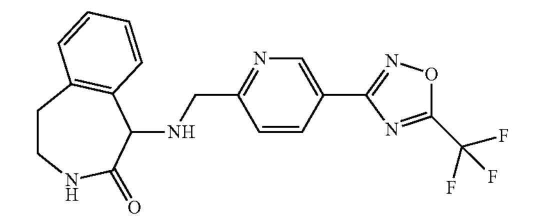 [SMILES: O=C1NCCc2ccccc2C1NCc1ccc(-c2noc(C(F)(F)F)n2)cn1] | 1-[({5-[5-(trifluoro-methyl)-1,2,4-oxa-diazol-3-yl]pyridin-2-yl}methyl)amino]-1,3,4,5-tetrahydro-2H-3-benzazepin-2-one | RACEMIC | 404.0 | 174 |
| 374 | 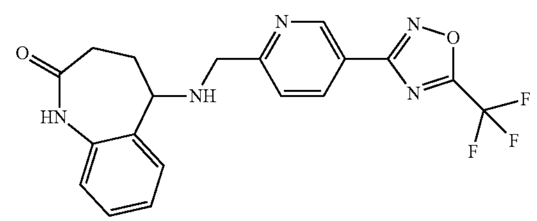 [SMILES: O=C1CCC(NCc2ccc(-c3noc(C(F)(F)F)n3)cn2)c2ccccc2N1] | 5-[({5-[5-(trifluoro-methyl)-1,2,4-oxa-diazol-3-yl]pyridin-2-yl}methyl)amino]-1,3,4,5-tetrahydro-2H-1-benzazepin-2-one | RACEMIC | 404.0 | 174 |
| 375 | 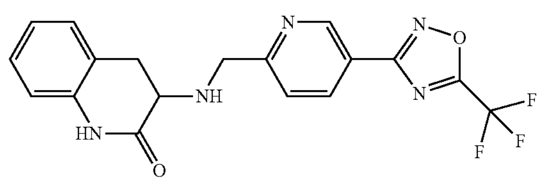 [SMILES: O=C1Nc2ccccc2CC1NCc1ccc(-c2noc(C(F)(F)F)n2)cn1] | 3-[({5-[5-(trifluoro-methyl)-1,2,4-oxa-diazol-3-yl]pyridin-2-yl}methyl)amino]-3,4-dihydro-quinolin-2(1H)-one | RACEMIC | 390.0 | 174 |
| 376 | 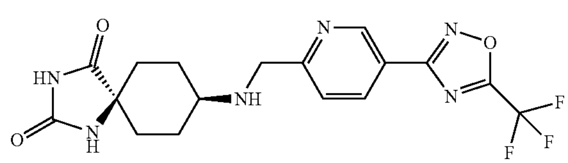 [SMILES: O=C1NC(=O)[C@]2(CC[C@H](NCc3ccc(-c4noc(C(F)(F)F)n4)cn3)CC2)N1] | (5s,8s)-8-[({5-[5-(trifluoro-methyl)-1,2,4-oxa-diazol-3-yl]pyridin-2-yl}methyl)amino]-1,3-diazaspiro[4.5]decane-2,4-dione | S, S | 411.0 | 174 |
| 377 | 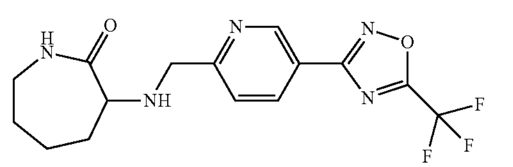 [SMILES: O=C1NCCCCC1NCc1ccc(-c2noc(C(F)(F)F)n2)cn1] | 3-[({5-[5-(trifluoro-methyl)-1,2,4-oxa-diazol-3-yl]pyridin-2-yl}methyl)amino]azepan-2-one | RACEMIC | 355.9 | 174 |

TABLE 2-continued

| Ex # | Structure | Name | Stereo-chemistry | [M + H]+ | General Procedures |
|---|---|---|---|---|---|
| 378 | 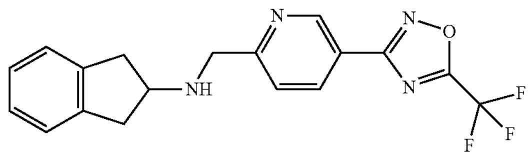 [SMILES: FC(F)(F)c1nc(-c2ccc(CNC3Cc4ccccc4C3)nc2)no1] | N-({5-[5-(trifluoro-methyl)-1,2,4-oxa-diazol-3-yl]pyridin-2-yl}methyl)-2,3-dihydro-1H-inden-2-amine | | 360.9 | 174 |
| 379 | 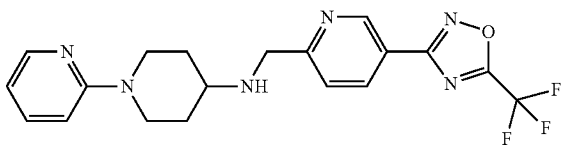 [SMILES: FC(F)(F)c1nc(-c2ccc(CNC3CCN(c4ccccn4)CC3)nc2)no1] | 1-(pyridin-2-yl)-N-({5-[5-(trifluoro-methyl)-1,2,4-oxa-diazol-3-yl]pyridin-2-yl}methyl)piperidin-4-amine | | 404.9 | 174 |
| 380 | 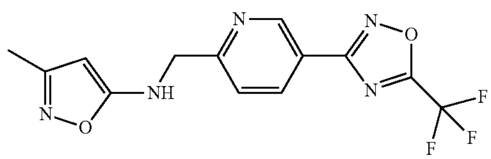 [SMILES: Cc1cc(NCc2ccc(-c3noc(C(F)(F)F)n3)cn2)on1] | 3-methyl-N-({5-[5-(trifluoro-methyl)-1,2,4-oxa-diazol-3-yl]pyridin-2-yl}methyl)-1,2-oxazol-5-amine | | 325.9 | 174 |
| 381 | 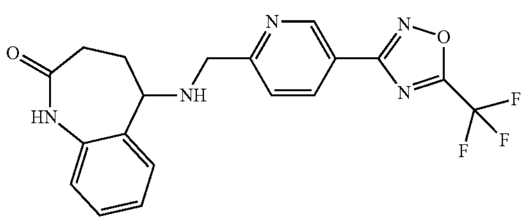 [SMILES: O=C1CCC(NCc2ccc(-c3noc(C(F)(F)F)n3)cn2)c2ccccc2N1] | 5-[({5-[5-(trifluoro-methyl)-1,2,4-oxa-diazol-3-yl]pyridin-2-yl}methyl)amino]-1,3,4,5-tetrahydro-2H-1-benzazepin-2-one | RACEMIC | 404.0 | 174 |
| 382 | 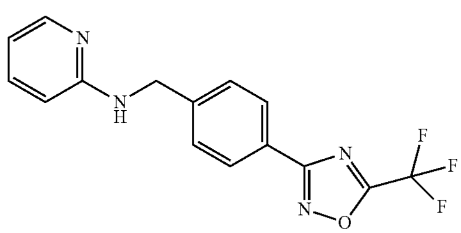 [SMILES: FC(F)(F)c1nc(-c2ccc(CNc3ccccn3)cc2)no1] | N-{4-[5-(trifluoro-methyl)-1,2,4-oxa-diazol-3-yl]benzyl}pyridin-2-amine | | 321.1 | 175 |
| 383 | 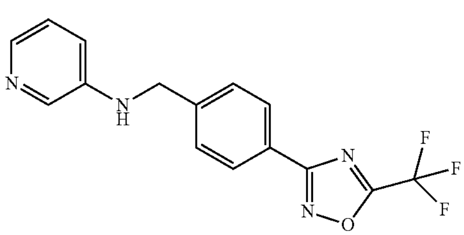 [SMILES: FC(F)(F)c1nc(-c2ccc(CNc3cccnc3)cc2)no1] | N-{4-[5-(trifluoro-methyl)-1,2,4-oxa-diazol-3-yl]benzyl}pyridin-3-amine | | 321.1 | 175 |

TABLE 2-continued

| Ex # | Structure | Name | Stereo-chemistry | [M + H]+ | General Procedures |
|---|---|---|---|---|---|
| 384 | 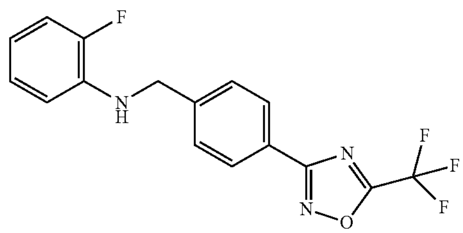 [SMILES: Fc1ccccc1NCc1ccc(-c2noc(C(F)(F)F)n2)cc1] | 2-fluoro-N-{4-[5-(trifluoro-methyl)-1,2,4-oxa-diazol-3-yl]benzyl}aniline | | 338.1 | 175 |
| 385 | 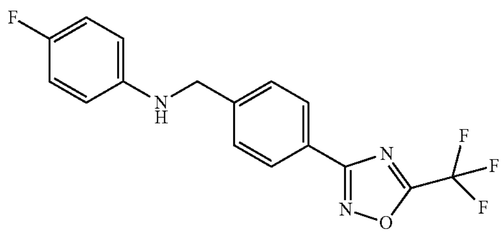 [SMILES: Fc1ccc(NCc2ccc(-c3noc(C(F)(F)F)n3)cc2)cc1] | 4-fluoro-N-{4-[5-(trifluoro-methyl)-1,2,4-oxa-diazol-3-yl]benzyl}aniline | | 338.1 | 175 |
| 386 | 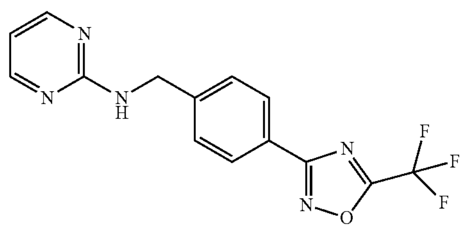 [SMILES: FC(F)(F)c1nc(-c2ccc(CNc3ncccn3)cc2)no1] | N-{4-[5-(trifluoro-methyl)-1,2,4-oxa-diazol-3-yl]benzyl}pyrimidin-2-amine | | 322.2 | 175 |
| 387 | 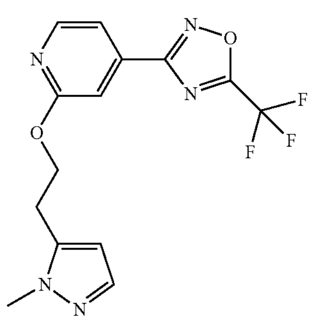 [SMILES: Cn1nccc1CCOc1cc(-c2noc(C(F)(F)F)n2)ccn1] | 2-[2-(1-methyl-1H-pyrazol-5-yl)ethoxy]-4-[5-(trifluoro-methyl)-1,2,4-oxa-diazol-3-yl]pyridine | | 340.1 | 24 |
| 388 | 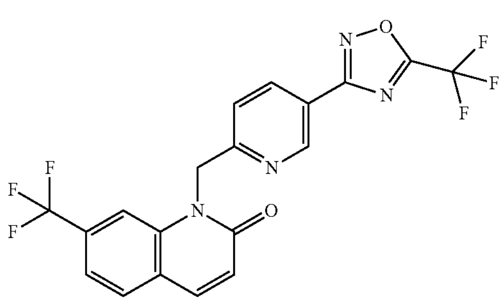 [SMILES: O=c1ccc2ccc(C(F)(F)F)cc2n1Cc1ccc(-c2noc(C(F)(F)F)n2)cn1] | 7-(trifluoro-methyl)-1-({5-[5-(trifluoro-methyl)-1,2,4-oxa-diazol-3-yl]pyridin-2-yl}methyl)quinolin-2(1H)-one | | 440.9 | 28 |

TABLE 2-continued

| Ex # | Structure | Name | Stereo-chemistry | [M + H]+ | General Procedures |
|---|---|---|---|---|---|
| 389 | 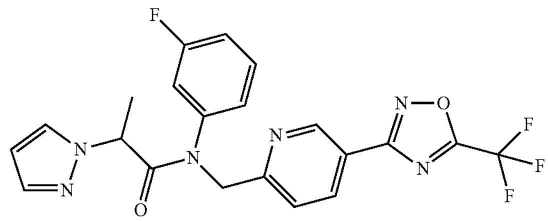 [SMILES: CC(C(=O)N(Cc1ccc(-c2noc(C(F)(F)F)n2)cn1)c1cccc(F)c1)n1cccn1] | N-(3-fluoro-phenyl)-2-(1H-pyrazol-1-yl)-N-({5-[5-(trifluoro-methyl)-1,2,4-oxa-diazol-3-yl]pyridin-2-yl}methyl)propanamide | RACEMIC | 461.2 | 30 |
| 390 | 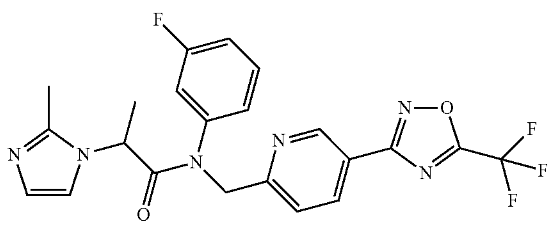 [SMILES: Cc1nccn1C(C)C(=O)N(Cc1ccc(-c2noc(C(F)(F)F)n2)cn1)c1cccc(F)c1] | N-(3-fluoro-phenyl)-2-(2-methyl-1H-imidazol-1-yl)-N-({5-[5-(trifluoro-methyl)-1,2,4-oxa-diazol-3-yl]pyridin-2-yl}methyl)propanamide | RACEMIC | 475.2 | 30 |
| 391 | 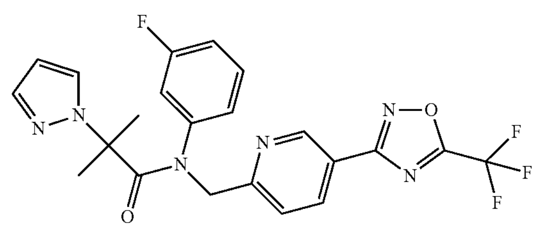 [SMILES: CC(C)(C(=O)N(Cc1ccc(-c2noc(C(F)(F)F)n2)cn1)c1cccc(F)c1)n1cccn1] | N-(3-fluoro-phenyl)-2-methyl-2-(1H-pyrazol-1-yl)-N-({5-[5-(trifluoro-methyl)-1,2,4-oxa-diazol-3-yl]pyridin-2-yl}methyl)propanamide | | 475.2 | 30 |
| 392 | 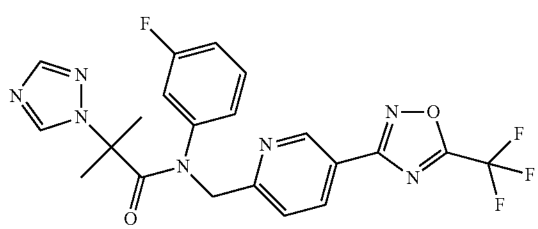 [SMILES: CC(C)(C(=O)N(Cc1ccc(-c2noc(C(F)(F)F)n2)cn1)c1cccc(F)c1)n1cncn1] | N-(3-fluoro-phenyl)-2-methyl-2-(1H-1,2,4-triazol-1-yl)-N-({5-[5-(trifluoro-methyl)-1,2,4-oxa-diazol-3-yl]pyridin-2-yl}methyl)propanamide | | 476.2 | 30 |
| 393 | 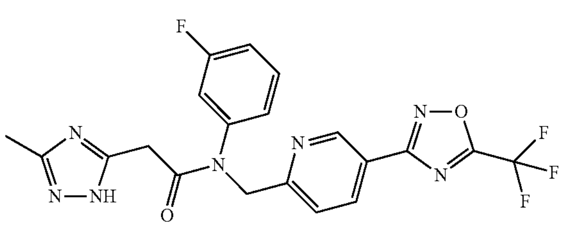 [SMILES: Cc1n[nH]c(CC(=O)N(Cc2ccc(-c3noc(C(F)(F)F)n3)cn2)c2cccc(F)c2)n1] | N-(3-fluoro-phenyl)-2-(3-methyl-1H-1,2,4-triazol-5-yl)-N-({5-[5-(trifluoro-methyl)-1,2,4-oxa-diazol-3-yl]pyridin-2-yl}methyl) | | 462.1 | 30 |

TABLE 2-continued

| Ex # | Structure | Name | Stereo-chemistry | [M + H]+ | General Procedures |
|---|---|---|---|---|---|
| | | acetamide | | | |
| 394 | 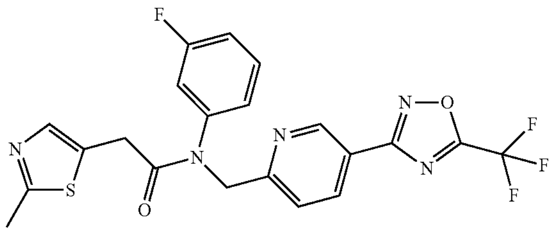 [SMILES: Cc1ncc(CC(=O)N(Cc2ccc(-c3noc(C(F)(F)F)n3)cn2)c2cccc(F)c2)s1] | N-(3-fluoro-phenyl)-2-(2-methyl-1,3-thiazol-5-yl)-N-({5-[5-(trifluoro-methyl)-1,2,4-oxa-diazol-3-yl]pyridin-2-yl}methyl)acetamide | | 478.1 | 30 |
| 395 | 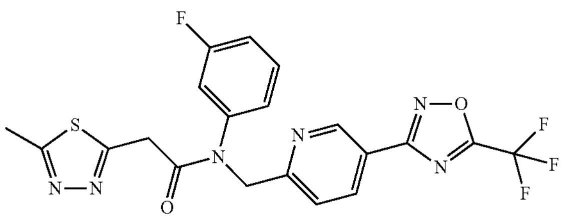 [SMILES: Cc1nnc(CC(=O)N(Cc2ccc(-c3noc(C(F)(F)F)n3)cn2)c2cccc(F)c2)s1] | N-(3-fluoro-phenyl)-2-(5-methyl-1,3,4-thiadiazol-2-yl)-N-({5-[5-(trifluoro-methyl)-1,2,4-oxa-diazol-3-yl]pyridin-2-yl}methyl)acetamide | | 479.1 | 30 |
| 396 | 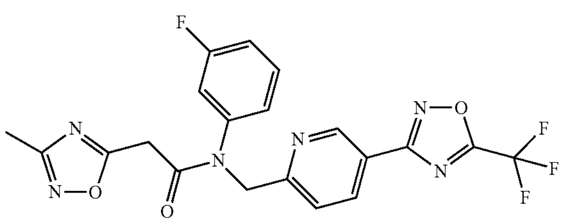 [SMILES: Cc1noc(CC(=O)N(Cc2ccc(-c3noc(C(F)(F)F)n3)cn2)c2cccc(F)c2)n1] | N-(3-fluoro-phenyl)-2-(3-methyl-1,2,4-oxa-diazol-5-yl)-N-({5-[5-(trifluoro-methyl)-1,2,4-oxa-diazol-3-yl]pyridin-2-yl}methyl)acetamide | | 463.1 | 30 |
| 397 | 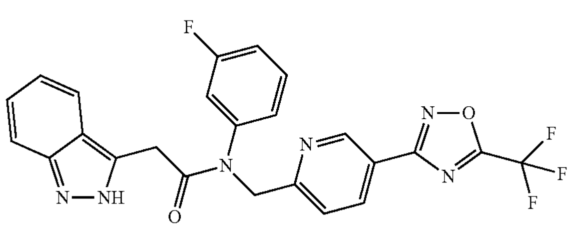 [SMILES: O=C(Cc1[nH]nc2ccccc12)N(Cc1ccc(-c2noc(C(F)(F)F)n2)cn1)c1cccc(F)c1] | N-(3-fluoro-phenyl)-2-(2H-indazol-3-yl)-N-({5-[5-(trifluoro-methyl)-1,2,4-oxa-diazol-3-yl]pyridin-2-yl}methyl)acetamide | | 497.2 | 30 |

TABLE 2-continued

| Ex # | Structure | Name | Stereo-chemistry | [M + H]⁺ | General Procedures |
|---|---|---|---|---|---|
| 398 | 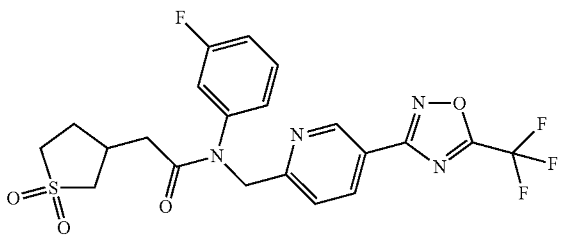 [SMILES: O=C(CC1CCS(=O)(=O)C1)N(Cc1ccc(-c2noc(C(F)(F)F)n2)cn1)c1cccc(F)c1] | 2-(1,1-dioxido-tetrahydro-thiophen-3-yl)-N-(3-fluoro-phenyl)-N-({5-[5-(trifluoro-methyl)-1,2,4-oxa-diazol-3-yl]pyridin-2-yl}methyl)acetamide | RACEMIC | 499.1 | 30 |
| 399 | 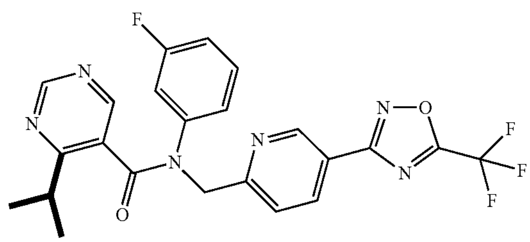 | N-(3-fluoro-phenyl)-4-(1-methyl-ethyl)-N-({5-[5-(trifluoro-methyl)-1,2,4-oxa-diazol-3-yl]pyridin-2-yl}methyl)pyrimidine-5-carbox-amide | | 487.2 | 30 |
| 400 | 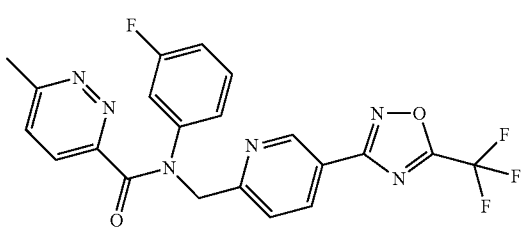 [SMILES: Cc1ccc(C(=O)N(Cc2ccc(-c3noc(C(F)(F)F)n3)cn2)c2cccc(F)c2)nn1] | N-(3-fluoro-phenyl)-6-methyl-N-({5-[5-(trifluoro-methyl)-1,2,4-oxa-diazol-3-yl]pyridin-2-yl}methyl)pyridazine-3-carbox-amide | | 459.1 | 30 |
| 401 | 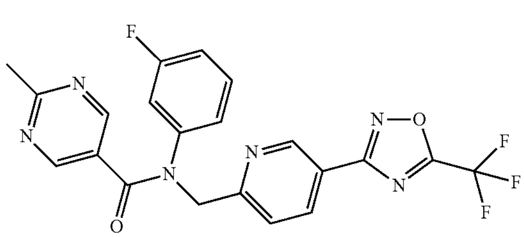 [SMILES: Cc1ncc(C(=O)N(Cc2ccc(-c3noc(C(F)(F)F)n3)cn2)c2cccc(F)c2)cn1] | N-(3-fluoro-phenyl)-2-methyl-N-({5-[5-(trifluoro-methyl)-1,2,4-oxa-diazol-3-yl]pyridin-2-yl}methyl)pyrimidine-5-carbox-amide | | 459.1 | 30 |

TABLE 2-continued

| Ex # | Structure | Name | Stereo-chemistry | [M + H]+ | General Procedures |
|---|---|---|---|---|---|
| 402 | 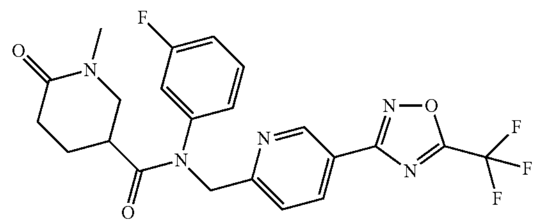 [SMILES: CN1CC(C(=O)N(Cc2ccc(-c3noc(C(F)(F)F)n3)cn2)c2cccc(F)c2)CCC1=O] | N-(3-fluorophenyl)-1-methyl-6-oxo-N-({5-[5-(trifluoromethyl)-1,2,4-oxadiazol-3-yl]pyridin-2-yl}methyl)piperidine-3-carboxamide | RACEMIC | 478.2 | 30 |
| 403 | 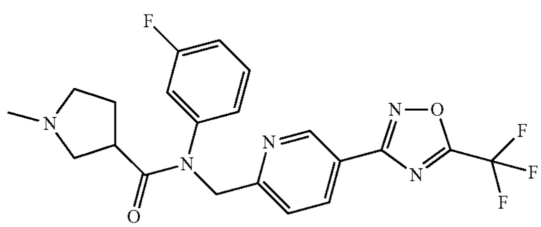 [SMILES: CN1CCC(C(=O)N(Cc2ccc(-c3noc(C(F)(F)F)n3)cn2)c2cccc(F)c2)C1] | N-(3-fluorophenyl)-1-methyl-N-({5-[5-(trifluoromethyl)-1,2,4-oxadiazol-3-yl]pyridin-2-yl}methyl)pyrrolidine-3-carboxamide | RACEMIC | 450.2 | 30 |
| 404 | 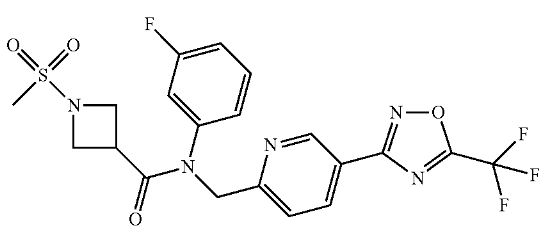 [SMILES: CS(=O)(=O)N1CC(C(=O)N(Cc2ccc(-c3noc(C(F)(F)F)n3)cn2)c2cccc(F)c2)C1] | N-(3-fluorophenyl)-1-(methylsulfonyl)-N-({5-[5-(trifluoromethyl)-1,2,4-oxadiazol-3-yl]pyridin-2-yl}methyl)azetidine-3-carboxamide | | 500.1 | 30 |
| 405 | 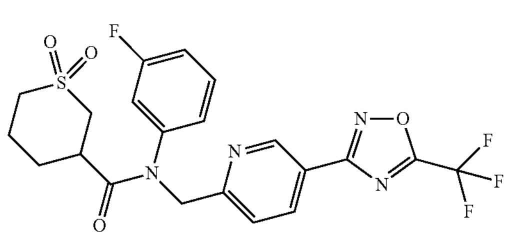 [SMILES: O=C(C1CCCS(=O)(=O)C1)N(Cc1ccc(-c2noc(C(F)(F)F)n2)cn1)c1cccc(F)c1] | N-(3-fluorophenyl)-N-({5-[5-(trifluoromethyl)-1,2,4-oxadiazol-3-yl]pyridin-2-yl}methyl)tetrahydro-2H-thiopyran-3-carboxamide 1,1-dioxide | RACEMIC | 499.1 | 30 |

TABLE 2-continued

| Ex # | Structure | Name | Stereo-chemistry | [M + H]+ | General Procedures |
|---|---|---|---|---|---|
| 406 | 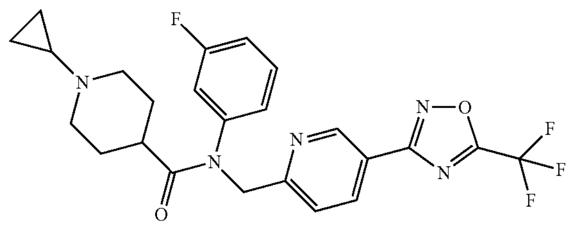 [SMILES: O=C(C1CCN(C2CC2)CC1)N(Cc1ccc(-c2noc(C(F)(F)F)n2)cn1)c1cccc(F)c1] | 1-cyclopropyl-N-(3-fluorophenyl)-N-({5-[5-(trifluoromethyl)-1,2,4-oxadiazol-3-yl]pyridin-2-yl}methyl)piperidine-4-carboxamide | | 490.2 | 30 |
| 407 | 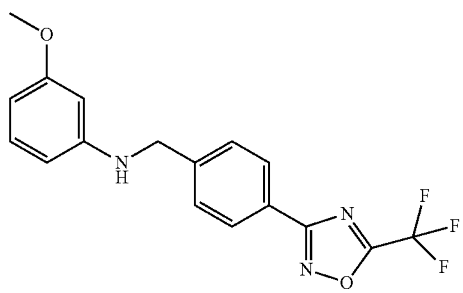 [SMILES: COc1cccc(NCc2ccc(-c3noc(C(F)(F)F)n3)cc2)c1] | 3-methoxy-N-{4-[5-(trifluoromethyl)-1,2,4-oxadiazol-3-yl]benzyl}aniline | | 350.1 | 175 |
| 408 | 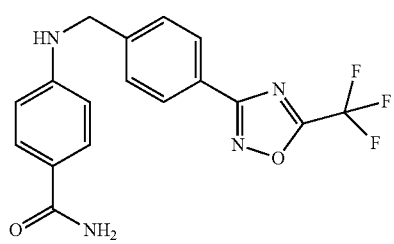 [SMILES: NC(=O)c1ccc(NCc2ccc(-c3noc(C(F)(F)F)n3)cc2)cc1] | 4-({4-[5-(trifluoromethyl)-1,2,4-oxadiazol-3-yl]benzyl}amino)benzamide | | 363.1 | 175 |
| 409 | 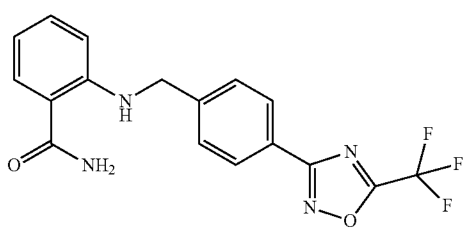 [SMILES: NC(=O)c1ccccc1NCc1ccc(-c2noc(C(F)(F)F)n2)cc1] | 2-({4-[5-(trifluoromethyl)-1,2,4-oxadiazol-3-yl]benzyl}amino)benzamide | | 363.1 | 175 |
| 410 | 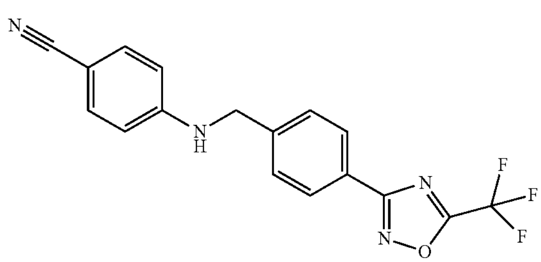 [SMILES: N#Cc1ccc(NCc2ccc(-c3noc(C(F)(F)F)n3)cc2)cc1] | 4-({4-[5-(trifluoromethyl)-1,2,4-oxadiazol-3-yl]benzyl}amino)benzonitrile | | 345.1 | 175 |

TABLE 2-continued

| Ex # | Structure | Name | Stereo-chemistry | [M + H]+ | General Procedures |
|---|---|---|---|---|---|
| 411 | 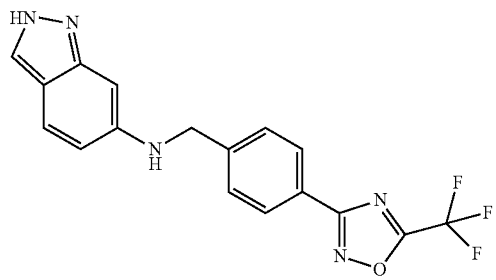 [SMILES: FC(F)(F)c1nc(-c2ccc(CNc3ccc4c[nH]nc4c3)cc2)no1] | N-{4-[5-(trifluoro-methyl)-1,2,4-oxa-diazol-3-yl]benzyl}-2H-indazol-6-amine | | 360.1 | 175 |
| 412 | 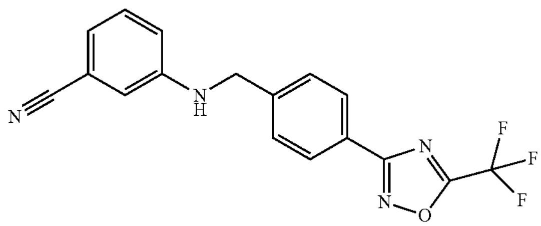 [SMILES: N#Cc1cccc(NCc2ccc(-c3noc(C(F)(F)F)n3)cc2)c1] | 3-({4-[5-(trifluoro-methyl)-1,2,4-oxa-diazol-3-yl]benzyl}amino)benzonitrile | | 345.1 | 175 |
| 413 | 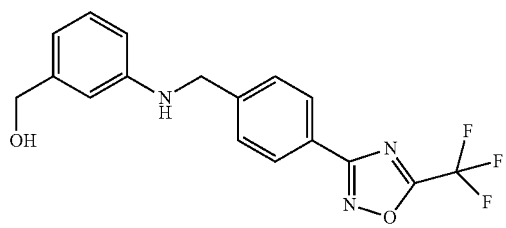 [SMILES: OCc1cccc(NCc2ccc(-c3noc(C(F)(F)F)n3)cc2)c1] | [3-({4-[5-(trifluoro-methyl)-1,2,4-oxa-diazol-3-yl]benzyl}amino)phenyl]methanol | | 350.1 | 175 |
| 414 | 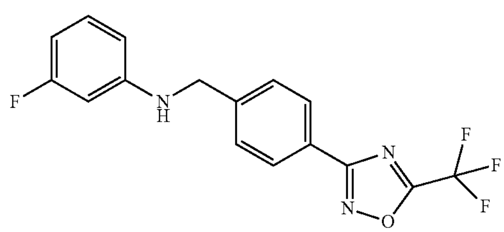 [SMILES: Fc1cccc(NCc2ccc(-c3noc(C(F)(F)F)n3)cc2)c1] | 3-fluoro-N-{4-[5-(trifluoro-methyl)-1,2,4-oxa-diazol-3-yl]benzyl}aniline | | 338.1 | 175 |
| 415 | 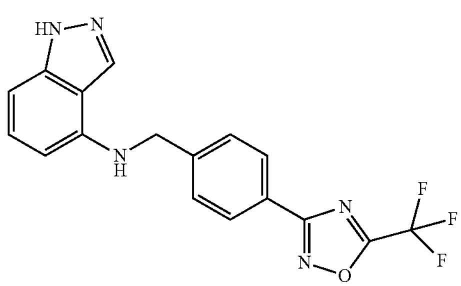 [SMILES: FC(F)(F)c1nc(-c2ccc(CNc3cccc4[nH]ncc34)cc2)no1] | N-{4-[5-(trifluoro-methyl)-1,2,4-oxa-diazol-3-yl]benzyl}-1H-indazol-4-amine | | 360.1 | 175 |

TABLE 2-continued

| Ex # | Structure | Name | Stereo-chemistry | [M + H]+ | General Procedures |
|---|---|---|---|---|---|
| 416 | 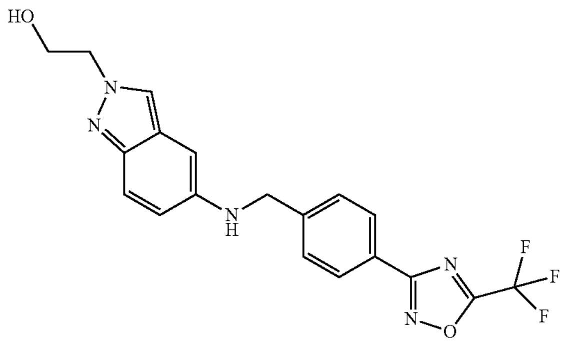 [SMILES: OCCn1cc2cc(NCc3ccc(-c4noc(C(F)(F)F)n4)cc3)ccc2n1] | 2-[5-({4-[5-(trifluoro-methyl)-1,2,4-oxa-diazol-3-yl]benzyl}amino)-2H-indazol-2-yl]ethanol | | 404.1 | 175 |
| 417 | 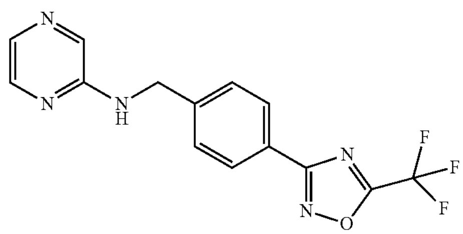 [SMILES: FC(F)(F)c1nc(-c2ccc(CNc3cnccn3)cc2)no1] | N-{4-[5-(trifluoro-methyl)-1,2,4-oxa-diazol-3-yl]benzyl}pyrazin-2-amine | | 322.0 | 175 |
| 418 | 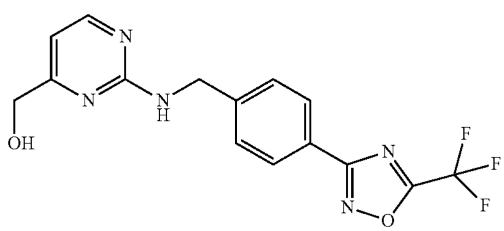 [SMILES: OCc1ccnc(NCc2ccc(-c3noc(C(F)(F)F)n3)cc2)n1] | [2-({4-[5-(trifluoro-methyl)-1,2,4-oxa-diazol-3-yl]benzyl}amino)pyrimidin-4-yl]methanol | | 352.1 | 175 |
| 419 | 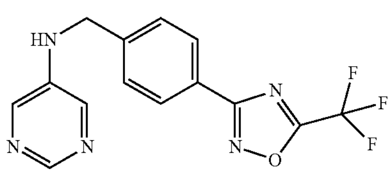 [SMILES: FC(F)(F)c1nc(-c2ccc(CNc3cncnc3)cc2)no1] | N-{4-[5-(trifluoro-methyl)-1,2,4-oxa-diazol-3-yl]benzyl}pyrimidin-5-amine | | 322.1 | 175 |
| 420 | 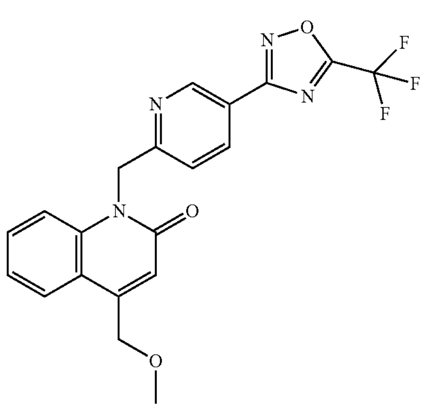 [SMILES: COCc1cc(=O)n(Cc2ccc(-c3noc(C(F)(F)F)n3)cn2)c2ccccc12] | 4-(methoxy-methyl)-1-({5-[5-(trifluoro-methyl)-1,2,4-oxa-diazol-3-yl]pyridin-2-yl}methyl)quinolin-2(1H)-one | | 417.0 | 185 |

TABLE 2-continued

| Ex # | Structure | Name | Stereo-chemistry | [M + H]+ | General Procedures |
|---|---|---|---|---|---|
| 421 | 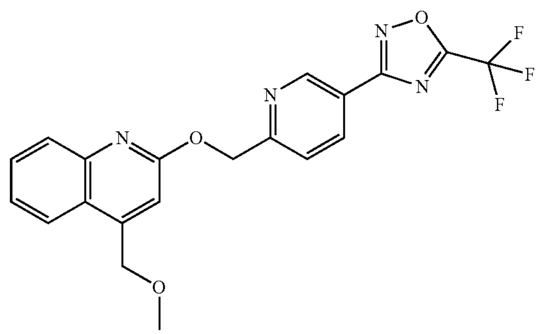 [SMILES: COCc1cc(OCc2ccc(-c3noc(C(F)(F)F)n3)cn2)nc2ccccc12] | 4-(methoxy-methyl)-2-({5-[5-(trifluoro-methyl)-1,2,4-oxa-diazol-3-yl]pyridin-2-yl}methoxy)quinoline | | 416.9 | 185 |
| 422 | 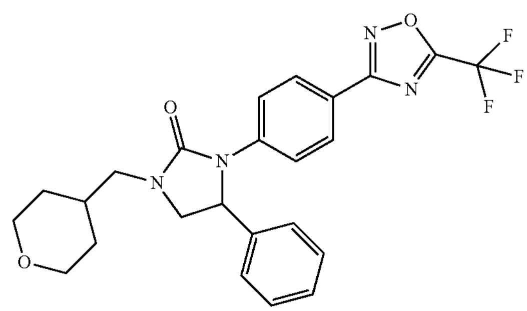 [SMILES: O=C1N(CC2CCOCC2)CC(c2ccccc2)N1c1ccc(-c2noc(C(F)(F)F)n2)cc1] | 4-phenyl-1-(tetra-hydro-2H-pyran-4-ylmethyl)-3-{4-[5-(trifluoro-methyl)-1,2,4-oxa-diazol-3-yl]phenyl}imida-zolidin-2-one | RACEMIC | 473.0 | 5 |
| 423 | 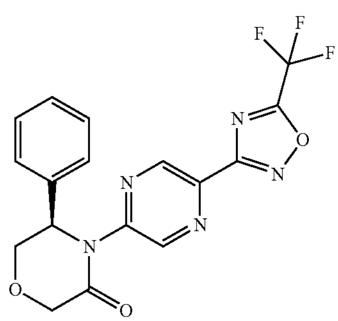 [SMILES: O=C1COC[C@@H](c2ccccc2)N1c1cnc(-c2noc(C(F)(F)F)n2)cn1] | (5R)-5-phenyl-4-{5-[5-(trifluoro-methyl)-1,2,4-oxa-diazol-3-yl]pyrazin-2-yl}morpholin-3-one | R | 391.9 | 1 |
| 424 | 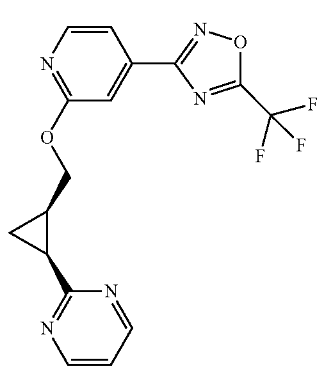 [SMILES: FC(F)(F)c1nc(-c2ccnc(OC[C@@H]3C[C@@H]3c3ncccn3)c2)no1] | 2-{(1S,2R)-2-[({4-[5-(trifluoro-methyl)-1,2,4-oxa-diazol-3-yl]pyridin-2-yl}oxy)methyl]cyclopropyl}pyrimidine | R, S | 364.1 | 24 |

TABLE 2-continued

| Ex # | Structure | Name | Stereo-chemistry | [M + H]+ | General Procedures |
|---|---|---|---|---|---|
| 425 | 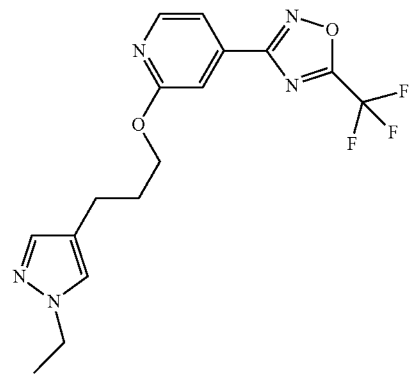 [SMILES: CCn1cc(CCCOc2cc(-c3noc(C(F)(F)F)n3)ccn2)cn1] | 2-[3-(1-ethyl-1H-pyrazol-4-yl)propoxy]-4-[5-(trifluoromethyl)-1,2,4-oxadiazol-3-yl]pyridine | | 368.1 | 24 |
| 426 | 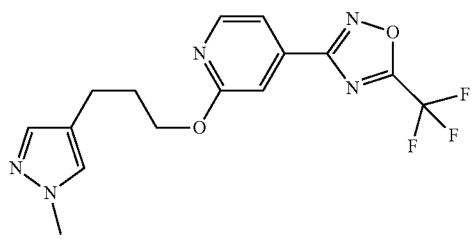 [SMILES: Cn1cc(CCCOc2cc(-c3noc(C(F)(F)F)n3)ccn2)cn1] | 2-[3-(1-methyl-1H-pyrazol-4-yl)propoxy]-4-[5-(trifluoromethyl)-1,2,4-oxadiazol-3-yl]pyridine | | 354.1 | 24 |
| 427 | 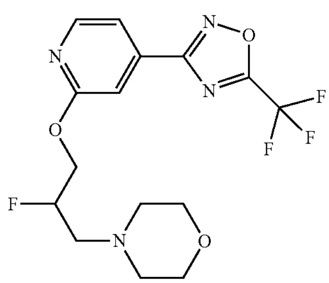 [SMILES: FC(COc1cc(-c2noc(C(F)(F)F)n2)ccn1)CN1CCOCC1] | 4-[2-fluoro-3-({4-[5-(trifluoromethyl)-1,2,4-oxadiazol-3-yl]pyridin-2-yl}oxy)propyl]morpholine | RACEMIC | 377.1 | 24 |
| 428 | 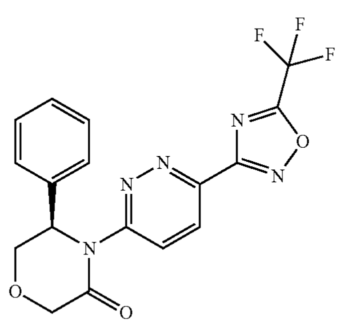 [SMILES: O=C1COC[C@@H](c2ccccc2)N1c1ccc(-c2noc(C(F)(F)F)n2)nn1] | (5R)-5-phenyl-4-{6-[5-(trifluoromethyl)-1,2,4-oxadiazol-3-yl]pyridazin-3-yl}morpholin-3-one | R | 391.9 | 1 |
| 429 | 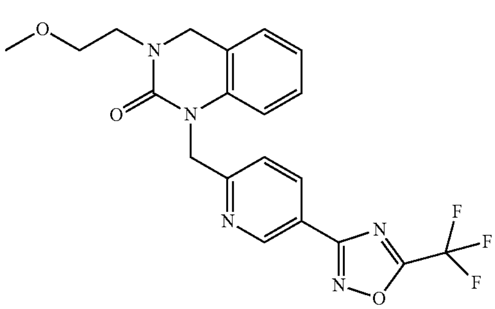 [SMILES: COCCN1Cc2ccccc2N(Cc2ccc(-c3noc(C(F)(F)F)n3)cn2)C1=O] | 3-(2-methoxyethyl)-1-({5-[5-(trifluoromethyl)-1,2,4-oxadiazol-3-yl]pyridin-2-yl}methyl)-3,4-dihydroquinazolin-2(1H)-one | | 434.0 | 28 |

TABLE 2-continued

| Ex # | Structure | Name | Stereo-chemistry | [M + H]+ | General Procedures |
|---|---|---|---|---|---|
| 430 | 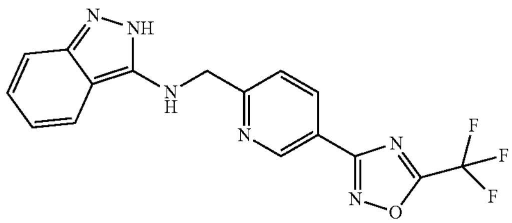 [SMILES: FC(F)(F)c1nc(-c2ccc(CNc3[nH]nc4ccccc34)nc2)no1] | N-({5-[5-(trifluoro-methyl)-1,2,4-oxa-diazol-3-yl]pyridin-2-yl}methyl)-2H-indazol-3-amine | | 361.1 | 174 |
| 431 | 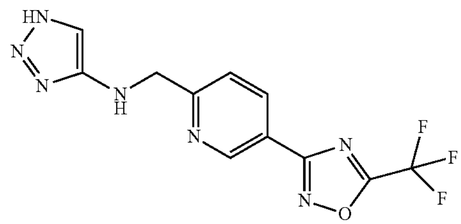 [SMILES: FC(F)(F)c1nc(-c2ccc(CNc3c[nH]nn3)nc2)no1] | N-({5-[5-(trifluoro-methyl)-1,2,4-oxa-diazol-3-yl]pyridin-2-yl}methyl)-1H-1,2,3-triazol-4-amine | | 312.1 | 174 |
| 432 | 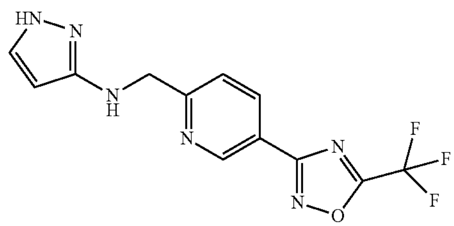 [SMILES: FC(F)(F)c1nc(-c2ccc(CNc3cc[nH]n3)nc2)no1] | N-({5-[5-(trifluoro-methyl)-1,2,4-oxa-diazol-3-yl]pyridin-2-yl}methyl)-1H-pyrazol-3-amine | | 311.1 | 174 |
| 433 | 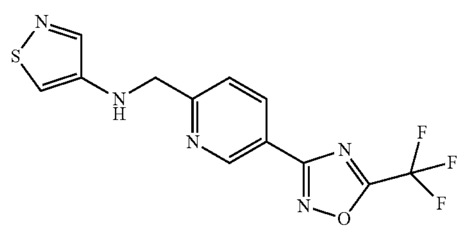 [SMILES: FC(F)(F)c1nc(-c2ccc(CNc3cnsc3)nc2)no1] | N-({5-[5-(trifluoro-methyl)-1,2,4-oxa-diazol-3-yl]pyridin-2-yl}methyl)isothiazol-4-amine | | 328.1 | 174 |
| 434 | 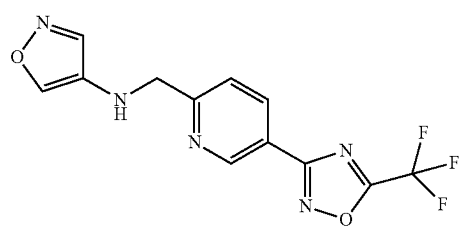 [SMILES: FC(F)(F)c1nc(-c2ccc(CNc3cnoc3)nc2)no1] | N-({5-[5-(trifluoro-methyl)-1,2,4-oxa-diazol-3-yl]pyridin-2-yl}methyl)isoxazol-4-amine | | 312.1 | 174 |
| 435 | 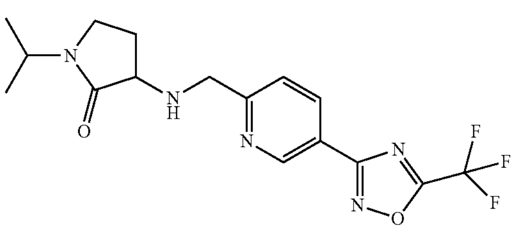 [SMILES: CC(C)N1CCC(NCc2ccc(-c3noc(C(F)(F)F)n3)cn2)C1=O] | 1-(1-methyl-ethyl)-3-[({5-[5-(trifluoro-methyl)-1,2,4-oxa-diazol-3-yl]pyridin-2-yl}methyl)amino]pyrrolidin-2-one | RACEMIC | 370.2 | 174 |

TABLE 2-continued

| Ex # | Structure | Name | Stereo-chemistry | [M + H]+ | General Procedures |
|---|---|---|---|---|---|
| 436 | 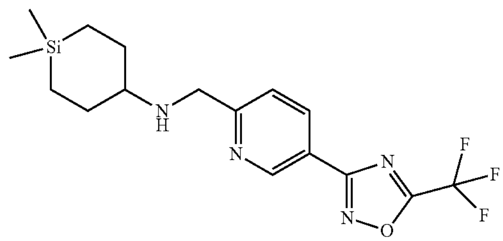 [SMILES: C[Si]1(C)CCC(NCc2ccc(-c3noc(C(F)(F)F)n3)cn2)CC1] | 1,1-dimethyl-N-({5-[5-(trifluoro-methyl)-1,2,4-oxa-diazol-3-yl]pyridin-2-yl}methyl)silinan-4-amine | | 371.2 | 174 |
| 437 | 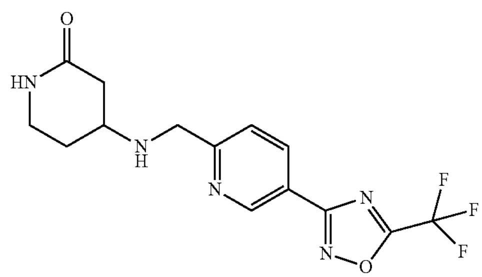 [SMILES: O=C1CC(NCc2ccc(-c3noc(C(F)(F)F)n3)cn2)CCN1] | 4-[({5-[5-(trifluoro-methyl)-1,2,4-oxa-diazol-3-yl]pyridin-2-yl}methyl)amino]piperidin-2-one | RACEMIC | 342.2 | 174 |
| 438 | 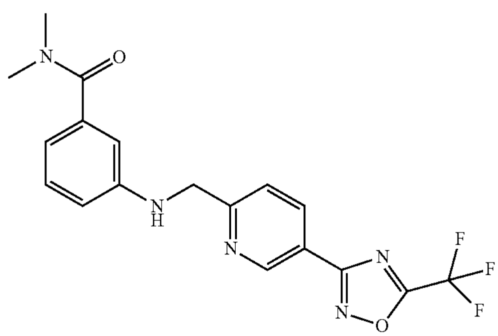 [SMILES: CN(C)C(=O)c1cccc(NCc2ccc(-c3noc(C(F)(F)F)n3)cn2)c1] | N,N-dimethyl-3-[({5-[5-(trifluoro-methyl)-1,2,4-oxa-diazol-3-yl]pyridin-2-yl}methyl)amino]benzamide | | 392.2 | 174 |
| 439 | 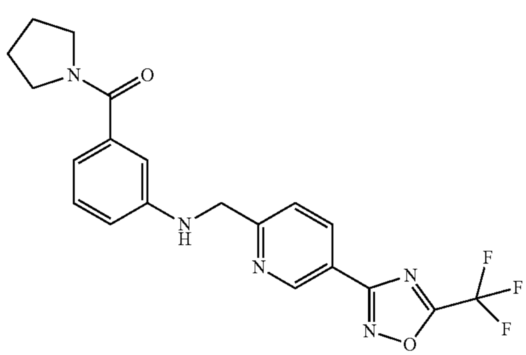 [SMILES: O=C(c1cccc(NCc2ccc(-c3noc(C(F)(F)F)n3)cn2)c1)N1CCCC1] | 3-(pyrrolidin-1-ylcarbonyl)-N-({5-[5-(trifluoro-methyl)-1,2,4-oxa-diazol-3-yl]pyridin-2-yl}methyl)aniline | | 418.2 | 174 |

TABLE 2-continued

| Ex # | Structure | Name | Stereo-chemistry | [M + H]+ | General Procedures |
|---|---|---|---|---|---|
| 440 | 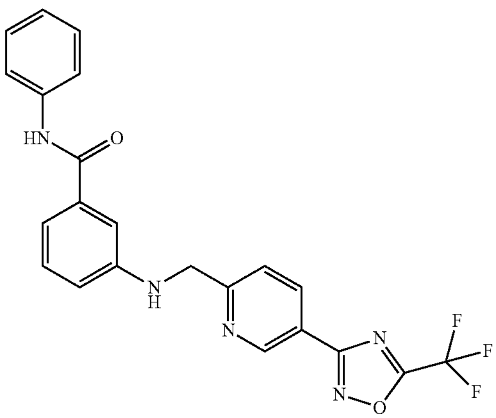 [SMILES: O=C(Nc1ccccc1)c1cccc(NCc2ccc(-c3noc(C(F)(F)F)n3)cn2)c1] | N-phenyl-3-[({5-[5-(trifluoro-methyl)-1,2,4-oxa-diazol-3-yl]pyridin-2-yl}methyl)amino]benzamide | | 440.2 | 174 |
| 441 | 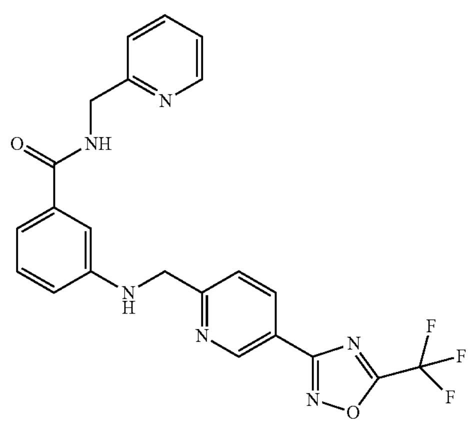 [SMILES: O=C(NCc1ccccn1)c1cccc(NCc2ccc(-c3noc(C(F)(F)F)n3)cn2)c1] | N-(pyridin-2-ylmethyl)-3-[({5-[5-(trifluoro-methyl)-1,2,4-oxa-diazol-3-yl]pyridin-2-yl}methyl)amino]benzamide | | 455.2 | 174 |
| 442 | 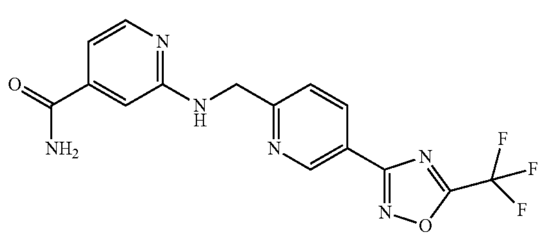 [SMILES: NC(=O)c1ccnc(NCc2ccc(-c3noc(C(F)(F)F)n3)cn2)c1] | 2-[({5-[5-(trifluoro-methyl)-1,2,4-oxa-diazol-3-yl]pyridin-2-yl}methyl)amino]pyridine-4-carbox-amide | | 365.1 | 174 |
| 443 | 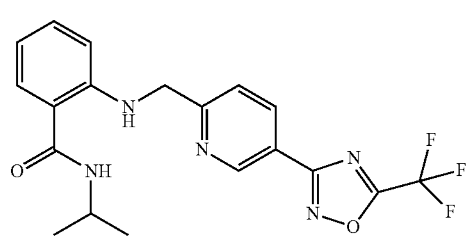 [SMILES: CC(C)NC(=O)c1ccccc1NCc1ccc(-c2noc(C(F)(F)F)n2)cn1] | N-(1-methyl-ethyl)-2-[({5-[5-(trifluoro-methyl)-1,2,4-oxa-diazol-3-yl]pyridin-2-yl}methyl)amino]benzamide | | 406.2 | 174 |

TABLE 2-continued

| Ex # | Structure | Name | Stereo-chemistry | [M + H]+ | General Procedures |
|---|---|---|---|---|---|
| 444 | 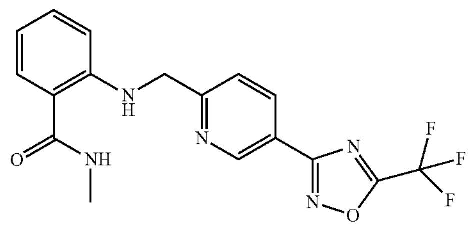 [SMILES: CNC(=O)c1ccccc1NCc1ccc(-c2noc(C(F)(F)F)n2)cn1] | N-methyl-2-[({5-[5-(trifluoromethyl)-1,2,4-oxadiazol-3-yl]pyridin-2-yl}methyl)amino]benzamide | | 378.2 | 174 |
| 445 | 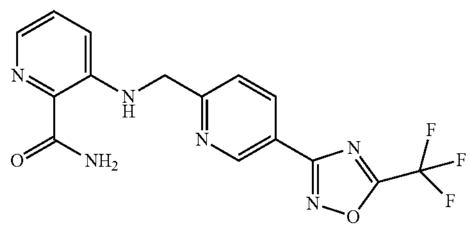 [SMILES: NC(=O)c1ncccc1NCc1ccc(-c2noc(C(F)(F)F)n2)cn1] | 3-[({5-[5-(trifluoromethyl)-1,2,4-oxadiazol-3-yl]pyridin-2-yl}methyl)amino]pyridine-2-carboxamide | | 365.1 | 174 |
| 446 | 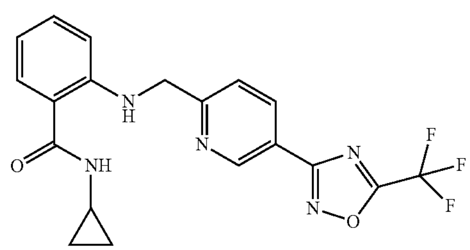 [SMILES: O=C(NC1CC1)c1ccccc1NCc1ccc(-c2noc(C(F)(F)F)n2)cn1] | N-cyclopropyl-2-[({5-[5-(trifluoromethyl)-1,2,4-oxadiazol-3-yl]pyridin-2-yl}methyl)amino]benzamide | | 404.2 | 174 |
| 447 | 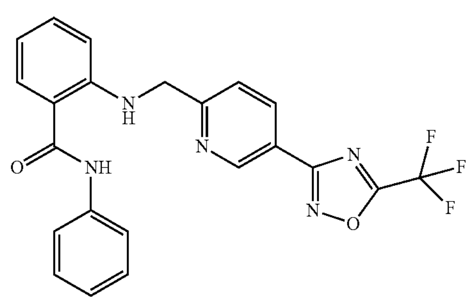 [SMILES: O=C(Nc1ccccc1)c1ccccc1NCc1ccc(-c2noc(C(F)(F)F)n2)cn1] | N-phenyl-2-[({5-[5-(trifluoromethyl)-1,2,4-oxadiazol-3-yl]pyridin-2-yl}methyl)amino]benzamide | | 440.2 | 174 |
| 448 | 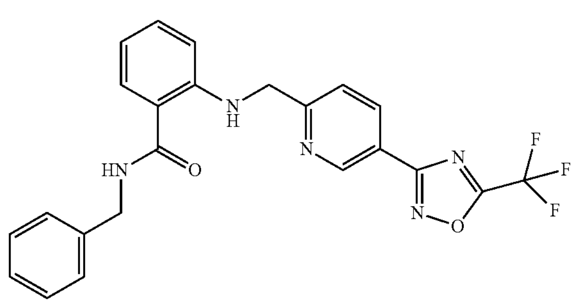 [SMILES: O=C(NCc1ccccc1)c1ccccc1NCc1ccc(-c2noc(C(F)(F)F)n2)cn1] | N-benzyl-2-[({5-[5-(trifluoromethyl)-1,2,4-oxadiazol-3-yl]pyridin-2-yl}methyl)amino]benzamide | | 454.2 | 174 |

TABLE 2-continued

| Ex # | Structure | Name | Stereo-chemistry | [M + H]+ | General Procedures |
|---|---|---|---|---|---|
| 449 | 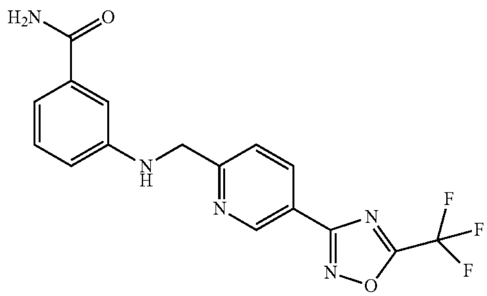 [SMILES: NC(=O)c1cccc(NCc2ccc(-c3noc(C(F)(F)F)n3)cn2)c1] | 3-[({5-[5-(trifluoromethyl)-1,2,4-oxadiazol-3-yl]pyridin-2-yl}methyl)amino]benzamide | | 364.1 | 174 |
| 450 | 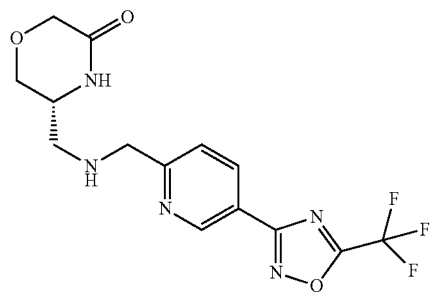 [SMILES: O=C1COC[C@@H](CNCc2ccc(-c3noc(C(F)(F)F)n3)cn2)N1] | (5R)-5-{[({5-[5-(trifluoromethyl)-1,2,4-oxadiazol-3-yl]pyridin-2-yl}methyl)amino]methyl}morpholin-3-one | R | 358.1 | 174 |
| 451 | 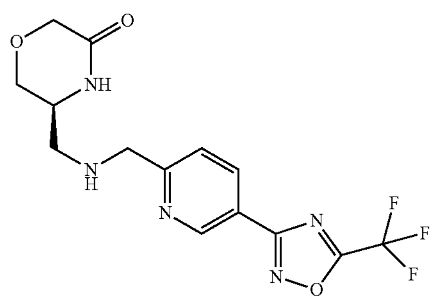 [SMILES: O=C1COC[C@H](CNCc2ccc(-c3noc(C(F)(F)F)n3)cn2)N1] | (5S)-5-{[({5-[5-(trifluoromethyl)-1,2,4-oxadiazol-3-yl]pyridin-2-yl}methyl)amino]methyl}morpholin-3-one | S | 358.1 | 174 |
| 452 | 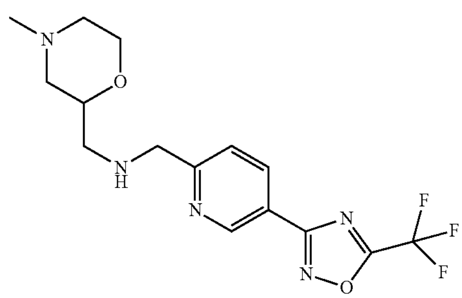 [SMILES: CN1CCOC(CNCc2ccc(-c3noc(C(F)(F)F)n3)cn2)C1] | 1-(4-methylmorpholin-2-yl)-N-({5-[5-(trifluoromethyl)-1,2,4-oxadiazol-3-yl]pyridin-2-yl}methyl)methanamine | RACEMIC | 358.2 | 174 |
| 453 | 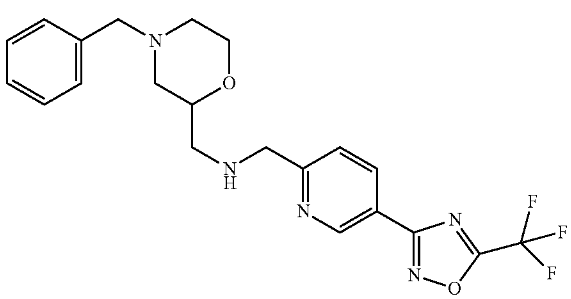 [SMILES: FC(F)(F)c1nc(-c2ccc(CNCC3CN(Cc4ccccc4)CCO3)nc2)no1] | 1-(4-benzylmorpholin-2-yl)-N-({5-[5-(trifluoromethyl)-1,2,4-oxadiazol-3-yl]pyridin-2-yl}methyl)methanamine | RACEMIC | 434.3 | 174 |

TABLE 2-continued

| Ex # | Structure | Name | Stereo-chemistry | [M + H]+ | General Procedures |
|------|-----------|------|------------------|----------|--------------------|
| 454 | 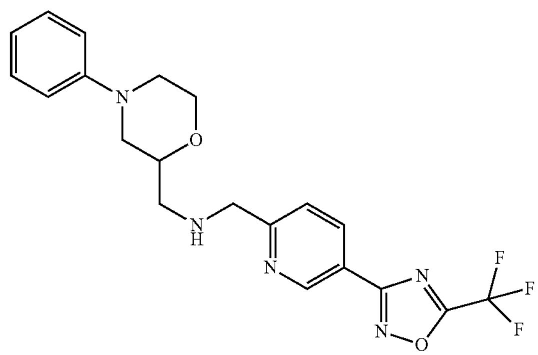 [SMILES: FC(F)(F)c1nc(-c2ccc(CNCC3CN(c4ccccc4)CCO3)nc2)no1] | 1-(4-phenyl-morpholin-2-yl)-N-({5-[5-(trifluoro-methyl)-1,2,4-oxa-diazol-3-yl]pyridin-2-yl}methyl)methanamine | RACEMIC | 420.2 | 174 |
| 455 | 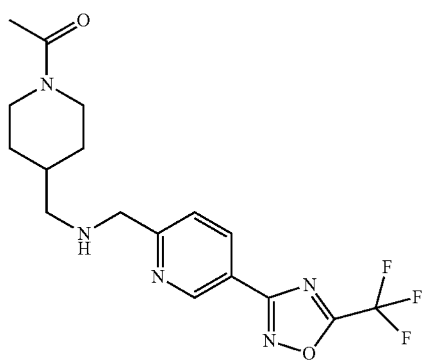 [SMILES: CC(=O)N1CCC(CNCc2ccc(-c3noc(C(F)(F)F)n3)cn2)CC1] | 1-(1-acetyl-piperidin-4-yl)-N-({5-[5-(trifluoro-methyl)-1,2,4-oxa-diazol-3-yl]pyridin-2-yl}methyl)methanamine | | 384.2 | 174 |
| 456 | 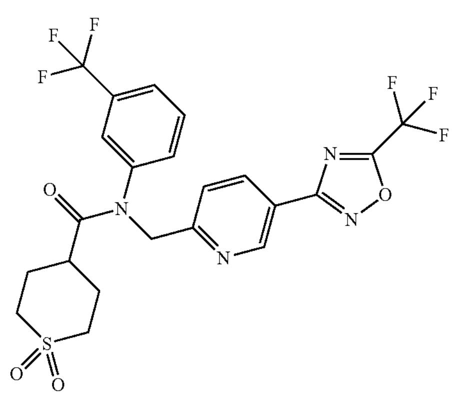 [SMILES: O=C(C1CCS(=O)(=O)CC1)N(Cc1ccc(-c2noc(C(F)(F)F)n2)cn1)c1cccc(C(F)(F)F)c1] | N-({5-[5-(trifluoro-methyl)-1,2,4-oxa-diazol-3-yl]pyridin-2-yl}methyl)-N-[3-(trifluoro-methyl)phenyl]tetrahydro-2H-thio-pyran-4-carboxa-mide 1,1-dioxide | | 548.9 | 30 |
| 457 | 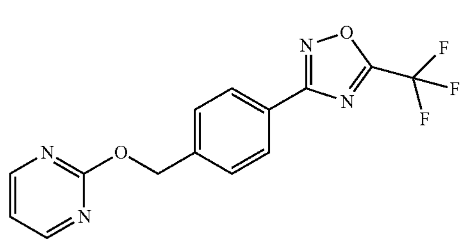 [SMILES: FC(F)(F)c1nc(-c2ccc(COc3ncccn3)cc2)no1] | 2-({4-[5-(trifluoro-methyl)-1,2,4-oxa-diazol-3-yl]benzyl}oxy)pyrimidine | | 323.0 | 168 |

TABLE 2-continued

| Ex # | Structure | Name | Stereo-chemistry | [M + H]+ | General Procedures |
|---|---|---|---|---|---|
| 458 | 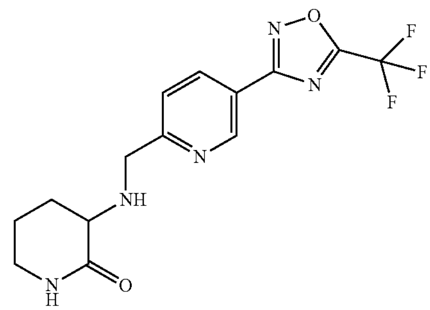 [SMILES: O=C1NCCCC1NCc1ccc(-c2noc(C(F)(F)F)n2)cn1] | 3-[({5-[5-(trifluoro-methyl)-1,2,4-oxa-diazol-3-yl]pyridin-2-yl}methyl)amino]piperidin-2-one | RACEMIC | 342.1 | 174 |
| 459 | 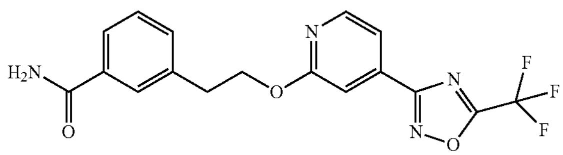 [SMILES: NC(=O)c1cccc(CCOc2cc(-c3noc(C(F)(F)F)n3)ccn2)c1] | 3-[2-({4-[5-(trifluoro-methyl)-1,2,4-oxa-diazol-3-yl]pyridin-2-yl}oxy)ethyl]benzamide | | 379.0 | 24 |
| 460 | 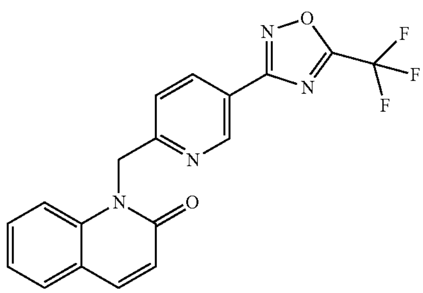 [SMILES: O=c1ccc2ccccc2n1Cc1ccc(-c2noc(C(F)(F)F)n2)cn1] | 1-({5-[5-(trifluoro-methyl)-1,2,4-oxa-diazol-3-yl]pyridin-2-yl}methyl)quinolin-2(1H)-one | | 372.9 | 28 |
| 461 | 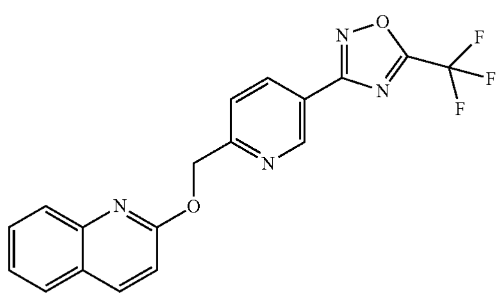 [SMILES: FC(F)(F)c1nc(-c2ccc(COc3ccc4ccccc4n3)nc2)no1] | 2-({5-[5-(trifluoro-methyl)-1,2,4-oxa-diazol-3-yl]pyridin-2-yl}methoxy)quinoline | | 373.0 | 185 |
| 462 | 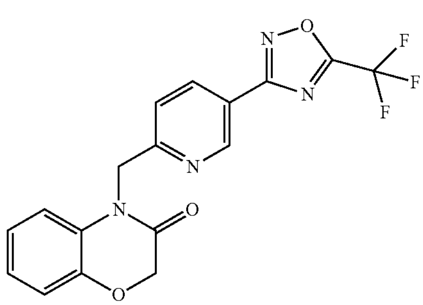 [SMILES: O=C1COc2ccccc2N1Cc1ccc(-c2noc(C(F)(F)F)n2)cn1] | 4-({5-[5-(trifluoro-methyl)-1,2,4-oxa-diazol-3-yl]pyridin-2-yl}methyl)-2H-1,4-benzoxazin-3(4H)-one | | 377.0 | 28 |

TABLE 2-continued

| Ex # | Structure | Name | Stereo-chemistry | [M + H]+ | General Procedures |
|---|---|---|---|---|---|
| 463 | 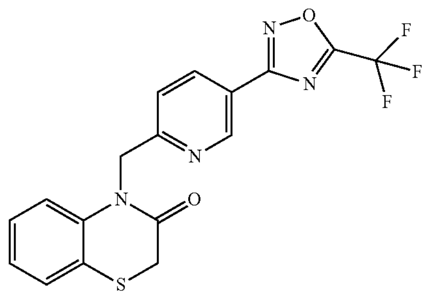 [SMILES: O=C1CSc2ccccc2N1Cc1ccc(-c2noc(C(F)(F)F)n2)cn1] | 4-({5-[5-(trifluoro-methyl)-1,2,4-oxa-diazol-3-yl]pyridin-2-yl}methyl)-2H-1,4-benzothiazin-3(4H)-one | | 392.9 | 28 |
| 464 | 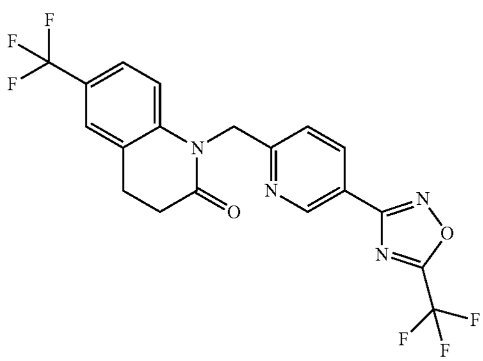 [SMILES: O=C1CCc2cc(C(F)(F)F)ccc2N1Cc1ccc(-c2noc(C(F)(F)F)n2)cn1] | 6-(trifluoro-methyl)-1-({5-[5-(trifluoro-methyl)-1,2,4-oxa-diazol-3-yl]pyridin-2-yl}methyl)-3,4-dihydro-quinolin-2(1H)-one | | 442.9 | 28 |
| 465 | 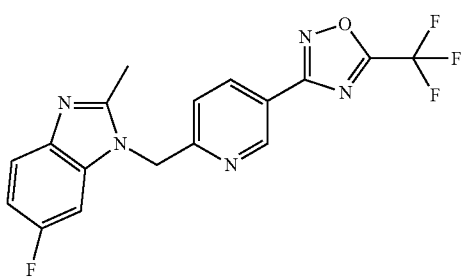 [SMILES: Cc1nc2ccc(F)cc2n1Cc1ccc(-c2noc(C(F)(F)F)n2)cn1] | 6-fluoro-2-methyl-1-({5-[5-(trifluoro-methyl)-1,2,4-oxa-diazol-3-yl]pyridin-2-yl}methyl)-1H-benz-imidazole | | 377.9 | 29 |
| 466 | 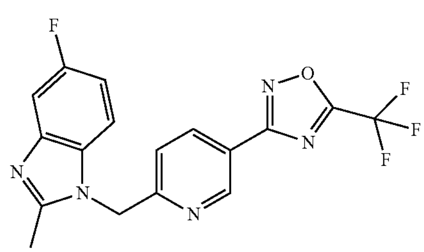 [SMILES: Cc1nc2cc(F)ccc2n1Cc1ccc(-c2noc(C(F)(F)F)n2)cn1] | 5-fluoro-2-methyl-1-({5-[5-(trifluoro-methyl)-1,2,4-oxa-diazol-3-yl]pyridin-2-yl}methyl)-1H-benz-imidazole | | 378.0 | 29 |
| 467 | 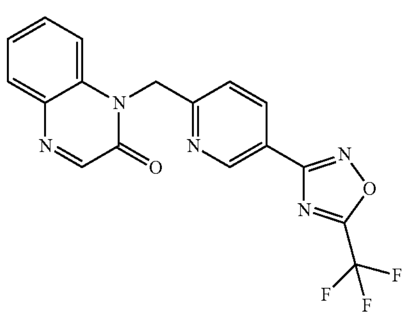 [SMILES: O=c1cnc2ccccc2n1Cc1ccc(-c2noc(C(F)(F)F)n2)cn1] | 1-({5-[5-(trifluoro-methyl)-1,2,4-oxa-diazol-3-yl]pyridin-2-yl}methyl)quinoxalin-2(1H)-one | | 374.0 | 28 |

TABLE 2-continued

| Ex # | Structure | Name | Stereo-chemistry | [M + H]+ | General Procedures |
|---|---|---|---|---|---|
| 468 | 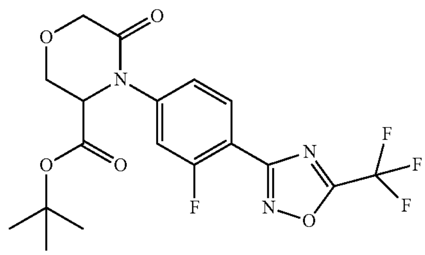 [SMILES: CC(C)(C)OC(=O)C1COCC(=O)N1c1ccc(-c2noc(C(F)(F)F)n2)c(F)c1] | tert-butyl 4-{3-fluoro-4-[5-(trifluoro-methyl)-1,2,4-oxa-diazol-3-yl]phenyl}-5-oxomor-pholine-3-carboxylate | S | 431.9 | 8 |
| 469 | 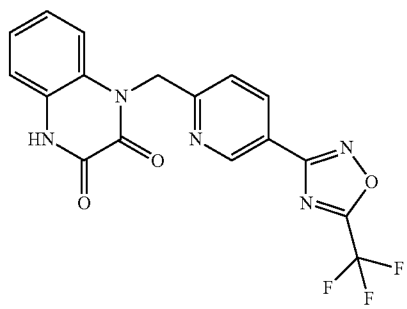 [SMILES: O=c1[nH]c2ccccc2n(Cc2ccc(-c3noc(C(F)(F)F)n3)cn2)c1=O] | 1-({5-[5-(trifluoro-methyl)-1,2,4-oxa-diazol-3-yl]pyridin-2-yl}methyl)-1,4-dihydro-quinoxaline-2,3-dione | | 389.9 | 28 |
| 470 | 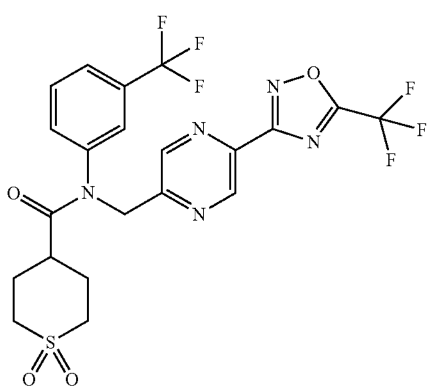 [SMILES: O=C(C1CCS(=O)(=O)CC1)N(Cc1cnc(-c2noc(C(F)(F)F)n2)cn1)c1cccc(C(F)(F)F)c1] | N-({5-[5-(trifluoro-methyl)-1,2,4-oxa-diazol-3-yl]pyrazin-2-yl}methyl)-N-[3-(trifluoro-methyl)phenyl]tetrahydro-2H-thio-pyran-4-carboxamide 1,1-dioxide | | 549.9 | 30 |
| 471 | 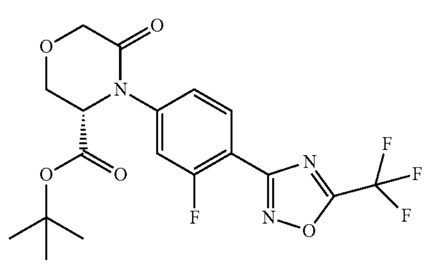 [SMILES: CC(C)(C)OC(=O)[C@@H]1COCC(=O)N1c1ccc(-c2noc(C(F)(F)F)n2)c(F)c1] | tert-butyl (3S)-4-{3-fluoro-4-[5-(trifluoro-methyl)-1,2,4-oxa-diazol-3-yl]phenyl}-5-oxomor-pholine-3-carboxylate | S | 431.9 | 8 |

TABLE 2-continued

| Ex # | Structure | Name | Stereo-chemistry | [M + H]⁺ | General Procedures |
|---|---|---|---|---|---|
| 472 | 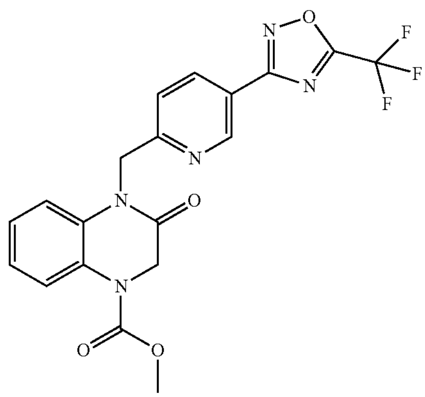 [SMILES: COC(=O)N1CC(=O)N(Cc2ccc(-c3noc(C(F)(F)F)n3)cn2)c2ccccc21] | methyl 3-oxo-4-({5-[5-(trifluoromethyl)-1,2,4-oxadiazol-3-yl]pyridin-2-yl}methyl)-3,4-dihydroquinoxaline-1(2H)-carboxylate | | 433.9 | 28 |
| 473 | 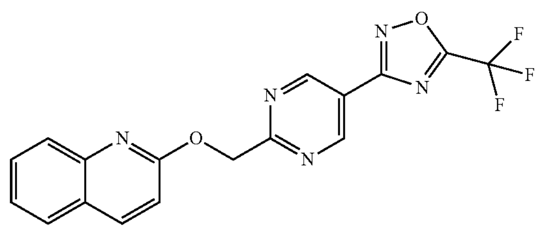 [SMILES: FC(F)(F)c1nc(-c2cnc(COc3ccc4ccccc4n3)nc2)no1] | 2-({5-[5-(trifluoromethyl)-1,2,4-oxadiazol-3-yl]pyrimidin-2-yl}methoxy)quinoline | | 373.9 | 185 |
| 474 | 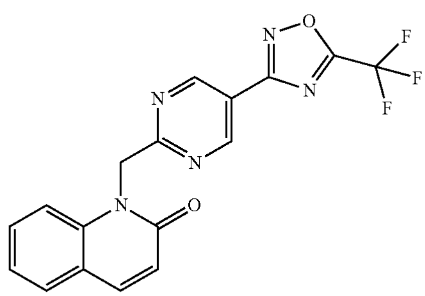 [SMILES: O=c1ccc2ccccc2n1Cc1ncc(-c2noc(C(F)(F)F)n2)cn1] | 1-({5-[5-(trifluoromethyl)-1,2,4-oxadiazol-3-yl]pyrimidin-2-yl}methyl)quinolin-2(1H)-one | | 373.9 | 28 |
| 475 | 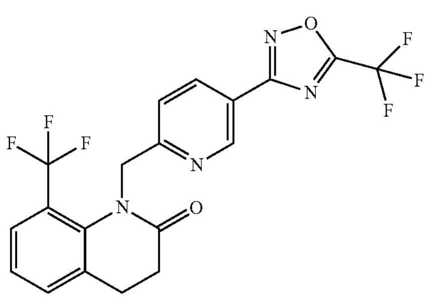 [SMILES: O=C1CCc2cccc(C(F)(F)F)c2N1Cc1ccc(-c2noc(C(F)(F)F)n2)cn1] | 8-(trifluoromethyl)-1-({5-[5-(trifluoromethyl)-1,2,4-oxadiazol-3-yl]pyridin-2-yl}methyl)-3,4-dihydroquinolin-2(1H)-one | | 442.9 | 28 |
| 476 | 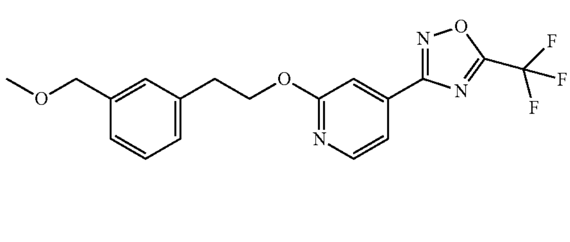 [SMILES: COCc1cccc(CCOc2cc(-c3noc(C(F)(F)F)n3)ccn2)c1] | 2-{2-[3-(methoxymethyl)phenyl]ethoxy}-4-[5-(trifluoromethyl)-1,2,4-oxadiazol-3-yl]pyridine | | 380.0 | 24 |

TABLE 2-continued

| Ex # | Structure | Name | Stereo-chemistry | [M + H]+ | General Procedures |
|---|---|---|---|---|---|
| 477 | 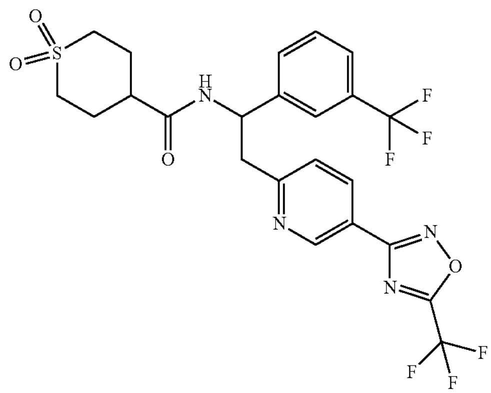 [SMILES: O=C(NC(Cc1ccc(-c2noc(C(F)(F)F)n2)cn1)c1cccc(C(F)(F)F)c1)C1CCS(=O)(=O)CC1] | 1,1-dioxo-N-(2-{5-[5-(trifluoromethyl)-1,2,4-oxadiazol-3-yl]pyridin-2-yl}-1-[3-(trifluoromethyl)phenyl]ethyl)-1lambda~6~-thiane-4-carboxamide | RACEMIC | 563.3 | 177 |
| 478 | 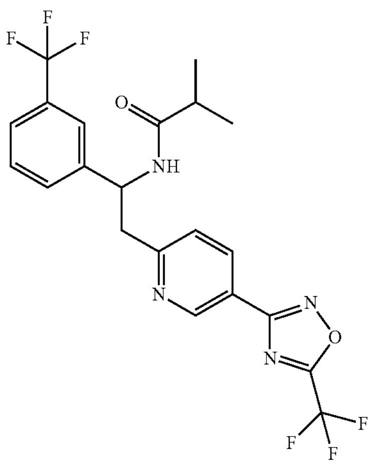 [SMILES: CC(C)C(=O)NC(Cc1ccc(-c2noc(C(F)(F)F)n2)cn1)c1cccc(C(F)(F)F)c1] | 2-methyl-N-(2-{5-[5-(trifluoromethyl)-1,2,4-oxadiazol-3-yl]pyridin-2-yl}-1-[3-(trifluoromethyl)phenyl]ethyl)propanamide | RACEMIC | 473.0 | 177 |
| 479 | 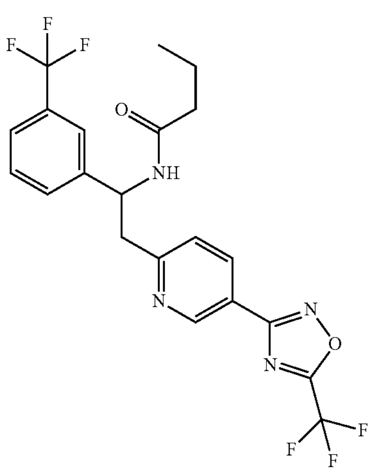 [SMILES: CCCC(=O)NC(Cc1ccc(-c2noc(C(F)(F)F)n2)cn1)c1cccc(C(F)(F)F)c1] | N-(2-{5-[5-(trifluoromethyl)-1,2,4-oxadiazol-3-yl]pyridin-2-yl}-1-[3-(trifluoromethyl)phenyl]ethyl)butanamide | RACEMIC | 472.9 | 177 |

TABLE 2-continued

| Ex # | Structure | Name | Stereo-chemistry | [M + H]⁺ | General Procedures |
|---|---|---|---|---|---|
| 480 | 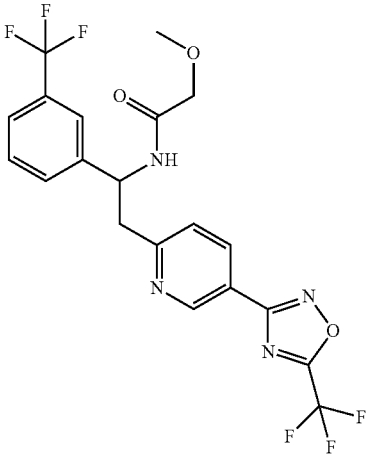 [SMILES: COCC(=O)NC(Cc1ccc(-c2noc(C(F)(F)F)n2)cn1)c1cccc(C(F)(F)F)c1] | 2-methoxy-N-(2-{5-[5-(trifluoro-methyl)-1,2,4-oxa-diazol-3-yl]pyridin-2-yl}-1-[3-(trifluoro-methyl)phenyl]ethyl)acetamide | RACEMIC | 474.9 | 177 |
| 481 | 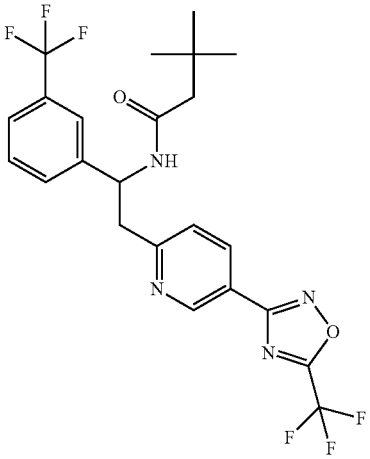 [SMILES: CC(C)(C)CC(=O)NC(Cc1ccc(-c2noc(C(F)(F)F)n2)cn1)c1cccc(C(F)(F)F)c1] | 3,3-dimethyl-N-(2-{5-[5-(trifluoro-methyl)-1,2,4-oxa-diazol-3-yl]pyridin-2-yl}-1-[3-(trifluoro-methyl)phenyl]ethyl)butanamide | RACEMIC | 501.0 | 177 |
| 482 | 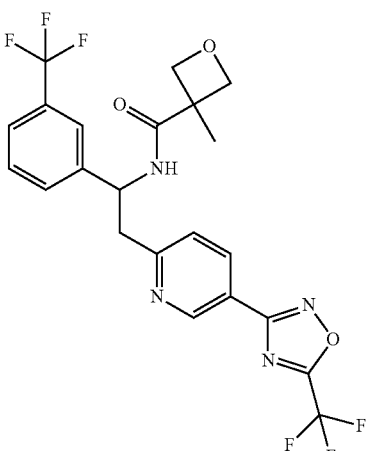 | 3-methyl-N-(2-{5-[5-(trifluoro-methyl)-1,2,4-oxa-diazol-3-yl]pyridin-2-yl}-1-[3-(trifluoro-methyl)phenyl]ethyl)oxetane-3-carboxamide | RACEMIC | 501.0 | 177 |

TABLE 2-continued

| Ex # | Structure | Name | Stereo-chemistry | [M + H]+ | General Procedures |
|---|---|---|---|---|---|
| 483 | 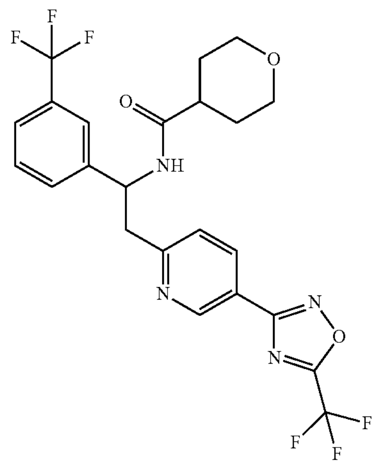 [SMILES: O=C(NC(Cc1ccc(-c2noc(C(F)(F)F)n2)cn1)c1cccc(C(F)(F)F)c1)C1CCOCC1] | N-(2-{5-[5-(trifluoro-methyl)-1,2,4-oxa-diazol-3-yl]pyridin-2-yl}-1-[3-(trifluoro-methyl)phenyl]ethyl)oxane-4-carboxamide | RACEMIC | 515.0 | 177 |
| 484 | 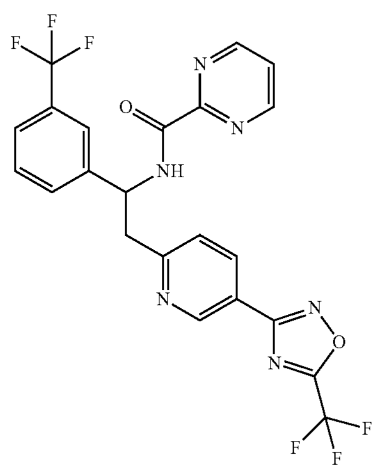 [SMILES: O=C(NC(Cc1ccc(-c2noc(C(F)(F)F)n2)cn1)c1cccc(C(F)(F)F)c1)c1ncccn1] | N-(2-{5-[5-(trifluoro-methyl)-1,2,4-oxa-diazol-3-yl]pyridin-2-yl}-1-[3-(trifluoro-methyl)phenyl]ethyl)pyrimidine-2-carbox-amide | RACEMIC | 509.0 | 177 |
| 485 | 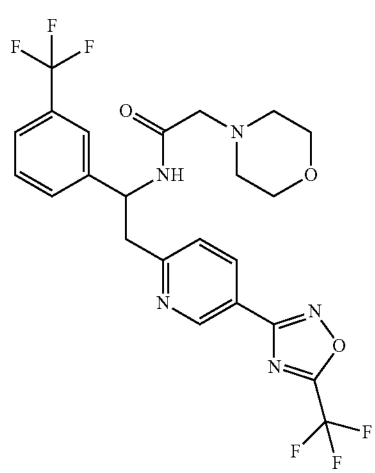 [SMILES: O=C(CN1CCOCC1)NC(Cc1ccc(-c2noc(C(F)(F)F)n2)cn1)c1cccc(C(F)(F)F)c1] | 2-(morpholin-4-yl)-N-(2-{5-[5-(trifluoro-methyl)-1,2,4-oxa-diazol-3-yl]pyridin-2-yl}-1-[3-(trifluoro-methyl)phenyl]ethyl)acetamide | RACEMIC | 530.0 | 177 |

TABLE 2-continued

| Ex # | Structure | Name | Stereo-chemistry | [M + H]+ | General Procedures |
|---|---|---|---|---|---|
| 486 | 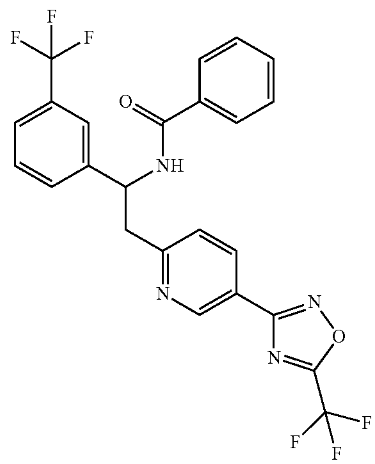 [SMILES: O=C(NC(Cc1ccc(-c2noc(C(F)(F)F)n2)cn1)c1cccc(C(F)(F)F)c1)c1ccccc1] | N-(2-{5-[5-(trifluoro-methyl)-1,2,4-oxa-diazol-3-yl]pyridin-2-yl}-1-[3-(trifluoro-methyl)phenyl]ethyl)benzamide | RACEMIC | 507.0 | 177 |
| 487 | 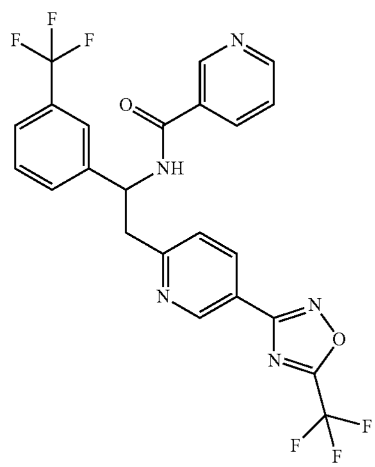 [SMILES: O=C(NC(Cc1ccc(-c2noc(C(F)(F)F)n2)cn1)c1cccc(C(F)(F)F)c1)c1cccnc1] | N-(2-{5-[5-(trifluoro-methyl)-1,2,4-oxa-diazol-3-yl]pyridin-2-yl}-1-[3-(trifluoro-methyl)phenyl]ethyl)pyridine-3-carboxamide | RACEMIC | 508.0 | 177 |
| 488 | 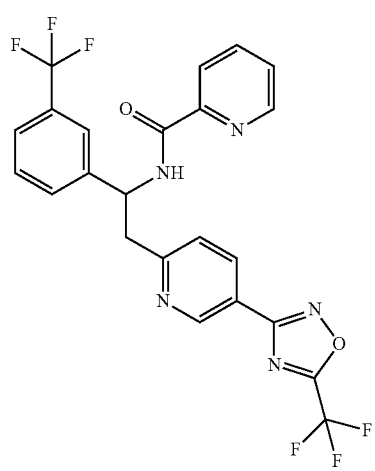 [SMILES: O=C(NC(Cc1ccc(-c2noc(C(F)(F)F)n2)cn1)c1cccc(C(F)(F)F)c1)c1ccccn1] | N-(2-{5-[5-(trifluoro-methyl)-1,2,4-oxa-diazol-3-yl]pyridin-2-yl}-1-[3-(trifluoro-methyl)phenyl]ethyl)pyridine-2-carboxamide | RACEMIC | 508.0 | 177 |

TABLE 2-continued

| Ex # | Structure | Name | Stereo-chemistry | [M + H]+ | General Procedures |
|---|---|---|---|---|---|
| 489 | 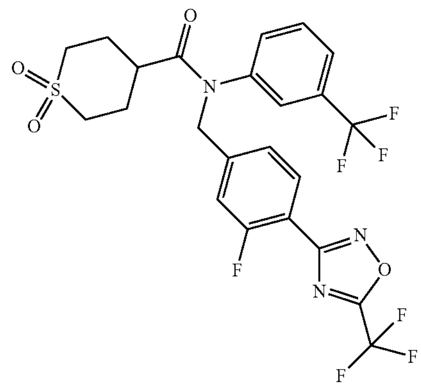 [SMILES: O=C(C1CCS(=O)(=O)CC1)N(Cc1ccc(-c2noc(C(F)(F)F)n2)c(F)c1)c1cccc(C(F)(F)F)c1] | N-({3-fluoro-4-[5-(trifluoro-methyl)-1,2,4-oxa-diazol-3-yl]phenyl}methyl)-1,1-dioxo-N-[3-(trifluoro-methyl)phenyl]-llambda~6~-thiane-4-carbox-amide | | 566.2 | 30 |
| 490 | 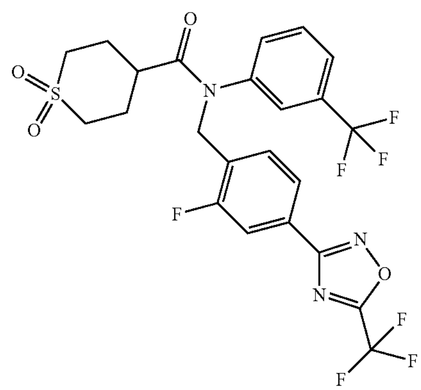 [SMILES: O=C(C1CCS(=O)(=O)CC1)N(Cc1ccc(-c2noc(C(F)(F)F)n2)cc1F)c1cccc(C(F)(F)F)c1] | N-({2-fluoro-4-[5-(trifluoro-methyl)-1,2,4-oxa-diazol-3-yl]phenyl}methyl)-1,1-dioxo-N-[3-(trifluoro-methyl)phenyl]-llambda~6~-thiane-4-carbox-amide | | 566.2 | 30 |
| 491 | 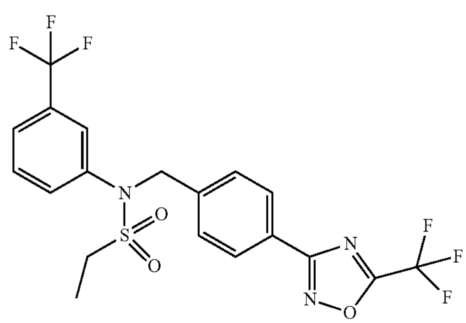 [SMILES: CCS(=O)(=O)N(Cc1ccc(-c2noc(C(F)(F)F)n2)cc1)c1cccc(C(F)(F)F)c1] | N-({4-[5-(trifluoro-methyl)-1,2,4-oxa-diazol-3-yl]phenyl}methyl)-N-[3-(trifluoro-methyl)phenyl]ethane-sulfonamide | | 479.9 | 183 |
| 492 | 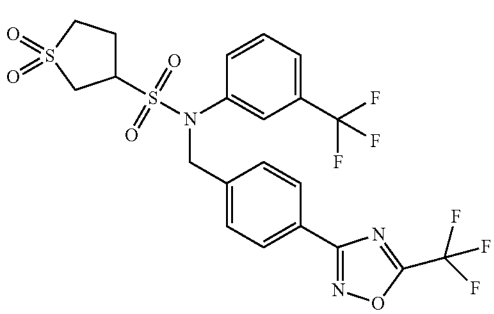 [SMILES: O=S1(=O)CCC(S(=O)(=O)N(Cc2ccc(-c3noc(C(F)(F)F)n3)cc2)c2cccc(C(F)(F)F)c2)C1] | 1,1-dioxo-N-({4-[5-(trifluoro-methyl)-1,2,4-oxa-diazol-3-yl]phenyl}methyl)-N-[3-(trifluoro-methyl)phenyl]-llambda~6~-thiolane-3-sulfonamide | RACEMIC | 569.6 | 183 |

Assay
Methods for HDAC Enzymatic Assays:
Compound potencies were determined versus HDAC1, 5, 6, and 8 isoforms with in vitro assays that measured inhibition of cleavage of a Fluor-de-Lys substrate.

HDAC1 and 6 reagents: FLAG-tagged HDACs 1 and 6 were prepared in-house by protein expression in HEK293F cells followed by anti-FLAG affinity purification. Assays were performed with buffer containing 20 mM HEPES, pH 8.0 [Boston BioProducts, catalog #BB-104, 1M stock], 137 mM NaCl [Sigma, catalog #S5150, 5M stock], 2.7 mM KCl [BioChemika, catalog #87526, 4M stock], 1 mM MgCl2 [Fluka, catalog #63020, 1M stock], and 0.05% BSA (Fraction V) [Invitrogen, catalog #15260, 7.5% stock]. In addition to the above buffer ingredients, TCEP [CalBiochem, catalog #580561, 500 mM stock] was added at a final concentration of 0.5 mM to the buffer for the HDAC6 assays. HDAC1, 2, 3, and 6 enzymes were run at the final concentrations of 0.3 nM, 1.5 nM, 0.3 nM, and 1.333 nM, respectively. Fluor-de-Lys substrate [BioMol Research Laboratories, catalog #KI-104], used to evaluate enzyme activity, was added at the final concentrations of 20 uM, 40 uM, 20 uM, and 2.5 uM for HDACs 1, 2, 3, and 6. To enable detection of the signal, Developer [BioMol Research Laboratories, catalog #KI-105] was added at a 1:250 dilution to the stop solution, which also included 10 uM SAHA [Sigma, catalog #SML0061] to ensure complete termination of the reaction.

HDAC5 reagents: N-terminal GST tagged HDAC5 was purchased from BPS Bioscience [catalog #50045]. Assays were performed with buffer containing 20 mM HEPES, pH 8.0 [Boston BioProducts, catalog #BB-104, 1M stock], 137 mM NaCl [Sigma, catalog #S5150, 5M stock], 2.7 mM KCl [BioChemika, catalog #87526, 4M stock], 1 mM MgCl2 [Fluka, catalog #63020, 1M stock], and 0.05% BSA (Fraction V) [Invitrogen, catalog #15260, 7.5% stock]. The HDAC5 enzyme was run at the final concentration of 0.447 nM. Boc-Lys(TFA)-AMC substrate [Bachem, catalog #1-1985.0050], used to evaluate enzyme activity, was added at the final concentration of 60 uM. To enable detection of the signal, Developer II [BioMol Research Laboratories, catalog #KI-176] was added at a 1:200 dilution to the stop solution, which also included 20 uM trichostatin A (TSA) [Sigma, catalog #T8552] to ensure complete termination of the reaction.

HDAC8 reagents: HDAC8 was purchased from Enzo Life Sciences [catalog #BML-SE145]. Assays were performed with buffer containing 20 mM HEPES, pH 8.0 [Boston BioProducts, catalog #BB-104, 1M stock], 100 mM NaCl [Sigma, catalog #S5150, 5M stock], 20 mM KCl [BioChemika, catalog #87526, 4M stock], 1 mM MgCl2 [Fluka, catalog #63020, 1M stock], 0.05% BSA (Fraction V) [Invitrogen, catalog #15260, 7.5% stock], and 0.1% n-Octyl-β-D-glucopyranoside (N-OG) [Anatrace, catalog #O311, 10% stock]. The HDAC8 enzyme was run at the final concentration of 1.333 nM. Fluor-de-Lys substrate [BioMol Research Laboratories, catalog #KI-178], used to evaluate enzyme activity, was added at the final concentration of 200 uM. To enable detection of the signal, Developer II [BioMol Research Laboratories, catalog #KI-176] was added at a 1:200 dilution to the stop solution, which also included 20 uM SAHA [Sigma, catalog #SML0061] to ensure complete termination of the reaction.

Assay protocol: In brief, compounds were titrated in 100% DMSO via accoustic dispensing directly to the assay plate using the ECHO 550 [Labcyte]. HDAC enzymes at the concentrations indicated above were added in assay buffer to the assay plates containing the compounds using a Combi [Thermo Scientific]. The wells were mixed, and the plates were allowed to pre-incubate at ambient temperature for 3 h. After the 3 h, the appropriate substrate, at the concentrations indicated above, was added to the wells using a Combi. The wells were mixed, and the plates were allowed to incubate at ambient temperature for 1 h. After the 1 h, the appropriate Developer/stop solution was added to the wells using a Combi. The wells were mixed, and the plates were allowed to incubate at ambient temperature for 1 h. The plates were then read on the EnVision [Perkin Elmer] using 380 nm excitiation and 460 nm emission. Data were analyzed using 4P curve fitting with Activity Base [IDBS] software.

TABLE 3 displays the HDAC inhibitory activity of representative HDAC isoforms for the illustrated examples.

TABLE 3

| Example # | HDAC6 $IC_{50}$ (nM) | HDAC1 $IC_{50}$ (nM) | HDAC5 $IC_{50}$ (nM) | HDAC8 $IC_{50}$ (nM) |
|---|---|---|---|---|
| 1 | 10 | 440 | 31 | 2000 |
| 2 | 5.3 | 480 | 18 | 4600 |
| 3 | 240 | | | 6100 |
| 4 | 18 | 210 | | 690 |
| 5 | 19 | 2300 | | 13000 |
| 6 | 73 | | | 2200 |
| 7 | 28 | 3200 | | 2400 |
| 8 | 7.2 | 680 | | 15000 |
| 9 | 3.9 | 1100 | 7.0 | 8300 |
| 10 | 320 | 9000 | | |
| 11 | 110 | 520 | | |
| 12 | 14 | 2000 | 11 | 6000 |
| 13 | 1300 | | | |
| 14 | 130 | | | |
| 15 | 32 | 2400 | 75 | 27000 |
| 16 | 5.6 | 1000 | 19 | 6000 |
| 17 | 5.0 | 97 | 5.0 | 290 |
| 18 | 1600 | >15000 | | |
| 19 | 7.5 | 7500 | 190 | 21000 |
| 20 | 120 | | | |
| 21 | 8.7 | 110 | | 660 |
| 22 | 4.7 | 32 | | 350 |
| 23 | 40 | 7200 | 200 | 2900 |
| 24 | 760 | | | |
| 25 | 8.1 | 220 | | 740 |
| 26 | 170 | 4600 | | 26000 |
| 27 | 160 | 3700 | | 4800 |
| 28 | 31 | 760 | | 1600 |
| 29 | 110 | 1600 | | 8200 |
| 30 | 43 | 1340 | 1200 | 4300 |
| 31 | 390 | | | |
| 32 | 43 | 440 | | 2300 |
| 33 | 140 | 5300 | | 3900 |
| 34 | 6.0 | 64 | | 280 |
| 35 | 6.0 | 55 | 2.0 | 400 |
| 36 | 82 | 16000 | | 5300 |
| 37 | 72 | 16000 | | 10000 |
| 38 | 26 | 4300 | | 16000 |
| 39 | 11 | 550 | 25 | 1600 |
| 40 | 8.7 | 410 | 34 | 800 |
| 41 | 6.1 | 610 | 19 | 6000 |
| 42 | 11 | 530 | 27 | 1400 |
| 43 | 13 | 1900 | 74 | 3600 |
| 44 | 7.3 | | | |
| 45 | 12 | | | |
| 46 | 14 | 100 | | 640 |
| 47 | 29 | 1500 | | 3000 |
| 48 | 29 | 2200 | | 1800 |
| 49 | 120 | 1000 | 1900 | 10000 |
| 50 | 69 | 240 | 820 | |
| 51 | 160 | | | |
| 52 | 120 | | | |
| 53 | 7.3 | 170 | | 1800 |
| 54 | 7.8 | 270 | | 2600 |
| 55 | 8.1 | 250 | 1100 | 2300 |
| 56 | 8.2 | 250 | | 3100 |
| 57 | 8.4 | 240 | | 2000 |
| 58 | 8.6 | 220 | 730 | 1700 |
| 59 | 9.2 | 210 | | 1500 |
| 60 | 9.9 | 230 | 650 | 2100 |
| 61 | 11 | 260 | | 2000 |
| 62 | 11 | 480 | | 3500 |
| 63 | 12 | 260 | | 1500 |
| 64 | 12 | 200 | | 2800 |
| 65 | 15 | 240 | | 3000 |
| 66 | 17 | 720 | | 1900 |
| 67 | 18 | | | |
| 68 | 19 | 690 | 500 | 2000 |
| 69 | 21 | 1300 | | 2600 |
| 70 | 24 | 960 | | 2200 |
| 71 | 26 | 670 | | 2800 |

TABLE 3-continued

| Example # | HDAC6 IC$_{50}$ (nM) | HDAC1 IC$_{50}$ (nM) | HDAC5 IC$_{50}$ (nM) | HDAC8 IC$_{50}$ (nM) |
|---|---|---|---|---|
| 72 | 28 | 1900 | | 2000 |
| 73 | 29 | 940 | | 2200 |
| 74 | 31 | 1000 | | 1900 |
| 75 | 31 | 860 | | 2300 |
| 76 | 34 | 1000 | | 2100 |
| 77 | 37 | 1400 | | 3300 |
| 78 | 39 | 890 | | 2300 |
| 79 | 39 | 1300 | | 3400 |
| 80 | 39 | 1600 | | 2800 |
| 81 | 41 | 1300 | | 4900 |
| 82 | 43 | 860 | | 2500 |
| 83 | 44 | 1200 | | 3500 |
| 84 | 44 | 950 | | 2400 |
| 85 | 46 | 1200 | | 2300 |
| 86 | 46 | 1200 | | 3300 |
| 87 | 46 | 1200 | | 1700 |
| 88 | 49 | 940 | | 3000 |
| 89 | 52 | 1100 | | 2000 |
| 90 | 54 | 1400 | | 2500 |
| 91 | 54 | 1300 | | 19000 |
| 92 | 62 | 3300 | | 10000 |
| 93 | 64 | 990 | | 2200 |
| 94 | 69 | 1400 | | 2300 |
| 95 | 75 | 1300 | | 2000 |
| 96 | 150 | 2400 | | 30000 |
| 97 | 150 | 2300 | | 2900 |
| 98 | 160 | 4200 | | 2300 |
| 99 | 56 | 1900 | | 5900 |
| 100 | 98 | | | |
| 101 | 97 | 20000 | | 17000 |
| 102 | 98 | | | |
| 103 | 120 | | | |
| 104 | 7.1 | 120 | | 440 |
| 105 | 10 | 710 | 18 | 6600 |
| 106 | 4.1 | | | |
| 107 | 12 | 300 | | 2200 |
| 108 | 22 | 2000 | 120 | 2900 |
| 109 | 79 | 1000 | | 2300 |
| 110 | 19 | | | |
| 111 | 42 | | | |
| 112 | 91 | | | |
| 113 | 7.2 | 130 | | 410 |
| 114 | 7.6 | 82 | | 270 |
| 115 | 21 | 1000 | | 920 |
| 116 | 90 | 1600 | | 14000 |
| 117 | 8.7 | 1800 | 140 | 3100 |
| 118 | 5.1 | 570 | 130 | 2500 |
| 119 | 15 | 720 | | 1300 |
| 120 | 25 | | 79 | |
| 121 | 64 | 26000 | | 29000 |
| 122 | 6.5 | 730 | 21 | 1400 |
| 123 | 18 | 1000 | | 5200 |
| 124 | 16 | 1300 | 17 | 7400 |
| 125 | 14 | 430 | | 6200 |
| 126 | 15 | 1400 | 190 | 5000 |
| 127 | 41 | 7300 | 360 | >45000 |
| 128 | 32 | 2900 | | 5100 |
| 129 | 130 | | | |
| 130 | 33 | 480 | 74 | 1500 |
| 131 | 75 | | | |
| 132 | 19 | | | 630 |
| 133 | 11 | 160 | 31 | 350 |
| 134 | 18 | 360 | | 2100 |
| 135 | 23 | 210 | | 1300 |
| 136 | 24 | | | 1800 |
| 137 | 25 | 440 | | 2300 |
| 138 | 26 | | | 1200 |
| 139 | 26 | 3400 | | 4600 |
| 140 | 26 | 930 | 150 | 1000 |
| 141 | 27 | 350 | | 1800 |
| 142 | 38 | 500 | | 1900 |
| 143 | 39 | 6200 | | 2800 |
| 144 | 42 | | | 2700 |
| 145 | 44 | | | |
| 146 | 48 | | | 20000 |
| 147 | 57 | | | 3200 |
| 148 | 57 | | | |
| 149 | 74 | | | |
| 150 | 81 | | | 1800 |
| 151 | 82 | | | 1600 |
| 152 | 92 | | | 840 |
| 153 | 9.6 | 124 | | 280 |
| 154 | 98 | | | 3400 |
| 155 | 100 | | | 1800 |
| 156 | 100 | | | |
| 157 | 110 | | | 3300 |
| 158 | 130 | | | 750 |
| 159 | 140 | | | 4000 |
| 160 | 42 | 1300 | 3.0 | 12000 |
| 161 | 14 | 390 | | 2100 |
| 162 | 18 | 850 | | 1400 |
| 163 | 34 | 1700 | | 4300 |
| 164 | 9.0 | 2900 | | 6100 |
| 165 | 50 | 28000 | | 21000 |
| 166 | 190 | | | |
| 167 | 200 | 2500 | 900 | 480 |
| 168 | 590 | 15000 | 1100 | |
| 169 | 46 | 5200 | 1300 | 12000 |
| 170 | 45 | 5300 | 7400 | 14000 |
| 171 | 59 | 5500 | 1600 | 10000 |
| 172 | 340 | 45000 | 760 | 45000 |
| 173 | 25 | 1100 | 8300 | 6300 |
| 174 | 2.1 | 300 | | 700 |
| 175 | 15 | 900 | | 1400 |
| 176 | 56 | 1300 | 320 | 45000 |
| 177 | 16 | 530 | 420 | 4500 |
| 178 | 21 | 410 | 320 | 3700 |
| 179 | 42 | 340 | 390 | |
| 180 | 48 | 650 | 650 | |
| 181 | 550 | 3300 | 1800 | |
| 182 | 92 | 1100 | 350 | |
| 183 | 50 | 690 | 140 | |
| 184 | 190 | 2300 | 1100 | 2700 |
| 185 | 81 | 4000 | 1400 | |
| 186 | 69 | 8100 | 850 | 3900 |
| 187 | 64 | 1500 | 220 | 1500 |
| 188 | 27 | 380 | | 38 |
| 189 | 170 | 15000 | 170 | 6900 |
| 190 | 100 | 2200 | 550 | 1100 |
| 191 | 82 | 2200 | 940 | 2900 |
| 192 | 23 | 660 | 640 | 1800 |
| 193 | 50 | 710 | | |
| 194 | 53 | 1700 | 610 | 1300 |
| 195 | 45 | 780 | 660 | 1600 |
| 196 | 16 | 6900 | 300 | 6300 |
| 197 | 17 | 1200 | 50 | 110 |
| 198 | 21 | 480 | 650 | 1300 |
| 199 | 30 | 4100 | 2100 | 9900 |
| 200 | 52 | 450 | 460 | 970 |
| 201 | 82 | 4000 | 1400 | 9200 |
| 202 | 75 | 2200 | 730 | 900 |
| 203 | 60 | 130 | 130 | 900 |
| 204 | 95 | 1000 | | |
| 205 | 73 | 720 | | |
| 206 | 93 | 4200 | | |
| 207 | 23 | 1500 | | 1300 |
| 208 | 97 | 3100 | | |
| 209 | 42 | 6800 | | 4400 |
| 210 | 52 | 1200 | | |
| 211 | 71 | 2500 | | |
| 212 | 86 | 1900 | | |
| 213 | 92 | 1900 | | |
| 214 | 66 | 1400 | | |
| 215 | 95 | 1200 | | |
| 216 | 86 | 1100 | | |
| 217 | 88 | 3800 | | |
| 218 | 66 | 870 | | |
| 219 | 73 | 920 | | |
| 220 | 57 | 1200 | | |
| 221 | 44 | 2800 | | 1600 |
| 222 | 95 | 3500 | | |
| 223 | 98 | 2400 | | |
| 224 | 91 | 1200 | | |
| 225 | 55 | 1500 | | 620 |

TABLE 3-continued

| Example # | HDAC6 IC$_{50}$ (nM) | HDAC1 IC$_{50}$ (nM) | HDAC5 IC$_{50}$ (nM) | HDAC8 IC$_{50}$ (nM) |
|---|---|---|---|---|
| 226 | 36 | 1100 | | 850 |
| 227 | 19 | 1500 | 65 | 730 |
| 228 | 38 | 4300 | 140 | 2000 |
| 229 | 95 | 3700 | 140 | 4800 |
| 230 | 67 | 8500 | 200 | 540 |
| 231 | 49 | 6900 | 110 | 45000 |
| 232 | 54 | 3000 | 67 | 1300 |
| 233 | 27 | 1600 | 170 | 2200 |
| 234 | 21 | 370 | 8.4 | 640 |
| 235 | 27 | 520 | 26 | 770 |
| 236 | 26 | 3100 | 42 | 2100 |
| 237 | 96 | 1800 | 230 | 5300 |
| 238 | 21 | 510 | 21 | 1300 |
| 239 | 74 | 5900 | 190 | 2400 |
| 240 | 26 | 1500 | 78 | 11000 |
| 241 | 92 | 3200 | 48 | 3000 |
| 242 | 51 | 2900 | 110 | 1700 |
| 243 | 79 | 1500 | 50 | 1600 |
| 244 | 44 | 3300 | 130 | 1900 |
| 245 | 54 | 1500 | 180 | 3400 |
| 246 | 54 | 2400 | 120 | 45000 |
| 247 | 94 | 5500 | 98 | 1400 |
| 248 | 73 | 2600 | 59 | 2600 |
| 249 | 49 | 3100 | 74 | 2300 |
| 250 | 97 | 3100 | 910 | |
| 251 | 29 | 1200 | 190 | 3500 |
| 252 | 51 | 2600 | 120 | 4500 |
| 253 | 35 | 1700 | 64 | 3900 |
| 254 | 33 | 1600 | 140 | 45000 |
| 255 | 91 | 1700 | 380 | 1600 |
| 256 | 56 | 3300 | 200 | 2300 |
| 257 | 83 | 6400 | 200 | |
| 258 | 61 | 1200 | 150 | |
| 259 | 28 | 4200 | 84 | |
| 260 | 47 | 12000 | 120 | |
| 261 | 29 | 850 | 24 | |
| 262 | 24 | 2900 | 120 | |
| 263 | 83 | 5300 | 240 | |
| 264 | 42 | 2200 | 90 | |
| 265 | 96 | 5600 | 280 | |
| 266 | 82 | 6600 | 250 | |
| 267 | 78 | 1100 | 200 | |
| 268 | 48 | 2900 | 120 | |
| 269 | 95 | 7100 | 500 | |
| 270 | 38 | 2300 | 160 | |
| 271 | 20 | 3700 | 85 | |
| 272 | 20 | 630 | 31 | |
| 273 | 25 | 720 | 28 | |
| 274 | 48 | 4000 | 160 | |
| 275 | 73 | 860 | 87 | |
| 276 | 84 | 1500 | 120 | |
| 277 | 16 | 2000 | 130 | |
| 278 | 21 | 780 | 86 | |
| 279 | 39 | 750 | 69 | |
| 280 | 85 | 2200 | 190 | |
| 281 | 93 | 2700 | 30 | |
| 282 | 16 | 720 | 7 | |
| 283 | 27 | 45000 | 75 | |
| 284 | 38 | 2200 | 260 | |
| 285 | 48 | 3400 | 280 | |
| 286 | 88 | 2700 | 50 | |
| 287 | 67 | 1800 | 150 | |
| 288 | 93 | 45000 | 280 | |
| 289 | 72 | 8400 | 680 | |
| 290 | 84 | 8100 | 660 | |
| 291 | 63 | 9300 | 190 | |
| 292 | 68 | 6500 | 540 | |
| 293 | 77 | 4500 | 510 | |
| 294 | 92 | 12000 | 410 | |
| 295 | 74 | 17000 | 500 | |
| 296 | 77 | 3700 | 49 | |
| 297 | 6.1 | 310 | 51 | |
| 298 | 16 | 1000 | 290 | |
| 299 | 42 | 1300 | 800 | |
| 300 | 25 | 1300 | 660 | |
| 301 | 19 | 280 | 37 | |
| 302 | 12 | 290 | 76 | |
| 303 | 23 | 990 | 170 | |
| 304 | 13 | 250 | 79 | |
| 305 | 82 | 2400 | 1700 | |
| 306 | 27 | 1300 | 220 | |
| 307 | 39 | 2200 | 620 | |
| 308 | 26 | 740 | 310 | |
| 309 | 98 | 4200 | 450 | |
| 310 | 71 | 2400 | 770 | |
| 311 | 27 | 880 | 540 | |
| 312 | 19 | 1400 | | 45000 |
| 313 | 5.1 | 570 | | 2500 |
| 314 | 51 | 11000 | | 6500 |
| 315 | 18 | 2100 | | 8000 |
| 316 | 25 | | | |
| 317 | 3.9 | | | |
| 318 | 9.9 | | | 1800 |
| 319 | 22 | 180 | | |
| 320 | 13 | 880 | | 12000 |
| 321 | 21 | 210 | | 2600 |
| 322 | 11 | 260 | | |
| 323 | 4.2 | 53 | | |
| 324 | 9.1 | 150 | | |
| 325 | 60 | 2500 | | |
| 326 | 50 | 35000 | | 45000 |
| 327 | 26 | 640 | | |
| 328 | 35 | 580 | | |
| 329 | 65 | 3900 | | 7900 |
| 330 | 95 | 3700 | | 18000 |
| 331 | 25 | 4900 | | 19000 |
| 332 | 14 | 4500 | | 4500 |
| 333 | 13 | 3300 | | 6700 |
| 334 | 79 | 4400 | | 19000 |
| 335 | 27 | 1200 | | 7400 |
| 336 | 59 | 10000 | | 26000 |
| 337 | 7.5 | 7500 | | 21000 |
| 338 | 91 | | | |
| 339 | 28 | 13000 | | 45000 |
| 340 | 36 | 31000 | 1800 | 27000 |
| 341 | 71 | 41000 | | 26000 |
| 342 | 97 | 45000 | | 25000 |
| 343 | 64 | 24000 | 3000 | 25000 |
| 344 | 67 | 45000 | 1900 | |
| 345 | 67 | 43000 | 1500 | |
| 346 | 53 | 1200 | | 15000 |
| 347 | 43 | 600 | | |
| 348 | 80 | 2400 | | |
| 349 | 62 | 730 | | 1400 |
| 350 | 72 | 1200 | | 250 |
| 351 | 66 | 520 | | 680 |
| 352 | 83 | 44 | | |
| 353 | 82 | 410 | | 900 |
| 354 | 85 | 1600 | | 680 |
| 355 | 83 | 48 | | |
| 356 | 16 | 280 | | 520 |
| 357 | 17 | 210 | | 960 |
| 358 | 26 | 890 | | 2400 |
| 359 | 8.0 | 430 | | 1800 |
| 360 | 4.8 | 7.6 | | |
| 361 | 17 | 520 | | 1600 |
| 362 | 57 | 1400 | | 2800 |
| 363 | 19 | 520 | | 3400 |
| 364 | 6.6 | 60 | | |
| 365 | 65 | 1200 | | 1800 |
| 366 | 26 | 1300 | | 2700 |
| 367 | 17 | 820 | | 870 |
| 368 | 25 | 1000 | | 890 |
| 369 | 17 | 930 | | 960 |
| 370 | 3.0 | 68 | | 860 |
| 371 | 30 | 450 | | 1600 |
| 372 | 29 | 400 | | 2900 |
| 373 | 36 | 1300 | | 2800 |
| 374 | 95 | 3200 | | 6900 |
| 375 | 17 | 1000 | | 2600 |
| 376 | 62 | 3400 | | 3900 |
| 377 | 64 | 7300 | | 3300 |
| 378 | 53 | 630 | | 4200 |
| 379 | 29 | 1900 | | 7700 |

TABLE 3-continued

| Example # | HDAC6 IC50 (nM) | HDAC1 IC50 (nM) | HDAC5 IC50 (nM) | HDAC8 IC50 (nM) |
|---|---|---|---|---|
| 380 | 24 | 930 | | 1400 |
| 381 | 16 | 520 | | 3900 |
| 382 | 32 | 1600 | | 2100 |
| 383 | 41 | 1700 | | 3100 |
| 384 | 83 | 4600 | | 13000 |
| 385 | 57 | 2100 | | 5000 |
| 386 | 59 | 5300 | | 3900 |
| 387 | 78 | 3100 | | 880 |
| 388 | 8.6 | 280 | | 4900 |
| 389 | 8.7 | 300 | | 1600 |
| 390 | 10 | 430 | | 1700 |
| 391 | 19 | 1400 | | 7400 |
| 392 | 8.8 | 480 | | 3100 |
| 393 | 9.2 | 410 | | 3400 |
| 394 | 19 | 730 | | 2400 |
| 395 | 9.4 | 330 | | 1300 |
| 396 | 13 | 380 | | 1000 |
| 397 | 18 | 420 | | 1100 |
| 398 | 7.7 | 410 | | 2300 |
| 399 | 26 | 930 | | 3100 |
| 400 | 8.2 | 260 | | 3200 |
| 401 | 5.8 | 290 | | 3300 |
| 402 | 9.0 | 340 | | 2600 |
| 403 | 8.3 | 250 | | 2000 |
| 404 | 8.3 | 280 | | 1300 |
| 405 | 8.4 | 220 | | 1600 |
| 406 | 11 | 270 | | 1800 |
| 407 | 64 | 1700 | | 5800 |
| 408 | 19 | 600 | | 1200 |
| 409 | 26 | 5500 | | 1200 |
| 410 | 76 | | | |
| 411 | 30 | 1000 | | 2200 |
| 412 | 30 | 1000 | | 5700 |
| 413 | 29 | 2000 | | 4300 |
| 414 | 67 | 3900 | | 12000 |
| 415 | 21 | 1600 | | 2500 |
| 416 | 77 | | | |
| 417 | 56 | 2600 | | 1900 |
| 418 | 49 | 3600 | | 3200 |
| 419 | 47 | 2600 | | 1900 |
| 420 | 3.8 | 110 | | 1000 |
| 421 | 17 | | | |
| 422 | 82 | 3400 | | 4000 |
| 423 | 9.0 | 2900 | | 6100 |
| 424 | 59 | 2600 | | 320 |
| 425 | 89 | | | |
| 426 | 95 | | | |
| 427 | 91 | 5100 | | 1000 |
| 428 | 50 | 28000 | | 21000 |
| 429 | 14 | 460 | | 2300 |
| 430 | 9.9 | 530 | | 2000 |
| 431 | 91 | 4300 | | 1900 |
| 432 | 98 | | | 1300 |
| 433 | 12 | 890 | | 900 |
| 434 | 40 | 1100 | | 1200 |
| 435 | 39 | 4400 | | 4600 |
| 436 | 34 | 1200 | | 4200 |
| 437 | 32 | 5400 | | 5100 |
| 438 | 12 | 520 | | 1000 |
| 439 | 54 | | | 1400 |
| 440 | 7.0 | | | 280 |
| 441 | 11 | 490 | | 740 |
| 442 | 7.3 | 280 | | 750 |
| 443 | 13 | 1200 | | 1400 |
| 444 | 5.3 | 350 | | 2500 |
| 445 | 4.4 | 850 | | 2200 |
| 446 | 4.7 | 240 | | 1600 |
| 447 | 17 | 970 | | 740 |
| 448 | 32 | | | 530 |
| 449 | 4.2 | 310 | | 1900 |
| 450 | 65 | 2800 | | 2800 |
| 451 | 72 | 2500 | | 2400 |
| 452 | 93 | 2800 | | 2400 |
| 453 | 66 | | | 1900 |
| 454 | 20 | | | 1700 |
| 455 | 100 | | | 3800 |
| 456 | 10 | 360 | 2700 | 2500 |
| 457 | 35 | 2600 | | 730 |
| 458 | 40 | 8300 | 290 | 2800 |
| 459 | 90 | 1800 | | |
| 460 | 4.5 | 99 | | |
| 461 | 33 | 500 | | 21000 |
| 462 | 5.1 | 150 | 9.6 | 2400 |
| 463 | 11 | 130 | | |
| 464 | 28 | 300 | | |
| 465 | 13 | 720 | 36 | 5600 |
| 466 | 27 | 840 | | |
| 467 | 8.8 | 170 | | |
| 468 | 19 | 940 | | 5500 |
| 469 | 3.4 | 86 | 22 | 1400 |
| 470 | 47 | 1100 | | 10000 |
| 471 | 22 | 870 | 54 | 3800 |
| 472 | 20 | 320 | | 1400 |
| 473 | 32 | 160 | | 45000 |
| 474 | 26 | 220 | | 6000 |
| 475 | 65 | 880 | | 5600 |
| 476 | 28 | 1900 | 780 | 3000 |
| 477 | 44 | 670 | 620 | |
| 478 | 25 | 680 | 500 | 45000 |
| 479 | 28 | 610 | 440 | 45000 |
| 480 | 22 | 670 | 620 | 5300 |
| 481 | 77 | 1100 | 710 | |
| 482 | 26 | 790 | 480 | 8500 |
| 483 | 27 | 630 | 510 | 6100 |
| 484 | 29 | 600 | 720 | 2500 |
| 485 | 37 | 1100 | 1100 | 11000 |
| 486 | 66 | 690 | 670 | |
| 487 | 27 | 670 | 380 | 5300 |
| 488 | 73 | 880 | 670 | |
| 489 | 34 | 950 | 760 | 6900 |
| 490 | 18 | 500 | 520 | 3400 |
| 491 | 53 | 820 | 140 | |
| 492 | 56 | 1200 | 390 | |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

What is claimed is:

1. A compound of formula (I):

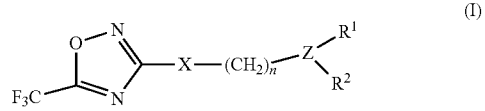

or a pharmaceutically acceptable salt thereof wherein;

X represents phenyl, wherein said phenyl is optionally substituted with one or two fluoro;

Z is —N;

$R^1$ and $R^2$ can combine together with the nitrogen atom to which they are attached to form a six membered monocyclic, heterocyclic non-aromatic ring optionally interrupted by 1 heteroatoms O, wherein said heterocyclic ring is optionally substituted with 1 to 2 groups of $R^a$;

R$^a$ is selected from the group consisting of H, phenyl and =O, wherein said phenyl is optionally substituted with 1 group R$^b$;

R$^b$ is halo, n represents 0.

2. The compound according to claim 1 wherein R$^1$ and R$^2$ combine together with the nitrogen atom to which they are attached to form optionally substituted morpholinyl, morpholinonyl, piperidinonyl, or piperidinyl, wherein said groups are optionally substituted with 1 to 2 R$^a$ selected from the group consisting of phenyl, or a pharmaceutically acceptable salt thereof.

3. The compound according to claim 2 wherein R$^1$ and R$^2$ combine together with the nitrogen atom to which they are attached to form morpholinyl, morpholinonyl, piperidinonyl, or piperidinyl, and at least one R$^a$ is present which is positioned adjacent to the nitrogen atom to which R$^1$ and R$^2$ originally are attached, or a pharmaceutically acceptable salt thereof.

4. The compound according to claim 3 wherein the R$^a$ substituent attached adjacent to the nitrogen atom to which R$^1$ and R$^2$ are originally attached is phenyl, or a pharmaceutically acceptable salt thereof.

5. The compound according to claim 1 as represented by structural formula II:

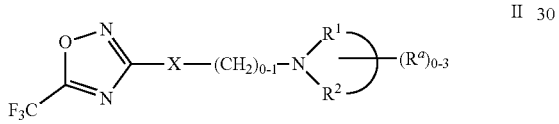

II or a pharmaceutically acceptable salt thereof, wherein

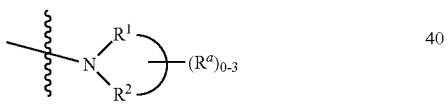

is defined as Q and Q is represented by structural formulas (c), (d), (e), or (f);

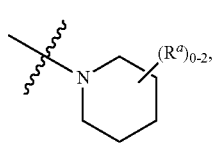 (c)

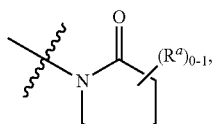 (d)

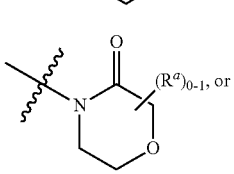 (e)

-continued

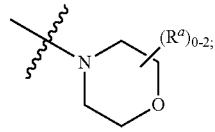 (f)

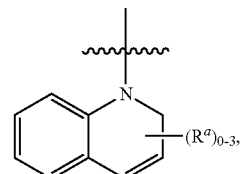 (k)

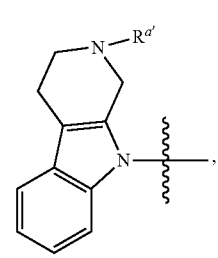 (l)

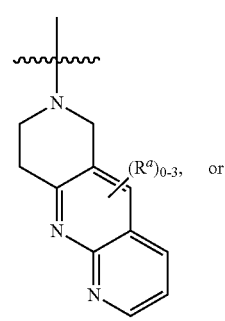 (m)

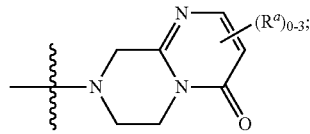 (n)

∿∿∿ represents the bond that links the nitrogen to which it is attached to the rest of the molecule;

and R$^{a\prime}$ is R$^a$ and R$^a$ is as defined in claim 1.

6. The compound according to claim 5 wherein Q is (c), (d), (e), or (f), at least one R$^a$ is attached and is phenyl, or a pharmaceutically acceptable salt thereof.

7. The compound according to claim 6 wherein at least one R$^a$ present, is phenyl, and is located on the carbon atom directly adjacent to the linking nitrogen atom, or a pharmaceutically acceptable salt thereof.

8. A compound which is selected from the group consisting of:

(R)-5-phenyl-4-(4-(5-(trifluoromethyl)-1,2,4-oxadiazol-3-yl)phenyl)morpholin-3-one, (R)-4-(3-fluoro-4-(5-(trifluoromethyl)-1,2,4-oxadiazol-3-yl)phenyl)-5-phenylmorpholin-3-one, (R)-4-(2,5-difluoro-4-(5-(trifluoromethyl)-1,2,4-oxadiazol-3-yl)phenyl)-5-phenylmorpholin-3-one, (R)-4-(2-fluoro-4-(5-(trifluoromethyl)-1,2,4-oxadiazol-3-yl)phenyl)-5-phenylmorpholin-3-one, or a pharmaceutically acceptable salt thereof.

9. A pharmaceutical composition comprising a compound of claim 1, or a pharmaceutically acceptable salt thereof and a pharmaceutically acceptable carrier.

\* \* \* \* \*